United States Patent [19]

Doumaux, Jr. et al.

[11] Patent Number: 5,202,489
[45] Date of Patent: Apr. 13, 1993

[54] AMINES CATALYSIS

[75] Inventors: Arthur R. Doumaux, Jr., Charleston; David J. Schreck, Cross Lanes, both of W. Va.; George A. Skoler, White Plains, N.Y.; Stephen W. King, Scott Depot, W. Va.

[73] Assignee: Union Carbide Chemicals & Plastics Technology Corporation, Danbury, Conn.

[21] Appl. No.: 390,829

[22] Filed: Aug. 8, 1989

Related U.S. Application Data

[63] Continuation-in-part of Ser. No. 136,615, Dec. 22, 1987, abandoned.

[51] Int. Cl.$^5$ ............................................. C07C 209/60
[52] U.S. Cl. ................... 564/479; 564/480; 564/512
[58] Field of Search .................. 564/512, 479, 480

[56] References Cited

FOREIGN PATENT DOCUMENTS

| | | |
|---|---|---|
| 0315189 | 11/1988 | European Pat. Off. |
| 0328101 | 2/1989 | European Pat. Off. |
| 0331396 | 2/1989 | European Pat. Off. |
| 0345955 | 5/1989 | European Pat. Off. |
| 326955 | 7/1954 | Switzerland |
| 1439838 | 7/1972 | United Kingdom |
| 2147896 | 10/1984 | United Kingdom |

Primary Examiner—C. Warren Ivy
Assistant Examiner—Raymond Covington
Attorney, Agent, or Firm—R. M. Allen

[57] ABSTRACT

Process of making amines by inter alia the (i) intramolecular condensation of an amino compound to an amine having a lower molecular weight or (ii) the intermolecular condensation of an amino compound with one or more of another amino compound or a compound containing an alcoholic hydroxyl group using a Group IVB metal oxide condensation catalyst. The preferred process involves the manufacture of alkyleneamines, most desirably polyalkylenepolyamines, by such condensation reactions utilizing catalysts containing titanium oxide, zirconium oxide or mixtures of them.

40 Claims, No Drawings

AMINES CATALYSIS

This application is a continuation-in-part of U.S. patent application Ser. No. 136,615, filed Dec. 22, 1987 now abandoned.

The following are related, commonly assigned applications, filed on an even date herewith: U.S. patent application Ser. No. 390,714; U.S. patent application Ser. No. 390,709 now U.S. Pat. No. 4,983,736 U.S patent application Ser. No. 390,706; U.S. patent application Ser. No. 390,828 now U.S. Pat. No. 5,101,074 and U.S. patent application Ser. No. 390,708 now abandoned; all incorporated herein by reference.

BRIEF SUMMARY OF THE INVENTION

1. Technical Field

A process of making amines which comprises condensing an amino compound in the presence of a Group IVB metal oxide condensation catalyst.

A catalyst composition comprising a high surface area Group IVB metal oxide condensation catalyst containing one or more performance modifiers.

2. Background of the Invention

There is a substantial body of literature directed to the use of acid catalysts to effect intramolecular and intermolecular condensation of amino compounds. U.S. Pat. No. 2,073,671 and U.S. Pat. No. 2,467,205 constitute early prior work on the use of acid condensation catalysts to condense amino compounds. U.S. Pat. No. 2,073,671 discusses, in a general fashion, the catalytic intermolecular condensation of alcohols and amines or ammonia using the same phosphate catalysts later favored by U.S. Pat. No. 2,467,205 for the intramolecular condensation of amines. The two patents are not in harmony over the use of other materials as catalysts. To illustrate this point, U.S. Pat. No. 2,073,671 states:

"Alumina, thoria, blue oxide of tungsten, titania, chromic oxide, blue oxide of molybdenum and zirconia have been mentioned in the literature for use as catalysts in carrying out these reactions but their effectiveness is so low that no practical application has been made of their use."

whereas U.S. Pat. No. 2,467,205 in describing the self-condensation of ethylenediamine (EDA) under vapor phase conditions, to initially produce ethyleneamines, but after recycle, eventually generates piperazine through multistep condensation reactions, followed by deamination, recommends "dehydration catalysts" which are thereafter characterized as "silica gel, titania gel, alumina, thoria, boron phosphate, aluminum phosphate, and the like."

U.S. Pat. No. 2,073,671 describes the condensation catalyst in the following terms:

". . . a heated catalyst or contact mass containing phosphorus and especially one or more of the oxygen acids of phosphorus, their anhydrides, their polymers, and their salts; for example, orthophosphoric acid, metaphosphoric acid, pyrophosphoric acid, phosphorous pentoxide, dimetaphosphoric acid, trimetaphosphoric acid primary ammonium phosphate, secondary ammonium phosphate, normal ammonium phosphate, ammonium metaphosphate, secondary ammonium pyrophosphate, normal ammonium pyrophosphate, aluminum phosphate, aluminum acid phosphate and mixtures of two or more of such materials."

whereas U.S. Pat. No. 2,467,205 describes one of the preferred catalysts as "basic aluminum phosphate".

U.S. Pat. No. 2,454,404 effects the "catalytic deamination of alkylene polyamines" by reacting diethylenetriamine (DETA) vapor over solid catalysts such as activated alumina, bauxite, certain aluminum silicates such as kaolin and oxides of thorium, titanium and zirconium.

U.S. Pat. Nos. 2,073,671 and 2,467,205 demonstrate a common experience in using aluminum phosphate as a condensation catalyst to produce aliphatic amines, and U.S. Pat. Nos. 2,454,404 and 2,467,205 contemplate the other solid catalysts for deamination of amines to make heterocyclic noncyclic amines. In general, the reaction conditions under which deamination to effect cyclization occurs are more severe than those employed for condensation to generate noncyclic molecules, all other factors being comparable.

It is suffice to state that neither of U.S. Pat. Nos. 2,467,205 and 2,454,404 show the actual use of oxides of Group IVB metals as catalysts for any purpose nor do they indicate the nature of these oxides in terms of properties in order to distinguish one oxide of the class form another. U.S. Pat. No. 2,073,671 suggests that the oxides of Group IVB metals would be ineffectual condensation catalysts.

U.S. Pat. Nos. 4,540,822, 4,584,406, and 4,588,842 depict the use of Group IVB metal oxides as supports for phosphorus catalysts used to effect the condensation of amino compounds with alkanolamines. They each show that the Group IVB metal oxide per se is essentially inactive as a catalyst. In other words, these patents specifically tested certain Group IVB metal oxides as condensation catalysts and found they were inert, i.e., they failed to affect the reactants or cause any condensation. U.S. Pat. No. 4,540,822 at Table I states that catalyst "5494-4" is titania ($TiO_2$) and at col. 9, lines 49–52, the patentee finds that titania is "essentially inert", see Table II. In Table IV, the patentee shows that the calcined phosphoric treated titania contained a small amount of sulfur impurity. Table VI is an analysis of the titania pellet and shows no detected sulfur. This can be interpreted as indicating that the sulfur impurity detected was associated with the phosphoric acid. U.S. Pat. No. 4,584,406 demonstrates that zirconia (No. "5484-37") is also inactive as a condensation catalyst, see Table II therein. The same data ca be found in U.S. Pat. No. 4,588,842.

U.S. Pat. No. 683,335 describes the use of tungstophosphoric acid, molybdophosphoric acid or mixtures deposited on titania as catalysts for the condensation of amines and alkanolamines to make polyalkylenepolyamines. Examples 2–7 characterize titania surface areas of 51, 60 and 120 $m^2/gm$. There is no description in the patent dealing with the use of the tiania support as a catalyst.

The only reasonable conclusion to be drawn from the above prior art is that titania is a favorable catalyst support material for the condensation of amines and has no catalytic activity for effecting condensation of amines.

U.S. Pat. Nos. 4,314,083, 4,316,840, 4,362,886 and 4,394,524 disclose the use of certain metal sulfates as useful catalysts for the condensation of alkanolamine and an amino compound. No distinction is made between the sulfur compounds in respect to catalytic efficacy. Sulfuric acid is as good as any metal sulfate, and all metal sulfates are treated as equivalents. At column 8 of U.S. Pat. No. 4,314,083, it is noted that boron sulfate "gave extremely high selectivity at a low level" of EDA. However, selectivity in general was shown to increase with an increase of EDA relative to MEA in the feed. The only specific metal sulfates disclosed in the patents are antimony sulfate, beryllium sulfate, iron sulfate and aluminum sulfate. No Group IVB metal oxide containing residual sulfur is described by these patents.

In the typical case of the manufacture of alkyleneamines, mixtures with other alkyleneamines (including a variety of polyalkylenepolyamines and cyclic alkylenepolyamines) are formed. The same holds true when the object of the process is to produce polyalkylenepolyamines whether acyclic or cyclic, in that a variety of amino compounds are also formed. Each of these cyclic and acyclic alkyleneamines can be isolated from the mixture.

The acid catalyzed condensation reaction involving the reaction of an alkanolamine with an amino compound in the presence of an acidic catalyst is believed to proceed through the mechanism of esterifying free surface hydroxyl groups on the acid catalyst with the alkanolamine and/or by protonating the alkanolamine in the presence of the acid catalyst, followed by loss of water and amine condensation of the ester or the hydrated species, as the case may be, to form the alkyleneamine. Illustrative prior art directed primarily to the cyclic polyalkylenepolyamines (heterocyclic polyamines), but not necessarily limited to the aforementioned acid condensation reaction, are: U.S. Pat. Nos. 2,937,176, 2,977,363, 2,977,364, 2,985,658, 3,056,788, 3,231,573, 3,167,555, 3,242,183, 3,297,701, 3,172,891, 3,369,019, 3,342,820, 3,956,329, 4,017,494, 4,092,316, 4,182,864, 4,405,784 and 4,514,567; European Pat. Applications 0 069 322, 0 111 928 and 0 158 319; East German Pat. No. 206,896; Japanese Pat. Publication No. 51-141895; and French Pat. No. 1,381,243. The evolution of the art to the use of the acid catalyzed condensation reaction to generate acyclic alkyleneamines, particular acyclic polyalkylenepolyamines, as the predominant products stemmed from the initial disclosure in U.S. Pat. No. 4,036,881, patented Jul. 19, 1977, though earlier patent literature fairly well characterized such an effect without labeling it so, see U.S. Pat. No. 2,467,205, supra. The acid catalysts are phosphorus compounds and the reaction is carried out in the liquid phase. The trend in this catalyst direction was early set as demonstrated by U.S. Pat. Nos. 2,073,671 and 2,467,205, supra. A modification of this route includes the addition of ammonia to the reaction, see, for example, U.S. Pat. No. 4,394,524, patented Jul. 19, 1983, and U.S. Pat. No. 4,463,193, patented Jul. 31, 1984, for the purpose of converting alkanolamine such as MEA in situ to alkylene amine such as EDA by reaction with ammonia, and the EDA is in situ reacted with MEA according to the process of U.S. Pat. No. 4,036,881 to form alkyleneamines.

A summary of the prior art employing acid catalysts for making alkyleneamines is set forth in Table 1 below.

TABLE 1

| CITATION | CATALYST TYPE | REACTANTS |
|---|---|---|
| U.S. Pat. No. 2,467,205 | Silica gel, titania gel, alumina, thoria, aluminum phosphate. Preferred catalyst is basic aluminum phosphate. | Vapor phase condensation of EDA over a fixed bed of the catalyst, multipass process shifts from polyethylenepolyamines with the first few cycles. |
| U.S. Pat. No. 4,036,881 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorous and phosphoric acids wherein said alkyl groups have from 1 to about 8 carbon atoms and said aryl groups have from 6 to about 20 carbon atoms, alkali metal monosalts of phosphoric acid, the thioanalogs of the foregoing, and mixtures of the above. | Alkanolamine and alkyleneamine in liquid phase reaction. |
| U.S. Pat. No. 4,044,053 | Phosphorus containing substances selected from the group consisting of acidic metal phosphates, phosphoric acid compounds and their anhydrides, phosphorus acid compounds and their anhydrides, alkyl or aryl phosphate esters, alkyl or aryl phosphate esters, alkyl or aryl substituted phosphorous acids and phosphoric acids wherein said alkyl groups have from 1 to about 8 carbon atoms and said aryl groups have from 6 to about 20 carbon atoms, alkali metal monosalts of phosphoric acid and mixtures of the above. | Alkanepolyols and alkyleneamine in liquid phase reaction. |
| U.S. Pat. No. 4,314,083 | Salt of a nitrogen or sulfur containing substance or the corresponding acid. | Alkanolamine and an alkyleneamine in liquid phase reaction. |

TABLE 1-continued

| CITATION | CATALYST TYPE | REACTANTS |
|---|---|---|
| U.S. Pat. No. 4,316,840 | Metal nitrates and sulfates including zirconium sulfate. | Reforming linear polyamines. |
| U.S. Pat. No. 4,316,841 | Phosphate, preferably boron phosphate. | Reforming linear polyamines. |
| U.S. Pat. No. 4,324,917 | Phosphorus-containing cation exchange resin. | Alkanolamine and an alkyleneamine in linquid phase reaction. |
| U.S. Pat. No. 4,362,886 | Arsenic, antimony or bismuth containing compounds. Antimony sulfate specifically disclosed. | Alkanolamine and an alkyleneamine in liquid phase reaction. |
| U.S. Pat. No. 4,399,308 | Lewis acid halide. | Alkanolamine and an alkyleneamine in liquid phase reaction. |
| U.S. Pat. No. 4,394,524 | Phosphorus-containing substance or salt of a sulfur-containing substance, or the corresponding acid | Ammonia, alkanolamine and an alkyleneamine in liquid phase reaction. |
| U.S. Pat. No. 4,448,997 | Reacts alumina with phosphoric acid, adds ammonium hydroxide. | EDA with MEA. |
| U.S. Pat. No. 4,463,193 | Group IIIB metal acid phosphate. | Ammonia, alkanolamine and an alkyleneamine. |
| U.S. Pat. No. 4,503,253 | Supported phosphoric acid. | Ammonia, alkanolamine and an alkyleneamine. |
| U.S. Pat. No. 4,521,600 | Select hydrogen phosphates and pyrophosphates. | Alkanolamine and an alkyleneamine. |
| U.S. Pat. No. 4,524,143 | Phosphorus impregnated onto zirconium silicate support. | Alkanolamine and an alkyleneamine. |
| U.S. Pat. No. 4,540,822 | Phosphorus compound deposited on a Group IVB metal oxide support. | Alkanolamine and an alkyleneamine, regenerates the catalyst with $O_2$-containing gas. |
| U.S. Pat. No. 4,547,591 | Silica-alumina alone or in combination with an acidic phosphorus cocatalyst. | An ethyleneamine and an alkanolamine; ethyleneamines; or ammonia and an alkanolamine |
| U.S. Pat. No. 4,550,209 | An intercalatively catalytically active tetravalent zirconium polymeric reaction product of an organo phosphonic acid or an ester thereof with a compound of tetravalent zirconium reactive therewith. | EDA and MEA. |
| U.S. Pat. No. 4,552,961 | Phosphorus amide compound. | Alkyleneamine and alkanolamine and/or alkylene glycol. |
| U.S. Pat. No. 4,555,582 | Phosphorus chemically bonded to a zirconium silicate support. | MEA and EDA. |
| U.S. Pat. No. 4,560,798 | Rare earth metal or strontium acid phosphate. | MEA. |
| U.S. Pat. No. 4,578,517 | Group IIIB metal acid phosphate. | Ammonia or p-/s-amine and alkanolamine. |
| U.S. Pat. No. 4,578,518 | Thermally activated, calcined, pelleted titania containing titanium triphosphate. ". . . the titania that was used was . . . anatase." (Col. 9, lines 18-19). | MEA and EDA. |
| U.S. Pat. No. 4,578,519 | Thermally activated, calcined, pelleted titania with chemically bonded phosphorus derived from polyphosphoric acid. | MEA and EDA with optional recycle of DETA. |
| U.S. Pat. No. 4,584,405 | Activated carbon, optionally treated to incorporate phosphorus. Activated carbon may be washed with strong mineral acid to remove impurities followed by water wash. Optional treatment follows. | MEA and EDA. |
| U.S. Pat. No. 4,584,406 | Pelleted Group IVB metal oxide with chemically bonded phosphorus derived from phosphoryl chloride or bromide. | MEA and EDA. |
| U.S. Pat. No. 4,588,842 | Thermally activated pelleted Group IVB metal oxide with chemically bonded phosphorus. | MEA and EDA. |
| U.S. Pat. No. 4,605,770 | Group IIA or IIIB metal acid phosphate. | Alkanolamine and an alkyleneamine "in liquid phase". |
| U.S. Pat. No. 4,609,761 | Thermally activated pelleted titania with chemically bonded phosphorus. | MEA and EDA. |
| U.S. Pat. No. 4,612,397 | Thermally activated pelleted titania with chemically bonded phosphorus. | MEA and EDA. |
| U.S. Pat. No. 4,617,418 | Acid catalysts, mentions "beryllium sulfate". | Ammonia, alkanolamine and an alkyleneamine "under |

TABLE 1-continued

| CITATION | CATALYST TYPE | REACTANTS |
|---|---|---|
| | | vapor phase conditions". |
| Japanese Patent Application #1983-185,871, Publication #1985-78,945 | Variety of phosphorus and metal phosphates including Group IVB phosphates. | Ammonia, alkanolamine and ethyleneamine, with ammonia/ alkanolamine molar ratio greater than 11. |
| U.S. Pat. No. 4,683,335 | Tungstophosphoric acid, molybdo-phosphoric acid or mixtures. deposited on titania. Examples 2-7 characterize titania surface areas of 51, 60 and 120 m$^2$/gm. | Claims reaction of MEA and EDA, but discloses self-condensation reaction of EDA and DETA. |
| Japanese Patent Application #1985-078,391, Publication #1986-236,752 | Group IVB metal oxide with bonded phosphorus. | Ammonia and MEA. |
| Japanese Patent Application #1985-078,392, Publication #1986-236,753 | Group IVB metal oxide with bonded phosphorus. | Ammonia and MEA. |
| U.S. Pat. No. 4,698,427 | Titania having phospshorus thermally chemically bonded to the surface thereof in the form of phosphate bonds. | Diethanolamine and/or hydroxyethyldiethylene-triamine in EDA. |
| U.S. Pat. No. 4,806,517 | Pelleted Group IVB metal oxide with phosphorus thermally chemically bonded to the surface thereof. | MEA and EDA. |

This invention is directed to a new process for condensing amino compounds which depends on the novel concept of using Group IVB (Periodic Table of the Elements, CAS version, Handbook of Chemistry and Physics, 67th Ed., 1986-1987, inside cover) metal oxide catalysts, preferably on high surface area Group IVB metal oxide catalysts. The invention also relates to new high surface area Group IVB metal oxide catalysts containing one or more performance moderators.

SUMMARY OF THE INVENTION

The invention relates to a process of making amines which comprises condensing an amino compound in the presence of a Group IVB metal oxide condensation catalyst.

This invention relates to a process of making amines by the (i) intramolecular condensation of an amino compound to an amine having a lower molecular weight or (ii) the intermolecular condensation of an amino compound with one or more of another amino compound or a compound containing an alcoholic hydroxyl group using solid Group IVB metal oxides as the condensation catalyst. In one preferred embodiment of the invention, the solid Group IVB metal oxides used as the condensation catalyst possess a high surface area. The preferred process involves the manufacture of alkyleneamines, most desirably polyalkylenepolyamines, by such condensation reactions utilizing titanium dioxide, titanium oxide, zirconium oxide, or mixtures of them, and the like, as the condensation catalyst.

The invention also relates to amines condensation catalysts comprising high surface area, solid Group IVB metal oxides, preferably in particulate form.

The invention is also directed to a catalyst composition comprising a high surface area Group IVB metal oxide condensation catalyst containing a performance modifier. The preferred catalyst is a solid, particulate high surface area Group IVB metal oxide condensation catalyst containing a performance modifier.

As used herein, the term "amino compound" embraces ammonia and any compound containing nitrogen to which is bonded an active hydrogen. Also, as used herein, the term "oxide" embraces oxides, hydroxides and/or mixtures thereof.

For purposes of this invention, the chemical elements are identified in accordance with the Periodic Table of the Elements, CAS version, Handbook of Chemistry and Physics, 67th Ed , 1986-87, inside cover. Also, for purposes of this invention, Group IIIB metal oxides embraces the lanthanides and actinides.

DETAILED DESCRIPTION

This invention contemplates the catalyzed condensation by (i) intramolecular condensation of an amino compound to an amine having a lower molecular weight and (ii) intermolecular condensation of an amino compound with one or more of another amino compound or a compound containing an alcohol hydroxyl group to an amine having a lower, same or higher molecular weight than the reactants in the presence of solid Group IVB metal oxide condensation catalyst, preferably a high surface area solid Group IVB metal oxide condensation catalyst.

The high surface area Group IVB metal oxide condensation catalyst suitable for use in the practice of this invention comprise any of their active forms. Such forms are characterized as a degree of metal oxide condensation which provides sufficient residual bound hydroxyl groups or other groupings which render the metal oxide active.

The Group IVB metal oxides are typically formed by the hydrolysis and condensation of a suitable Group IVB metal in a hydrolyzable form, such as

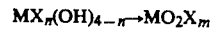

wherein M is a Group IVB metal such as titanium, zirconium or the like; X is a hydrolyzable group such as hydroxyl, halogen, sulfonyl or sulfate, phosphonyl, phosphoryl or phosphate, nitroso or nitrate, alkoxy of 1 to 8 carbon atoms, and the like; a is 3 or 4; n is a number less than about 2; and m has a value which constitutes less than about 10 weight percent of $MO_2X_m$.

The level of activity of the catalyst of the invention is that level which of itself makes the catalyst at least as active in the condensation of amines as, for example, is phosphoric acid on an equivalent basis. Preferably, the Group IVB metal oxide catalyst has a surface area greater than about 70 m²/gm to as high as about 260 m²/gm or greater depending upon which Group IVB metal oxide that is employed. In the case of titanium oxides, the surface area should be greater than about 140 m²/gm to as high as about 260 m²/gm, more preferably, greater than about 160 m²/gm to as high as about 260 m²/gm, determined according to the single point $N_2$ method. In the case of zirconia oxides, the surface area should be greater than about 70 m²/gm to as high as about 150 m²/gm, more preferably, greater than about 90 m² gm to as high as about 135 m²/gm, determined according to the single point $N_2$ method. It is appreciated that the metal oxides described below which can be used in association with the Group IVB metal oxide and the performance moderators described below can affect the surface area of the Group IVB metal oxide catalyst. While surface areas described above may be preferred, for purposes of this invention, the surface area of the Group IVB metal oxide catalyst should be sufficient to contribute to product selectivity, catalytic activity and/or mechanical or dimensional strength of the catalyst.

Embraced within the scope of the Group IVB metal oxide catalysts of this invention are mixed metal oxides wherein at least one of the metals is titanium, zirconium or the like. Preferred metal oxides are amphoteric or slightly acidic or slightly basic. Illustrative of such metal oxides which may be utilized in association with the Group IVB metal oxide catalyst include, for example, one or more of the following: Group IA metal oxides, Group IIA metal oxides, Group IIIB metal oxides (including lanthanides and actinides), Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides and other Group IVB metal oxides or mixtures thereof. For mixed metal oxides in which at least one of the metals is titanium, suitable metals in association with titanium may include, for example, one or more of the following: Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IIIA metals such as boron, aluminum, gallium and indium, Group IVA metals such as silicon, germanium, tin and lead, Group VA metals such as arsenic, antimony and bismuth, and Group IVB metals such as zirconium and hafnium. For mixed metal oxides in which at least one of the metals is zirconium, suitable metals in association with zirconium may include, for example, one or more of the following: Group IVA metals such as silicon, germanium, tin and lead, Group VB metals such as niobium and tantalum, and Group VIB metals such as chromium, molybdenum and tungsten. The virtue of these metal oxides is that they demonstrate higher mechanical strength than the Group IVB metal oxide component per se and can contribute to product selectivity and catalytic activity.

Illustrative of mixed metal oxide catalysts embraced within the scope of this invention include, for example, $TiO_2$—$SiO_2$, $TiO_2$—$Al_2O_3$, $TiO_2$—$CdO$, $TiO_2$—$Bi_2O_3$, $TiO_2$—$Sb_2O_5$, $TiO_2$—$SnO_2$, $TiO_2$—$ZrO_2$, $TiO_2$—$BeO$, $TiO_2MgO$, $TiO_2$—$CaO$, $TiO_2$—$SrO$, $TiO_2$—$ZnO$, $TiO_2$—$Ga_2O_3$, $TiO_2$—$Y_2O_3$, $TiO_2$—$La_2O_3$, $TiO_2$—$MoO_3$, $TiO_2$—$Mn_2O_3$, $TiO_2$—$Fe_2O_3$, $TiO_2$—$Co_3O_4$, $TiO_2$—$WO_3$, $TiO_2$—$V_2O_5$, $TiO_2$—$Cr_2O_3$, $TiO_2$—$ThO_2$, $TiO_2$—$Na_2O$, $TiO_2$—$BaO$, $TiO_2$—$CaO$, $TiO_2$—$HfO_2$, $TiO_2$—$Li_2O$, $TiO_2$—$Nb_2O_5$, $TiO_2$—$Ta_2O_5$, $TiO_2$—$Gd_2O_3$, $TiO_2$—$Lu_2O_3$, $TiO_2$—$Yb_2O_3$, $TiO_2$—$CeO_2$, $TiO_2$—$Sc_2O_3$, $TiO_2$—$PbO$, $TiO_2$—$NiO$, $TiO_2$—$CuO$, $TiO_2$—$CoO$, $TiO_2$—$B_2O_3$, $ZrO_2$—$SiO_2$, $ZrO_2$—$Al_2O_3$, $ZrO_2$—$SnO$, $ZrO_2$—$PbO$, $ZrO_2$—$Nb_2O_5$, $ZrO_2$—$Ta_2O_5$, $ZrO_2$—$Cr_2O_3$, $ZrO_2$—$MoO_3$, $ZrO_2$—$WO_3$, $ZrO_2$—$TiO_2$, $ZrO_2$—$HfO_2$, $TiO_2$—$SiO_2$—$Al_2O_3$, $TiO_2$—$SiO_2$—$ZnO$, $TiO_2$—$SiO_2$—$ZrO_2$, $TiO_2$—$SiO_2$—$CuO$, $TiO_2$—$SiO_2$—$MgO$, $TiO_2$—$SiO_2$—$Fe_2O_3$, $TiO_2$—$SiO_2$—$B_2O_3$, $TiO_2$—$SiO_2$—$WO_3$, $TiO_2$—$SiO_2$—$Na_2O$, $TiO_2$—$SiO_2$—$MgO$, $TiO_2$—$SiO_2$—$La_2O_3$, $TiO_2$—$SiO_2$—$Nb_2O_5$, $TiO_2$—$SiO_2$—$Mn_2O_3$, $TiO_2$—$SiO_2$—$Co_3O_4$, $TiO_2$—$SiO_2$—$NiO$, $TiO_2$—$SiO_2$—$PbO$, $TiO_2$—$SiO_2$—$Bi_2O_3$, $TiO_2$—$Al_2O_3$—$ZnO$, $TiO_2$—$Al_2O_3$—$ZrO_2$, $TiO_2$—$Al_2O_3$—$Fe_2O_3$, $TiO_2$—$Al_2O_3$—$WO_3$, $TiO_2$—$Al_2O_3$—$La_2O_3$, $TiO_2$—$Al_2O_3$—$Co_3O_4$, $ZrO_2$—$SiO_2$—$Al_2O_3$, $ZrO_2$—$SiO_2$—$SnO$, $ZrO_2$—$SiO_2$—$Nb_2O_5$, $ZrO_2$—$SiO_2$—$WO_3$, $ZrO_2$—$SiO_2$—$TiO_2$, $ZrO_2$—$SiO_2$—$MoO_3$, $ZrO_2$—$SiO_2$—$HfO_2$, $ZrO_2$—$SiO_2$—$Ta_2O_5$, $ZrO_2$—$Al_2O_3$—$SiO_2$, $ZrO_2$—$Al_2O_3$—$PbO$, $ZrO_2$—$Al_2O_3$—$Nb_2O_5$, $ZrO_2$—$Al_2O_3$—$WO_3$, $ZrO_2$—$Al_2O_3$—$TiO_2$, $ZrO_2$—$Al_2O_3$—$MoO_3$, $ZrO_2$—$HfO_2$—$Al_2O_3$, $ZrO_2$—$HfO_2$—$TiO_2$, and the like. Other suitable mixed metal oxide catalysts embraced within the scope of this invention are disclosed by Tanabe et al., Bulletin of the Chemical Society of Japan, Vol. 47(5), pp. 1,064–1,066 (1974).

The metal oxides described herein which can be used in association with the Group IVB metal oxide may contribute to product selectivity and/or catalytic activity of the reaction and/or stability of the catalyst. The catalyst structure can comprise from about 0 to about 50 percent by weight of the metal oxide, preferably from about 0 to about 25 percent by weight of the metal oxide, and more preferably from about 0 to about 10 percent by weight of the metal oxide, the remainder being the weight of the Group IVB metal oxide. For mixed metal oxides containing titania, higher concentrations of titania can provide very desirable product selectivities including acyclic to cyclic selectivities and linear to branched selectivities of higher polyalkylene polyamine products. As discussed hereinafter, the Group IVB metal oxide catalyst of this invention may also contain support(s), binding agent(s) or other additives to stabilize or otherwise help in the manufacture of the catalyst.

Though the Group IVB metal oxide catalyst of the invention provides sufficient activity to effect the condensation reaction, certain combinations of reactants and/or product formation are benefited by treating the catalyst with a catalyst moderator, hereinafter termed "performance moderator." Catalyst moderators are widely used to control the performance of catalysts in areas of selectivity to certain products and the repression of a catalyst's proclivity to generate a broad range of reaction products. It has been found that there are a range of materials that impact the Group IVB metal oxide catalysts of this invention in the variety of reaction products. The performance moderator may be any material which impacts the Group IVB metal oxide catalyst's selection of reaction products or which changes the proportion of any one or more of the reaction products which the Group IVB metal oxide catalyst generates at comparable processing conditions In addition to contributing to product selectivity, the performance moderator may be any material which contributes to catalytic activity and/or catalyst stability (mechanical or dimensional strength).

A preferred performance moderator is a mineral acid or a compound derived from a mineral acid. Suitable for use as performance moderators are one or more phosphoric acid or a salt of phosphoric acid, hydrogen fluoride, hydrofluoric acid or a fluoride salt, sulfuric acid or a salt of sulfuric acid, and the like. The moderator may also be organic esters of phosphoric acid or a salt of phosphoric acid, hydrogen fluoride organic complexes, hydrofluoric acid organic complexes or a fluoride salt organic complexes, organic esters of sulfuric acid or a salt of sulfuric acid, and the like. Suitable salts of phosphoric acid include sodium dihydrogen phosphate, disodium hydrogen phosphate, sodium phosphate and the like. Other preferred performance moderators include the metal oxides described above which can be used in association with the Group IVB metal oxide and also metallic phosphates which may or may not have a cyclic structure and metallic polyphosphates which may or may not have a condensed structure described below such as sodium trimetaphosphate, sodium tripolyphosphate, disodium dihydrogen pyrophosphate and the like including mixtures thereof.

It has been noted that the selectivity to a particular reaction product can be materially influenced by a particular performance moderator. For example, the addition of ammonium fluoride or diammonium sulfate to the Group IVB metal oxide catalyst of the invention produces diethylenetriamine (DETA) almost exclusively from the reaction of ammonia and ethylenediamine (EDA) with aminoethylethanolamine (AEEA). No other performance moderator has been found to have such an effect on the Group IVB metal oxide catalyst of this invention.

The metal oxides described hereinabove which can be used in association with the Group IVB metal oxide can also be used as performance moderators in accordance with this invention. The metal oxides can contribute to product selectivity, catalytic activity and/or catalyst stability (mechanical strength).

The metallic phosphates and polyphosphates are preferred performance moderators for use in this invention. The metallic phosphate and polyphosphate condensation catalysts may or may not have a cyclic structure and may or may not have a condensed structure. Suitable metallic phosphates having a cyclic structure or an acyclic structure are disclosed in U.S. patent application Ser. No. 390,706, filed on an even date herewith and incorporated herein by reference. Suitable metallic polyphosphates having a condensed structure are disclosed in U.S. patent application Ser. No. 390,709, filed on an even date herewith and incorporated herein by reference. Illustrative of metallic phosphates which may or may not have a cyclic structure and metallic polyphosphates which may or may not have a condensed structure include, for example, metallic orthophosphates ($PO_4^{-3}$), metallic pyrophosphates $P_2O_7^{-4}$), metallic polyphosphates (including tripolyphosphates ($P_3O_{10}^{-5}$), tetrapolyphosphates ($P_4O_{13}^{-6}$), pentapolyphosphates ($P_5O_{16}^{-7}$) and higher polyphosphates), metallic metaphosphates (including trimetaphosphates ($P^3O_9^{-3}$), tetrametaphosphates ($P_4O_{12}^{-4}$) and other lower and higher metaphosphates) and metallic ultraphosphates (condensed phosphates containing more $P_2O_5$ than corresponds to the metaphosphate structure). Corresponding metallic metaphosphimates, metallic phosphoramidates and metallic amido- and imidophosphates of the above may also be used as performance moderators in accordance with this invention. Suitable metals which can be incorporated into the performance moderators include, for example, Group IA metals, Group IIA metals, Group IIIB metals, Group IVB metals, Group VB metals, Group VIB metals, Group VIIB metals, Group VIII metals, Group IB metals, Group IIB metals, Group IIIA metals, Group IVA metals, Group VA metals, Group VIA metals and mixtures thereof. Such metallic phosphates and metallic polyphosphates can contribute to product selectivity, catalytic activity and/or catalyst stability (mechanical strength).

Illustrative of metallic orthophosphates which may be utilized in this invention include, for example, $NaH_2PO_4$, $KH_2PO_4$, $RbH_2PO_4$, $LiH_2PO_4$, $MgHPO_4$, $CaHPO_4$, $YPO_4$, $CePO_4$, $LaPO_4$, $ThPO_4$, $MnPO_4$, $FePO_4$, $BPO_4$, $AlPO_4$, $BiPO_4$, $Mg(H_2PO_4)_2$, $Ba(H_2PO_4)_2$, $Mg(NH_4)_2PO_4$, $Ca(H_2PO_4)_2$, $La(H_2PO_4)_3$ and the like. Illustrative of metallic pyrophosphates which may be utilized in this invention include, for example, $dNa_2H_2P_2O_7$, $K_2H_2P_2O_7$, $Ca_2P_2O_7$, $Mg_2P_2O_7$, $KMnP_2O_7$, $AgMnP_2O_7$, $BaMnP_2O_7$, $NaMnP_2O_7$, $KCrP_2O_7$, $NaCrP_2O_7$, $Na_4P_2O_7$, $K_4P_2O_7$, $Na_3HP_2O_7$, $NaH_3P_2O_7$, $SiP_2O_7$, $ZrP_2O_7$, $Na_6Fe_2(P_2O_7)_3$, $Na_8Fe_4(P_2O_7)_5$, $Na_6Cu(P_2O_7)_2$, $Na_{32}Cu_{14}(P_2O_7)_{15}$, $Na_4Cu_{18}(P_2O_7)_5$, $Na_2(NH_4)_2P_2O_7$, $Ca(NH_4)_2P_2O_7$, $MgH_2P_2O_7$, $Mg(NH_4)_2P_2O_7$ and the like. Illustrative of metallic polyphosphates which may be utilized in this invention include, for example, $NaSr_2P_3P_{10}$, $NaCa_2P_3O_{10}$, $Na_2Ni_2P_3O_{10}$, $Na_5P_3O_{10}$, $K_5P_3O_{10}$, $Na_3MgP_3O_{10}$, $Na_3CuP_3O_{10}$, $Cu_5(P_3O_{10})_2$, $Na_3ZnP_3O_{10}$, $Na_3CdP_3O_{10}$, $Na_6Pb(P_3O_{10})_2$, $Na_3CoP_3O_{10}$, $K_3CoP_3O_{10}$, $Na_3NiP_3O_{10}$, $K_2(NH_4)_3P_3O_{10}$, $Ca(NH_4)_2P_3O_{10}$, $La(NH_4)_2P_3O_{10}$, $NaMgH_2P_3O_{10}$ and the like. Illustrative of metallic metaphosphates which may be utilized in this invention include, for example, $Na_3P_3O_9$, $K_3P_3O_9$, $Ag_3P_3O_9$, $Na_4P_4O_{12}$, $K_4P_4O_{12}$, $Na_2HP_3O_9$, $Na_4Mg(P_3O_9)_2$, $NaSrP_3O_9$, $NaCaP_3O_9$, $NaBaP_3O_9$, $KBaP_3O_9$, $Ca_3(P_3O_9)_2$, $Ba(P_3O_9)_2$, $Na_2Ni_2(P_3O_9)_2$, $Na_4Co(P_3O_9)_2$, $Na_4Cd(P_3O_9)_2$ and the like. Illustrative of metallic ultraphosphates which may be utilized in this invention include, for example, $CaP_4O_{11}$, $Ca_2P_6O_{17}$, $Na_8P_{10}O_{29}$, $Na_6P_8O_{23}$, $Na_2CaP_6O_{17}$, $Na_2P_4O_{11}$, $NaBaP_7O_{18}$, $Na_2P_8O_{21}$, $K_4P_6O_{17}$ and the like. Preferred performance moderators for use in this invention include Group IA metal dihydrogen orthophosphates, Group IA metal metaphosphates and Group IA metal dihydrogen pyrophosphates, more preferably $NaH_2PO_4$, $Na_3P_3O_9$ and $Na_2H_2P_2O_7$. Other suitable metallic phosphates and metallic polyphosphates which are embraced within the scope of this invention are disclosed by Van Wazer, J. R., Phosphorus and Its Compounds, Vol. 1, Interscience Publishers, Inc., New York (1958).

Group VIB metal-containing substances may be used as performance moderators in accordance with this invention. Suitable Group VIB metal-containing substances are disclosed in U.S. patent application Ser. No.

390,708, filed on an even date herewith and incorporated herein by reference. Illustrative of Group VIB metal-containing performance moderators include, for example, one or more oxides of tungsten, chromium, molybdenum or mixtures thereof.

A variety of conventional phosphorus-containing substances may be suitable for use as performance moderators in this invention. The conventional substances should be capable of functioning as a performance moderator. Illustrative of conventional phosphorus-containing substances may include, for example, those disclosed in U.S. Pat. No. 4,036,881, U.S. Pat. No. 4,806,517, U.S. Pat. No. 4,617,418, U.S. Pat. No. 4,720,588, U S. Pat. No. 4,394,524, U.S. Pat. No 4,540,822, U.S. Pat. No. 4,588,842, U.S. Pat. No. 4,605,770, U.S. Pat. No. 4,683,335, U.S. Pat. No. 4,316,841, U.S. Pat. No. 4,463,193, U.S. Pat. No. 4,503,253, U.S. Pat. No. 4,560,798 and U.S. Pat. No. 4,578,517.

Suitable conventional phosphorus-containing substances which may be employed as performance moderators in this invention include acidic metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures of any of the above.

The amount of the performance moderator of the mineral acid type used with the Group IVB metal oxide catalyst of the invention is not narrowly critical. Generally, the amount does not exceed 25 weight percent of the weight of the catalyst. As a rule, it is desirable to use at least 0.01 weight percent of the weight of the catalyst. Preferably, the amount of performance moderator, when used, will range from about 0.2 to about 10 weight percent of the weight of the catalyst. Most preferably, the amount of performance moderator, when used, will range from about 0.5 to about 5 weight percent of the weight of the catalyst.

The amount of performance moderator other than the mineral acid type used with the Group IVB metal oxide catalyst is not narrowly critical. Generally, the amount does not exceed 50 weight percent of the weight of the catalyst. The amount of performance moderator can range from about 0 to about 50 weight percent of the weight of the catalyst, preferably from about 0 to about 25 weight percent of the weight of the catalyst, and more perferably from about 0 to about 15 weight percent of the weight of the catalyst. Most preferably, the amount of performance moderator, when used, will range from about 0.5 to about 10 weight percent of the weight of the catalyst.

This invention also embraces the use of vicinal di(-hetero)alkylene organometalates in the preparation of amines. Suitable vicinal di(hetero)alkylene organometalates in U.S. patent application Ser. No. 390,828, filed on an even date herewith and incorporated herein by reference.

The performance moderator can be provided to the Group IVB metal oxide catalyst by conventional procedures known in the art. For example, the performance moderator can be provided to the catalyst by impregnating particles or monolithic structures comprising the Group IVB metal oxide catalyst with liquid comprising the performance moderator. This is a well known procedure in the art for incorporating additives to a solid support material. The Group IVB metal oxide catalyst of the invention may be utilized as solid powders, such as a pigment form of the Group IVB metal oxide, or as fused, bonded or compressed solid pellets, or larger structures comprising the Group IVB metal oxide, or as coated, fused, bonded or compressed solid pellets, or larger structures, composited with one or more support materials, comprising the Group IVB metal oxide. These solid structures may be treated with the performance moderator by mixing a liquid body of the performance moderator with the solid structure. For example, the Group IVB metal oxide solids may be slurried in the performance moderator, drained, washed and suctioned to remove excess performance moderator, and then dried with heat to remove any volatiles accompanying the performance moderator. The drying temperature chosen will depend on the nature of the volatiles to be removed. Usually, the time/temperature for effecting drying will be below the conditions for effecting dehydration to remove bound water from the Group IVB metal oxide. Normally the drying temperature will be greater than about 120° C. and below about 600° C. The drying time will generally go down as the drying temperature rises and vice versus, and may extend from 5 seconds to about 24 hours.

Alternatively, the performance moderator can be provided to the catalyst at the time of preparing the Group IVB metal oxide. For example, the Group IVB metal oxide and one or more other metal oxides may be condensed from their respective hydrolyzable monomers described below to the desired oxides to form oxide powders which can thereafter be blended and compressed to form pellets and larger structures of the Group IVB metal oxide catalyst of this invention. The one or more metal oxides which can be used in association with the Group IVB metal oxide in accordance with this invention can be provided from metal salts which can be heated to form the metal oxide as illustrated in the Examples hereinafter. It is appreciated that the performance moderator can be incorporated into the molecular bonding configuration of the Group IVB metal oxide by conventional procedures known in the art.

The Group IVB metal oxide catalysts of the invention prior to the optional treatment of the performance moderator may be prepared in a wide variety of ways. The Group IVB metal oxide may be provided as a partial condensate to the $MO_2X_q$ state, where q has a higher value than m, supra, on a support, such as a silica or alpha, beta or gamma alumina, silicon carbide, and the like, and then condensed to the desired degree of acidity by heating to effect polymerization to the desired oxide form. The Group IVB metal oxide may be condensed from the hydrolyzable monomers characterized above to the desired oxide, indeed, to form an oxide powder which can thereafter be compressed in the presence of binding agents to form pellets and larger structures of the Group IVB metal oxide catalyst of the invention. A blend of the powder and binding agent can be made into a shapeable paste which can be extruded and cut into pellets according to conventional procedures. The extrudate may thereafter be fired to cure the binding agent and fix the structure. The cut extrudate may be blended with a support material such as those characterized above, and the blend fired to fuse the Group IVB metal oxide catalyst to the support.

A preferred catalyst structure comprises the Group IVB metal oxide having a surface area of at least 140 m²/gm bonded to a support material. The term "support," as used herein and in the claims, means a solid structure which does not adversely affect the catalytic properties of the Group IVB metal oxide and is at least as stable as the Group IVB metal oxide catalyst to the reaction medium. The support can function as an amine condensation catalyst independent of the Group IVB metal oxide, although it may have lower catalytic activity to the reaction The support may act in concert with the catalyst to moderate the reaction. It has been noted that some supports, such as gamma-alumina, appear to contribute to the selectivity of the reaction. The catalyst structure can comprise from about 2 to about 50 percent by weight or greater of the support, preferably from about 2 to about 25 percent by weight of the support, and more preferably from about 2 to about 10 percent by weight of the support, the remainder being the weight of the Group IVB metal oxide catalyst. Included in the weight of the support is the weight of any binding agent such as phosphates, sulfates, silicates, fluorides, and the like, and any other additive provided to stabilize or otherwise help in the manufacture of the catalyst. The support may be particles as large or larger than the catalyst component and "glued" to the catalytic Group IVB metal oxide by virtue of a binding medium.

The support may constitute a separate phase in the process of extruding the catalytic structure. In this embodiment, the support forming material, preferably as a paste is blended with a paste of the Group IVB metal oxide or a partial condensate thereof. The paste may comprise the oxide forms of the support and the oxide catalyst, each blended with water, and/or binding agents. The extrudate of the blend is passed through a multiorificed die and chopped into pellets of the desired size. The particles may be doughnut shaped, spherical, and the like. Then the particles are calcined to dry them and complete any condensation reaction in the support and/or the Group IVB metal oxide catalyst.

The use of supports for the Group IVB metal oxide catalyst provides a number of significant advantages. It has been determined that some of the Group IVB metal oxides are not as stable in the amines reaction media when utilized over an extended period of time. When the reaction is effected as a batch reaction, this matter is not a problem. However, when the reaction is effected with the Group IVB metal oxide catalyst as part of a fixed bed in a tubular reactor, the preferred procedure for carrying out the invention, it is desirable to have the catalyst be more stable. When the catalyst is combined with the support, the catalyst has greater stability for the reaction medium, and therefore, it is better able to be used in a fixed bed of a continuous reactor. The supported catalysts suffer from none of the leaching problems that the catalyst per se may have or the problems that are associated with the prior art catalysts, such as acidic phosphorus compounds on silica.

The reactants used in the condensation process of the invention may be ammonia or organic compound containing —NH— and any compound possessing an alcoholic hydroxyl group, subject to the following: the intramolecular condensation of an amino compound produces an amine having a lower molecular weight, and the intermolecular condensation of an amino compound with one or more of another amino compound or a compound containing an alcoholic hydroxyl group produces an amine having a lower, same or higher molecular weight than the reactants.

Illustrative of suitable reactants in effecting the process of the invention, include by way of example:

Ammonia

MEA—monoethanolamine
EDA—ethylenediamine
MeEDA—methylethylenediamine
EtEDA—ethylethylenediamine
AEEA—N-(2-aminoethyl)ethanolamine
HEP—N-(2-hydroxyethyl)piperazine
DETA—diethylenetriamine
AEP—N-(2-aminoethyl)piperazine
TAEA—trisaminoethylamine
TETA—triethylenetetramine
TEPA—tetraethylenepentamine
PEHA—pentaethylenehexamine TETA Isomers TAEA—trisaminoethylamine
TETA—triethylenetetramine
DPE—dipiperazinoethane
DAEP—diaminoethylpiperazine
PEEDA—piperazinoethylethylenediamine TEPA Isomers AETAEA—trisaminoethylamine
TEPA—tetraethylenepentamine
AEDPE—aminoethyldipiperazinoethane
AEPEEDA—aminoethylpiperazinoethylethylenediamine
iAEPEEDA—isoaminoethylpiperazinoethylethylenediamine
AEDAEP—aminoethyldiaminoethylpiperazine
BPEA bispiperazinoethylamine The foregoing also can represent the products of the reaction. For example, ammonia and MEA are frequently employed to produce EDA along with a variety of other amines, most of which are set forth above. The higher polyalkylene polyamines prepared by the process of this invention such as TETA, TEPA and PEHA are very useful commercial products for a variety of applications including fuel oil additives, corrosion inhibitors, fabric softeners, fungicides and others.

Glycol compounds can also be employed in the preparation of amines in accordance with this invention. For purposes of this invention, glycol compounds embrace diols and polyols. Illustrative of suitable glycol compounds include alkylene glycols such as ethylene glycol, propylene glycol, 1,3-propane diol or mixtures thereof.

The process may be effected in the liquid or vapor or supercritical liquid states or mixtures thereof though the actual reaction is believed to occur on the catalyst's solid surface in the absorbed state. In this context, the vapor phase reaction is intended to refer to the general vapor state of the reactants. Though the reaction conditions may range from subatmospheric to superatmospheric conditions, it is desirable to run the reaction from about 50 psig to about 3,000 psig, preferably from about 200 psig to about 2,000 psig.

The temperature of the reaction may be as low as about 125° C. to about 400° C. Preferably, the reaction temperature ranges from about 150° C. to about 350° C., and most preferably from about 225° C. to about 325° C.

The reaction may be effected by the incremental addition of one of the reactants to the other or by the joint addition of the reactants to the catalyst. The preferred process effects the reaction in a continuous manner over a fixed bed of the Group IVB metal oxide catalyst in a tubular reactor. However, the reaction may be carried out by slurrying the catalyst in the reactants or in a batch mode in an autoclave. An inert such as nitrogen, methane and the like can be used in the reaction process.

The preferred process involves the formation of alkyleneamines from the intermolecular condensation of alkanolamines and alkyleneamines or the intramolecular condensation of alkyleneamines or alkanolamines. Illustrative of such reactions are the following reactant combinations:

| REACTANT | REACTANT | PRODUCTS |
|---|---|---|
| Ammonia | Methanol | Monomethylamine Dimethylamine Trimethylamine |
| Ammonia | MEA | EDA, DETA, AEEA, TETA, TEPA, PIP |
| Ammonia | AEEA | DETA, PIP |
| MEA, Ammonia | EDA | EDA, AEEA, HEP, DETA, AEP, TETA, TEPA, PEHA, TETA Isomers: TAEA, TETA; DAEP, PEEDA, DPE TEPA, TEPA Isomers: AETAEA, AEPEEDA, AEDAEP, AEDPE, BPEA |
| MEA | EDA | AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| EDA | AEEA | HEP, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| DETA | AEEA | TEPA Isomers, AEP |
| EDA | EDA | DETA, TETA and TEPA Isomers |

It is appreciated that the Group IVB metal oxide condensation catalysts of this invention may also be useful in the production of alkylamines. For example, an alcohol and at least one of ammonia, a primary amine, a secondary amine or a tertiary amine may be contacted in the presence of a Group IVB metal oxide condensation catalyst under conditions effective to produce alkylamines.

This invention is further illustrated by certain of the following examples:

EXAMPLES

In the examples set forth in Tables I-XXIV and XLV-LXXI below, the catalyst of choice was placed in a tubular reactor having an outside diameter of 1 inch and an overall length of 30 inches. The catalyst portion of the reactor comprised a length of 24 inches, accommodating 150 cubic centimeters of catalyst. The reactor was made of 316 stainless steel. In the examples set forth in Tables XXV-XLIV and LXXII-LXXIX, the catalyst of choice was placed in one of three tubular reactors, each having an outside diameter of 1 inch, and heated by a sand bath. The catalyst portion of the reactor comprised a length of 24 inches, accommodating 100 cubic centimeters of catalyst. As used herein, AB1 refers to a material obtained from Norton Company, Akron, Ohio, which is a mixture of sodium trimetaphosphate and sodium tripolyphosphate. As used in the tables below, acyclic (N4)/cyclic ($\leq$N4) refers to the weight ratio of TETA+TAEA to PIP+AEP+PEEDA+DAEP+DPE, and acyclic (N5)/cyclic ($\leq$N5) refers to the weight ratio of TEPA+AETAEA to PIP+AEP+PEEDA+DAEP+DPE+AEPEEDA+iAEPEEDA+AEDAEP+AEDPE+BPEA. The catalysts employed are identified as follows:

| DESIGNATION | COMPOSITION | PHYSICAL PROPERTIES |
|---|---|---|
| A | Titanium dioxide (anatase), 2% sulfur (presumed to be —OSO$_3$H) content | Particle size: 1/16" cylindrical extrudates: Surface area: 188.4 m$^2$/gm; Pore vol. Hg, cc/gm: 0.274; Med. Pore Diam., 0.0092; Crush strength, FPCS, LBS.: 10.8. |
| B | TiO$_2$(anatase)-$\gamma$-Al$_2$O$_3$ | Particle size: 1/16" cylindrical extrudates TiO$_2$-$\gamma$-Al$_2$O$_3$; Catalyst surface area: 162.8 m$_2$/gm.; Pore vol. N$_2$, cc/gm.: 0.338. |
| C | TiO$_2$(anatase)-SiO$_2$ | Particle size: 1/16: cylindrical extrudates; TiO$_2$—SiO$_2$; Catalyst surface area: 210.9 m$^2$/gm.; Pore vol. N$_2$, cc/gm.: 0.334. |
| D | Catalyst B/small amount of H$_3$PO$_4$ from diammonium hydrogen phosphate | Particle size: 1/16" cylindrical extrudates TiO$_2$-$\gamma$-Al$_2$O$_3$; Catalyst surface area: 162.8 m$_2$/gm.; Pore vol. N$_2$, cc/gm.: 0.338. |
| E | Catalyst C/small amount of H$_3$PO$_4$ from diammonium hydrogen phosphate | Particle size: 1/16" cylindrical extrudates TiO$_2$—SiO$_2$; Catalyst surface area: 210.9 m$^2$/gm.; Pore vol. N$_2$, cc/gm.: 0.334. |
| F | Catalyst B/small amount of HF from NH$_4$F | Particle size: 1/16" cylindrical extrudates TiO$_2$-$\gamma$-Al$_2$O$_3$; Catalyst surface area: 162.8 m$_2$/gm.; Pore vol. N$_2$, cc/gm.: |

-continued

| DESIGNATION | COMPOSITION | PHYSICIAL PROPERTIES |
|---|---|---|
| | | 0.338. |
| G | Catalyst B/small amount of $H_2SO_4$ from $(NH_4)_2SO_4$ | Particle size: 1/16" cylindrical extrudates $TiO_2$-$\gamma$-$Al_2O_3$; Catalyst surface area: 162.8 $m_2$/gm.; Pore vol. $N_2$, cc/gm.: 0.338. |
| H | Catalyst C/small amount of HF from $NH_4F$ | Particle size: 1/16: cylindrical extrudates; $TiO_2$—$SiO_2$; Catalyst surface area: 210.9 $m^2$/gm.; Pore vol. $N_2$, cc/gm.: 0.334. |
| I | Catalyst C/small amount of $H_2SO_4$ from $(NH_4)_2SO_4$ | Particle size: 1/16: cylindrical extrudates; $TiO_2$—$SiO_2$; Catalyst surface area: 210.9 $m^2$/gm.; Pore vol. $N_2$, cc/gm.: 0.334. |
| J | $TiO_2$ (anatase)/$Al_2O_3$/ SnO | Particle size: 1/16 inch cylindrical extrudates; Catalyst surface area: 125.0 $m^2$/gm. |
| K | $TiO_2$ (anatase)/$SiO_2$/ $H_3BO_3$ | Particle size: 1/16 inch cylindrical extrudates; Catalyst surface area: 154.0 $m^2$/gm. |
| L | $TiO_2$ (anatase)/$Al_2O_3$/ $Nb_2O_5$/$H_3VO_4$ | Particle size: 1/16 inch cylindrical extrudates; Catalyst surface area: 111.0 $m^2$/gm. |
| M | $TiO_2$ (anatase)/$SiO_2$/ $La_2O_3$/$H_3PO_4$ | Particle size: 1/16 inch cylindrical extrudates; Catalyst surface area: 136.0 $m^2$/gm. |
| N | $TiO_2$ (anatase)/$SiO_2$/ $La_2O_3$ | Particle size: 1/16 inch cylindrical extrudates; Catalyst surface area: 136.0 $m^2$/gm. |
| O | $TiO_2$ (anatase)/$Al_2O_3$/ $Nb_2O_5$/$H_3BO_3$ | Particle size: 1/16 inch cylindrical extrudates; Catalyst surface area: 111.0 $m^2$/gm. |
| P | $TiO_2$ (anatase)/$SiO_2$/ $H_3VO_4$ | Particle size: 1/16 inch cylindrical extrudates; Catalyst surface area: 149 $m^2$/gm. |
| Q | $TiO_2$ (anatase)/$Al_2O_3$/ SnO/$H_3PO_4$ | Particle size: 1/16 inch cylindrical extrudates; Catalyst surface area: 125 $m^2$/gm. |
| R | $TiO_2$ (anatase)/$Al_2O_3$ | Particle size: 1/16 inch cylindrical extrudates; Catalyst surface area: 185 $m^2$/gm. |
| S | $TiO_2$ (anatase)/$SiO_2$/ SnO/$H_3BO_3$ | Particle size: 1/16 inch cylindrical extrudates; Catalyst surface area: 141 $m^2$/gm. |
| T | $TiO_2$ (anatase)/$Al_2O_3$/ $La_2O_3$/$H_3VO_4$ | Particle size: 1/16 inch cylindrical extrudates; Catalyst surface area: 148 $m^2$/gm. |
| U | $TiO_2$ (anatase)/$SiO_2$/ $Nb_2O_5$/$H_3PO_4$ | Particle size: 1/16 inch cylindrical extrudates; Catalyst surface area: 129 $m^2$/gm. |
| V | $TiO_2$ (anatase)/$SiO_2$/ $Nb_2O_5$ | Particle size: 1/16 inch cylindrical extrudates; Catalyst surface area: 146 $m^2$/gm. |
| W | $TiO_2$ (anatase)/$Al_2O_3$/ $La_2O_3$/$H_3BO_3$ | Particle size: 1/16 inch cylindrical extrudates; Catalyst surface area: 135 $m^2$/gm. |
| X | $TiO_2$ (anatase)/$SiO_2$/ SnO/$H_3VO_4$ | Particle size: 1/16 inch cylindrical extrudates; Catalyst surface area: 143 $m^2$/gm. |
| Y | $TiO_2$ (anatase)/$Al_2O_3$/ $H_3PO_4$ | Particle size: 1/16 inch cylindrical extrudates; Catalyst surface area: 150 $m^2$/gm. |
| Z | $TiO_2$ (anatase)/$Al_2O_3$/ $La_2O_3$/$H_3PO_4$ | Particle size: 1/16 inch cylindrical extrudates; Catalyst surface area: 139 $m^2$gm. |
| AA | $TiO_2$ (anatase)/$SiO_2$/ $Na_2B_4O_7$ | Particle size: 1/16 inch cylindrical extrudates; Catalyst surface area: 99 $m^2$/gm. |
| BB | $TiO_2$ (anatase)/$SiO_2$/ $Na_2SnO_6$ | Particle size: 1/16 inch cylindrical extrudates; Catalyst surface area: 112 $m^2$/gm. |
| CC | $ZrO_2$/$SiO_2$ | Particle size: 1/16 inch cylindrical extrudates; Catalyst surface area: 127 $m^2$/gm. |
| DD | $ZrO_2$/$SiO_2$/ $Nb_2O_5$ | Particle size: 1/16 inch cylindrical extrudates; Catalyst surface area: 126 $m^2$/gm. |
| EE | $ZrO_2$/$SiO_2$/ $H_3BO_3$ | Particle size: 1/16 inch cylindrical extrudates; Catalyst surface area: 126 $m^2$/gm. |
| FF | $ZrO_2$/$SiO_2$/ | Particle size: 1/16 inch |

-continued

| DESIGNATION | COMPOSITION | PHYSICAL PROPERTIES |
|---|---|---|
| | $NH_4VO_3$ (2 wt. % as $V_2O_5$) | cylindrical extrudates; Catalyst surface area: 169 $m^2$/gm. |
| GG | $TiO_2$(anatase)/$SiO_2$ | Particle size: 1/16 inch cylindrical extrudates; Catalyst surface area: 169 $m^2$/gm. |
| HH | $TiO_2$(anatase)/$SiO_2$/ $Al_2O_3$ | Particle size: 1/16 inch cylindrical extrudates; Catalyst surface area: 204 $m^2$/gm. |
| II | $TiO_2$(anatase)/$SiO_2$/ $B_2O_3$ | Particle size: 1/16 inch cylindrical extrudates; Catalyst surface area: 219 $m^2$/gm. |
| JJ | $TiO_2$(anatase)/$SiO_2$/ $NH_4HB_2O_7$ (2 wt. % as $B_2O_3$) | Particle size: 1/16 inch cylindrical extrudates; Catalyst surface area: 146 $m^2$/gm. |
| KK | $TiO_2$(anatase)/$SiO_2$/ $NH_4HB_4O_7$/$WO_3$ | Particle size: 1/16 inch cylindrical extrudates; Catalyst surface area: 148 $m^2$/gm. |
| LL | $TiO_2$(anatase)/$SiO_2$/ $NH_4HB_4O_7$/$NH_4VO_3$ | Particle size: 1/16 inch cylindrical extrudates; Catalyst surface area: 142 $m^2$/gm. |
| MM | $TiO_2$ (anatase)/$SiO_2$/ $NH_4HB_4O_7$/$NH_4VO_3$ | Particle size: 1/16 inch cylindrical extrudates; Catalyst surface area: 144 $m^2$/gm. |
| NN | $TiO_2$ (anatase)/$SiO_2$/ $NH_4HB_4O_7$/$NaVO_3$ | Particle size: 1/16 inch cylindrical extrudates; Catalyst surface area: 110 $m^2$/gm. |
| OO | $TiO_2$ (anatase)/$SiO_2$/ $(NH_4) W_{12}O_{41}$ | Particle size: 1/16 inch cylindrical extrudates; Catalyst surface area: 141 $m^2$/gm. |
| PP | $TiO_2$ (anatase)/$SiO_2$/ $(NH_4)_6H_2W_{12}O_{41}$ (8 wt. %) | Particle size: 1/16 inch cylindrical extrudates; Catalyst surface area: 156 $m^2$/gm. |
| QQ | $TiO_2$ (anatase)/$SiO_2$/ $Na_2WO_4.9WO_3$ (2 wt. % as $WO_3$) | Particle size: 1/16 inch cylindrical extrudates; Catalyst surface area: 145 $m^2$/gm. |
| RR | $TiO_2$ (anatase)/$SiO_2$/ $V_2O_5$ | Particle size: 1/16 inch cylindrical extrudates; Catalyst surface area: 127 $m^2$/gm. |
| SS | $TiO_2$ (anatase)/$SiO_2$/ $NaVO_3$ (2 wt. %) | Particle size: 1/16 inch cylindrical extrudates; Catalyst surface area: 83 $m^2$/gm. |
| TT | $TiO_2$ (anatase)/$SiO_2$/ $La_2O_3$/$B_2O_5$/$WO_3$ | Particle size: 1/16 inch cylindrical extrudates; Catalyst surface area: 152 $m^2$/gm. |
| UU | $ZrO_2$/$SiO_2$/$TiO_2$ | Particle size: 1/16 inch cylindrical extrudates; Catalyst surface area: 127 $m^2$/gm. |
| VV | $ZrO_2$/$SiO_2$/ $(NH_4)_6H_2W_{12}O_{40}$ (2 wt. % as $WO_3$) | Particle size: 1/16 inch cylindrical extrudates; Catalyst surface area: 120 $m^2$/gm. |
| WW | $TiO_2$ (anatase)/ $(NH_4)_2HPO_4$ | Particle size: 1/16 inch cylindrical extrudates; Catalyst surface area: 100 $m^2$/gm. |
| XX | $TiO_2$ (rutile)/ $(NH_4)_2HPO_4$ | Particle size: 1/16 inch cylindrical extrudates; Catalyst surface area: 0.34 $m^2$/gm. |
| YY | $TiO_2$ (rutile)/ $H_3PO_4$ | Particle size: 1/16 inch cylindrical extrudates; Catalyst surface area: 1.08 $m^2$/gm. |
| ZZ | $TiO_2$ (anatase) | Particle size: 1/16 inch cylindrical extrudates; Catalyst surface area: 188.4 $m^2$/gm. |
| AAA | $TiO_2$ (anatase)/$SiO_2$ | Particle size: 1/16 inch cylindrical extrudates; Catalyst surface area: 186 $m^2$/gm. |
| BBB | $TiO_2$ (anatase)/$SiO_2$/ $H_3BO_3$ | Particle size: 1/16 inch cylindrical extrudates; Catalyst surface area: 154 $m^2$/gm. |
| CCC | $TiO_2$ (anatase)/$SiO_2$/ $H_3VO_4$ | Particle size: 1/16 inch cylindrical extrudates; Catalyst surface area: 146 $m^2$/gm. |
| DDD | $TiO_2$ (anatase)/$SiO_2$/ $NH_4BF_4$/$H_3PO_4$ | Particle size: 1/16 inch cylindrical extrudates; Catalyst surface area: 94 $m^2$/gm. |
| EEE | $TiO_2$ (anatase)/$SiO_2$/ $NaBF_4$ | Particle size: 1/16 inch cylindrical extrudates; Catalyst surface area: 107 $m^2$/gm. |
| FFF | $TiO_2$ (anatase)/$SiO_2$/ $H_2B_4O_7$/$H_3PO_4$ | Particle size: 1/16 inch cylindrical extrudates; Catalyst surface area: 142 $m^2$/gm. |
| GGG | $TiO_2$ (anatase)/$SiO_2$/ | Particle size: 1/16 inch |

-continued

| DESIGNATION | COMPOSITION | PHYSICAL PROPERTIES |
|---|---|---|
| | $Nb_2O_5$ | cylindrical extrudates; Catalyst surface area: 151 $m^2$/gm. |
| HHH | $TiO_2$ (anatase)/$SiO_2$/ $ZrO_2$ | Particle size: 1/16 inch cylindrical extrudates; Catalyst surface area: 151 $m^2$/gm. |
| III | $TiO_2$ (anatase)/$SiO_2$/ $Fe_2O_3$ | Particle size: 1/16 inch cylindrical extrudates; Catalyst surface area: 142 $m^2$/gm. |
| JJJ | $TiO_2$ (anatase)/$SiO_2$/ SnO | Particle size: 1/16 inch cylindrical extrudates; Catalyst surface area: 253 $m^2$/gm. |
| KKK | $TiO_2$ (anatase)/$SiO_2$/ $H_3BO_3$/$H_3VO_4$ | Particle size: 1/16 inch cylindrical extrudates; Catalyst surface area: 152 $m^2$/gm. |
| LLL | $TiO_2$ (anatase)/$SiO_2$/ $Na_2O$ | Particle size: 1/16 inch cylindrical extrudates; Catalyst surface area: 151 $m^2$/gm. |
| MMM | $TiO_2$ (anatase)/$SiO_2$/ ZnO | Particle size: 1/16 inch cylindrical extrudates; Catalyst surface area: 137 $m^2$/gm. |
| NNN | $TiO_2$ (anatase)/$SiO_2$/ $La_2O_3$ | Particle size: 1/16 inch cylindrical extrudates; Catalyst surface area: 134 $m^2$/gm. |
| OOO | $TiO_2$ (anatase)/$SiO_2$/ $Li_2O$ | Particle size: 1/16 inch cylindrical extrudates; Catalyst surface area: 127 $m^2$/gm. |
| PPP | $TiO_2$ (anatase)/$Al_2O_3$ | Particle size: 1/16 inch cylindrical extrudates; Catalyst surface area: 185 $m^2$/gm. |
| QQQ | $TiO_2$ (anatase)/$Al_2O_3$/ $Na_2O$ | Particle size: 1/16 inch cylindrical extrudates; Catalyst surface area: 117 $m^2$/gm. |
| RRR | $TiO_2$ (anatase)/$Al_2O_3$/ $La_2O_3$ | Particle size: 1/16 inch cylindrical extrudates; Catalyst surface area: 142 $m^2$/gm. |
| SSS | $TiO_2$ (anatase)/$Al_2O_3$/ $La_2O_3$/$H_3PO_4$ | Particle size: 1/16 inch cylindrical extrudates; Catalyst surface area: 115 $m^2$/gm. |
| TTT | $TiO_2$ (anatase)/$Al_2O_3$/ MgO | Particle size: 1/16 inch cylindrical extrudates; Catalyst surface area: 137 $m^2$/gm. |
| UUU | $TiO_2$ (anatase)/$Al_2O_3$/ $Li_2O$ | Particle size: 1/16 inch cylindrical extrudates; Catalyst surface area: 105 $m^2$/gm. |
| VVV | $TiO_2$ (anatase)/$Al_2O_3$/ $NaBF_4$ | Particle size: 1/16 inch cylindrical extrudates; Catalyst surface area: 138 $m^2$/gm. |
| WWW | $TiO_2$ (anatase)/$Al_2O_3$/ SrO | Particle size: 1/16 inch cylindrical extrudates; Catalyst surface area: 141 $m^2$/gm. |
| XXX | $TiO_2$ (anatase)/$Al_2O_3$/ $H_3BO_3$ | Particle size: 1/16 inch cylindrical extrudates; Catalyst surface area: 159 $m^2$/gm. |
| YYY | $TiO_2$ (anatase)/$Al_2O_3$/ ZnO | Particle size: 1/16 inch cylindrical extrudates; Catalyst surface area: 141 $m^2$/gm. |
| ZZZ | $TiO_2$ (anatase)/$Al_2O_3$/ SnO | Particle size: 1/16 inch cylindrical extrudates; Catalyst surface area: 125 $m^2$/gm. |
| AAAA | $TiO_2$ (anatase)/$Al_2O_3$/ $Fe_2O_3$ | Particle size: 1/16 inch cylindrical extrudates; Catalyst surface area: 147 $m^2$/gm. |
| BBBB | Titanium dioxide (anatase)/ sodium trimetaphosphate; Ti:P atom ratio = 5.7:1 | Particle size: 1/16 inch cylindrical extrudates; Catalyst surface area: 133.3 $m^2$/gm; Pore volume $N_2$: 0.344 cc/gm; Pore area: 83.5 $m^2$/gm; Bulk density: 1.55 gm/cc. |
| CCCC | Titanium dioxide (anatase)/ sodium tripolyphosphate; Ti:P atom ratio = 5.7:1 | Particle size: 1/16 inch cylindrical extrudates; Catalyst surface area: 80.3 $m^2$/gm; Pore volume $N_2$: 0.236 cc/gm; Pore area: 54.2 $m^2$/gm; Bulk density: 1.72 gm/cc. |
| DDDD | Titanium dioxide (anatase)/ AB1; Ti:P atom ratio = 5.7:1 | Particle size: 1/16 inch cylindrical extrudates; Catalyst surface area: 115.0 $m^2$/gm; Pore volume $N_2$: 0.429 cc/gm; Pore area: 87.4 $m^2$/gm; Bulk density: 1.39 gm/cc. |
| EEEE | Titanium dioxide (anatase)/ | Particle size: 1/16 inch |

| DESIGNATION | COMPOSITION | PHYSICAL PROPERTIES |
|---|---|---|
| | sodium pyrophosphate; Ti:P atom ratio = 5.7:1 | cylindrical extrudates; Catalyst surface area: 78.6 m²/gm; Pore volume N₂: 0.339 cc/gm; Pore area: 72.1 m²/gm; Bulk density: 1.59 gm/cc. |
| FFFF | Titanium dioxide (anatase)/sodium dihydrogen phosphate; Ti:P atom ratio = 5.7:1 | Particle size: 1/16 inch cylindrical extrudates; Catalyst surface area: 117.1 m²/gm; Pore volume N₂: 0.321 cc/gm; Pore area: 85.7 m²/gm; Bulk density: 1.64 gm/cc. |
| GGGG | Titanium dioxide (anatase)/disodium dihydrogen pyrophosphate; Ti:P atom ratio = 5.7:1 | Particle size: 1/16 inch cylindrical extrudates; Catalyst surface area: 133.5 m²/gm; Pore N₂: 0.291 cc/gm; Pore area: 89.6 m²/gm; Bulk density: 1.66 gm/cc. |
| HHHH | Titanium dioxide (anatase)/disodium hydrogen phosphate; Ti:P atom ratio = 5.7:1 | Particle size: 1/16 inch cylindrical extrudates; Catalyst surface area: 117/4 m²/gm; Pore volume N₂: 0.346 cc/gm; Pore area 86.5 m²/gm; Bulk density: 1.53 gm/cc. |
| IIII | Titanium dioxide (anatase)/sodium phosphate; Ti:P atom ratio = 5.7:1 | Particle size: 1/16 inch cylindrical extrudates: Catalyst surface area: 88.4 m²/gm; Pore volume N₂: 0.365 cc/gm; Pore area: 76.90 m²/gm; Bulk density: 1.48 gm/cc. |

For each run the tubular reaction system was brought up to the designated conditions. The ammonia feed was established first, then the EDA-MEA, DETA-AEEA or DETA-MEA feed, as appropriate. After a sufficient line out period, a two hour timed run was conducted, then the experiment was run overnight and sampled. The feed was changed to another reactant set and the above procedure repeated.

Performance moderator additions

Diammonium hydrogen phosphate preparation to provide a performance moderator: Catalyst pellets (150 cc) were added to a saturated solution of diammonium hydrogen phosphate in water. Enough solution was added to completely immerse the pellets. The slurry was allowed to stand at a temperature of 55°-60° C. for a period of 8 hours. The catalyst was filtered, washed with water until the wash water was neutral, dried at a temperature of 100° C., and then calcined at a temperature of 600° C. for a period of 6-8 hours.

Hydrogen fluoride preparation to provide a performance moderator: Catalyst pellets (150 cc) were added to a saturated solution of ammonium fluoride in water. Enough solution was added to completely immerse the pellets. The slurry was allowed to stand at a temperature of 55°-60° C. for a period of 8 hours. The catalyst was filtered, washed with water until the wash water was neutral, dried at a temperature of 100° C., and then calcined at a temperature of 600° C. for a period of 6-8 hours.

Sulfuric acid preparation to provide a performance moderator: Catalyst pellets (150 cc) were added to a saturated solution of ammonium sulphate in water. Enough solution was added to completely immerse the pellets. The slurry was allowed to stand at a temperature of 55°-60° C. for a period of 8 hours. The catalyst was filtered, washed with water until the wash water was neutral, dried at a temperature of 100° C., and then calcined at a temperature of 600° C. for a period of 6-8 hours.

Catalyst J Preparation: Tin (II) ethylene glycoxide (9.88 grams) was dissolved in 150 milliliters of monoethanolamine. The resulting solution was diluted with isopropanol (80 milliliters) and the TiO₂/Al₂O₃ support (280 grams) was impregnated. The support turned yellow. After a period of 1 hour, the catalyst was filtered and washed with excess isopropanol, dried and then calcined at a temperature of 600° C. for a period of 16 hours. The catalyst was divided into 2 equal parts—one part was used to make Catalyst Q.

Catalyst K Preparation: Boric acid (2.86 grams) was dissolved in just enough water to impregnate the TiO₂/SiO₂ support (140 grams). The catalyst was dried at a temperature of 100° C. and then calcined at a temperature of 400° C. for a period of 16 hours.

Catalyst L Preparation: The TiO₂/Al₂O₃ support (280 grams) was impregnated with niobium pentoxide-toluene solution (13.68 grams of niobium pentoxide). Excess toluene was removed under reduced pressure on a Buchi rotary evaporator. The catalyst was dried at a temperature of 100° C. and then calcined at a temperature of 400° C. for a period of 16 hours. The catalyst was divided into 2 equal parts. One part was impreqnated with ammonium vanadate (2.83 grams) dissolved in water. This catalyst was dried at a temperature of 100° C. and then calcined at a temperature of 400° C. for a period of 16 hours. The second part was used to make Catalyst O described below.

Catalyst M Preparation: The TiO₂/SiO₂ support (280 grams) was impreqnated with lanthanum nitrate (7.59 grams) in sufficient water to wet all of the support. The wet catalyst was dried at a temperature of 100° C. and then calcined at a temperature of 400° C. for a period of 16 hours. The catalyst (140 grams) was then soaked in 85% phosphoric acid for a period of 1 hour and washed with water until neutral. The catalyst was dried at a temperature of 100° C. and then calcined at a temperature of 400° C. for a period of 16 hours.

Catalyst N Preparation: The TiO₂/SiO₂ support (280 grams) was impreqnated with lanthanum nitrate (7.59 grams) in sufficient water to wet all of the support. The wet catalyst was dried at a temperature of 100° C. and then calcined at a temperature of 400° C. for a period of 16 hours.

Catalyst O Preparation: The second part of Catalyst L greenware was impregnated with boric acid (2.86 grams) in sufficient water to wet the support. The catalyst was dried at a temperature of 100° C. and then calcined at a temperature of 400° C. for a period of 16 hours.

Catalyst P Preparation: Ammonium vanadate (2.83 grams) was dissolved in sufficient water to impregnate the $TiO_2/SiO_2$ support (140 grams). The wet catalyst was dried at a temperature of 100° C. and then calcined at a temperature of 400° C. for a period of 16 hours.

Catalyst Q Preparation: The second part of Catalyst J greenware was impreqnated with 85% phosphoric acid for a period of 1 hour and then washed with water until neutral. The catalyst was dried at a temperature of 100° C. and then calcined at a temperature of 400° C. for a period of 16 hours.

Catalyst R Preparation: The $TiO_2/Al_2O_3$ support was used without further treatment.

Catalyst S Preparation: Tin (II) ethylene glycoxide (9.88 grams) was dissolved in 150 milliliters of monoethanolamine and the $TiO_2/SiO_2$ support (280 grams) was impregnated therewith. The $TiO_2/SiO_2$ support turned yellow. After a period of 1 hour, the catalyst was filtered and washed with excess isopropanol to remove excess monoethanolamine. The catalyst was dried at a temperature of 100° C. and then calcined at a temperature of 400° C. for a period of 16 hours. The catalyst was divided into 2 equal parts. One part was impregnated with boric acid (2.86 grams) dissolved in sufficient water to wet the support. This catalyst was dried at a temperature of 100° C. and then calcined at a temperature of 400° C. for a period of 16 hours. The second part was used to make Catalyst X described below.

Catalyst T Preparation: The $TiO_2/Al_2O_3$ support (280 grams) was impregnated with lanthanum nitrate (7.59 grams) in sufficient water to wet the support. The catalyst was dried at a temperature of 100° C. and then calcined at a temperature of 400° C. for a period of 16 hours. The catalyst was then impregnated with ammonium vanadate (2.83 grams) in sufficient water to wet the support. The catalyst was dried at a temperature of 100° C. and then calcined at a temperature of 400° C. for a period of 16 hours.

Catalyst U Preparation: The $TiO_2/SiO_2$ support (280 grams) was impregnated with niobium pentoxide in toluene (13.68 grams). Excess toluene was removed under reduced pressure on a Buchi rotary evaporator. The catalyst was dried at a temperature of 100° C. and then calcined at a temperature of 400° C. for a period of 16 hours. The catalyst was divided into 2 equal parts. One portion was impregnated with 85% phosphoric acid for a period of 1 hour and then washed with water until neutral. The wet catalyst was dried at a temperature of 100° C. and then calcined at a temperature of 400° C. for a period of 16 hours. The second part was used as Catalyst V described below.

Catalyst V Preparation: The second part of Catalyst U prior to impregnation with phosphoric acid was used without further treatment.

Catalyst W Preparation: The $TiO_2/Al_2O_3$ support (280 grams) was impregnated with lanthanum nitrate (7.59 grams) in sufficient water to wet the support. The catalyst was dried at a temperature of 100° C. and then calcined at a temperature of 400° C. for a period of 16 hours. The catalyst was then impregnated with boric acid (2.86 grams) in sufficient water to wet the support. The catalyst was dried at a temperature of 100° C. and then calcined at a temperature of 400° C. for a period of 16 hours.

Catalyst X Preparation: The second part of Catalyst S greenware was impregnated with ammonium vanadate (2.83 grams) in sufficient water to wet the support. The catalyst was dried at a temperature of 100° C. and then calcined at a temperature of 400° C. for a period of 16 hours.

Catalyst Y Preparation: The $TiO_2/Al_2O_3$ support (140 grams) was impreqnated with 85% phosphoric acid for a period of 1 hour and then washed with water until neutral. The wet catalyst was dried at a temperature of 100° C. and then calcined at a temperature of 400° C. for a period of 16 hours.

Catalyst Z Preparation: The $TiO_2/Al_2O_3$ support (280 grams) was impreqnated with lanthanum nitrate (7.59 grams) in sufficient water to wet all of the support. The wet catalyst was dried at a temperature of 100° C. and then calcined at a temperature of 400° C. for a period of 16 hours. The catalyst (140 grams) was then soaked in 85% phosphoric acid for a period of 1 hour and washed with water until neutral. The catalyst was dried at a temperature of 100° C. and then calcined at a temperature of 400° C. for a period of 16 hours.

Catalyst AA Preparation: Sodium tetraborate (21 grams) was dissolved in water (112 grams) and used to impregnate the $TiO_2/SiO_2$ support (140 grams). After a period of 1 hour, excess liquid was decanted and the material dried at a temperature of 100° C. for a period of 1 hour. The catalyst was then calcined at a temperature of 400° C. for a period of 16 hours.

Catalyst BB Preparation: Sodium stannate (21 grams) was dissolved in just enough water (56.4 grams) to impregnate the $TiO_2/SiO_2$ support (140 grams). After a period of 1 hour, the catalyst was calcined at a temperature of 400° C. for a period of 16 hours.

Catalyst CC Preparation: The $ZrO_2/SiO_2$ support was used without further treatment.

Catalyst DD Preparation: A solution of niobium pentethoxide (25.28 grams) in toluene (84.18 grams) was prepared. The $ZrO_2/SiO_2$ support (140 grams) was slurried with toluene (75 milliliters) and then the niobium pentethoxide solution (29.6 grams) was added. Excess toluene was removed under reduced pressure and the catalyst was dried at a temperature of 100° C. for a period of 1 hour. The catalyst was then calcined at a temperature of 400° C. for a period of 16 hours.

Catalyst EE Preparation: Boric acid (2.86 grams) was dissolved in methanol (75 milliliters) and the $ZrO_2/SiO_2$ support (140 grams) was impregnated with this solution. The catalyst was dried at a temperature of 100° C. for a period of 1 hour and then calcined at a temperature of 400° C. for a period of 16 hours.

Catalyst FF Preparation: Ammonium metavanadate (2.86 grams) was dissolved in water (75 milliliters) and the $ZrO_2/SiO_2$ support (140 grams) was impregnated with this solution. The catalyst was dried at a temperature of 100° C. for a period of 1 hour and then calcined at a temperature of 400° C. for a period of 16 hours.

Catalyst GG Preparation: The $TiO_2/SiO_2$ support was used without further treatment.

Catalyst HH Preparation: The $TiO_2/SiO_2/Al_2O_3$ support was used without further treatment.

Catalyst II Preparation: Boric acid (2.86 grams) was dissolved in just enough water to impregnate the TiO$_2$/SiO$_2$ support (140 grams). The catalyst was dried at a temperature of 100° C. for a period of 1 hour and the calcined at a temperature of 400° C. for a period of 16 hours.

Catalyst JJ Preparation: Ammonium hydrogentetraborate (4.19 grams) was dissolved in water (104.3 grams) to wet the TiO$_2$/SiO$_2$ support (140 grams). After an impregnation period of 1 hour, the catalyst was dried at a temperature of 100° C. for a period of 1 hour and then calcined at a temperature of 400° C. for a period of 16 hours.

Catalyst KK Preparation: Ammonium hydrogentetraborate (4.19 grams) and ammonium tungstate (5.89 grams) were dissolved in sufficient water (95.45 grams) to wet the TiO$_2$/SiO$_2$ support (140 grams). After an impregnation period of 1 hour at room temperature, the catalyst was dried at a temperature of 100° C. for a period of 1 hour and then calcined at a temperature of 400° C. for a period of 16 hours.

Catalyst LL Preparation: Ammonium hydrogentetraborate (4.19 grams) and ammonium vanadate (5.62 grams) were dissolved in sufficient water (170.2 grams) to dissolve the inorganic salts. The TiO$_2$/SiO$_2$ support (140 grams) was immersed in this solution for a period of 1 hour. Excess liquid was decanted and the catalyst was dried at a temperature of 100° C. for a period of 1 hour. The catalyst was then calcined at a temperature of 600° C. for a period of 16 hours.

Catalyst MM Preparation: Ammonium hydrogentetraborate (4.19 grams) and ammonium vanadate (5.62 grams) were dissolved in sufficient hot water (176 grams). The TiO$_2$/SiO$_2$ support (140 grams) was added to the hot solution, stirred well and then allowed to cool to room temperature. The catalyst slurry was transferred to a round bottom flask and stripped under reduced pressure using a Buchi evaporator. The catalyst was dried at a temperature of 100° C. for a period of 1 hour and then calcined at a temperature of 400° C. for a period of 16 hours.

Catalyst NN Preparation: Ammonium hydrogentetraborate (4.19 grams) was dissolved in sufficient water (94 grams) to wet the TiO$_2$/SiO$_2$ support (140 grams). After an impregnation period of 1 hour, the catalyst was dried at a temperature of 100° C. and then calcined at a temperature of 400° C. for a period of 16 hours. Sodium vanadate (5.85 grams) was dissolved in water (94 grams) sufficient to wet the calcined material. After an impregnation period of 1 hour, the catalyst was redried at a temperature of 100° C. and calcined at a temperature of 400° C. for a period of 16 hours.

Catalyst OO Preparation: Ammonium metatungstate (3.12 grams) was dissolved in a sufficient amount of water (103 grams) to wet the TiO$_2$/SiO$_2$ support (140 grams). The catalyst was dried at a temperature of 100° C. for a period of 1 hour and then calcined at a temperature of 400° C. for a period of 16 hours.

Catalyst PP Preparation: Ammonium metatungstate (12.26 grams) was dissolved in a sufficient amount of water (94 grams) to wet the Ti)$_2$/SiO$_2$ support (140 grams). The catalyst was dried at a temperature of 100° C. for a period of 1 hour and then calcined at a temperature of 400° C. for a period of 16 hours.

Catalyst QQ Preparation: Sodium metatungstate (2.86 grams) was dissolved in sufficient water (88.4 grams) to wet the TiO$_2$/SiO$_2$ support (140 grams). After an impregnation period of 1 hour at room temperature, the catalyst was dried at a temperature of 100° C. for a period of 1 hour and then calcined at a temperature of 400° C. for a period of 16 hours.

Catalyst RR Preparation: A solution of vanadium triisopropoxide (7.60) grams in toluene (76.85 grams) was prepared and added to the TiO$_2$/SiO$_2$ support (140 grams) in a round bottom flask on a Buchi evaporator. After mixing for a period of 1 hour, excess toluene was removed under reduced pressure and the catalyst was calcined at a temperature of 400° C. for a period of 16 hours.

Catalyst SS Preparation: Sodium vanadate (21 grams) was dissolved in water (84.3 grams). A small amount (2.55 grams) did not dissolve and this was removed by filtration. The solution was poured over the TiO$_2$/SiO$_2$ support with stirring. Excess liquid (14.85 grams) was removed and the catalyst was calcined at a temperature of 400° C. for a period of 16 hours.

Catalyst TT Preparation: Boric acid (2.97 grams), lanthanum nitrate (10.39 grams) and ammonium tungstate (6.13 grams) were dissolved in water (94 grams) and the TiO$_2$/SiO$_2$ support (140 grams) was impregnated with the solution. The catalyst was dried at a temperature of 100° C. for a period of 1 hour and then calcined at a temperature of 400° C. for a period of 16 hours.

Catalyst UU Preparation: Titanium isopropoxide (10.25 grams) was dissolved in toluene (45.44 grams). This solution was used to impregnate the ZrO$_2$/SiO$_2$ support (140 grams). Excess toluene was removed under reduced pressure. The catalyst was dried at a temperature of 100° C. for a period of 1 hour and then calcined at a temperature of 400° C. for a period of 16 hours.

Catalyst VV Preparation: Ammonium tungstate (3.12 grams) was dissolved in a sufficient amount of water (63.24 grams) to wet the ZrO$_2$/SiO$_2$ support (140 grams). After impregnation for a period of 1 hour at room temperature, the catalyst was dried at a temperature of 100° C. for a period of 1 hour and then calcined at a temperature of 400° C. for a period of 16 hours.

Catalyst WW Preparation: Diammonium hydrogen phosphate (65 grams) was dissolved in water (50 grams) in a round bottom flask and anatase TiO$_2$ (150 cubic centimeters) was added to the flask. The flask was rotated on a Buchi rotary evaporator under reduced pressure for a period of 2 hours. The resulting slurry was filtered, washed with water (100 milliliters) and dried at a temperature of 100° C. for a period of 1 hour and then at a temperature of 250° C. for overnight.

Catalyst XX Preparation: Diammonium hydrogen phosphate (65 grams) was dissolved in water (50 grams) in a round bottom flask and rutile TiO$_2$ (150 cubic centimeters) was added to the flask. The flask was rotated on a Buchi rotary evaporator under reduced pressure for a period of 2 hours. The resulting slurry was filtered, washed with water (100 milliliters) and dried at a temperature of 100° C. for a period of 1 hour and then at a temperature of 250° C. for overnight.

Catalyst YY Preparation: Orthophosphoric acid (52 grams), water (50 grams) and TiO$_2$ (171.11 grams) were placed in a flask on a Buchi rotary evaporator at a pressure of 210 millimeters Hg for a period of 2 hours. The catalyst was filtered and washed with distilled water (2500 milliliters) to pH 6, dried at a temperature of 100° C. for a period of 1 hour and then at a temperature of 250° C. for a period of 16 hours. The resulting catalyst (171.11 grams) was slurried with phosphoric acid (52.37 grams) and water (50.05 grams) for a period of 2 hours on a Buchi rotary evaporator at a pressure of 310 mm Hg, filtered, washed with water (100 milliliters), evaporated dry and heated at a temperature of 100° C. for a period of 1 hour and then at a temperature of 250° C. for a period of 16 hours.

Catalyst ZZ Preparation: The $TiO_2$ support was used without further treatment.

Catalyst AAA Preparation: Obtained from Norton Company, Akron, Ohio.

Catalyst BBB Preparation: Boric acid (1.81 grams) was mixed in sufficient water to wet the $TiO_2/SiO_2$ support (100 grams). After an impregnation period of 1 hour, the catalyst was calcined at a temperature of 400° C. for a period of 16 hours.

Catalyst CCC Preparation: Ammonium vanadate (2.63 grams) was mixed in sufficient water to wet the $TiO_2/SiO_2$ support (140 grams). After an impregnation period of 1 hour at room temperature, the catalyst was calcined at a temperature of 400° C. for a period of 16 hours.

Catalyst DDD Preparation: Ammonium tetrafluoroborate (8.39 grams) and diammonium hydrogen phosphate (10.52 grams) were dissolved in sufficient water to wet the $TiO_2/SiO_2$ support (140 grams). After an impregnation period of 1 hour at room temperature, the catalyst was dried at a temperature of 100° C. for a period of 1 hour and then calcined at a temperature of 400° C. for a period of 16 hours.

Catalyst EEE Preparation: Sodium tetrafluoroborate (2.86 grams) was dissolved in sufficient water to wet the $TiO_2/SiO_2$ support (140 grams). After an impregnation period of 1 hour, the catalyst was calcined at a temperature of 400° C. for a period of 16 hours.

Catalyst FFF Preparation: Ammonium hydrogen tetraborate (4.18 grams) and diammonium hydrogen phosphate (10.52 grams) were dissolved in sufficient water to wet the $TiO_2/SiO_2$ support (140 grams). After an impregnation period of 1 hour at room temperature, the catalyst was dried at a temperature of 100° C. for a period of 8 hours and then calcined at a temperature of 400° C. for a period of 16 hours.

Catalyst GGG Preparation: Niobium pentoxide (13.67 grams) dissolved in toluene (approximately 200 milliliters) was used to wet the $TiO_2/SiO_2$ support (280 grams). After an impregnation period of 15 minutes at room temperature, toluene was removed under reduced pressure and the catalyst was dried at a temperature of 100° C. for a period of 8 hours and then calcined at a temperature of 400° C. for a period of 16 hours.

Catalyst HHH Preparation: Zirconium n-propoxide (7.59 grams) dissolved in toluene (62 grams) was used to wet the $TiO_2/SiO_2$ support (140 grams). After standing overnight under a cover at room temperature, the catalyst was stripped under reduced pressure and then calcined at a temperature of 400° C. for a period of 16 hours.

Catalyst III Preparation: Ferric nitrate. $9H_2O$ (7.21 grams) was dissolved in sufficient water to wet the $TiO_2/SiO_2$ support (140 grams). After an impregnation period of 1 hour, the catalyst was calcined at a temperature of 400° C. for a period of 16 hours.

Catalyst JJJ Preparation: Tin (II) acetate (95%) (4.42 grams) was dissolved in sufficient water to wet the $TiO_2/SiO_2$ support (140 grams). After an impregnation period of 1 hour, the catalyst was calcined at a temperature of 400° C. for a period of 16 hours.

Catalyst KKK Preparation: Ammonium hydrogen borate (2.53 grams) and ammonium vanadate (5.62 grams) were dissolved at a temperature of 75° C. in excess water to wet the $TiO_2/SiO_2$ support (140 grams). The excess water was then evaporated. After an impregnation period of 1 hour, the catalyst was calcined at a temperature of 400° C. for a period of 16 hours.

Catalyst LLL Preparation: Sodium bicarbonate (4.15 grams) was dissolved in sufficient water to wet the $TiO_2/SiO_2$ support (100 grams). After an impregnation period of 1 hour at room temperature, the catalyst was calcined at a temperature of 400° C. for a period of 16 hours.

Catalyst MMM Preparation: Zinc nitrate hexahydrate (10.44 grams) was dissolved in sufficient water to wet the $TiO_2/SiO_2$ support (140 grams). After an impregnation period of 1 hour at room temperature, the catalyst was calcined at a temperature of 400° C. for a period of 16 hours.

Catalyst NNN Preparation: Lantanum nitrate hexahydrate (3.79 grams) was dissolved in sufficient water to wet the $TiO_2/SiO_2$ support (140 grams). After an impregnation period of 1 hour at room temperature, the catalyst was calcined at a temperature of 400° C. for a period of 16 hours.

Catalyst OOO Preparation: Lithium acetate dihydrate (9.74 grams) was dissolved in sufficient water to wet the $TiO_2/SiO_2$ support (140 grams). After an impregnation period of 1 hour at room temperature, the catalyst was calcined at a temperature of 400° C. for a period of 16 hours.

Catalyst PPP Preparation: Obtained from Norton Company, Akron, Ohio.

Catalyst QQQ Preparation: Sodium bicarbonate (4.15 grams) was dissolved in sufficient water to wet the $TiO_2/Al_2O_3$ support (100 grams). After an impregnation period of 1 hour at room temperature, the catalyst was calcined at a temperature of 400° C. for a period of 16 hours.

Catalyst RRR Preparation: Lanthanum nitrate hexahydrate (3.79 grams) was dissolved in sufficient water to wet the $TiO_2/Al_2O_3$ support (140 grams). After an impregnation period of 1 hour at room temperature, the catalyst was calcined at a temperature of 400° C. for a period of 16 hours.

Catalyst SSS Preparation: Lanthanum nitrate hexahydrate (4.29 grams) was dissolved in sufficient water to wet the $TiO_2/Al_2O_3$ support (160 grams). After an impregnation period of 1 hour at room temperature, the catalyst was calcined at a temperature of 400° C. for a period of 16 hours. This material (140 grams) was slurried with 85% phosphoric acid (90 milliliters) for a period of 1 hour, filtered, washed with water until pH of 6.5 and then calcined at a temperature of 400° C. for a period of 16 hours.

Catalyst TTT Preparation: Magnesium nitrate hexahydrate (18.17 grams) was dissolved in sufficient water to wet the $TiO_2/Al_2O_3$ support (140 grams). After an impregnation period of 1 hour at room temperature, the catalyst was calcined at a temperature of 400° C. for a period of 16 hours.

Catalyst UUU Preparation: Lithium acetate dihydrate (9.74 grams) was dissolved in sufficient water to wet the $TiO_2/Al_2O_3$ support (140 grams). After an impregnation period of 1 hour at room temperature, the catalyst calcined at a temperature of 400° C. for a period of 16 hours.

Catalyst VVV Preparation: Sodium tetrafluoroborate (2.86 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst WWW Preparation: Strontium nitrate (5.84 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst XXX Preparation: Boric acid (1.81 grams) was dissolved in sufficient water to wet the TiO$_2$/Al$_2$O$_3$ support (100 grams). After an impregnation period of 1 hour at room temperature, the catalyst was calcined at a temperature of 400° C. for a period of 16 hours.

Catalyst YYY Preparation: Zinc nitrate hexahydrate (10.44 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst ZZZ Preparation: Stannous acetate (95%) (4.42 grams) was dissolved in hot monoethanolamine diluted with isopropanol (30 grams) and slurried with the TiO support (140 grams). After an impregnation period of 1 hour at room temperature, the catalyst was dried at a temperature of 100° C. for a period of 1 hour. Excess liquid was then drained off. The catalyst was washed with isopropanol and then calcined at a temperature of 400° C. for a period of 16 hours.

Catalyst AAAA Preparation: Ferric nitrate. 9H$_2$O (7.21 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst BBBB: Obtained from Norton Company, Akron, Ohio.

Catalyst CCCC: Obtained from Norton Company, Akron, Ohio.

Catalyst DDDD: Obtained from Norton Company, Akron, Ohio.

Catalyst EEEE: Obtained from Norton Company, Akron, Ohio.

Catalyst FFFF: Obtained from Norton Company, Akron, Ohio.

Catalyst GGGG: Obtained from Norton Company, Akron, Ohio.

Catalyst HHHH: Obtained from Norton Company, Akron, Ohio.

Catalyst IIII: Obtained from Norton Company, Akron, Ohio.

TABLE I

| Example No. | 1 | 2 | 3 | 4 | 5 |
|---|---|---|---|---|---|
| Catalyst Type | A | A | A | A | A |
| TEMP., °C.; ave. | 228 | 241 | 290 | 294 | 268 |
| PRES., psia | 1172.7 | 1214.7 | 1214.7 | 1214.7 | 914.7 |
| AEEA SV; M/kg cat/hr. | 1.61 | 1.44 | 1.5 | 1.56 | 0.9 |
| EDA/AEEA Mole Ratio | 1.5 | 1.5 | 2 | 2 | 5 |
| NH$_3$/AEEA Mole Ratio | 24.2 | 45.83 | 34.9 | 36.33 | 55.94 |
| H$_2$O/AEEA Mole Ratio | 0.86 | 0.86 | 0.66 | 1.38 | 1.18 |
| Wt % H$_2$O | 7.4 | 7.4 | 5 | 10 | 5 |
| % Conversion AEEA | 70.4 | 73.2 | 97 | 61.8 | 97.3 |
| ANALYTICAL, area % | | | | | |
| EDA | 62.81 | 65.97 | 60.95 | 62.65 | 77.39 |
| MEA | 0.92 | 0.41 | 0.12 | 0.13 | 0 |
| PIP | 5.52 | 5.84 | 9.66 | 6.36 | 5.23 |
| DETA | 2.33 | 2.58 | 3.68 | 1.24 | 3.49 |
| AEEA | 15.51 | 14.19 | 1.36 | 17.33 | 0.7 |
| AEP | 0.89 | 1.03 | 2.13 | 0.35 | 2.49 |
| HEP | 0.17 | 0.13 | 0.1 | 0.14 | 0.04 |
| TETA | 5.1 | 4.45 | 4.47 | 1.78 | 4.64 |
| DAEP | 1.70 | 1.77 | 4.42 | 3.10 | 2.00 |
| PEEDA | 1.99 | 2.11 | 5.00 | 3.02 | 2.15 |
| DPE | 0 | 0.56 | 0.14 | 0.19 | 0.07 |
| Total TETAS | 8.79 | 8.38 | 14.02 | 8.08 | 8.91 |
| Total TEPAS | 0.87 | 0.77 | 2.01 | 0.29 | 0.96 |
| Total Byproducts | 2.19 | 0.72 | 5.98 | 3.43 | 0.79 |
| % Water | 16.68 | 21.18 | 13.75 | 13.94 | 10.66 |

TABLE I-continued

| Example No. | 6 | 7 | 8 | 9 |
|---|---|---|---|---|
| Catalyst Type | A | A | A | A |
| TEMP., °C.; ave. | 242 | 247 | 295 | 270 |
| PRES., psia | 1214.7 | 1214.7 | 414.7 | 614.7 |
| AEEA SV; M/kg cat/hr. | 0.57 | 0.69 | 1.18 | 2.21 |
| EDA/AEEA Mole Ratio | 8 | 8 | 2 | 0.8 |
| NH$_3$/AEEA Mole Ratio | 107.9 | 91.22 | 66.88 | 30.36 |
| H$_2$O/AEEA Mole Ratio | 3.61 | 3.61 | 0.66 | 0.44 |
| Wt % H$_2$O | 10 | 10 | 5 | 5 |
| % Conversion AEEA | 43.3 | 23.3 | 98.6 | 27 |
| ANALYTICAL, area % | | | | |
| EDA | 87.72 | 84.11 | 60.49 | 43.42 |
| MEA | 0 | 0 | 0 | 0 |
| PIP | 0.68 | 0.64 | 11.37 | 3.72 |
| DETA | 0 | 0.13 | 4.03 | 0 |
| AEEA | 9.96 | 13.57 | 0.63 | 49.49 |
| HEP | 0 | 0.01 | 0.1 | 0.06 |
| AEP | 0.06 | 0.05 | 3.82 | 0.06 |
| TETA | 0.40 | 0.46 | 3.36 | 0.20 |
| DAEP | 0.16 | 0.16 | 5.78 | 1.52 |
| PEEDA | 0.12 | 0.10 | 5.09 | 1.01 |
| DPE | 0 | 0 | 0.32 | — |
| Total TETAS | 0.68 | 0.71 | 14.26 | 2.72 |
| Total TEPAS | 0.22 | 0.14 | 1.62 | 0.04 |
| Total Byproducts | 0.68 | 0.64 | 3.67 | 0.49 |
| % Water | 12 | 9.97 | 17.34 | 12.18 |

| Example No. | 10 | 11 | 12 |
|---|---|---|---|
| Catalyst Type | F | G | D |
| Temp. °C. | 172 | 178 | 258 |
| Press. psig | 614 | 614.7 | 614.7 |
| Space velocity g mol/kg-cat/hr | 2.2 | 2.4 | 2.2 |
| Feed Comp. | EDA/AEEA/NH$_3$ | EDA/AEEA/NH$_3$ | EDA/AEEA/NH$_3$ |
| Feed Mole Ratio | 2/1/37 | 2/1/12.5 | 2/1/10.8 |
| % water; feed | 5 | 0 | 5 |
| % Conv. | 40.4 | 40.7 | 41.5 |
| R$_x$ Outlet Comp. Area % GG | | | |
| EDA | 32.94 | 46.98 | 39.1 |
| MEA | 0.38 | 0 | 0.66 |
| PIP | 0.03 | 0 | 8.95 |
| DETA | 8.03 | 24.37 | 1.3 |
| AEEA | 57.53 | 27.91 | 27.01 |
| AEP | 0.98 | 0.72 | 0.85 |
| nc-TETA[2] | 0.02 | 0 | 7.96 |
| c-TETA[3] | | 0 | 6.68 |
| TEPA's | 0.02 | 0 | 1.73 |
| HPA/ UNKNOWNS | 0.06 | 0.02 | 5.55 |

| Example No. | 13 | 14 |
|---|---|---|
| Catalyst Type | D | B |
| Temp. °C. | 261 | 284 |
| Press. psig | 614.7 | 614.7 |
| Space velocity g mol/kg-cat/hr | 3.3 | 2 |
| Feed Comp. | DETA/MEA/NH$_3$ | DETA/MEA/NH$_3$ |
| Feed Mole Ratio | 2/1/11.9 | 2/1/10.7 |
| % water; feed | 5 | 5 |
| % Conv. | 34.5(DETA) | 66.7 |
| R$_x$ Outlet Comp. | | |

TABLE I-continued

| Area % GG | | |
|---|---|---|
| EDA | 1.63 | 1.45 |
| MEA | 24.16 | 7.75 |
| PIP | 0.93 | 0.77 |
| DETA | 50.93 | 75.48 |
| AEEA | 2.22 | 0.19 |
| AEP | 7.76 | 1.54 |
| nc-TETA | 8.21 | 9.67 |
| c-TETA | 0.89 | 0.55 |
| TEPA's | 1.88 | 1.13 |
| HPA/UNKNOWNS | 1.35 | 1.45 |

| Example No. | 15 | 16 | 17 |
|---|---|---|---|
| Catalyst Type | H | E | E |
| Temp. °C. | 180 | 268 | 266 |
| Press. psig | 614.7 | 614.7 | 614.7 |
| Space velocity g mol/kg-cat/hr | 3.3 | 2.4 | 2.1 |
| Feed Comp. | EDA/AEEA/NH$_3$ | EDA/AEEA/NH$_3$ | DETA/MEA/NH$_3$ |
| Feed Mole Ratio | 2/1/9.5 | 2/1/18.5 | 2/1/16.2 |
| % water; feed | 0 | 0 | 0 |
| % Conv. | 23.5 | 96.2 | 42.9 |
| R$_x$ Outlet Comp. Area % GG | | | |
| EDA | 58.46 | 43.41 | 2.32 |
| MEA | 0.03 | 0.14 | 13.14 |
| PIP | 0.05 | 16.67 | 2.28 |
| DETA | 6.12 | 5.16 | 42.38 |
| AEEA | 35.27 | 1.74 | 0.96 |
| AEP | 0 | 2.17 | 8.87 |
| nc-TETA[2] | 0 | 8.3 | 14.84 |
| c-TETA[3] | 0 | 12.17 | 3.46 |
| TEPA's | 0 | 2.61 | 7.08 |
| HPA/UNKNOWNS | 0.07 | 7.55 | 4.48 |

| Example No. | 18 | 19 | 20 |
|---|---|---|---|
| Catalyst Type | C | C | B |
| Temp. °C. | 257 | 279 | 259 |
| Press. psig | 614.7 | 614.7 | 614.7 |
| Space velocity g mol/kg-cat/hr | 2.4 | 2.3 | 2.1 |
| Feed Comp. | DETA/MEA/NH$_3$ | DETA/MEA/NH$_3$ | EDA/AEEA/NH$_3$ |
| Feed Mole Ratio | 2/1/11.7 | 2/1/13.2 | 2/1/10.0 |
| % water; feed | 0 | 0 | 5 |
| % Conv. | 45.3 | 75 | 21.8 |
| R$_x$ Outlet Comp. Area % GG | | | |
| EDA | .56 | 1.02 | 44.38 |
| MEA | 12.7 | 5.71 | 0 |
| PIP | 0.47 | 1.32 | 2.25 |
| DETA | 80.17 | 78.73 | 8.92 |
| AEEA | 0.35 | 0 | 37.01 |
| AEP | 0.84 | 1.77 | 0.21 |
| nc-TETA[2] | 3.95 | 6.43 | 5.64 |
| c-TETA[3] | 0.17 | 0.55 | 0.58 |
| TEPA's | 0.34 | 0.93 | 0.45 |
| HPA/UNKNOWNS | 0.4 | 3.04 | 0.47 |

| Example No. | 21 | 22 |
|---|---|---|
| Catalyst Type | I | C |
| Temp. °C. | 179 | 274 |
| Press. psig | 614.7 | 614.7 |
| Space velocity g mol/kg-cat/hr | 2.4 | 4.7 |
| Feed Comp. | EDA/AEEA/NH$_3$ | EDA/MEA/NH$_3$ |
| Feed Mole Ratio | 2/1/11.1 | 1/1/5.3 |
| % water; feed | 0 | 0 |
| % Conv. | 42.3 | 42 |
| R$_x$ Outlet Comp. Area % GG | | |
| EDA | 61.7 | 56.03 |
| MEA | 0 | 29.12 |
| PIP | 0 | 1.83 |
| DETA | 10.43 | 4.58 |
| AEEA | 25.84 | 1.44 |
| AEP | 0.5 | 1.92 |
| nc-TETA | 0 | 1.00 |
| c-TETA | 0 | 0.99 |
| TEPA's | 0 | 0.53 |
| HPA/UNKNOWNS | 1.53 | 2.54 |

[2] nc = noncyclics
[3] c = cyclics

TABLE II

| Example No. | 23 | 24 | 25 | 26 | 27 | 28 | 29 | 30 | 31 |
|---|---|---|---|---|---|---|---|---|---|
| Catalyst Type | J | J | J | J | J | J | J | J | J |
| Catalyst weight, gm | 81.0 | 81.0 | 81.0 | 81.0 | 81.0 | 81.0 | 81.0 | 81.0 | 81.0 |
| Pressure, psig | 600 | 600 | 600 | 600 | 600 | 600 | 600 | 600 | 600 |
| Temperature, °C. | 269.7 | 269.5 | 280.7 | 260.2 | 270.9 | 258.8 | 279.7 | 268.7 | 268.9 |
| Time on organics, hrs. | 25.0 | 27.0 | 30.0 | 47.5 | 53.0 | 72.5 | 78.5 | 96.0 | 104.0 |
| Duration of run, hrs. | 2 | 2 | 2 | 2 | 2 | 2 | 2 | 2 | 2 |
| MEA SV, gmol/hr/kgcat | 4.65 | 4.99 | 5.19 | 4.45 | 4.75 | 3.91 | 4.36 | 4.43 | 4.87 |
| NH$_3$ feedrate, gm/hr | 40.6 | 43.8 | 46.3 | 36.7 | 38.6 | 30.9 | 35.8 | 38.5 | 42.3 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.06 | 0.96 | 1.65 | 0.58 | 0.93 | 0.44 | 1.29 | 0.76 | 0.71 |
| MeEDA | 0 | 0 | 0 | 0 | 0 | 0 | 0 | 0 | 0 |
| MEA | 27.97 | 29.69 | 25.97 | 33.84 | 31.26 | 33.34 | 25.75 | 31.85 | 32.53 |
| EtEDA | 0 | 0 | 0 | 0 | 0 | 0 | 0 | 0 | 0 |
| PIP | 0.41 | 0.35 | 0.65 | 0.13 | 0.26 | 0.09 | 0.38 | 0.15 | 0.12 |
| DETA | 48.20 | 49.21 | 45.95 | 52.63 | 51.53 | 56.05 | 49.30 | 52.04 | 53.16 |
| AEEA | 3.81 | 4.35 | 3.82 | 3.19 | 4.30 | 2.48 | 4.17 | 3.47 | 3.39 |
| AEP | 0.47 | 0.36 | 0.67 | 0.22 | 0.30 | 0.17 | 0.47 | 0.26 | 0.25 |
| HEP | 0 | 0 | 0 | 0 | 0 | 0 | 0 | 0 | 0 |
| TETA's | 10.10 | 8.61 | 10.77 | 5.04 | 7.01 | 3.88 | 9.98 | 5.75 | 4.72 |
| TEPA's | 3.39 | 1.88 | 3.55 | 0.11 | 0.82 | 0 | 2.63 | 0.63 | 0.44 |
| MEA Conversion % | 22.93 | 17.73 | 26.84 | 5.52 | 13.89 | 7.65 | 28.09 | 10.64 | 8.96 |
| Acyclic (N4)/cyclic (< = N4), weight ratio | 43.8 | 46.8 | 41.4 | 100 | 119 | AL | 32.1 | 80.5 | AL |
| Acyclic (N5)/cyclic (< = N5), weight ratio | 19.5 | AL | 60.6 | AL | AL | — | AL | 0.2 | AC |

TABLE II-continued

| Example No. | 23 | 24 | 25 | 26 | 27 | 28 | 29 | 30 | 31 |
|---|---|---|---|---|---|---|---|---|---|
| $\Sigma(N5)/\Sigma(N4)$, weight ratio | 0.26 | 0.17 | 0.25 | 0.02 | 0.09 | 0 | 0.20 | 0.08 | 0.07 |

AL = All linear
AC = All cyclic

TABLE III

| Example No. | 32 | 33 | 34 | 35 | 36 | 37 | 38 | 39 | 40 | 41 | 42 | 43 |
|---|---|---|---|---|---|---|---|---|---|---|---|---|
| Catalyst Type | K | K | K | K | K | K | K | K | K | K | K | K |
| Catalyst weight, gm | 69.8 | 86.2 | 69.8 | 86.2 | 69.8 | 86.2 | 69.8 | 69.8 | 69.8 | 69.8 | 69.8 | 69.8 |
| Pressure, psig | 600 | 600 | 600 | 600 | 600 | 600 | 600 | 600 | 600 | 600 | 600 | 600 |
| Temperature, °C. | 269.0 | 269.9 | 270.1 | 269.8 | 280.3 | 280.8 | 260.0 | 270.4 | 260.6 | 280.7 | 270.0 | 270.5 |
| Time on organics, hrs. | 7.0 | 25.0 | 28.2 | 27.0 | 32.0 | 30.0 | 51.0 | 55.5 | 76.0 | 80.0 | 98.0 | 100.0 |
| Duration of run, hrs. | 2 | 2 | 2.2 | 2 | 2 | 2 | 2 | 1 | 1 | 2 | 2 | 2 |
| MEA SV, gmol/hr/kgcat | 6.58 | 4.13 | 5.83 | 4.39 | 6.07 | 3.45 | 5.23 | 1.85 | 5.05 | 5.44 | 5.46 | 5.60 |
| $NH_3$ feedrate, gm/hr | 57.2 | 38.4 | 52.1 | 41.1 | 48.5 | 32.7 | 40.3 | 15.1 | 19.8 | 21.6 | 44.6 | 46.2 |
| Liquid feed composition, wt. % | | | | | | | | | | | | |
| DETA | 62.81 | 62.81 | 62.81 | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 | 37.19 | 37.19 | 37.19 |
| Liquid product composition, wt. % | | | | | | | | | | | | |
| EDA | 1.24 | 1.60 | 0.95 | 1.21 | 1.43 | 1.80 | 0.74 | 0.74 | 0.74 | 1.34 | 0.74 | 0.87 |
| MeEDA | 0 | 0 | 0 | 0 | 0 | 0 | 0 | 0 | 0 | 0 | 0 | 0 |
| MEA | 19.67 | 22.54 | 26.20 | 25.34 | 19.49 | 20.13 | 29.73 | 29.73 | 29.73 | 23.12 | 28.77 | 29.57 |
| EtEDA | 0 | 0 | 0 | 0 | 0 | 0 | 0 | 0 | 0 | 0 | 0 | 0 |
| PIP | 0.65 | 1.03 | 0.53 | 0.72 | 0.93 | 1.19 | 0.38 | 0.38 | 0.38 | 0.86 | 0.40 | 0.44 |
| DETA | 55.44 | 45.02 | 50.44 | 47.30 | 46.80 | 44.02 | 51.65 | 51.65 | 51.65 | 48.33 | 52.65 | 50.62 |
| AEEA | 2.25 | 3.72 | 4.05 | 4.52 | 2.91 | 3.70 | 3.10 | 3.10 | 3.10 | 2.98 | 3.53 | 3.82 |
| AEP | 0.70 | 1.12 | 0.49 | 0.69 | 1.01 | 1.09 | 0.37 | 0.37 | 0.37 | 0.82 | 0.34 | 0.38 |
| HEP | 0 | 0 | 0 | 0 | 0 | 0 | 0 | 0 | 0 | 0 | 0 | 0 |
| TETA's | 9.65 | 11.96 | 9.66 | 10.63 | 12.87 | 13.06 | 6.39 | 6.39 | 6.39 | 11.07 | 7.31 | 6.58 |
| TEPA's | 4.85 | 6.85 | 2.52 | 3.79 | 7.21 | 6.64 | 1.70 | 1.70 | 1.70 | 5.04 | 0.69 | 1.22 |
| MEA Conversion % | 46.11 | 37.81 | 27.53 | 29.68 | 45.85 | 43.35 | 16.29 | 16.29 | 16.29 | 35.76 | 19.42 | 16.21 |
| Acyclic (N4)/cyclic (< = N4), weight ratio | 27.7 | 12.2 | 32.7 | 35.6 | 21.4 | 23.5 | 29.0 | 29.0 | 54.2 | 21.4 | 24.9 | 26.3 |
| Acyclic (N5)/cyclic (< = N5), weight ratio | 24.3 | 16.4 | AL | 42.8 | 14.0 | 17.2 | AL | AL | 1.0 | 22.0 | 1.2 | 4.0 |
| $\Sigma(N5)/\Sigma(N4)$, weight ratio | 0.39 | 0.44 | 0.20 | 0.28 | 0.43 | 0.39 | 0.21 | 0.21 | 0.21 | 0.35 | 0.07 | 0.14 |

AL = All linear

TABLE IV

| Example No. | 44 | 45 | 46 | 47 | 48 | 49 | 50 | 51 | 52 |
|---|---|---|---|---|---|---|---|---|---|
| Catalyst Type | L | L | L | L | L | L | L | L | L |
| Catalyst weight, gm | 81.0 | 81.0 | 81.0 | 81.0 | 81.0 | 81.0 | 81.0 | 81.0 | 81.0 |
| Pressure, psig | 600 | 600 | 600 | 600 | 600 | 600 | 600 | 600 | 600 |
| Temperature, °C. | 270.0 | 280.0 | 260.0 | 270.0 | 261.1 | 281.0 | 270.0 | 271.1 | 280.8 |
| Time on organics, hrs. | 5.5 | 8.5 | 25.5 | 30.5 | 49.0 | 55.0 | 63.0 | 65.0 | 83.5 |
| Duration of run, hrs. | 1 | 2 | 2 | 2 | 2 | 2 | 2 | 2 | 2 |
| MEA SV, gmol/hr/kgcat | 4.82 | 2.44 | 5.36 | 5.37 | 5.39 | 5.95 | 5.42 | 5.82 | 5.02 |
| $NH_3$ feedrate, gm/hr | 21.8 | 22.1 | 55.8 | 54.8 | 55.0 | 69.9 | 57.3 | 61.5 | 56.6 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 2.69 | 2.69 | 1.29 | 1.35 | 1.28 | 3.69 | 2.47 | 2.35 | 4.26 |
| MeEDA | 0 | 0 | 0 | 0 | 0 | 0 | 0 | 0 | 0 |
| MEA | 26.60 | 26.60 | 35.62 | 32.63 | 34.35 | 25.96 | 31.23 | 30.52 | 27.27 |
| EtEDA | 0 | 0 | 0 | 0 | 0 | 0 | 0 | 0 | 0 |
| PIP | 0.37 | 0.37 | 0.08 | 0.14 | 0.05 | 0.19 | 0.09 | 0.08 | 0.14 |
| DETA | 47.58 | 47.58 | 53.88 | 52.05 | 56.50 | 53.83 | 57.32 | 55.41 | 53.05 |
| AEEA | 2.60 | 2.60 | 1.47 | 1.73 | 1.17 | 1.43 | 1.35 | 1.26 | 1.21 |
| AEP | 0.43 | 0.43 | 0.20 | 0.26 | 0.19 | 0.38 | 0.27 | 0.27 | 0.44 |
| HEP | 0 | 0 | 0 | 0 | 0 | 0 | 0 | 0 | 0 |
| TETA's | 10.73 | 10.73 | 3.22 | 5.26 | 1.92 | 6.33 | 1.69 | 2.44 | 3.03 |
| TEPA's | 1.91 | 1.91 | 0 | 0.28 | 0 | 0.67 | 0 | 1.71 | 1.16 |
| MEA Conversion % | 24.56 | 24.56 | 0.03 | 6.94 | 3.40 | 25.65 | 11.47 | 13.43 | 19.76 |
| Acyclic (N4)/cyclic (< = N4), weight ratio | 151.7 | 21.9 | 14.4 | 19.4 | 7.9 | 25.5 | 3.0 | 5.5 | 4.7 |
| Acyclic (N5)/cyclic (< = N5), weight ratio | 4.0 | 7.9 | — | 2.1 | — | 1.2 | — | 1.4 | 1.6 |
| $\Sigma(N5)/\Sigma(N4)$, weight ratio | 0.14 | 0.13 | 0 | 0.04 | 0 | 0.08 | 0 | 0.54 | 0.30 |

TABLE V

| Example No. | 53 | 54 | 55 | 56 | 57 | 58 | 59 | 60 | 61 |
|---|---|---|---|---|---|---|---|---|---|
| Catalyst Type | M | M | M | M | M | M | M | M | M |
| Catalyst weight, gm | 85.2 | 85.2 | 85.2 | 85.2 | 85.2 | 85.2 | 85.2 | 85.2 | 85.2 |
| Pressure, psig | 600 | 600 | 600 | 600 | 600 | 600 | 600 | 600 | 600 |
| Temperature, °C. | 270.0 | 280.0 | 260.0 | 270.0 | 260.8 | 280.5 | 270.0 | 271.1 | 280.3 |
| Time on organics, hrs. | 5.5 | 8.5 | 25.5 | 30.5 | 49.0 | 55.0 | 63.0 | 65.0 | 83.5 |
| Duration of run, hrs. | 1 | 2 | 2 | 2 | 2 | 2 | 2 | 2 | 2 |
| MEA SV, gmol/hr/kgcat | 5.28 | 5.07 | 5.48 | 5.84 | 5.52 | 6.52 | 5.81 | 6.13 | 5.44 |
| $NH_3$ feedrate, gm/hr | 24.7 | 48.6 | 56.6 | 61.3 | 58.5 | 58.5 | 62.6 | 66.0 | 62.2 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.32 | 2.15 | 0.85 | 1.26 | 0.90 | 2.02 | 1.37 | 1.38 | 2.33 |
| MeEDA | 0 | 0 | 0 | 0 | 0 | 0 | 0 | 0 | 0 |
| MEA | 15.57 | 10.16 | 24.66 | 18.69 | 22.60 | 8.57 | 15.60 | 15.52 | 7.94 |
| EtEDA | 0 | 0 | 0 | 0 | 0 | 0 | 0 | 0 | 0 |
| PIP | 1.21 | 1.79 | 0.67 | 1.08 | 0.67 | 1.48 | 1.10 | 1.14 | 1.74 |
| DETA | 41.58 | 39.29 | 46.91 | 43.53 | 49.14 | 40.82 | 44.78 | 45.27 | 38.44 |
| AEEA | 2.20 | 1.15 | 2.85 | 2.14 | 2.98 | 0.66 | 1.62 | 1.56 | 0.56 |
| AEP | 1.22 | 1.98 | 0.54 | 1.04 | 0.61 | 1.67 | 1.07 | 1.11 | 1.93 |
| HEP | 0 | 0 | 0 | 0 | 0 | 0 | 0 | 0 | 0 |
| TETA's | 16.72 | 18.77 | 11.96 | 15.23 | 12.45 | 17.75 | 16.10 | 16.16 | 17.53 |
| TEPA's | 11.40 | 12.43 | 4.91 | 8.93 | 4.19 | 15.36 | 10.78 | 10.47 | 17.18 |
| MEA Conversion % | 56.69 | 71.01 | 31.16 | 47.92 | 37.24 | 75.81 | 57.10 | 57.41 | 77.50 |
| Acyclic (N4)/cyclic (< = N4), weight ratio | 28.1 | 10.7 | 39.8 | 27.5 | 58.3 | 10.0 | 28.4 | 20.2 | 7.7 |
| Acyclic (N5)/cyclic (< = N5), weight ratio | 17.8 | 11.1 | AL | 28.1 | AL | 9.6 | 20.8 | 20.2 | 7.7 |
| Σ(N5)/Σ(N4), weight ratio | 0.53 | 0.51 | 0.32 | 0.45 | 0.26 | 0.67 | 0.52 | 0.50 | 0.76 |

AL = All linear

TABLE VI

| Example No. | 62 | 63 | 64 | 65 | 66 | 67 | 68 | 69 | 70 |
|---|---|---|---|---|---|---|---|---|---|
| Catalyst Type | N | N | N | N | N | N | N | N | N |
| Catalyst weight, gm | 77.8 | 77.8 | 77.8 | 77.8 | 77.8 | 77.8 | 77.8 | 77.8 | 77.8 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.0 | 270.0 |
| Time on organics, hrs. | 5.7 | 24.0 | 29.9 | 46.7 | 50.7 | 70.0 | 73.2 | 94.5 | 96.2 |
| Duration of run, hrs. | 1 | 2 | 2 | 2 | 2 | 2 | 1 | 1.5 | 1.5 |
| AEEA SV, gmol/hr/kgcat | 6.67 | 4.63 | 4.91 | 3.59 | 2.96 | 2.58 | 3.91 | 3.41 | 3.48 |
| $NH_3$ feedrate, gm/hr | 21.8 | 50.0 | 46.9 | 32.5 | 28.0 | 23.2 | 18.2 | 22.2 | 22.7 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 0.44 | 0.39 | 0.77 | 0.24 | 0.48 | 0.24 | 0.87 | 0.49 | 0.48 |
| MeEDA | 0 | 0 | 0 | 0 | 0 | 0 | 0 | 0 | 0 |
| MEA | 0.09 | 0 | 0.08 | 0 | 0 | 0 | 0.07 | 0.08 | 0.08 |
| EtEDA | 0 | 0 | 0 | 0 | 0 | 0 | 0 | 0 | 0 |
| PIP | 4.44 | 4.13 | 5.87 | 3.20 | 4.67 | 3.53 | 6.10 | 4.40 | 4.40 |
| DETA | 43.18 | 42.76 | 43.32 | 44.28 | 43.52 | 42.38 | 42.49 | 42.87 | 42.71 |
| AEEA | 26.48 | 26.78 | 16.71 | 37.36 | 26.70 | 34.34 | 16.74 | 27.84 | 28.30 |
| AEP | 0.39 | 0.35 | 0.55 | 0.17 | 0.36 | 0.18 | 0.54 | 0.34 | 0.32 |
| HEP | 0 | 0 | 0 | 0 | 0 | 0 | 0 | 0 | 0 |
| TETA's | 3.69 | 4.01 | 5.95 | 1.76 | 3.48 | 2.16 | 5.38 | 3.50 | 3.11 |
| TEPA's | 15.71 | 15.98 | 19.62 | 9.10 | 14.81 | 12.31 | 18.59 | 13.57 | 13.51 |
| AEEA Conversion % | 45.75 | 45.11 | 65.52 | 23.95 | 45.05 | 29.69 | 64.66 | 42.02 | 40.92 |
| Acyclic (N4)/cyclic (< = N4), weight ratio | 0.1 | 0.1 | 0.1 | 0.1 | 0.1 | 0.1 | 0.1 | 0.1 | 0.1 |
| Acyclic (N5)/cyclic (< = N5), | 34.1 | 27.3 | 26.5 | 28.9 | 32.0 | 5.2 | 31.0 | 31.9 | 38.4 |
| Σ(N5)/Σ(N4), weight ratio | 4.3 | 4.0 | 3.3 | 5.2 | 4.3 | 5.7 | 3.5 | 3.9 | 4.3 |

TABLE VII

| Example No. | 71 | 72 | 73 | 74 | 75 | 76 | 77 | 78 | 79 |
|---|---|---|---|---|---|---|---|---|---|
| Catalyst Type | O | O | O | O | O | O | O | O | O |
| Catalyst weight, gm | 79.2 | 79.2 | 79.2 | 79.2 | 79.2 | 79.2 | 79.2 | 79.2 | 79.2 |
| Pressure, psig | 600 | 600 | 600 | 600 | 600 | 600 | 600 | 600 | 600 |
| Temperature, °C. | 270.0 | 270.0 | 283.0 | 258.0 | 270.9 | 260.0 | 280.8 | 270.3 | 270.9 |
| Time on organics, hrs. | 5.5 | 24.0 | 29.5 | 48.2 | 54.0 | 72.0 | 77.0 | 96.0 | 98.0 |
| Duration of run, hrs. | 2 | 2 | 1 | 2.2 | 2 | 2 | 2 | 2 | 2 |
| AEEA SV, gmol/hr/kgcat | — | — | — | — | — | — | — | — | — |

TABLE VII-continued

| Example No. | 71 | 72 | 73 | 74 | 75 | 76 | 77 | 78 | 79 |
|---|---|---|---|---|---|---|---|---|---|
| $NH_3$ feedrate, gm/hr | 23.9 | 44.4 | 23.5 | 60.7 | 63.0 | 38.0 | 50.5 | 43.3 | 42.4 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 0.72 | 0.52 | 1.19 | 0.21 | 0.27 | 0 | 0.86 | 0.49 | 0.45 |
| MeEDA | 0 | 0 | 0 | 0 | 0 | 0 | 0 | 0 | 0 |
| MEA | 0.18 | 0 | 0.10 | 0 | 0 | 0 | 0.12 | 0.07 | 0.08 |
| EtEDA | 0 | 0 | 0 | 0 | 0 | 0 | 0 | 0 | 0 |
| PIP | 3.26 | 3.37 | 5.01 | 1.95 | 2.53 | 1.91 | 4.25 | 3.00 | 2.84 |
| DETA | 44.51 | 41.52 | 43.07 | 43.76 | 42.61 | 42.89 | 43.51 | 44.61 | 43.96 |
| AEEA | 21.05 | 28.04 | 18.66 | 41.43 | 34.60 | 41.04 | 22.86 | 32.99 | 33.50 |
| AEP | 0.51 | 0.40 | 0.69 | 0.17 | 0.30 | 0.17 | 0.46 | 0.30 | 0.30 |
| HEP | 0 | 0 | 0 | 0 | 0 | 0 | 0 | 0 | 0 |
| TETA's | 4.12 | 3.89 | 5.55 | 1.56 | 2.66 | 1.64 | 4.87 | 2.56 | 2.65 |
| TEPA's | 16.72 | 15.50 | 16.20 | 6.95 | 11.77 | 8.80 | 15.08 | 9.19 | 10.75 |
| AEEA Conversion % | 55.29 | 41.70 | 60.26 | 15.17 | 28.72 | 16.50 | 51.95 | 30.81 | 30.79 |
| Acyclic (N4)/cyclic ($\leq$ N4), weight ratio | 0.1 | 0.2 | 0.2 | 0.2 | 0.1 | 0.2 | 0.2 | 0.1 | 0.1 |
| Acyclic (N5)/cyclic ($\leq$ N5), weight ratio | 21.9 | 28.0 | 18.9 | 18.8 | 35.8 | 32.4 | 25.2 | 26.1 | 16.9 |
| $\Sigma(N5)/\Sigma(N4)$, weight ratio | 4.1 | 4.0 | 2.9 | 4.5 | 4.4 | 3.1 | 3.1 | 3.6 | 4.1 |

TABLE VIII

| Example No. | 80 | 81 | 82 | 83 | 84 | 85 | 86 | 87 | 88 |
|---|---|---|---|---|---|---|---|---|---|
| Catalyst Type | P | P | P | P | P | P | P | P | P |
| Catalyst weight, gm | 70.3 | 70.3 | 70.3 | 70.3 | 70.3 | 70.3 | 70.3 | 70.3 | 70.3 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.8 | 270.6 | 269.0 |
| Time on organics, hrs. | 5.5 | 22.5 | 29.0 | 52.0 | 54.5 | 72.2 | 78.0 | 96.5 | 98.5 |
| Duration of run, hrs. | 2 | 1 | 2 | 1 | 1 | 2 | 2 | 2 | 2 |
| AEEA SV, gmol/hr/kgcat | — | — | — | — | — | — | — | — | — |
| $NH_3$ feedrate, gm/hr | 21.6 | 14.3 | 32.8 | 30.7 | 29.8 | 50.4 | 43.6 | 38.0 | 38.9 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 2.46 | 1.29 | 1.46 | 0.41 | 0.59 | 0.36 | 0.24 | 0.75 | 0.70 |
| MeEDA | 0 | 0 | 0 | 0 | 0 | 0 | 0 | 0 | 0 |
| MEA | 1.52 | 0.91 | 0.77 | 0.43 | 0.40 | 0.21 | 0.22 | 0.23 | 0.17 |
| EtEDA | 0 | 0 | 0 | 0 | 0 | 0 | 0 | 0 | 0 |
| PIP | 4.80 | 3.83 | 4.36 | 2.11 | 2.78 | 2.01 | 4.12 | 3.40 | 3.25 |
| DETA | 37.58 | 41.15 | 42.68 | 44.21 | 41.99 | 43.58 | 39.66 | 43.51 | 41.45 |
| AEEA | 16.78 | 26.05 | 23.62 | 42.66 | 33.98 | 43.20 | 23.91 | 34.37 | 33.86 |
| AEP | 1.48 | 0.54 | 0.55 | 0.14 | 0.31 | 0.14 | 0.42 | 0.29 | 0.20 |
| HEP | 0 | 0 | 0 | 0 | 0 | 0 | 0 | 0 | 0 |
| TETA's | 7.37 | 3.99 | 3.66 | 0.85 | 2.68 | 1.01 | 4.52 | 2.37 | 2.61 |
| TEPA's | 16.17 | 14.01 | 13.88 | 5.45 | 10.84 | 5.68 | 18.03 | 9.38 | 10.95 |
| AEEA Conversion % | 63.30 | 44.80 | 49.70 | 12.60 | 29.00 | 11.50 | 49.67 | 28.70 | 29.10 |
| Acyclic (N4)/cyclic ($\leq$ N4), weight ratio | 0.9 | 0.3 | 0.1 | 0.1 | 0.1 | 0.3 | 0.1 | 0.1 | 0.1 |
| Acyclic (N5)/cyclic ($\leq$ N5), weight ratio | 11.8 | 20.5 | 23.8 | 22.6 | 22.9 | 24.2 | 13.2 | 30.5 | 18.2 |
| $\Sigma(N5)/\Sigma(N4)$, weight ratio | 2.2 | 3.5 | 3.8 | 6.4 | 4.0 | 5.6 | 4.0 | 4.0 | 4.2 |

TABLE IX

| Example No. | 89 | 90 | 91 | 92 | 93 | 94 | 95 | 96 | 97 |
|---|---|---|---|---|---|---|---|---|---|
| Catalyst Type | Q | Q | Q | Q | Q | Q | Q | Q | Q |
| Catalyst weight, gm | 92.4 | 92.4 | 92.4 | 92.4 | 92.4 | 92.4 | 92.4 | 92.4 | 92.4 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.0 | 270.0 |
| Time on organics, hrs. | 5.7 | 24.0 | 29.0 | 46.7 | 50.7 | 70.0 | 73.2 | 94.5 | 96.2 |
| Duration of run, hrs. | 1 | 2 | 2 | 2 | 2 | 2 | 1 | 1.5 | 1.5 |
| AEEA SV, gmol/hr/kgcat | — | — | — | — | — | — | — | — | — |
| $NH_3$ feedrate, gm/hr | 20.7 | 54.6 | 46.1 | 39.5 | 43.8 | 36.2 | 19.9 | 23.6 | 24.5 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |

TABLE IX-continued

| Example No. | 89 | 90 | 91 | 92 | 93 | 94 | 95 | 96 | 97 |
|---|---|---|---|---|---|---|---|---|---|
| EDA | 0.62 | 0.77 | 1.43 | 0.35 | 0.65 | 0.34 | 1.54 | 0.85 | 0.85 |
| MeEDA | 0 | 0 | 0 | 0 | 0 | 0 | 0 | 0 | 0 |
| MEA | 0.05 | 0.05 | 0.12 | 0 | 0 | 0 | 0.12 | 0.05 | 0.05 |
| EtEDA | 0 | 0 | 0 | 0 | 0 | 0 | 0 | 0 | 0 |
| PIP | 5.03 | 5.21 | 6.86 | 3.37 | 4.62 | 3.56 | 6.78 | 5 | 4.91 |
| DETA | 41.13 | 41.09 | 41.25 | 41.84 | 41.18 | 42.24 | 40.18 | 40.78 | 40.48 |
| AEEA | 22.03 | 21.43 | 12.01 | 33.20 | 23.91 | 32.48 | 12.42 | 22.88 | 23.37 |
| AEP | 0.50 | 0.51 | 1.00 | 0.32 | 0.47 | 0.32 | 0.94 | 0.49 | 0.47 |
| HEP | 0 | 0 | 0 | 0 | 0 | 0 | 0 | 0 | 0 |
| TETA's | 4.09 | 4.42 | 6.08 | 2.05 | 3.98 | 1.87 | 4.49 | 3.99 | 3.92 |
| TEPA's | 20.24 | 20.45 | 22.65 | 14.14 | 19.44 | 13.37 | 20.88 | 18.77 | 18.49 |
| AEEA Conversion % | 54.80 | 56.17 | 74.97 | 32.22 | 51.14 | 32.91 | 72.86 | 52.54 | 51.35 |
| Acyclic (N4)/cyclic (< = N4), weight ratio | 0.2 | 0.2 | 0.2 | 0.2 | 0.2 | 0.2 | 0.3 | 0.2 | 0.2 |
| Acyclic (N5)/cyclic (< = N5), weight ratio | 37.8 | 37.9 | 37.9 | 28.4 | 39.5 | 22.2 | 22.3 | 40.8 | 36.2 |
| Σ(N5)/Σ(N4), weight ratio | 5.0 | 4.6 | 4.6 | 6.9 | 4.9 | 7.2 | 4.7 | 4.7 | 4.7 |

TABLE X

| Example No. | 98 | 99 | 100 | 101 | 102 | 103 | 104 | 105 | 106 |
|---|---|---|---|---|---|---|---|---|---|
| Catalyst Type | R | R | R | R | R | R | R | R | R |
| Catalyst weight, gm | 83.0 | 83.0 | 83.0 | 83.0 | 83.0 | 83.0 | 83.0 | 83.0 | 83.0 |
| Pressure, psig | 600 | 600 | 600 | 600 | 600 | 600 | 600 | 600 | 600 |
| Temperature, °C. | 269.3 | 269.2 | 280.3 | 260.0 | 270.7 | 258.8 | 279.4 | 268.5 | 268.9 |
| Time on organics, hrs. | 25.0 | 27.0 | 30.0 | 47.5 | 53.0 | 72.5 | 78.5 | 96.0 | 104.0 |
| Duration of run, hrs. | 2 | 2 | 2 | 2 | 2 | 2 | 2 | 2 | 2 |
| MEA SV, gmol/hr/kgcat | 4.36 | 5.83 | 4.87 | 4.24 | 4.63 | 4.25 | 4.23 | 4.49 | 4.84 |
| NH₃ feedrate, gm/hr | 3.93 | 42.6 | 44.5 | 35.7 | 38.8 | 34.3 | 35.5 | 39.3 | 42.8 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.48 | 1.57 | 2.02 | 0.69 | 1.06 | 0.53 | 1.45 | 0.83 | 0.78 |
| MeEDA | 0 | 0 | 0 | 0 | 0 | 0 | 0 | 0 | 0 |
| MEA | 22.85 | 29.24 | 17.65 | 29.77 | 25.97 | 31.82 | 20.10 | 27.71 | 29.07 |
| EtEDA | 0 | 0 | 0 | 0 | 0 | 0 | 0 | 0 | 0 |
| PIP | 0.64 | 0.66 | 0.94 | 0.22 | 0.41 | 0.15 | 0.60 | 0.26 | 0.23 |
| DETA | 45.36 | 55.10 | 42.59 | 50.64 | 49.02 | 53.67 | 45.37 | 50.33 | 50.69 |
| AEEA | 4.02 | 5.66 | 3.65 | 4.36 | 4.97 | 3.75 | 4.15 | 4.75 | 4.55 |
| AEP | 0.79 | 0.77 | 1.15 | 0.28 | 0.45 | 0.23 | 0.79 | 0.79 | 0.30 |
| HEP | 0 | 0 | 0 | 0 | 0 | 0 | 0 | 0 | 0 |
| TETA's | 12.73 | 15.31 | 14.61 | 7.65 | 9.90 | 5.99 | 13.50 | 8.57 | 7.66 |
| TEPA's | 5.73 | 6.96 | 8.41 | 1.55 | 2.93 | 0.37 | 6.56 | 2.11 | 1.74 |
| MEA Conversion % | 36.63 | 34.01 | 50.31 | 17.19 | 28.09 | 12.29 | 43.92 | 23.51 | 19.12 |
| Acyclic (N4)/cyclic (< = N4), weight ratio | 26.3 | 37 | 19.1 | 59.2 | 49.2 | 73.5 | 30.6 | 56.3 | 91.8 |
| Acyclic (N5)/cyclic (< = N5), weight ratio | 16.6 | 26.7 | 17.3 | AL | AL | Al | 16.1 | AL | AL |
| Σ(N5)/Σ(N4), weight ratio | 0.35 | 0.35 | 0.44 | 0.16 | 0.23 | 0.05 | 0.38 | 0.19 | 0.18 |

AL = All linear

TABLE XI

| Example No. | 107 | 108 | 109 | 110 | 111 | 112 | 113 | 114 | 115 |
|---|---|---|---|---|---|---|---|---|---|
| Catalyst Type | S | S | S | S | S | S | S | S | S |
| Catalyst weight, gm | 87.0 | 87.0 | 87.0 | 87.0 | 87.0 | 87.0 | 87.0 | 87.0 | 87.0 |
| Pressure, psig | 600 | 600 | 600 | 600 | 600 | 600 | 600 | 600 | 600 |
| Temperature, °C. | 270.0 | 280.0 | 260.0 | 270.0 | 260.0 | 280.2 | 270.0 | 270.8 | 279.6 |
| Time on organics, hrs. | 5.5 | 8.5 | 25.5 | 30.5 | 49.0 | 55.0 | 63.0 | 65.0 | 83.5 |
| Duration of run, hrs. | 1 | 2 | 2 | 2 | 2 | 2 | 2 | 2 | 2 |
| MEA SV, gmol/hr/kgcat | 4.98 | 3.19 | 5.17 | 5.40 | 4.94 | 5.17 | 2.91 | 3.20 | 2.01 |
| NH₃ feedrate, gm/hr | 23.8 | 22.8 | 28.4 | 28.8 | 26.7 | 31.6 | 16.1 | 17.5 | 11.7 |
| Liquid feed composition, wt. % | | | | | | | | | |
| DETA | 62.81 | 62.81 | 62.81 | 62.81 | 62.81 | 62.81 | 62.81 | 62.81 | 62.81 |
| AEEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.41 | 2.05 | 0.56 | 0.87 | 0.58 | 1.66 | 1.73 | 1.61 | 3.20 |
| MeEDA | 0 | 0 | 0 | 0 | 0 | 0 | 0 | 0 | 0 |
| MEA | 19.33 | 14.89 | 32.59 | 28.88 | 30.91 | 19.92 | 22.47 | 22.59 | 14.36 |
| EtEDA | 0 | 0 | 0 | 0 | 0 | 0 | 0 | 0 | 0 |
| PIP | 0.90 | 1.42 | 0.34 | 0.61 | 0.30 | 1.17 | 1.29 | 1.22 | 2.55 |
| DETA | 52.52 | 49.03 | 53.57 | 50.73 | 55.21 | 50.05 | 49.40 | 49.57 | 40.30 |

TABLE XI-continued

| Example No. | 107 | 108 | 109 | 110 | 111 | 112 | 113 | 114 | 115 |
|---|---|---|---|---|---|---|---|---|---|
| AEEA | 3.10 | 2.24 | 2.82 | 3.11 | 2.59 | 2.54 | 2.81 | 2.84 | 1.84 |
| AEP | 0.85 | 1.56 | 0.26 | 0.44 | 0.23 | 1.07 | 0.95 | 0.90 | 2.16 |
| HEP | 0 | 0 | 0 | 0 | 0 | 0 | 0 | 0 | 0 |
| TETA's | 9.47 | 11.11 | 5.40 | 8.10 | 5.43 | 11.41 | 10.18 | 10.98 | 13.32 |
| TEPA's | 5.10 | 7.91 | 0.97 | 2.28 | 0.46 | 5.29 | 4.71 | 5.15 | 11.87 |
| MEA Conversion % | 46.07 | 57.87 | 10.12 | 19.83 | 14.19 | 44.75 | 37.61 | 38.21 | 59.43 |
| Acyclic (N4)/cyclic (< = N4), weight ratio | 27.7 | 11.6 | 29.1 | 31.2 | 29.4 | 19.7 | 18.6 | 24.8 | 5.9 |
| Acyclic (N5)/cyclic (< = N5), weight ratio | 24.3 | 7.9 | 3.8 | AL | 0.5 | 12.4 | 13.9 | 20.6 | 8.8 |
| Σ(N5)/Σ(N4), weight ratio | 0.42 | 0.55 | 0.14 | 0.22 | 0.07 | 0.36 | 0.36 | 0,.36 | 0.69 |

AL = All linear

TABLE XII

| Example No. | 116 | 117 | 118 | 119 | 120 | 121 | 122 | 123 | 124 |
|---|---|---|---|---|---|---|---|---|---|
| Catalyst Type | T | T | T | T | T | T | T | T | T |
| Catalyst weight, gm | 70.3 | 70.3 | 70.3 | 70.3 | 70.3 | 70.3 | 70.3 | 70.3 | 70.3 |
| Pressure, psig | 600 | 600 | 600 | 600 | 600 | 600 | 600 | 600 | 600 |
| Temperature, °C. | 269.6 | 269.8 | 280.0 | 260.0 | 269.9 | 259.9 | 280.0 | 270.0 | 269.8 |
| Time on organics, hrs. | 7.0 | 28.2 | 32.0 | 51.0 | 55.5 | 76.0 | 80.0 | 98.0 | 100.0 |
| Duration of run, hrs. | 2 | 2.2 | 2 | 2 | 2 | 1 | 1 | 2 | 2 |
| MEA SV, gmol/hr/kgcat | 6.41 | 5.47 | 5.54 | 5.55 | 5.99 | 4.94 | 4.87 | 5.13 | 5.09 |
| NH3 feedrate, gm/hr | 57.0 | 50.0 | 47.4 | 42.9 | 51.0 | 19.5 | 20.2 | 42.8 | 42.6 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.76 | 1.72 | 2.79 | 1.20 | 1.54 | 1.03 | 3.28 | 1.62 | 1.77 |
| MeEDA | 0 | 0 | 0 | 0 | 0 | 0 | 0 | 0 | 0 |
| MEA | 28.93 | 31.18 | 25.30 | 34.17 | 32.94 | 36.96 | 29.76 | 34.70 | 34.76 |
| EtEDA | 0 | 0 | 0 | 0 | 0 | 0 | 0 | 0 | 0 |
| PIP | 0.31 | 0.20 | 0.35 | 0.11 | 0.13 | 0.05 | 0.26 | 0.08 | 0.08 |
| DETA | 51.86 | 51.84 | 47.27 | 52.54 | 50.53 | 55.52 | 49.86 | 54.14 | 52.26 |
| AEEA | 2.46 | 2.38 | 2.35 | 1.71 | 1.94 | 1.39 | 2.21 | 1.69 | 1.72 |
| AEP | 0.34 | 0.26 | 0.43 | 0.27 | 0.22 | 0.18 | 0.37 | 0.23 | 0.23 |
| HEP | 0 | 0 | 0 | 0 | 0 | 0 | 0 | 0 | 0 |
| TETA's | 8.21 | 6.88 | 8.88 | 4.83 | 4.02 | 0.75 | 6.01 | 1.23 | 2.76 |
| TEPA's | 1.20 | 0.40 | 1.93 | 0.61 | 0.28 | 0 | 0.77 | 0.75 | 0.69 |
| MEA Conversion % | 19.48 | 12.50 | 25.30 | 4.19 | 3.61 | 3.96 | 14.28 | 1.23 | 0.93 |
| Acyclic (N4)/cyclic (< = N4), weight ratio | 61.5 | 34.2 | 29.6 | 8.2 | 10.8 | 5.2 | 15.9 | 5.1 | 10.0 |
| Acyclic (N5)/cyclic (< = N5), weight ratio | 8.7 | 2.5 | 6.9 | 3.1 | 1.0 | — | 1.6 | 0.8 | 0.9 |
| Σ(N5)/Σ(N4), weight ratio | 0.11 | 0.04 | 0.18 | 0.10 | 0.05 | 0.00 | 0.10 | 0.47 | 0.19 |

TABLE XIII

| Example No. | 125 | 126 | 127 | 128 | 129 | 130 | 131 | 132 | 133 |
|---|---|---|---|---|---|---|---|---|---|
| Catalyst Type | U | U | U | U | U | U | U | U | U |
| Catalyst weight, gm | 80.0 | 80.0 | 80.0 | 80.0 | 80.0 | 80.0 | 80.0 | 80.0 | 80.0 |
| Pressure, psig | 600 | 600 | 600 | 600 | 600 | 600 | 600 | 600 | 600 |
| Temperature, °C. | 269.2 | 270.6 | 280.0 | 260.0 | 270.6 | 260.3 | 280.3 | 270.0 | 270.4 |
| Time on organics, hrs. | 7.0 | 28.2 | 32.0 | 51.0 | 55.5 | 76.0 | 80.0 | 98.0 | 100.0 |
| Duration of run, hrs. | 2 | 2.2 | 2 | 2 | 2 | 1 | 1 | 2 | 2 |
| MEA SV, gmol/hr/kgcat | 5.80 | 5.38 | 5.30 | 5.18 | 5.59 | 4.76 | 4.64 | 4.77 | 4.93 |
| NH3 feedrate, gm/hr | 58.1 | 55.5 | 50.5 | 45.4 | 52.8 | 21.4 | 21.7 | 44.7 | 46.5 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.49 | 1.58 | 2.41 | 1.49 | 1.60 | 1.33 | 3.12 | 1.81 | 1.94 |
| MeEDA | 0 | 0 | 0 | 0 | 0 | 0 | 0 | 0 | 0 |
| MEA | 15.80 | 15.60 | 7.88 | 21.06 | 16.72 | 23.31 | 8.72 | 16.63 | 16.40 |
| EtEDA | 0 | 0 | 0 | 0 | 0 | 0 | 0 | 0 | 0 |
| PIP | 1.24 | 1.29 | 1.79 | 1.18 | 1.30 | 1.03 | 2.25 | 1.45 | 1.52 |
| DETA | 43.99 | 41.88 | 35.04 | 44.83 | 41.24 | 45.12 | 38.12 | 42.49 | 42.23 |
| AEEA | 1.68 | 1.76 | 0.69 | 2.11 | 1.79 | 2.59 | 0.65 | 1.94 | 1.78 |
| AEP | 1.28 | 1.32 | 2.09 | 1.44 | 1.21 | 0.82 | 2.32 | 1.36 | 1.42 |
| HEP | 0 | 0 | 0 | 0 | 0 | 0 | 0 | 0 | 0 |
| TETA's | 16.06 | 16.67 | 18.12 | 12.97 | 15.56 | 12.51 | 17.44 | 15.73 | 15.55 |
| TEPA's | 10.63 | 11.12 | 17.85 | 7.24 | 9.80 | 5.36 | 14.78 | 9.38 | 9.35 |
| MEA Conversion % | 56.44 | 56.59 | 77.25 | 41.21 | 52.29 | 34.25 | 75.14 | 53.32 | 53.67 |
| Acyclic (N4)/cyclic (< = N4), weight ratio | 45.2 | 22.5 | 7.5 | 21.2 | 22.4 | 34.8 | 8.8 | 23.5 | 22.7 |

TABLE XIII-continued

| Example No. | 125 | 126 | 127 | 128 | 129 | 130 | 131 | 132 | 133 |
|---|---|---|---|---|---|---|---|---|---|
| Catalyst Type | U | U | U | U | U | U | U | U | U |
| Acyclic (N5)/cyclic (< = N5), weight ratio | 22.8 | 18.1 | 7.8 | 16.0 | 18.1 | 30.1 | 9.5 | 16.3 | 16.1 |
| $\Sigma(N5)/\Sigma(N4)$, weight ratio | 0.51 | 0.52 | 0.76 | 0.43 | 0.48 | 0.33 | 0.65 | 0.46 | 0.46 |

TABLE XIV

| Example No. | 134 | 135 | 136 | 137 | 138 | 139 | 140 | 141 | 142 |
|---|---|---|---|---|---|---|---|---|---|
| Catalyst Type | V | V | V | V | V | V | V | V | V |
| Catalyst weight, gm | 73.7 | 73.7 | 73.7 | 73.7 | 73.7 | 73.7 | 73.7 | 73.7 | 73.7 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.7 | 270.0 |
| Time on organics, hrs. | 5.5 | 22.5 | 29.0 | 52.0 | 54.5 | 72.2 | 78.0 | 96.5 | 98.5 |
| Duration of run, hrs. | 2 | 1 | 2 | 1 | 1 | 2 | 2 | 2 | 2 |
| AEEA SV, gmol/hr/kgcat | 6.67 | 4.63 | 4.91 | 3.59 | 2.96 | 2.58 | 3.91 | 3.41 | 3.48 |
| NH3 feedrate, gm/hr | 23.9 | 9.9 | 48.8 | 23.5 | 28.5 | 31.0 | 25.0 | 26.9 | 26.3 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 1.79 | 1.51 | 1.41 | 0.34 | 0.50 | 0.35 | 1.70 | 0.78 | 0.74 |
| MeEDA | 0 | 0 | 0 | 0 | 0 | 0 | 0 | 0 | 0 |
| MEA | 1.07 | 1.17 | 0.74 | 0.25 | 0.33 | 0.24 | 0.04 | 0.16 | 0.15 |
| EtEDA | 0 | 0 | 0 | 0 | 0 | 0 | 0 | 0 | 0 |
| PIP | 5.52 | 3.76 | 5.76 | 2.81 | 3.63 | 3.64 | 6.92 | 5.05 | 4.86 |
| DETA | 35.90 | 41.93 | 41.57 | 41.16 | 41.76 | 42.48 | 39.49 | 41.16 | 39.75 |
| AEEA | 12.93 | 27.03 | 18.11 | 36.99 | 28.20 | 33.45 | 13.29 | 23.75 | 23.90 |
| AEP | 1.55 | 0.45 | 0.89 | 0.18 | 0.37 | 0.30 | 0.97 | 0.44 | 0.40 |
| HEP | 0 | 0 | 0 | 0 | 0 | 0 | 0 | 0 | 0 |
| TETA's | 8.53 | 3.5 | 6.04 | 2.12 | 3.43 | 2.57 | 7.05 | 4.24 | 3.96 |
| TEPA's | 20.89 | 12.30 | 16.43 | 11.31 | 14.45 | 12.09 | 20.16 | 16.39 | 16.70 |
| AEEA Conversion % | 71.98 | 42.53 | 61.68 | 24.04 | 40.94 | 31.50 | 71.70 | 50.18 | 49.03 |
| Acyclic (N4)/cyclic (< = N4), weight ratio | 0.6 | 0.3 | 0.3 | 0.1 | 0.1 | 0.1 | 0.2 | 0.1 | 0.1 |
| Acyclic (N5)/cyclic (< = N5), weight ratio | 11.5 | 23.0 | 21.5 | 29.0 | 36.6 | 40.9 | 21.5 | 38.7 | 40.6 |
| $\Sigma(N5)/\Sigma(N4)$, weight ratio | 2.4 | 3.5 | 2.7 | 5.3 | 4.2 | 4.7 | 2.9 | 3.9 | 4.2 |

TABLE XV

| Example No. | 143 | 144 | 145 | 146 | 147 | 148 | 149 | 150 | 151 |
|---|---|---|---|---|---|---|---|---|---|
| Catalyst Type | W | W | W | W | W | W | W | W | W |
| Catalyst weight, gm | 73.4 | 73.4 | 73.4 | 73.4 | 73.4 | 73.4 | 73.4 | 73.4 | 73.4 |
| Pressure, psig | 600 | 600 | 600 | 600 | 600 | 600 | 600 | 600 | 600 |
| Temperature, °C. | 270.0 | 270.0 | 283.0 | 258.0 | 270.9 | 260.0 | 280.8 | 270.3 | 270.9 |
| Time on organics, hrs. | 6.0 | 24.0 | 29.5 | 48.2 | 54.0 | 72.0 | 77.0 | 96.0 | 98.0 |
| Duration of run, hrs. | 2 | 2 | 1 | 2.2 | 2 | 2 | 2 | 2 | 2 |
| AEEA SV, gmol/hr/kgcat | — | — | — | — | — | — | — | — | — |
| NH3 feedrate, gm/hr | 49.4 | 47.0 | 25.3 | 63.8 | 66.2 | 40.9 | 55.0 | 45.8 | 45.5 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 0.59 | 0.51 | 1.22 | 0.19 | 0.25 | 0.17 | 0.76 | 0.44 | 0.45 |
| MeEDA | 0 | 0 | 0 | 0 | 0 | 0 | 0 | 0 | 0 |
| MEA | 0.20 | 0.07 | 0.09 | 0 | 0 | 0 | 0.12 | 0.07 | 0.07 |
| EtEDA | 0 | 0 | 0 | 0 | 0 | 0 | 0 | 0 | 0 |
| PIP | 2.85 | 3.05 | 4.72 | 1.66 | 2.14 | 1.61 | 3.58 | 2.65 | 2.63 |
| DETA | 45.65 | 41.32 | 44.05 | 44.34 | 42.13 | 42.52 | 43.04 | 44.85 | 44.90 |
| AEEA | 24.65 | 30.56 | 20.44 | 43.92 | 36.81 | 42.99 | 25.69 | 25.38 | 36.09 |
| AEP | 0.44 | 0.40 | 0.82 | 0.17 | 0.31 | 0.16 | 0.51 | 0.32 | 0.31 |
| HEP | 0 | 0 | 0 | 0 | 0 | 0 | 0 | 0 | 0 |
| TETA's | 3.12 | 2.96 | 4.96 | 0.73 | 1.76 | 0.98 | 4.05 | 1.48 | 1.46 |
| TEPA's | 14.38 | 15.11 | 15.08 | 6.05 | 11.07 | 7.67 | 15.97 | 8.80 | 8.72 |
| AEEA Conversion % | 47.86 | 36.83 | 56.81 | 10.83 | 23.78 | 12.00 | 46.91 | 40.95 | 25.27 |
| Acyclic (N4)/cyclic (< = N4), weight ratio | 0.2 | 0.2 | 0.3 | 0.1 | 0.1 | 0.2 | 0.2 | 0.1 | 0.1 |
| Acyclic (N5)/cyclic (< = N5), weight ratio | 29.2 | 29.9 | 16.2 | 33.1 | 34.6 | 30.5 | 23.6 | 23.1 | 24.5 |
| $\Sigma(N5)/\Sigma(N4)$, weight ratio | 4.6 | 5.1 | 3.0 | 8.3 | 6.3 | 7.8 | 3.9 | 6.0 | 6.0 |

TABLE XVI

| Example No. | 152 | 153 | 154 | 155 | 156 | 157 | 158 | 159 | 160 |
|---|---|---|---|---|---|---|---|---|---|
| Catalyst Type | X | X | X | X | X | X | X | X | X |
| Catalyst weight, gm | 84.4 | 84.4 | 84.4 | 84.4 | 84.4 | 84.4 | 84.4 | 84.4 | 84.4 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.8 | 270.6 | 270.0 |
| Time on organics, hrs. | 5.5 | 22.5 | 29.0 | 52.0 | 54.5 | 72.2 | 78.0 | 96.5 | 98.5 |
| Duration of run, hrs. | 2 | 1 | 2 | 1 | 1 | 2 | 2 | 2 | 2 |
| AEEA SV, gmol/hr/kgcat | — | — | — | — | — | — | — | — | — |
| NH$_3$ feedrate, gm/hr | 22.1 | 22.5 | 49.2 | 28.0 | 28.5 | 49.7 | 46.8 | 44.6 | 47.7 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 2.27 | 4.55 | 1.74 | 0.58 | 0.94 | 0.50 | 1.87 | 1.19 | 0.98 |
| MeEDA | 0 | 0 | 0 | 0 | 0 | 0 | 0 | 0 | 0 |
| MEA | 1.91 | 0.49 | 0.96 | 0.60 | 0.48 | 0.27 | 0.22 | 0.28 | 0.28 |
| EtEDA | 0 | 0 | 0 | 0 | 0 | 0 | 0 | 0 | 0 |
| PIP | 4.38 | 8.82 | 4.05 | 1.76 | 2.73 | 1.76 | 4.35 | 3.33 | 3.06 |
| DETA | 38.78 | 30.56 | 43.07 | 43.47 | 43.02 | 41.40 | 40.62 | 43.07 | 43.67 |
| AEEA | 18.03 | 6.55 | 25.13 | 44.40 | 34.37 | 41.62 | 22.92 | 33.81 | 36.22 |
| AEP | 1.04 | 3.42 | 0.47 | 0.13 | 0.29 | 0.13 | 0.45 | 0.29 | 0.20 |
| HEP | 0 | 0 | 0 | 0 | 0 | 0 | 0 | 0 | 0 |
| TETA's | 6.08 | 12.34 | 3.31 | 0.97 | 2.18 | 1.33 | 4.49 | 1.70 | 2.15 |
| TEPA's | 15.92 | 19.32 | 12.10 | 4.88 | 8.78 | 6.37 | 13.97 | 9.45 | 8.66 |
| AEEA Conversion % | 60.54 | 85.60 | 46.11 | 9.39 | 27.39 | 12.20 | 50.03 | 28.95 | 25.46 |
| Acyclic (N4)/cyclic (< = N4), weight ratio | 0.6 | 0.4 | 0.1 | 0.5 | 0.3 | 0.4 | 0.1 | 0.4 | 0.3 |
| Acyclic (N5)/cyclic (< = N5), weight ratio | 11.7 | 4.9 | 20.9 | 19.5 | 28.4 | 21.5 | 8.5 | 25.7 | 24.0 |
| Σ(N5)/Σ(N4), weight ratio | 2.6 | 1.6 | 3.7 | 5.0 | 4.0 | 4.8 | 3.1 | 3.1 | 4.0 |

TABLE XVII

| Example No. | 161 | 162 | 163 | 164 | 165 | 166 | 167 | 168 | 169 |
|---|---|---|---|---|---|---|---|---|---|
| Catalyst Type | Y | Y | Y | Y | Y | Y | Y | Y | Y |
| Catalyst weight, gm | 78.3 | 78.3 | 78.3 | 78.3 | 78.3 | 78.3 | 78.3 | 78.3 | 78.3 |
| Pressure, psig | 600 | 600 | 600 | 600 | 600 | 600 | 600 | 600 | 600 |
| Temperature, °C. | 270.0 | 270.0 | 283.0 | 258.0 | 270.9 | 260.0 | 280.8 | 270.3 | 270.9 |
| Time on organics, hrs. | 6.0 | 24.0 | 29.5 | 48.2 | 54.0 | 72.0 | 77.0 | 96.0 | 98.0 |
| Duration of run, hrs. | 2 | 2 | 1 | 2.2 | 2 | 2 | 2 | 2 | 2 |
| AEEA SV, gmol/hr/kgcat | — | — | — | — | — | — | — | — | — |
| NH$_3$ feedrate, gm/hr | 47.8 | 42.9 | 23.8 | 60.8 | 63.8 | 38.3 | 51.1 | 44.1 | 43.5 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 1.79 | 0.84 | 2.05 | 0.26 | 0.49 | 0.27 | 1.47 | 0.88 | 0.81 |
| MeEDA | 0 | 0 | 0 | 0 | 0 | 0 | 0 | 0 | 0 |
| MEA | 0.07 | 0.08 | 0.15 | 0 | 0 | 0 | 0.13 | 0.12 | 0.12 |
| EtEDA | 0 | 0 | 0 | 0 | 0 | 0 | 0 | 0 | 0 |
| PIP | 5.48 | 5.20 | 7.62 | 3.16 | 4.17 | 3.14 | 6.53 | 5.51 | 5.21 |
| DETA | 40.75 | 39.06 | 40.46 | 42.44 | 41.21 | 41.62 | 39.57 | 44.13 | 42.64 |
| AEEA | 21.03 | 20.82 | 10.49 | 34.11 | 26.14 | 34.43 | 12.94 | 23.33 | 23.17 |
| AEP | 0.61 | 0.59 | 1.43 | 0.32 | 0.45 | 0.31 | 1.03 | 0.58 | 0.53 |
| HEP | 0 | 0 | 0 | 0 | 0 | 0 | 0 | 0 | 0 |
| TETA's | 4.60 | 5.02 | 7.77 | 1.84 | 3.81 | 2.33 | 7.05 | 3.48 | 3.34 |
| TEPA's | 19.42 | 20.43 | 18.20 | 12.67 | 16.32 | 13.13 | 21.97 | 15.04 | 14.97 |
| AEEA Conversion % | 56.84 | 56.59 | 77.33 | 29.89 | 45.43 | 29.60 | 72.79 | 51.60 | 50.71 |
| Acyclic (N4)/cyclic (< = N4), weight ratio | 0.2 | 0.2 | 0.3 | 0.1 | 0.2 | 0.2 | 0.3 | 0.1 | 0.1 |
| Acyclic (N5)/cyclic (< = N5), weight ratio | 30.5 | 30.6 | 14.2 | 41.1 | 35.1 | 47.8 | 18.1 | 25.1 | 25.8 |
| Σ(N5)/Σ(N4), weight ratio | 4.2 | 4.1 | 2.3 | 6.9 | 4.3 | 5.6 | 3.1 | 4.3 | 4.5 |

TABLE XVIII

| Example No. | 170 | 171 | 172 | 173 | 174 | 175 | 176 | 177 | 178 |
|---|---|---|---|---|---|---|---|---|---|
| Catalyst Type | Z | Z | Z | Z | Z | Z | Z | Z | Z |
| Catalyst weight, gm | 84.8 | 84.8 | 84.8 | 84.8 | 84.8 | 84.8 | 84.8 | 84.8 | 84.8 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.0 | 270.0 |
| Time on organics, hrs. | 5.7 | 24.0 | 29.0 | 46.7 | 50.7 | 70.0 | 73.2 | 94.5 | 96.2 |
| Duration of run, hrs. | 1 | 2 | 2 | 2 | 2 | 2 | 1 | 1.5 | 1.5 |
| AEEA SV, gmol/hr/kgcat | — | — | — | — | — | — | — | — | — |
| NH$_3$ feedrate, gm/hr | 23.3 | 50.0 | 45.6 | 37.3 | 41.3 | 34.5 | 19.1 | 23.4 | 23.3 |
| Liquid feed composition, wt. % | | | | | | | | | |

TABLE XVIII-continued

| Example No. | 170 | 171 | 172 | 173 | 174 | 175 | 176 | 177 | 178 |
|---|---|---|---|---|---|---|---|---|---|
| Catalyst Type | Z | Z | Z | Z | Z | Z | Z | Z | Z |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 0.46 | 0.56 | 1.34 | 0.26 | 0.50 | 0.25 | 1.36 | 0.64 | 0.65 |
| MeEDA | 0 | 0 | 0 | 0 | 0 | 0 | 0 | 0 | 0 |
| MEA | 0 | 0.09 | 0.11 | 0 | 0 | 0 | 0.09 | 0 | 0 |
| EtEDA | 0 | 0 | 0 | 0 | 0 | 0 | 0 | 0 | 0 |
| PIP | 4.46 | 4.64 | 6.90 | 3.48 | 4.69 | 3.53 | 8.83 | 4.93 | 4.96 |
| DETA | 38.35 | 39.67 | 40.51 | 42.49 | 41.05 | 41.84 | 39.34 | 40.20 | 40.66 |
| AEEA | 21.70 | 22.16 | 12.36 | 33.12 | 23.84 | 32.81 | 12.26 | 22.74 | 23.22 |
| AEP | 0.54 | 0.54 | 1.08 | 0.35 | 0.51 | 0.36 | 1.06 | 0.54 | 0.53 |
| HEP | 0 | 0 | 0 | 0 | 0 | 0 | 0 | 0 | 0 |
| TETA's | 4.66 | 4.54 | 5.86 | 1.96 | 4.12 | 1.95 | 6.78 | 4.09 | 3.94 |
| TEPA's | 22.98 | 21.35 | 22.56 | 13.30 | 18.84 | 13.34 | 21.88 | 19.39 | 18.23 |
| AEEA Conversion % | 55.33 | 54.49 | 74.09 | 32.14 | 50.92 | 32.17 | 74.60 | 52.73 | 51.51 |
| Acyclic (N4)/cyclic ($\leq$ N4), weight ratio | 0.2 | 0.2 | 0 | 0.2 | 0.2 | 0.1 | 0.2 | 0.2 | 0.2 |
| Acyclic (N5)/cyclic ($\leq$ N5), weight ratio | 33.9 | 27.1 | 19.1 | 18.8 | 36.7 | 14.2 | 18.5 | 32.2 | 36.5 |
| $\Sigma(N5)/\Sigma(N4)$, weight ratio | 4.9 | 4.7 | 3.9 | 4.5 | 4.6 | 6.8 | 3.2 | 4.7 | 4.6 |

TABLE XIX

| Example No. | 179 | 180 | 181 | 182 | 183 | 184 | 185 | 186 |
|---|---|---|---|---|---|---|---|---|
| Catalyst Type | AA | AA | AA | AA | AA | AA | AA | AA |
| Catalyst weight, gm | 127.9 | 127.9 | 127.9 | 127.9 | 127.9 | 127.9 | 127.9 | 127.9 |
| Pressure, psig | 600 | 600 | 600 | 600 | 600 | 600 | 600 | 600 |
| Temperature, °C. | 252.8 | 252.5 | 252.8 | 273.3 | 271.5 | 274.3 | 273.8 | 273.3 |
| Time on organics, hrs. | 3.5 | 18.0 | 20.0 | 42.0 | 44.5 | 51.5 | 66.4 | 68.5 |
| Duration of run, hrs. | 2 | 14.5 | 2 | 16.5 | 2.5 | 2 | 14.8 | 2.1 |
| MEA SV, gmol/hr/kgcat | 1.82 | 1.81 | 1.82 | 1.75 | 1.79 | 1.39 | 1.52 | 1.63 |
| NH$_3$ feedrate, gm/hr | 49.0 | 59.9 | 59.9 | 50.7 | 48.4 | 55.0 | 48.0 | 67.5 |
| Liquid feed composition, wt. % | | | | | | | | |
| DETA | 77.16 | 77.16 | 77.16 | 77.16 | 77.16 | 66.46 | 66.46 | 66.46 |
| MEA | 22.84 | 22.84 | 22.84 | 22.84 | 22.84 | — | — | — |
| AEEA | — | — | — | — | — | 33.54 | 33.54 | 33.54 |
| Liquid product composition, wt. % | | | | | | | | |
| EDA | 0.44 | 0 | 0 | 0.57 | 0.56 | 0.53 | 0.55 | 0.64 |
| MeEDA | 0 | 0 | 0 | 0 | 0 | 0 | 0 | 0 |
| MEA | 19.06 | 20.36 | 20.38 | 16.79 | 17.14 | 1.82 | 0 | 0 |
| EtEDA | 0 | 0 | 0 | 0 | 0 | 0 | 0 | 0 |
| PIP | 0.35 | 0.17 | 0.13 | 0.55 | 0.56 | 5.29 | 5.83 | 6.16 |
| DETA | 73.70 | 76.19 | 77.06 | 74.38 | 74.02 | 70.73 | 66.69 | 69.84 |
| AEEA | 0 | 0 | 0 | 0 | 0 | 5.43 | 8.01 | 8.11 |
| AEP | 0.35 | 0.27 | 0.25 | 0.62 | 0.63 | 0.79 | 0.58 | 0.60 |
| HEP | 0 | 0 | 0 | 0 | 0 | 0 | 0 | 0 |
| TETA's | 3.10 | 3.40 | 1.18 | 3.97 | 3.94 | 3.94 | 4.98 | 4.71 |
| TEPA's | 0.75 | 0 | 0 | 0.92 | 0.97 | 6.54 | 8.17 | 8.30 |
| ROH Conversion % | 15.38 | 11.83 | 10.33 | 25.88 | 24.31 | 83.30 | 75.45 | 76.02 |
| Acyclic (N4)/cyclic ($\leq$ N4), weight ratio | AL | AL | AL | 23.21 | 23.20 | 0.32 | 0.11 | 0.12 |
| Acyclic (N5)/cyclic ($\leq$ N5), weight ratio | AL | — | — | AL | AL | 12.43 | 18.50 | 41.50 |
| $\Sigma(N5)/\Sigma(N4)$, weight ratio | 0.24 | 0 | 0 | 0.23 | 0.24 | — | — | — |

AL = All linear

TABLE XX

| Example No. | 187 | 188 | 189 | 190 | 191 | 192 | 193 | 194 |
|---|---|---|---|---|---|---|---|---|
| Catalyst Type | BB | BB | BB | BB | BB | BB | BB | AA |
| Catalyst weight, gm | 125.7 | 125.7 | 125.7 | 125.7 | 125.7 | 125.7 | 125.7 | 125.7 |
| Pressure, psig | 600 | 600 | 600 | 600 | 600 | 600 | 600 | 600 |
| Temperature, °C. | 260.8 | 260.0 | 280.5 | 280.5 | 281.5 | 281.3 | 279.8 | 260.5 |
| Time on organics, hrs. | 16.7 | 18.7 | 24.1 | 41.1 | 48.1 | 64.8 | 66.8 | 88.7 |
| Duration of run, hrs. | 15.7 | 2 | 2 | 16.7 | 2 | 15.8 | 2 | 15.7 |
| MEA SV, gmol/hr/kgcat | 1.77 | 2.02 | 1.77 | 1.76 | 1.77 | 1.63 | 1.62 | 1.60 |
| NH$_3$ feedrate, gm/hr | 58.2 | 55.5 | 49.0 | 52.7 | 49.0 | 52.5 | 54.5 | 60.0 |
| Liquid feed composition, wt. % | | | | | | | | |
| DETA | 77.16 | 77.16 | 77.16 | 77.16 | 77.16 | 66.46 | 66.46 | 77.16 |
| MEA | 22.84 | 22.84 | 22.84 | 22.84 | 22.84 | — | — | 22.84 |
| AEEA | — | — | — | — | — | 33.54 | 33.54 | — |
| Liquid product composition, wt. % | | | | | | | | |
| EDA | 0 | 0 | 1.64 | 1.13 | 1.40 | 2.21 | 2.12 | 0 |
| MeEDA | 0 | 0 | 0 | 0 | 0 | 0 | 0 | 0 |

TABLE XX-continued

| Example No. | 187 | 188 | 189 | 190 | 191 | 192 | 193 | 194 |
|---|---|---|---|---|---|---|---|---|
| Catalyst Type | BB | BB | BB | BB | BB | BB | BB | AA |
| MEA | 24.27 | 24.79 | 18.55 | 15.91 | 20.12 | 0 | 0 | 29.98 |
| EtEDA | 0 | 0 | 0 | 0 | 0 | 0 | 0 | 0 |
| PIP | 0.48 | 0.31 | 1.35 | 1.37 | 1.20 | 7.44 | 6.49 | 0.49 |
| DETA | 71.40 | 72.05 | 67.88 | 71.46 | 67.32 | 70.71 | 71.20 | 66.77 |
| AEEA | 0 | 0 | 0 | 0 | 0 | 0 | 0 | 0 |
| AEP | 0.34 | 0.32 | 1.14 | 1.08 | 0.98 | 1.10 | 1.08 | 0.25 |
| HEP | 0 | 0 | 0 | 0 | 0 | 0 | 0 | 0 |
| TETA's | 2.39 | 2.45 | 5.92 | 5.54 | 5.28 | 6.49 | 5.66 | 0.44 |
| TEPA's | 0.93 | 0 | 2.51 | 2.18 | 2.79 | 11.91 | 12.44 | 0.99 |
| ROH Conversion % | 6.29 | 8.67 | 19.20 | 30.97 | 12.19 | 100.00 | 100.00 | 0 |
| Acyclic (N4)/cyclic (< = N4), weight ratio | AL | AL | 8.42 | 8.58 | 8.53 | 0.23 | 0.25 | 3.97 |
| Acyclic (N5)/cyclic (< = N5), weight ratio | AL | — | 4.53 | AL | 6.19 | 10.77 | 11.11 | AL |
| Σ(N5)/Σ(N4), weight ratio | 0.39 | 0 | 0.42 | 0.39 | 0.53 | — | — | 2.25 |

AL = All linear

TABLE XXI

| Example No. | 195 | 196 | 197 | 198 | 199 |
|---|---|---|---|---|---|
| Catalyst Type | CC | CC | CC | CC | CC |
| Catalyst weight, gm | 132.3 | 132.3 | 132.3 | 132.3 | 132.3 |
| Pressure, psig | 600 | 600 | 600 | 600 | 600 |
| Temperature, °C. | 255.5 | 253.5 | 253.3 | 277.3 | 276.3 |
| Time on organics, hrs. | 5.5 | 22.2 | 24.2 | 29.7 | 46.5 |
| Duration of run, hrs. | 2 | 15.4 | 2 | 1.2 | 16 |
| MEA SV, gmol/hr/kgcat | 1.76 | 1.79 | 1.80 | 3.05 | 1.80 |
| NH3 feedrate, gm/hr | 56 | 53 | 58 | 80 | 57.9 |
| Liquid feed composition, wt. % | | | | | |
| DETA | 77.16 | 77.16 | 77.16 | 77.16 | 77.16 |
| MEA | 22.84 | 22.84 | 22.84 | 22.84 | 22.84 |
| Liquid product composition, wt. % | | | | | |
| EDA | 0.72 | 0.57 | 0.61 | 4.72 | 5.56 |
| MeEDA | 0 | 0 | 0 | 0 | 0 |
| MEA | 19.39 | 18.82 | 18.97 | 10.58 | 10.88 |
| EtEDA | 0 | 0 | 0 | 0 | 0 |
| PIP | 0.58 | 0.75 | 0.78 | 4.57 | 5.28 |
| DETA | 74.48 | 72.48 | 73.22 | 60.61 | 57.25 |
| AEEA | 1.14 | 0.55 | 0 | 0 | 0 |
| AEP | 0.59 | 0.73 | 0.75 | 4.56 | 5.02 |
| HEP | 0 | 0 | 0 | 0 | 0 |
| TETA's | 3.51 | 4.43 | 4.30 | 8.20 | 8.44 |
| TEPA's | 0.74 | 1.50 | 1.20 | 4.98 | 5.47 |
| ROH Conversion % | 16.90 | 18.49 | 17.80 | 54.71 | 53.33 |
| Acyclic (N4)/cyclic (< = N4), weight ratio | AL | 14.38 | 14.15 | 1.84 | 1.69 |
| Acyclic (N5)/cyclic (< = N5), weight ratio | AL | AL | AL | 1.17 | 1.13 |
| Σ(N5)/Σ(N4), weight ratio | — | — | — | — | |

AL = All linear
AC = All cyclic

TABLE XXII

| Example No. | 200 | 201 | 202 | 203 | 204 | 205 | 206 | 207 | 208 | 209 | 210 | 211 |
|---|---|---|---|---|---|---|---|---|---|---|---|---|
| Catalyst Type | DD | DD | DD | DD | DD | DD | DD | DD | DD | DD | DD | DD |
| Catalyst weight, gm | 119.0 | 119.0 | 119.0 | 119.0 | 119.0 | 119.0 | 119.0 | 119.0 | 119.0 | 119.0 | 119.0 | 119.0 |
| Pressure, psig | 600 | 600 | 600 | 600 | 600 | 600 | 600 | 600 | 600 | 600 | 600 | 600 |
| Temperature, °C. | 256.8 | 262.3 | 258.5 | 277.3 | 280.8 | 280.8 | 280.8 | 255.8 | 274.8 | 280.3 | 280.0 | 259.0 |
| Time on organics, hrs. | 4.5 | 20.5 | 22.5 | 27.5 | 35.5 | 57.0 | 59.0 | 80.5 | 87.5 | 104.5 | 106.5 | 111.5 |
| Duration of run, hrs. | 2 | 16 | 2 | 2 | 1.5 | 21 | 2 | 20.7 | 2 | 16 | 2 | 2 |
| MEA SV, gmol/hr/kgcat | 1.77 | 1.92 | 1.93 | 1.93 | 1.92 | 1.67 | 1.60 | 1.71 | 1.64 | 1.66 | 1.72 | 1.90 |
| NH3 feedrate, gm/hr | 70.0 | 65.8 | 53.0 | 61.5 | 50.6 | 55.5 | 51.0 | 55.1 | 57 | 56.1 | 58 | 74.5 |
| Liquid feed composition, wt. % | | | | | | | | | | | | |
| DETA | 77.16 | 77.16 | 77.16 | 77.16 | 77.16 | 66.46 | 66.46 | 66.46 | 66.46 | 66.46 | 66.46 | 66.46 |
| MEA | 22.84 | 22.84 | 22.84 | 22.84 | 22.84 | — | — | — | — | — | — | — |
| AEEA | — | — | — | — | — | 33.54 | 33.54 | 33.54 | 33.54 | 33.54 | 33.54 | 33.54 |
| Liquid product composition, wt. % | | | | | | | | | | | | |
| EDA | 0.44 | 0.46 | 0.48 | 2.39 | 5.14 | 4.62 | 4.73 | 0.69 | 3.82 | 4.27 | 4.42 | 0.75 |
| MeEDA | 0 | 0 | 0 | 0 | 0 | 0 | 0 | 0 | 0 | 0 | 0 | 0 |
| MEA | 17.17 | 16.69 | 16.56 | 11.29 | 8.13 | 0.93 | 0 | 0.35 | 0 | 0 | 0 | 18.51 |
| EtEDA | 0 | 0 | 0 | 0 | 0 | 0 | 0 | 0 | 0 | 0 | 0 | 0 |
| PIP | 0.62 | 0.74 | 0.75 | 2.63 | 4.42 | 9.83 | 10.45 | 5.60 | 9.71 | 10.22 | 10.06 | 1.17 |

TABLE XXII-continued

| Example No. | 200 | 201 | 202 | 203 | 204 | 205 | 206 | 207 | 208 | 209 | 210 | 211 |
|---|---|---|---|---|---|---|---|---|---|---|---|---|
| Catalyst Type | DD | DD | DD | DD | DD | DD | DD | DD | DD | DD | DD | DD |
| DETA | 71.04 | 70.74 | 70.92 | 64.82 | 58.99 | 58.30 | 57.95 | 64.75 | 60.92 | 58.93 | 58.24 | 68.48 |
| AEEA | 0.48 | 0.48 | 0.48 | 0.48 | 0.48 | 0.48 | 0.48 | 9.57 | 0 | 0 | 0 | 0.52 |
| AEP | 0.60 | 0.70 | 0.71 | 2.82 | 4.88 | 3.71 | 3.66 | 0.61 | 3.10 | 3.40 | 3.52 | 0.94 |
| HEP | 0 | 0 | 0 | 0 | 0 | 0 | 0 | 0 | 0 | 0 | 0 | 0 |
| TETA's | 5.44 | 5.34 | 6.10 | 9.66 | 10.38 | 9.60 | 9.73 | 4.33 | 9.27 | 10.07 | 10.19 | 6.01 |
| TEPA's | 1.89 | 2.14 | 2.19 | 4.62 | 5.30 | 8.66 | 9.12 | 11.34 | 8.91 | 8.88 | 9.52 | 3.26 |
| ROH Conversion % | 24.22 | 26.14 | 27.45 | 51.68 | 65.20 | 100.00 | 98.57 | 71.43 | 100.0 | 100.0 | 100.0 | 20.00 |
| Acyclic (N4)/cyclic (< = N4), weight ratio | AL | 20.27 | 18.61 | 2.93 | 2.23 | 0.39 | 0.33 | 0.13 | 0.30 | 0.33 | 0.38 | 9.99 |
| Acyclic (N5)/cyclic (< = N5), weight ratio | AL | AL | AL | 2.51 | 1.23 | 1.67 | 1.62 | 27.57 | 1.85 | 1.65 | 1.72 | 4.18 |
| Σ(N5)/Σ(N4), weight ratio | — | — | — | — | — | — | — | — | — | — | — | — |

AL = All linear

TABLE XXIII

| Example No. | 212 | 213 | 214 | 215 | 216 | 217 | 218 | 219 | 220 | 221 |
|---|---|---|---|---|---|---|---|---|---|---|
| Catalyst Type | EE | EE | EE | EE | EE | EE | EE | EE | EE | EE |
| Catalyst weight, gm | 117.0 | 117.0 | 117.0 | 117.0 | 117.0 | 117.0 | 117.0 | 117.0 | 117.0 | 117.0 |
| Pressure, psig | 600 | 600 | 600 | 600 | 600 | 600 | 600 | 600 | 600 | 600 |
| Temperature, °C. | 263.3 | 264.5 | 264.5 | 282.3 | 283.0 | 283.8 | 283.3 | 277.5 | 282.8 | 262.8 |
| Time on organics, hrs. | 15 | 17 | 17 | 23 | 39 | 41 | 45 | 63.5 | 65.5 | 70.5 |
| Duration of run, hrs. | 14 | 2 | 2 | 2 | 15 | 2 | 2 | 17.5 | 2 | 2 |
| MEA SV, gmol/hr/kgcat | 1.80 | 1.87 | 1.68 | 1.74 | 1.82 | 1.76 | 1.60 | 1.57 | 1.58 | 1.66 |
| NH3 feedrate, gm/hr | 69.3 | 61.0 | 61.0 | 107.5 | 66.8 | 61.5 | 62.0 | 53.2 | 60.5 | 70 |
| Liquid feed composition, wt. % | | | | | | | | | | |
| DETA | 77.16 | 77.16 | 77.16 | 77.16 | 77.16 | 77.16 | 66.46 | 66.46 | 66.46 | 66.46 |
| MEA | 22.84 | 22.84 | 22.84 | 22.84 | 22.84 | 22.84 | — | — | — | — |
| AEEA | — | — | — | — | — | — | 33.54 | 33.54 | 33.54 | 33.54 |
| Liquid product composition, wt. % | | | | | | | | | | |
| EDA | 0.34 | 0.33 | 0.31 | 1.45 | 1.71 | 1.75 | 2.27 | 2.48 | 2.68 | 0.50 |
| MeEDA | 0 | 0 | 0 | 0 | 0 | 0 | 0 | 0 | 0 | 0 |
| MEA | 19.00 | 19.14 | 18.85 | 13.73 | 13.66 | 13.73 | 1.37 | 0.78 | 0.82 | 0.68 |
| EtEDA | 0 | 0 | 0 | 0 | 0 | 0 | 0 | 0 | 0 | 0 |
| PIP | 0.45 | 0.45 | 0.44 | 1.77 | 2.06 | 2.14 | 6.70 | 6.85 | 7.15 | 3.66 |
| DETA | 74.32 | 74.61 | 74.55 | 69.65 | 68.47 | 68.83 | 64.69 | 61.15 | 60.88 | 66.11 |
| AEEA | 0.76 | 0.67 | 0.71 | 0.35 | 0.33 | 0.29 | 2.61 | 2.71 | 2.64 | 15.68 |
| AEP | 0.51 | 0.49 | 0.51 | 2.02 | 2.23 | 2.30 | 2.23 | 2.42 | 2.52 | 0.46 |
| HEP | 0 | 0 | 0 | 0 | 0 | 0 | 0.09 | 0.10 | 0.11 | 0.10 |
| TETA's | 3.45 | 3.22 | 3.39 | 6.74 | 6.78 | 6.65 | 7.65 | 8.09 | 8.08 | 5.03 |
| TEPA's | 1.05 | 0.96 | 1.09 | 3.63 | 3.95 | 3.89 | 9.99 | 10.75 | 10.78 | 7.59 |
| ROH Conversion % | 17.59 | 16.93 | 18.24 | 41.12 | 41.39 | 41.33 | 92.30 | 91.79 | 92.00 | 53.98 |
| Acryclic (N4)/cyclic (< = N4), weight ratio | 30.61 | 34.71 | 19.41 | 20.90 | 3.06 | 3.12 | 0.32 | 0.29 | 0.31 | 0.60 |
| Acryclic (N5)/cyclic (< = N5), weight ratio | AL | AL | AL | 1.83 | 1.60 | 1.53 | 1.98 | 1.79 | 1.77 | 19.83 |
| Σ(N5)/Σ(N4), weight ratio | 0.30 | 0.30 | 0.32 | 0.54 | 0.58 | 0.50 | — | — | — | — |

Al = All linear

TABLE XXIV

| Example No. | 222 | 223 | 224 | 225 | 226 | 227 | 228 | 229 | 230 | 231 |
|---|---|---|---|---|---|---|---|---|---|---|
| Catalyst Type | FF | FF | FF | FF | FF | FF | FF | FF | FF | FF |
| Catalyst weight, gm | 119.4 | 119.4 | 119.4 | 119.4 | 119.4 | 119.4 | 119.4 | 119.4 | 119.4 | 119.4 |
| Pressure, psig | 600 | 600 | 600 | 600 | 600 | 600 | 600 | 600 | 600 | 600 |
| Temperature, °C. | 232.8 | 230.0 | 231.8 | 248.5 | 244.0 | 247.3 | 248.8 | 250.5 | 249.5 | 230.3 |
| Time on organics, hrs. | 4.0 | 19.7 | 22.2 | 27.1 | 43.7 | 45.7 | 51.0 | 68.0 | 70 | 93 |
| Duration of run, hrs. | 2 | 15.7 | 2.6 | 2.2 | 15.7 | 2 | 2 | 16 | 2 | 21 |
| MEA SV, gmol/hr/kgcat | 1.95 | 1.85 | 1.96 | 1.68 | 1.71 | 1.79 | 1.54 | 1.49 | 1.64 | 1.63 |
| NH3 feedrate, gm/hr | 59.0 | 52.1 | 74.8 | 63.8 | 54.2 | 65.5 | 54.0 | 55.6 | 59 | 73 |
| Liquid feed composition, wt. % | | | | | | | | | | |
| DETA | 77.16 | 77.16 | 77.16 | 77.16 | 77.16 | 77.16 | 66.46 | 66.46 | 66.46 | 66.46 |
| MEA | 22.84 | 22.84 | 22.84 | 22.84 | 22.84 | 22.84 | — | — | — | — |
| AEEA | — | — | — | — | — | — | 33.54 | 33.54 | 33.54 | 33.54 |
| Liquid product composition, wt. % | | | | | | | | | | |
| EDA | 1.32 | 1.44 | 1.38 | 4.97 | 4.71 | 4.33 | 3.75 | 4.12 | 4.10 | 0.88 |
| MeEDA | 0 | 0 | 0 | 0 | 0 | 0 | 0 | 0 | 0 | 0 |
| MEA | 22.49 | 22.38 | 23.57 | 16.24 | 15.26 | 16.13 | 0.96 | 0.79 | 0.89 | 0.46 |
| EtEDA | 0 | 0 | 0 | 0 | 0 | 0 | 0 | 0 | 0 | 0 |
| PIP | 0.15 | 0.16 | 0.15 | 0.66 | 0.70 | 0.68 | 4.48 | 4.55 | 4.47 | 1.85 |

TABLE XXIV-continued

| Example No. | 222 | 223 | 224 | 225 | 226 | 227 | 228 | 229 | 230 | 231 |
|---|---|---|---|---|---|---|---|---|---|---|
| Catalyst Type | FF | FF | FF | FF | FF | FF | FF | FF | FF | FF |
| DETA | 71.90 | 71.93 | 72.75 | 66.24 | 65.86 | 67.79 | 65.70 | 65.25 | 63.53 | 66.74 |
| AEEA | 0 | 0 | 0 | 0 | 0 | 0 | 7.29 | 6.78 | 7.30 | 23.94 |
| AEP | 0.30 | 0.29 | 0.28 | 0.71 | 0.71 | 0.73 | 0.85 | 1.01 | 0.83 | 0.27 |
| HEP | 0 | 0 | 0 | 0 | 0 | 0 | 0 | 0 | 0 | 0 |
| TETA's | 1.74 | 1.84 | 1.76 | 4.20 | 4.28 | 4.17 | 4.03 | 4.23 | 4.21 | 1.31 |
| TEPA's | 0 | 0 | 0 | 1.02 | 1.00 | 1.02 | 5.49 | 5.53 | 6.01 | 3.03 |
| ROH Conversion % | 0.60 | 0.05 | 3.44 | 24.99 | 28.48 | 26.24 | 76.87 | 78.43 | 76.53 | 28.00 |
| Acyclic (N4)/cyclic ($\leq$ N4), weight ratio | AL | AL | AL | 9.42 | 10.16 | 9.87 | 0.41 | 0.41 | 0.40 | 0.49 |
| Acyclic (N5)/cyclic ($\leq$ N5), weight ratio | — | — | — | 3.61 | 3.28 | 3.95 | 11.99 | 12.16 | 7.62 | AL |
| $\Sigma$(N5)/$\Sigma$(N4), weight ratio | 0 | 0 | 0 | 0.24 | 0.23 | 0.24 | — | — | — | — |

AL = All linear

TABLE XXV

| Example No. | 232 | 233 | 234 | 235 | 236 | 237 | 238 | 239 | 240 |
|---|---|---|---|---|---|---|---|---|---|
| Catalyst Type | GG | GG | GG | GG | GG | GG | GG | GG | GG |
| Catalyst weight, gm | 71.7 | 71.7 | 71.7 | 71.7 | 71.7 | 71.7 | 71.7 | 71.7 | 71.7 |
| Pressure, psig | 600 | 600 | 600 | 600 | 600 | 600 | 600 | 600 | 600 |
| Temperature, °C. | 270 | 270 | 280 | 260 | 270 | 260 | 280 | 270 | 269.4 |
| Time on organics, hrs. | 5.5 | 24.0 | 29.5 | 48.5 | 53.5 | 72.0 | 77.5 | 93.0 | 94.0 |
| Duration of run, hrs. | 2 | 2 | 2 | 2 | 2 | 2 | 2 | 1 | 1 |
| MEA SV, gmol/hr/kgcat | 4.14 | 4.46 | 4.36 | 5.52 | 4.51 | 4.41 | 4.26 | 4.15 | 4.18 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.411 | 2.048 | 2.803 | 0.721 | 0.985 | 0.509 | 2.082 | 1.210 | 1.044 |
| MEA | 16.945 | 15.112 | 10.441 | 24.560 | 21.874 | 32.907 | 18.277 | 27.514 | 28.346 |
| PIP | 1.144 | 1.466 | 1.969 | 0.566 | 0.916 | 0.444 | 1.962 | 1.108 | 1.004 |
| DETA | 51.236 | 51.808 | 51.005 | 56.963 | 56.336 | 50.564 | 48.639 | 48.512 | 49.317 |
| AEEA | 1.633 | 0.750 | 0.471 | 2.854 | 1.334 | 3.313 | 0.761 | 3.022 | 2.993 |
| AEP | 1.408 | 1.792 | 2.383 | 0.570 | 0.907 | 0.527 | 2.313 | 1.179 | 1.053 |
| HEP | 0.000 | 0.000 | 0.000 | 0.000 | 0.000 | 0.000 | 0.000 | 0.000 | 0.000 |
| TAEA | 0.906 | 1.541 | 1.048 | 0.803 | 0.704 | 0.531 | 0.684 | 0.714 | 0.712 |
| 1-TETA | 10.823 | 10.188 | 9.970 | 6.179 | 6.720 | 4.624 | 7.721 | 6.104 | 5.767 |
| DAEP | 0.338 | 0.535 | 0.797 | 0.105 | 0.195 | 0.111 | 0.723 | 0.309 | 0.262 |
| PEEDA | 0.223 | 0.461 | 0.644 | 0.087 | 0.173 | 0.000 | 0.675 | 0.341 | 0.227 |
| DPE | 0.000 | 0.000 | 0.111 | 0.000 | 0.000 | 0.000 | 0.110 | 0.067 | 0.000 |
| AE-TAEA | 1.379 | 1.180 | 1.543 | 0.441 | 0.741 | 0.374 | 1.397 | 0.543 | 0.462 |
| 1-TEPA | 4.588 | 3.926 | 4.570 | 1.388 | 1.867 | 0.952 | 3.120 | 2.724 | 1.606 |
| AE-DAEP | 0.244 | 0.289 | 0.620 | 0.000 | 0.100 | 0.000 | 0.570 | 0.111 | 0.092 |
| AE-PEEDA | 0.105 | 0.109 | 0.209 | 0.000 | 0.00 | 0.00 | 0.260 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.173 | 0.272 | 0.386 | 0.000 | 0.073 | 0.000 | 0.000 | 0.121 | 0.081 |
| Others | 0.204 | 1.075 | 1.532 | 0.612 | 0.554 | 0.444 | 1.746 | 1.371 | 1.233 |
| MEA Conversion, % | 53.39 | 58.54 | 71.07 | 33.10 | 39.32 | 8.35 | 48.80 | 23.43 | 21.10 |
| DETA Conversion, % | 16.24 | 15.52 | 16.01 | 7.78 | 7.12 | 16.31 | 19.02 | 19.77 | 18.42 |
| Acyclic (N4), % | 95.43 | 92.18 | 87.66 | 97.32 | 95.28 | 97.90 | 84.79 | 90.50 | 92.98 |
| Acrylic (N5), % | 91.95 | 88.40 | 83.42 | 100.00 | 93.78 | 100.00 | 84.48 | 90.71 | 92.29 |
| $\Sigma$(N5)/$\Sigma$(N4), weight ratio | 0.53 | 0.45 | 0.58 | 0.25 | 0.36 | 0.25 | 0.54 | 0.33 | 0.32 |
| Acrylic (N4)/cyclic ($\leq$ N4), weight ratio | 3.77 | 2.76 | 1.87 | 5.26 | 3.39 | 4.77 | 1.45 | 2.27 | 2.54 |

TABLE XXVI

| Example No. | 241 | 242 | 243 | 244 | 245 | 246 | 247 | 248 | 249 |
|---|---|---|---|---|---|---|---|---|---|
| Catalyst Type | HH | HH | HH | HH | HH | HH | HH | HH | HH |
| Catalyst weight, gm | 73 | 73 | 73 | 73 | 73 | 73 | 73 | 73 | 73 |
| Pressure, psig | 600 | 600 | 600 | 600 | 600 | 600 | 600 | 600 | 600 |
| Temperature, °C. | 267.3 | 271.6 | 280.4 | 260.3 | 269.1 | 261.9 | 278.4 | 268.9 | 268.5 |
| Time on organics, hrs. | 6.5 | 25.5 | 30.5 | 49.5 | 54.5 | 73.5 | 78.5 | 97.0 | 99.2 |
| Duration of run, hrs. | 2 | 2 | 2 | 2 | 2 | 2 | 2 | 2 | 2 |
| MEA SV, gmol/hr/kgcat | 3.79 | 3.55 | 3.59 | 3.31 | 3.30 | 3.15 | 3.16 | 2.93 | 3.01 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.819 | 1.510 | 2.684 | 0.504 | 0.224 | 0.583 | 2.338 | 1.353 | 1.183 |
| MEA | 19.544 | 21.769 | 15.677 | 27.977 | 25.881 | 29.371 | 18.842 | 24.539 | 25.072 |
| PIP | 2.131 | 1.958 | 2.907 | 0.791 | 1.591 | 0.810 | 2.955 | 1.830 | 1.645 |
| DETA | 50.736 | 54.179 | 44.864 | 59.947 | 57.394 | 60.159 | 52.360 | 57.664 | 58.300 |
| AEEA | 1.308 | 1.561 | 0.890 | 1.790 | 1.759 | 1.755 | 1.156 | 1.824 | 1.888 |
| AEP | 2.087 | 1.610 | 2.837 | 0.614 | 0.959 | 0.559 | 2.442 | 1.151 | 1.012 |

TABLE XXVI-continued

| Example No. | 241 | 242 | 243 | 244 | 245 | 246 | 247 | 248 | 249 |
|---|---|---|---|---|---|---|---|---|---|
| Catalyst Type | HH | HH | HH | HH | HH | HH | HH | HH | HH |
| HEP | 0.000 | 0.000 | 0.000 | 0.000 | 0.000 | 0.000 | 0.000 | 0.000 | 0.000 |
| TAEA | 0.474 | 0.468 | 0.382 | 0.280 | 0.349 | 0.222 | 0.415 | 0.272 | 0.294 |
| 1-TETA | 7.326 | 7.199 | 7.828 | 4.424 | 5.292 | 3.705 | 7.135 | 5.363 | 5.018 |
| DAEP | 0.724 | 0.483 | 1.000 | 0.210 | 0.231 | 0.161 | 0.542 | 0.359 | 9.292 |
| PEEDA | 0.625 | 0.332 | 1.108 | 0.086 | 0.180 | 0.101 | 0.599 | 0.000 | 0.173 |
| DPE | 0.419 | 0.000 | 0.165 | 0.000 | 0.000 | 0.000 | 0.000 | 0.161 | 0.000 |
| AE-TAEA | 0.941 | 0.687 | 1.356 | 0.000 | 0.305 | 0.000 | 0.786 | 1.117 | 0.287 |
| 1-TEPA | 3.854 | 2.896 | 4.945 | 0.160 | 0.979 | 0.000 | 3.242 | 0.000 | 0.839 |
| AE-DAEP | 0.454 | 0.209 | 0.781 | 0.000 | 0.000 | 0.000 | 0.386 | 0.000 | 0.000 |
| AE-PEEDA | 0.243 | 0.101 | 1.082 | 0.000 | 0.000 | 0.000 | 0.209 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.138 | 0.000 | 0.372 | 0.000 | 0.000 | 0.000 | 0.000 | 0.000 | 0.000 |
| BPEA | 0.000 | 0.000 | 0.648 | 0.000 | 0.000 | 0.000 | 0.000 | 0.656 | 0.000 |
| Others | 1.377 | 0.788 | 3.906 | 0.418 | 0.685 | 0.294 | 1.783 | 0.000 | 0.667 |
| MEA Conversion, % | 47.04 | 41.40 | 57.92 | 24.31 | 30.19 | 20.72 | 49.47 | 33.74 | 32.35 |
| DETA Conversion, % | 18.29 | 13.32 | 28.42 | 3.61 | 7.99 | 3.49 | 16.55 | 7.46 | 6.51 |
| Acyclic (N4), % | 81.52 | 90.39 | 78.32 | 94.08 | 93.21 | 93.74 | 86.87 | 91.55 | 91.94 |
| Acrylic (N5), % | 85.16 | 92.04 | 68.62 | 100.00 | 100.00 | 0.00 | 87.13 | 62.99 | 100.00 |
| Σ(N5)/Σ(N4), weight ratio | 0.59 | 0.46 | 0.88 | 0.03 | 0.21 | 0.00 | 0.53 | 0.29 | 0.19 |
| Acrylic (N4)/cyclic (< = N4), weight ratio | 1.30 | 1.75 | 1.02 | 2.77 | 1.91 | 2.41 | 1.15 | 1.61 | 1.70 |

TABLE XXVII

| Example No. | 250 | 251 | 252 | 253 | 254 | 255 | 256 | 257 | 258 |
|---|---|---|---|---|---|---|---|---|---|
| Catalyst Type | II | II | II | II | II | II | II | II | II |
| Catalyst weight, gm | 81.2 | 81.2 | 81.2 | 81.2 | 81.2 | 81.2 | 81.2 | 81.2 | 81.2 |
| Pressure, psig | 600 | 600 | 600 | 600 | 600 | 600 | 600 | 600 | 600 |
| Temperature, °C. | 274.4 | 274.4 | 280.9 | 259.8 | 270.6 | 259.9 | 281.6 | 270.4 | 270.4 |
| Time on organics, hrs. | 22.0 | 26.0 | 45.5 | 50.5 | 69.0 | 74.5 | 95.0 | 119.0 | 120.0 |
| Duration of run, hrs. | 2 | 2 | 2 | 2 | 2 | 2 | 2 | 1 | 1 |
| MEA SV, gmol/hr/kgcat | 2.91 | 2.63 | 2.50 | 2.66 | 2.59 | 2.54 | 1.88 | 5.74 | 2.90 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.736 | 1.042 | 2.004 | 0.059 | 0.914 | 0.285 | 2.016 | 0.695 | 0.525 |
| MEA | 21.968 | 25.193 | 18.576 | 29.894 | 25.669 | 27.372 | 16.604 | 25.555 | 23.517 |
| PIP | 0.596 | 0.702 | 1.478 | 0.343 | 0.603 | 0.232 | 1.461 | 0.441 | 0.380 |
| DETA | 56.344 | 55.631 | 51.168 | 57.632 | 56.035 | 63.408 | 49.886 | 55.967 | 57.620 |
| AEEA | 3.232 | 3.031 | 2.286 | 2.679 | 3.151 | 1.296 | 2.181 | 2.896 | 3.070 |
| AEP | 0.919 | 0.802 | 1.485 | 0.437 | 0.730 | 0.367 | 1.549 | 0.662 | 0.582 |
| HEP | 0.000 | 0.000 | 0.000 | 0.000 | 0.000 | 0.000 | 0.000 | 0.000 | 0.000 |
| TAEA | 1.205 | 1.108 | 1.349 | 0.407 | 0.739 | 0.402 | 1.529 | 0.684 | 0.604 |
| 1-TETA | 7.587 | 6.573 | 10.443 | 4.085 | 6.496 | 2.782 | 9.613 | 6.122 | 6.727 |
| DAEP | 0.164 | 0.130 | 0.275 | 0.056 | 0.100 | 0.000 | 0.490 | 0.102 | 0.089 |
| PEEDA | 0.116 | 0.097 | 0.252 | 0.036 | 0.072 | 0.138 | 0.496 | 0.074 | 0.057 |
| DPE | 0.000 | 0.000 | 0.000 | 0.000 | 0.000 | 0.000 | 0.000 | 0.000 | 0.000 |
| AE-TAEA | 0.283 | 0.253 | 0.369 | 0.000 | 0.132 | 0.000 | 0.958 | 0.123 | 0.173 |
| 1-TEPA | 0.935 | 0.989 | 2.771 | 0.078 | 0.737 | 0.000 | 3.253 | 0.664 | 0.581 |
| AE-DAEP | 0.000 | 0.000 | 0.161 | 0.000 | 0.000 | 0.000 | 0.196 | 0.075 | 0.000 |
| AE-PEEDA | 0.000 | 0.000 | 0.125 | 0.000 | 0.000 | 0.000 | 0.156 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 0.666 | 0.639 | 1.229 | 1.336 | 0.741 | 0.467 | 2.672 | 0.616 | 0.819 |
| MEA Conversion, % | 39.80 | 31.57 | 49.29 | 18.66 | 30.14 | 25.57 | 54.52 | 29.35 | 35.28 |
| DETA Conversion, % | 8.23 | 10.19 | 16.98 | 6.80 | 9.36 | 2.48 | 18.80 | 8.04 | 5.76 |
| Acyclic (N4), % | 96.92 | 97.13 | 95.72 | 98.01 | 97.29 | 93.00 | 91.57 | 96.87 | 97.18 |
| Acrylic (N5), % | 100.00 | 100.00 | 91.66 | 100.00 | 100.00 | 0.00 | 92.28 | 91.26 | 100.00 |
| Σ(N5)/Σ(N4), weight ratio | 0.13 | 0.16 | 0.28 | 0.02 | 0.12 | 0.00 | 0.38 | 0.12 | 0.10 |
| Acrylic (N4)/cyclic (< = N4), weight ratio | 4.90 | 4.44 | 3.38 | 5.16 | 4.71 | 3.80 | 2.76 | 5.14 | 6.24 |

TABLE XXVIII

| Example No. | 259 | 260 | 261 | 262 | 263 | 264 | 265 | 266 | 267 |
|---|---|---|---|---|---|---|---|---|---|
| Catalyst Type | JJ | JJ | JJ | JJ | JJ | JJ | JJ | JJ | JJ |
| Catalyst weight, gm | 70.6 | 70.6 | 70.6 | 70.6 | 70.6 | 70.6 | 70.6 | 70.6 | 70.6 |
| Pressure, psig | 600 | 600 | 600 | 600 | 600 | 600 | 600 | 600 | 600 |
| Temperature, °C. | 267.9 | 267.8 | 277.8 | 259.9 | 270.1 | 259.9 | 280.1 | 269.6 | 269 |
| Time on organics, hrs. | 5.0 | 7.5 | 26.0 | 31.5 | 50.0 | 55.5 | 74.0 | 78.0 | 80.0 |
| Duration of run, hrs. | 1 | 1 | 2 | 2 | 2 | 2 | 2 | 2 | 1.5 |
| MEA SV, gmol/hr/kgcat | 7.43 | 7.71 | 3.55 | 3.61 | 3.27 | 3.62 | 3.67 | 3.54 | 3.54 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |

TABLE XXVIII-continued

| Example No. | 259 | 260 | 261 | 262 | 263 | 264 | 265 | 266 | 267 |
|---|---|---|---|---|---|---|---|---|---|
| Catalyst Type | JJ | JJ | JJ | JJ | JJ | JJ | JJ | JJ | JJ |
| Crude product composition, wt. % | | | | | | | | | |
| EDA | 0.791 | 0.623 | 1.276 | 0.399 | 0.923 | 0.398 | 1.559 | 0.813 | 0.864 |
| MEA | 26.509 | 30.058 | 23.663 | 33.991 | 28.444 | 31.796 | 22.061 | 26.996 | 27.146 |
| PIP | 1.147 | 0.517 | 1.058 | 0.224 | 0.638 | 0.217 | 1.106 | 0.510 | 0.513 |
| DETA | 47.682 | 54.106 | 51.834 | 56.779 | 55.100 | 57.812 | 53.839 | 55.907 | 56.086 |
| AEEA | 0.876 | 3.177 | 3.108 | 1.987 | 3.003 | 2.067 | 1.970 | 2.801 | 2.726 |
| AEP | 1.015 | 0.506 | 1.073 | 0.246 | 0.586 | 0.243 | 0.935 | 0.458 | 0.457 |
| HEP | 0.000 | 0.000 | 0.000 | 0.000 | 0.000 | 0.000 | 0.000 | 0.000 | 0.000 |
| TAEA | 1.944 | 0.557 | 0.833 | 0.309 | 0.576 | 0.340 | 0.831 | 0.577 | 0.572 |
| 1-TETA | 9.028 | 4.870 | 7.412 | 2.839 | 4.781 | 2.784 | 7.153 | 4.597 | 4.540 |
| DAEP | 0.183 | 0.000 | 0.187 | 0.000 | 0.086 | 0.000 | 0.082 | 0.095 | 0.087 |
| PEEDA | 0.136 | 0.000 | 0.165 | 0.000 | 0.000 | 0.000 | 0.169 | 0.000 | 0.069 |
| DPE | 0.000 | 0.000 | 0.000 | 0.000 | 0.000 | 0.000 | 0.000 | 0.000 | 0.000 |
| AE-TAEA | 1.392 | 0.209 | 0.543 | 0.000 | 0.357 | 0.119 | 0.545 | 0.238 | 0.228 |
| 1-TEPA | 2.723 | 0.634 | 2.000 | 0.109 | 0.910 | 0.179 | 1.995 | 0.719 | 0.686 |
| AE-DAEP | 0.000 | 0.000 | 0.000 | 0.000 | 0.000 | 0.000 | 0.000 | 0.000 | 0.000 |
| AE-PEEDA | 0.000 | 0.000 | 0.000 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.194 | 0.000 | 0.000 |
| Others | 0.293 | 0.493 | 0.939 | 0.196 | 0.758 | 0.426 | 1.662 | 0.989 | 1.025 |
| MEA Conversion, % | 26.38 | 17.06 | 34.61 | 6.67 | 22.13 | 12.36 | 39.22 | 25.04 | 24.86 |
| DETA Conversion, % | 21.30 | 11.27 | 14.88 | 7.35 | 10.35 | 5.30 | 11.85 | 7.74 | 7.73 |
| Acyclic (N4), % | 97.18 | 100.00 | 95.91 | 100.00 | 98.42 | 100.00 | 96.96 | 98.19 | 97.03 |
| Acyclic (N5), % | 100.00 | 100.00 | 100.00 | 100.00 | 100.00 | 100.00 | 92.92 | 100.00 | 100.00 |
| $\Sigma(N5)/\Sigma(N4)$, weight ratio | 0.36 | 0.16 | 0.30 | 0.03 | 0.23 | 0.10 | 0.33 | 0.18 | 0.17 |
| Acrylic (N4)/cyclic ($<$ = N4), weight ratio | 4.42 | 5.30 | 3.32 | 6.42 | 4.09 | 6.79 | 3.48 | 4.87 | 4.54 |

TABLE XXIX

| Example No. | 268 | 269 | 270 | 271 | 272 | 273 | 274 | 275 | 276 |
|---|---|---|---|---|---|---|---|---|---|
| Catalyst Type | KK | KK | KK | KK | KK | KK | KK | KK | KK |
| Catalyst weight, gm | 75.7 | 75.7 | 75.7 | 75.7 | 75.7 | 75.7 | 75.7 | 75.7 | 75.7 |
| Pressure, psig | 600 | 600 | 600 | 600 | 600 | 600 | 600 | 600 | 600 |
| Temperature, °C. | 269.6 | 272.7 | 279.9 | 260.3 | 268.3 | 261.4 | 278.9 | 270.6 | 271.7 |
| Time on organics, hrs. | 7.5 | 26.0 | 31.0 | 47.0 | 53.0 | 58.5 | 73.0 | 78.0 | 80.0 |
| Duration of run, hrs. | 2 | 2 | 2 | 2 | 2 | 2.5 | 2 | 2 | 2 |
| MEA SV, gmol/hr/kgcat | 3.78 | 3.60 | 4.14 | 2.88 | 4.21 | 4.57 | 4.11 | 4.29 | 4.20 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.512 | 2.957 | 2.611 | 0.873 | 1.230 | 0.581 | 2.105 | 1.136 | 1.147 |
| MEA | 19.636 | 15.858 | 13.674 | 24.751 | 22.713 | 28.289 | 17.328 | 24.549 | 24.295 |
| PIP | 0.850 | 1.545 | 1.281 | 0.362 | 0.559 | 0.213 | 0.983 | 0.499 | 0.466 |
| DETA | 53.823 | 48.802 | 49.039 | 57.674 | 55.152 | 58.393 | 51.571 | 56.716 | 56.142 |
| AEEA | 1.077 | 0.809 | 1.020 | 2.059 | 1.793 | 1.783 | 1.230 | 1.886 | 1.876 |
| AEP | 0.980 | 2.034 | 1.569 | 0.409 | 0.641 | 0.321 | 1.189 | 0.550 | 0.582 |
| HEP | 0.000 | 0.000 | 0.000 | 0.000 | 0.000 | 0.000 | 0.000 | 0.000 | 0.000 |
| TAEA | 1.511 | 1.463 | 1.689 | 0.877 | 1.037 | 0.668 | 1.665 | 0.917 | 0.952 |
| 1-TETA | 9.931 | 10.166 | 10.473 | 6.953 | 8.198 | 5.375 | 10.489 | 7.020 | 7.339 |
| DAEP | 0.209 | 0.694 | 0.560 | 0.075 | 0.134 | 0.000 | 0.248 | 0.095 | 0.105 |
| PEEDA | 0.118 | 0.559 | 0.497 | 0.000 | 0.091 | 0.000 | 0.182 | 0.000 | 0.067 |
| DPE | 0.000 | 0.157 | 0.076 | 0.000 | 0.000 | 0.000 | 0.068 | 0.000 | 0.000 |
| AE-TAEA | 1.152 | 1.307 | 1.509 | 0.447 | 0.967 | 0.273 | 1.060 | 0.599 | 0.651 |
| 1-TEPA | 2.758 | 3.629 | 3.880 | 0.863 | 1.812 | 0.388 | 3.088 | 0.995 | 1.169 |
| AE-DAEP | 0.000 | 0.343 | 0.336 | 0.000 | 0.000 | 0.000 | 0.222 | 0.000 | 0.000 |
| AE-PEEDA | 0.000 | 0.145 | 0.157 | 0.000 | 0.000 | 0.000 | 0.112 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.334 | 0.000 | 0.000 | 0.000 | 0.000 | 0.000 | 0.000 |
| BPEA | 0.000 | 0.099 | 0.291 | 0.000 | 0.000 | 0.000 | 0.106 | 0.000 | 0.000 |
| Others | 1.043 | 2.132 | 3.402 | 0.377 | 0.694 | 0.316 | 1.555 | 0.738 | 0.659 |
| MEA Conversion, % | 46.54 | 56.52 | 62.58 | 32.37 | 37.89 | 22.83 | 52.40 | 32.99 | 33.57 |
| DETA Conversion, % | 12.92 | 20.49 | 20.25 | 6.35 | 10.36 | 5.33 | 15.81 | 7.99 | 8.76 |
| Acyclic (N4), % | 97.22 | 89.18 | 91.48 | 99.05 | 97.62 | 100.00 | 96.06 | 98.82 | 97.97 |
| Acyclic (N5), % | 100.00 | 89.36 | 82.82 | 100.00 | 100.00 | 100.00 | 90.40 | 100.00 | 100.00 |
| $\Sigma(N5)/\Sigma(N4)$, weight ratio | 0.33 | 0.42 | 0.49 | 0.17 | 0.29 | 0.11 | 0.36 | 0.20 | 0.22 |
| Acrylic (N4)/cyclic ($<$ = N4), weight ratio | 5.31 | 2.33 | 3.05 | 9.26 | 6.48 | 11.31 | 4.55 | 6.94 | 6.80 |

TABLE XXX

| Example No. | 277 | 278 | 279 | 280 | 281 | 282 | 283 | 284 | 285 |
|---|---|---|---|---|---|---|---|---|---|
| Catalyst Type | LL | LL | LL | LL | LL | LL | LL | LL | LL |
| Catalyst weight, gm | 70.6 | 70.6 | 70.6 | 70.6 | 70.6 | 70.6 | 70.6 | 70.6 | 70.6 |
| Pressure, psig | 600 | 600 | 600 | 600 | 600 | 600 | 600 | 600 | 600 |
| Temperature, °C. | 267.9 | 267.8 | 277.8 | 259.9 | 270.1 | 259.9 | 280.1 | 269.6 | 269 |
| Time on organics, hrs. | 5.0 | 7.5 | 26.0 | 31.5 | 50.0 | 55.5 | 74.0 | 78.0 | 80.0 |
| Duration of run, hrs. | 1 | 1 | 2 | 2 | 2 | 2 | 2 | 2 | 1.5 |
| MEA SV, gmol/hr/kgcat | 0.39 | 8.50 | 4.10 | 4.26 | 3.89 | 4.41 | 4.10 | 4.07 | 4.13 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.167 | 2.266 | 4.396 | 1.162 | 2.491 | 1.273 | 4.640 | 2.530 | 2.433 |
| MEA | 28.978 | 28.688 | 26.446 | 33.928 | 28.222 | 33.924 | 23.574 | 29.868 | 29.121 |
| PIP | 0.494 | 0.372 | 0.461 | 0.092 | 0.207 | 0.083 | 0.544 | 0.212 | 0.203 |
| DETA | 48.084 | 52.021 | 51.406 | 57.383 | 55.479 | 56.855 | 50.221 | 53.418 | 55.210 |
| AEEA | 1.425 | 1.525 | 1.038 | 1.006 | 1.321 | 1.043 | 1.027 | 1.313 | 1.296 |
| AEP | 0.568 | 0.441 | 0.564 | 0.230 | 0.352 | 0.215 | 0.561 | 0.299 | 0.305 |
| HEP | 0.000 | 0.000 | 0.000 | 0.000 | 0.000 | 0.000 | 0.000 | 0.000 | 0.000 |
| TAEA | 0.506 | 0.561 | 0.265 | 0.113 | 0.219 | 0.139 | 0.375 | 0.264 | 0.266 |
| l-TETA | 7.871 | 6.131 | 3.828 | 1.714 | 4.080 | 1.741 | 5.218 | 3.019 | 3.221 |
| DAEP | 0.101 | 0.000 | 0.095 | 0.124 | 0.000 | 0.000 | 0.085 | 0.000 | 0.000 |
| PEEDA | 0.100 | 0.080 | 0.203 | 0.117 | 0.000 | 0.093 | 0.111 | 0.114 | 0.072 |
| DPE | 0.117 | 0.000 | 0.254 | 0.107 | 0.132 | 0.000 | 0.309 | 0.118 | 0.097 |
| AE-TAEA | 0.530 | 0.252 | 0.150 | 0.000 | 0.133 | 0.000 | 0.191 | 0.000 | 0.000 |
| 1-TEPA | 1.837 | 0.607 | 0.160 | 0.000 | 0.131 | 0.000 | 0.719 | 0.000 | 0.000 |
| AE-DAEP | 0.100 | 0.000 | 0.000 | 0.000 | 0.000 | 0.000 | 0.112 | 0.000 | 0.000 |
| AE-PEEDA | 0.000 | 0.157 | 0.147 | 0.000 | 0.000 | 0.000 | 0.178 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.101 | 0.093 |
| BPEA | 0.000 | 0.000 | 0.000 | 0.000 | 0.000 | 0.000 | 0.000 | 0.000 | 0.000 |
| Others | 2.103 | 1.740 | 5.237 | 1.773 | 2.532 | 1.674 | 5.777 | 2.917 | 2.755 |
| MEA Conversion, % | 19.77 | 20.18 | 26.43 | 7.46 | 21.73 | 6.67 | 34.14 | 15.86 | 18.88 |
| DETA Conversion, % | 20.89 | 13.97 | 15.01 | 6.98 | 8.55 | 7.04 | 16.62 | 10.56 | 8.60 |
| Acyclic (N4), % | 96.35 | 98.82 | 88.13 | 84.00 | 97.03 | 95.30 | 91.72 | 93.42 | 95.39 |
| Acrylic (N5), % | 95.93 | 84.54 | 67.84 | 0.00 | 100.00 | 0.00 | 75.87 | 0.00 | 0.00 |
| Σ(N5)/Σ(N4), weight ratio | 0.28 | 0.15 | 0.10 | 0.00 | 0.06 | 0.00 | 0.20 | 0.03 | 0.03 |
| Acrylic (N4)/cyclic (< = N4), weight ratio | 6.07 | 7.50 | 2.60 | 2.72 | 6.22 | 4.81 | 3.47 | 4.42 | 5.16 |

TABLE XXXI

| Example No. | 286 | 287 | 288 | 289 | 290 | 291 | 292 | 293 | 294 |
|---|---|---|---|---|---|---|---|---|---|
| Catalyst Type | MM | MM | MM | MM | MM | MM | MM | MM | MM |
| Catalyst weight, gm | 80.1 | 80.1 | 80.1 | 80.1 | 80.1 | 80.1 | 80.1 | 80.1 | 80.1 |
| Pressure, psig | 600 | 600 | 600 | 600 | 600 | 600 | 600 | 600 | 600 |
| Temperature, °C. | 270.1 | 270 | 280.2 | 259.7 | 270.1 | 259.6 | 280 | 270 | 270 |
| Time on organics, hrs. | 5.0 | 7.5 | 26.5 | 31.5 | 49.7 | 54.0 | 74.0 | 77.5 | 80.0 |
| Duration of run, hrs. | 2 | 2 | 2 | 2 | 2 | 2 | 2 | 2 | 2 |
| MEA SV, gmol/hr/kgcat | 3.81 | 3.85 | 3.23 | 4.01 | 3.93 | 4.12 | 3.71 | 3.87 | 3.79 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude prodict composition, wt. % | | | | | | | | | |
| EDA | 1.935 | 2.148 | 4.938 | 0.907 | 1.895 | 0.879 | 4.006 | 2.166 | 1.951 |
| MEA | 18.750 | 21.318 | 20.112 | 30.534 | 28.213 | 31.731 | 24.388 | 29.089 | 28.221 |
| PIP | 0.553 | 0.373 | 0.726 | 0.053 | 0.150 | 0.043 | 0.410 | 0.190 | 0.179 |
| DETA | 50.396 | 52.368 | 51.336 | 60.802 | 57.134 | 60.506 | 53.455 | 57.017 | 58.930 |
| AEEA | 0.561 | 0.915 | 0.707 | 0.796 | 1.023 | 0.782 | 0.908 | 1.152 | 1.167 |
| AEP | 0.744 | 0.572 | 0.748 | 0.309 | 0.383 | 0.307 | 0.625 | 0.384 | 0.410 |
| HEP | 0.000 | 0.000 | 0.000 | 0.000 | 0.000 | 0.000 | 0.000 | 0.000 | 0.000 |
| TAEA | 1.214 | 1.199 | 0.429 | 0.429 | 0.192 | 0.365 | 0.366 | 0.265 | 0.266 |
| l-TETA | 9.307 | 8.213 | 5.708 | 1.341 | 2.862 | 1.182 | 4.049 | 2.751 | 2.937 |
| DAEP | 0.134 | 0.098 | 0.388 | 0.083 | 0.164 | 0.000 | 0.099 | 0.107 | 0.177 |
| PEEDA | 0.113 | 0.091 | 0.487 | 0.000 | 0.168 | 0.097 | 0.310 | 0.113 | 0.134 |
| DPE | 0.111 | 0.074 | 0.489 | 0.000 | 0.145 | 0.000 | 0.313 | 0.141 | 0.126 |
| AE-TAEA | 0.592 | 0.135 | 0.282 | 0.140 | 0.151 | 0.000 | 0.279 | 0.118 | 0.152 |
| 1-TEPA | 2.145 | 1.256 | 0.907 | 0.000 | 0.137 | 0.000 | 0.116 | 0.111 | 0.000 |
| AE-DAEP | 0.105 | 0.097 | 0.165 | 0.000 | 0.000 | 0.000 | 0.000 | 0.000 | 0.000 |
| AE-PEEDA | 0.221 | 0.227 | 0.312 | 0.000 | 0.000 | 0.000 | 0.129 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.085 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 7.869 | 5.765 | 6.160 | 1.656 | 2.354 | 1.509 | 5.848 | 2.786 | 2.669 |
| MEA Conversion, % | 49.20 | 41.78 | 44.57 | 16.55 | 21.53 | 13.41 | 32.99 | 20.19 | 23.49 |
| DETA Conversion, % | 18.85 | 15.01 | 15.92 | 1.24 | 5.56 | 1.86 | 12.71 | 7.03 | 5.05 |
| Acyclic (N4), % | 96.71 | 97.29 | 81.81 | 95.55 | 86.50 | 94.12 | 85.94 | 89.31 | 88.02 |
| Acrylic (N5), % | 89.37 | 81.10 | 67.94 | 100.00 | 100.00 | 0.00 | 75.42 | 100.00 | 100.00 |
| Σ(N5)/Σ(N4), weight ratio | 0.28 | 0.18 | 0.23 | 0.08 | 0.08 | 0.00 | 0.10 | 0.07 | 0.04 |
| Acrylic (N4)/cyclic | 6.36 | 7.80 | 2.16 | 3.98 | 3.03 | 3.47 | 2.51 | 3.23 | 3.12 |

TABLE XXXI-continued

| Example No. | 286 | 287 | 288 | 289 | 290 | 291 | 292 | 293 | 294 |
|---|---|---|---|---|---|---|---|---|---|
| Catalyst Type | MM | MM | MM | MM | MM | MM | MM | MM | MM |
| (< = N4), weight ratio | | | | | | | | | |

TABLE XXXII

| Example No. | 295 | 296 | 297 | 298 | 299 | 300 | 301 | 302 | 303 |
|---|---|---|---|---|---|---|---|---|---|
| Catalyst Type | NN | NN | NN | NN | NN | NN | NN | NN | NN |
| Catalyst weight, gm | 81.2 | 81.2 | 81.2 | 81.2 | 81.2 | 81.2 | 81.2 | 81.2 | 81.2 |
| Pressure, psig | 600 | 600 | 600 | 600 | 600 | 600 | 600 | 600 | 600 |
| Temperature, °C. | 269.9 | 272.7 | 279.9 | 260.3 | 268.3 | 261.4 | 278.9 | 270.6 | 271.7 |
| Time on organics, hrs. | 7.5 | 26.0 | 31.0 | 47.0 | 53.0 | 58.5 | 73.0 | 78.0 | 80.0 |
| Duration of run, hrs. | 2 | 2 | 2 | 2 | 2 | 2.5 | 2 | 2 | 2 |
| MEA SV, gmol/hr/kgcat | 3.80 | 3.43 | 3.59 | 3.68 | 3.75 | 4.01 | 3.56 | 3.87 | 3.87 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.775 | 2.809 | 2.208 | 1.431 | 2.058 | 0.987 | 4.151 | 1.948 | 1.942 |
| MEA | 28.020 | 25.978 | 11.404 | 32.207 | 28.431 | 31.510 | 25.905 | 30.029 | 29.693 |
| PIP | 0.108 | 0.150 | 0.000 | 0.069 | 0.120 | 0.040 | 0.254 | 0.118 | 0.112 |
| DETA | 59.798 | 58.058 | 46.899 | 58.424 | 57.923 | 59.289 | 52.433 | 57.883 | 58.062 |
| AEEA | 0.541 | 0.675 | 1.138 | 0.696 | 0.890 | 0.677 | 0.840 | 0.882 | 0.858 |
| AEP | 0.313 | 0.348 | 1.766 | 0.248 | 0.320 | 0.252 | 0.449 | 0.311 | 0.322 |
| HEP | 0.000 | 0.000 | 0.000 | 0.000 | 0.000 | 0.000 | 0.000 | 0.000 | 0.000 |
| TAEA | 0.092 | 0.169 | 1.615 | 0.393 | 0.129 | 0.398 | 0.234 | 0.129 | 0.128 |
| l-TETA | 3.144 | 3.193 | 10.766 | 1.341 | 2.981 | 1.076 | 3.031 | 2.141 | 2.296 |
| DAEP | 0.168 | 0.096 | 0.685 | 0.064 | 0.076 | 0.099 | 0.109 | 0.146 | 0.166 |
| PEEDA | 0.243 | 0.153 | 0.635 | 0.058 | 0.167 | 0.147 | 0.177 | 0.113 | 0.141 |
| DPE | 0.184 | 0.207 | 0.122 | 0.098 | 0.172 | 0.095 | 0.253 | 0.136 | 0.160 |
| AE-TAEA | 0.203 | 0.120 | 2.095 | 0.000 | 0.159 | 0.000 | 0.298 | 0.115 | 0.142 |
| l-TEPA | 0.216 | 0.000 | 5.688 | 0.179 | 0.000 | 0.121 | 0.099 | 0.000 | 0.000 |
| AE-DAEP | 0.000 | 0.000 | 0.571 | 0.000 | 0.000 | 0.000 | 0.000 | 0.000 | 0.000 |
| AE-PEEDA | 0.000 | 0.000 | 0.651 | 0.000 | 0.000 | 0.000 | 0.098 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.469 | 0.000 | 0.000 | 0.000 | 0.000 | 0.000 | 0.000 |
| BPEA | 0.000 | 0.000 | 0.532 | 0.000 | 0.000 | 0.000 | 0.000 | 0.000 | 0.000 |
| Others | 2.095 | 3.752 | 4.778 | 2.591 | 3.333 | 2.170 | 6.088 | 2.749 | 2.847 |
| MEA Conversion, % | 23.74 | 28.57 | 68.94 | 12.45 | 22.42 | 13.61 | 27.80 | 17.72 | 18.86 |
| DETA Conversion, % | 3.28 | 5.12 | 24.09 | 5.62 | 6.07 | 3.39 | 13.14 | 5.74 | 5.71 |
| Acyclic(N4), % | 84.47 | 88.05 | 89.57 | 88.73 | 88.23 | 81.18 | 85.84 | 85.16 | 83.84 |
| Acyclic(N5), % | 100.00 | 100.00 | 77.78 | 100.00 | 100.00 | 100.00 | 80.24 | 100.00 | 100.00 |
| Σ(N5)/Σ(N4), weight ratio | 0.11 | 0.03 | 0.72 | 0.09 | 0.05 | 0.07 | 0.13 | 0.04 | 0.05 |
| Acyclic(N4)/cyclic (< = N4), weight ratio | 3.19 | 3.52 | 3.86 | 3.23 | 3.64 | 2.33 | 2.63 | 2.75 | 2.69 |

TABLE XXXIII

| Example No. | 304 | 305 | 306 | 307 | 308 | 309 | 310 | 311 | 312 |
|---|---|---|---|---|---|---|---|---|---|
| Catalyst Type | OO | OO | OO | OO | OO | OO | OO | OO | OO |
| Catalyst weight, gm | 76.3 | 76.3 | 76.3 | 76.3 | 76.3 | 76.3 | 76.3 | 76.3 | 76.3 |
| Pressure, psig | 600 | 600 | 600 | 600 | 600 | 600 | 600 | 600 | 600 |
| Temperature, °C. | 269.9 | 272.7 | 279.9 | 260.3 | 268.3 | 261.4 | 278.9 | 270.6 | 271.7 |
| Time on organics, hrs. | 7.5 | 26.0 | 31.0 | 47.0 | 53.0 | 58.5 | 73.0 | 78.0 | 80.0 |
| Duration of run, hrs. | 2 | 2 | 2 | 2 | 2 | 2.5 | 2 | 2 | 2 |
| MEA SV, gmol/hr/kgcat | 3.99 | 3.68 | 4.09 | 2.65 | 1.23 | 0.96 | 3.38 | 3.80 | 3.31 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.574 | 1.791 | 4.858 | 0.968 | 2.024 | 2.100 | 2.080 | 0.921 | 0.937 |
| MEA | 18.061 | 16.725 | 23.777 | 24.322 | 13.187 | 16.037 | 16.072 | 23.937 | 22.805 |
| PIP | 1.056 | 0.060 | 0.323 | 0.500 | 1.357 | 1.136 | 1.291 | 0.528 | 0.587 |
| DETA | 52.716 | 51.336 | 50.891 | 55.597 | 51.804 | 51.667 | 51.643 | 57.189 | 56.650 |
| AEEA | 1.515 | 1.794 | 0.774 | 3.457 | 3.008 | 2.269 | 1.717 | 2.377 | 3.256 |
| AEP | 1.413 | 1.302 | 0.469 | 0.517 | 1.435 | 1.300 | 1.360 | 0.518 | 0.660 |
| HEP | 0.000 | 0.000 | 0.000 | 0.000 | 0.000 | 0.000 | 0.000 | 0.000 | 0.000 |
| TAEA | 1.676 | 1.719 | 0.290 | 0.781 | 1.672 | 1.529 | 1.523 | 0.820 | 0.879 |
| l-TETA | 11.477 | 11.388 | 3.548 | 6.608 | 11.810 | 11.030 | 10.185 | 6.667 | 7.190 |
| DAEP | 0.280 | 0.282 | 0.141 | 0.080 | 0.263 | 0.294 | 0.263 | 0.097 | 0.107 |
| PEEDA | 0.193 | 0.215 | 0.257 | 0.000 | 0.192 | 0.203 | 0.206 | 0.000 | 0.067 |
| DPE | 0.000 | 0.000 | 0.366 | 0.000 | 0.000 | 0.072 | 0.000 | 0.000 | 0.000 |
| AE-TAEA | 0.773 | 0.861 | 0.327 | 0.406 | 0.810 | 0.775 | 0.789 | 0.456 | 0.513 |
| l-TEPA | 3.017 | 3.327 | 0.123 | 0.963 | 3.541 | 3.449 | 2.992 | 1.036 | 1.135 |
| AE-DAEP | 0.088 | 0.115 | 0.110 | 0.000 | 0.227 | 0.177 | 0.222 | 0.000 | 0.000 |
| AE-PEEDA | 0.000 | 0.000 | 0.176 | 0.000 | 0.115 | 0.135 | 0.110 | 0.000 | 0.000 |

TABLE XXXIII-continued

| Example No. | 304 | 305 | 306 | 307 | 308 | 309 | 310 | 311 | 312 |
|---|---|---|---|---|---|---|---|---|---|
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.094 | 0.000 | 0.000 | 0.072 | 0.098 | 0.058 | 0.000 | 0.000 |
| Others | 0.509 | 0.841 | 7.550 | 0.461 | 1.103 | 0.677 | 1.461 | 0.555 | 0.534 |
| MEA Conversion, % | 50.94 | 53.95 | 33.72 | 32.83 | 63.87 | 55.94 | 55.35 | 34.29 | 37.73 |
| DETA Conversion, % | 14.90 | 15.99 | 15.70 | 8.75 | 15.64 | 15.63 | 14.74 | 6.69 | 8.06 |
| Acyclic(N4), % | 96.53 | 96.35 | 83.41 | 98.93 | 96.73 | 95.66 | 96.15 | 98.72 | 97.88 |
| Acyclic(N5), % | 97.72 | 95.24 | 61.11 | 100.00 | 91.31 | 91.12 | 90.64 | 100.00 | 100.00 |
| $\Sigma(N5)/\Sigma(N4)$, weight ratio | 0.28 | 0.32 | 0.16 | 0.18 | 0.34 | 0.35 | 0.34 | 0.20 | 0.20 |
| Acyclic(N4)/cyclic (< = N4), weight ratio | 4.47 | 4.59 | 2.47 | 6.74 | 4.15 | 4.18 | 3.75 | 6.55 | 5.67 |

TABLE XXXIV

| Example No. | 313 | 314 | 315 | 316 | 317 | 318 | 319 | 320 | 321 |
|---|---|---|---|---|---|---|---|---|---|
| Catalyst Type | PP | PP | PP | PP | PP | PP | PP | PP | PP |
| Catalyst weight, gm | 76.1 | 76.1 | 76.1 | 76.1 | 76.1 | 76.1 | 76.1 | 76.1 | 76.1 |
| Pressure, psig | 600 | 600 | 600 | 600 | 600 | 600 | 600 | 600 | 600 |
| Temperature, °C. | 270 | 270 | 280 | 260 | 270 | 260 | 280 | 270 | 269.4 |
| Time on organics, hrs. | 5.5 | 24.0 | 29.5 | 48.5 | 53.5 | 72.0 | 77.5 | 93.0 | 94.0 |
| Duration of run, hrs. | 2 | 2 | 2 | 2 | 2 | 2 | 2 | 1 | 1 |
| MEA SV, gmol/hr/kgcat | 4.03 | 3.42 | 4.57 | 5.42 | 4.80 | 4.26 | 4.14 | 4.21 | 1.91 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.718 | 0.000 | 3.456 | 1.014 | 1.450 | 0.805 | 3.050 | 1.886 | 1.860 |
| MEA | 13.198 | 13.705 | 10.445 | 24.724 | 21.688 | 32.394 | 18.370 | 26.238 | 25.429 |
| PIP | 1.176 | 1.217 | 1.276 | 0.318 | 0.501 | 0.279 | 1.161 | 0.667 | 0.651 |
| DETA | 44.099 | 47.849 | 45.082 | 54.434 | 53.648 | 46.319 | 42.468 | 43.338 | 42.572 |
| AEEA | 1.298 | 1.149 | 0.783 | 1.841 | 1.512 | 2.946 | 1.159 | 2.722 | 2.762 |
| AEP | 1.774 | 1.847 | 1.906 | 0.410 | 0.649 | 0.391 | 1.624 | 0.861 | 0.848 |
| HEP | 0.000 | 0.000 | 0.000 | 0.000 | 0.000 | 0.000 | 0.000 | 0.000 | 0.000 |
| TAEA | 1.744 | 1.923 | 1.704 | 1.507 | 1.720 | 1.323 | 1.037 | 1.629 | 1.656 |
| 1-TETA | 12.612 | 12.764 | 11.841 | 8.466 | 10.127 | 7.262 | 9.928 | 9.641 | 10.039 |
| DAEP | 0.762 | 0.661 | 0.856 | 0.081 | 0.169 | 0.072 | 0.671 | 0.224 | 0.201 |
| PEEDA | 0.511 | 0.477 | 0.625 | 0.000 | 0.110 | 0.000 | 0.510 | 0.153 | 0.129 |
| DPE | 0.135 | 0.166 | 0.089 | 0.000 | 0.000 | 0.000 | 0.101 | 0.076 | 0.073 |
| AE-TAEA | 2.518 | 1.883 | 2.119 | 0.797 | 1.392 | 0.705 | 1.873 | 1.397 | 1.507 |
| 1-TEPA | 6.017 | 4.679 | 5.227 | 1.495 | 2.798 | 1.149 | 4.035 | 2.862 | 3.120 |
| AE-DAEP | 0.397 | 0.354 | 0.577 | 0.000 | 0.000 | 0.000 | 0.486 | 0.102 | 0.214 |
| AE-PEEDA | 0.098 | 0.000 | 0.207 | 0.000 | 0.000 | 0.000 | 0.102 | 0.000 | 0.103 |
| iAE-PEEDA | 0.000 | 0.000 | 0.000 | 0.000 | 0.000 | 0.000 | 0.000 | 0.000 | 0.000 |
| AE-DPE | 0.180 | 0.219 | 0.363 | 0.000 | 0.000 | 0.000 | 0.246 | 0.303 | 0.151 |
| BPEA | 0.182 | 0.198 | 0.325 | 0.000 | 0.000 | 0.000 | 0.200 | 0.174 | 0.113 |
| Others | 1.581 | 2.529 | 4.320 | 0.513 | 0.856 | 0.383 | 4.070 | 1.426 | 1.246 |
| MEA Conversion, % | 63.48 | 62.41 | 71.33 | 32.51 | 41.96 | 8.72 | 48.56 | 27.14 | 28.62 |
| DETA Conversion, % | 27.47 | 22.01 | 26.47 | 11.69 | 14.67 | 22.43 | 29.33 | 28.48 | 28.98 |
| Acyclic(N4), % | 91.07 | 91.84 | 89.61 | 99.19 | 97.70 | 99.17 | 89.54 | 96.14 | 97.25 |
| Acyclic(N5), % | 90.88 | 89.49 | 83.31 | 100.00 | 100.00 | 100.00 | 85.10 | 88.03 | 88.85 |
| $\Sigma(N5)/\Sigma(N4)$, weight ratio | 0.60 | 0.46 | 0.58 | 0.23 | 0.35 | 0.21 | 0.57 | 0.41 | 0.43 |
| Acyclic(N4)/cyclic (< = N4), weight ratio | 3.29 | 3.36 | 2.85 | 12.33 | 8.29 | 11.56 | 2.70 | 5.69 | 6.40 |

TABLE XXXV

| Example No. | 322 | 323 | 324 | 325 | 326 | 327 | 328 | 329 | 330 |
|---|---|---|---|---|---|---|---|---|---|
| Catalyst Type | QQ | QQ | QQ | QQ | QQ | QQ | QQ | QQ | QQ |
| Catalyst weight, gm | 78.5 | 78.5 | 78.5 | 78.5 | 78.5 | 78.5 | 78.5 | 78.5 | 78.5 |
| Pressure, psig | 600 | 600 | 600 | 600 | 600 | 600 | 600 | 600 | 600 |
| Temperature, °C. | 270.3 | 270.8 | 280.9 | 259.5 | 270.8 | 261.4 | 282.6 | 273.4 | 270.8 |
| Time on organics, hrs. | 4.0 | 7.0 | 26.0 | 31.0 | 50.0 | 55.0 | 74.0 | 79.0 | 99.5 |
| Duration of run, hrs. | 2 | 2 | 2 | 2 | 2 | 2 | 2 | 2 | 2 |
| MEA SV, gmol/hr/kgcat | 3.42 | 3.32 | 3.47 | 3.50 | 3.64 | 3.76 | 3.58 | 3.51 | 3.64 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.064 | 1.889 | 2.436 | 0.860 | 0.798 | 0.344 | 1.077 | 0.453 | 0.663 |
| MEA | 14.084 | 15.810 | 12.462 | 36.060 | 25.744 | 30.392 | 15.607 | 22.241 | 25.522 |
| PIP | 1.454 | 1.307 | 1.613 | 0.473 | 0.583 | 0.199 | 0.827 | 0.380 | 0.467 |
| DETA | 51.792 | 51.235 | 52.756 | 54.948 | 56.753 | 59.500 | 53.106 | 59.354 | 60.415 |
| AEEA | 0.857 | 1.123 | 0.758 | 1.393 | 0.172 | 1.675 | 1.251 | 1.785 | 0.264 |

TABLE XXXV-continued

| Example No. | 322 | 323 | 324 | 325 | 326 | 327 | 328 | 329 | 330 |
|---|---|---|---|---|---|---|---|---|---|
| AEP | 2.286 | 1.884 | 2.151 | 0.372 | 0.645 | 0.390 | 1.366 | 0.626 | 0.647 |
| HEP | 0.000 | 0.000 | 0.000 | 0.000 | 0.000 | 0.000 | 0.000 | 0.000 | 0.000 |
| TAEA | 1.116 | 0.989 | 1.006 | 0.279 | 0.629 | 0.401 | 1.612 | 0.804 | 0.629 |
| 1-TETA | 12.082 | 10.881 | 10.297 | 2.687 | 6.508 | 4.381 | 11.880 | 6.933 | 5.481 |
| DAEP | 0.742 | 0.738 | 0.685 | 0.000 | 0.135 | 0.000 | 0.271 | 0.099 | 0.151 |
| PEEDA | 0.468 | 0.513 | 0.507 | 0.000 | 0.071 | 0.000 | 0.256 | 0.087 | 0.127 |
| DPE | 0.000 | 0.133 | 0.000 | 0.000 | 0.000 | 0.000 | 0.000 | 0.000 | 0.000 |
| AE-TAEA | 1.823 | 1.579 | 1.601 | 0.000 | 0.441 | 0.000 | 0.202 | 0.000 | 0.380 |
| 1-TEPA | 5.194 | 4.155 | 4.031 | 0.000 | 0.624 | 0.000 | 3.427 | 0.617 | 0.349 |
| AE-DAEP | 0.472 | 0.373 | 0.373 | 0.000 | 0.000 | 0.000 | 0.230 | 0.000 | 0.000 |
| AE-PEEDA | 0.179 | 0.155 | 0.159 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.109 | 0.154 | 0.117 | 0.000 | 0.000 | 0.000 | 0.186 | 0.000 | 0.000 |
| BPEA | 0.000 | 0.000 | 0.000 | 0.000 | 0.000 | 0.000 | 0.000 | 0.000 | 0.000 |
| Others | 0.428 | 0.801 | 1.358 | 0.429 | 2.397 | 0.417 | 2.141 | 1.419 | 2.054 |
| MEA Conversion, % | 62.62 | 57.18 | 65.91 | 1.08 | 29.53 | 17.71 | 57.46 | 38.96 | 31.32 |
| DETA Conversion, % | 18.31 | 17.53 | 14.23 | 10.42 | 7.67 | 4.25 | 13.98 | 3.19 | 3.37 |
| Acyclic(N4), % | 91.61 | 89.56 | 90.46 | 100.00 | 97.20 | 100.00 | 96.24 | 97.65 | 95.65 |
| Acyclic(N5), % | 90.22 | 89.36 | 89.68 | 0.00 | 100.00 | 0.00 | 89.72 | 100.00 | 100.00 |
| Σ(N5)/Σ(N4), weight ratio | 0.54 | 0.48 | 0.50 | 0.00 | 0.14 | 0.00 | 0.29 | 0.08 | 0.11 |
| Acyclic(N4)/cyclic (< = N4), weight ratio | 2.67 | 2.59 | 2.28 | 3.51 | 4.98 | 8.11 | 4.96 | 6.49 | 4.39 |

TABLE XXXVI

| Example No. | 331 | 332 | 333 | 334 | 335 | 336 | 337 | 338 | 339 |
|---|---|---|---|---|---|---|---|---|---|
| Catalyst Type | RR | RR | RR | RR | RR | RR | RR | RR | RR |
| Catalyst weight, gm | 74.5 | 74.5 | 74.5 | 74.5 | 74.5 | 74.5 | 74.5 | 74.5 | 74.5 |
| Pressure, psig | 600 | 600 | 600 | 600 | 600 | 600 | 600 | 600 | 600 |
| Temperature, °C. | 267.3 | 271.6 | 280.4 | 260.3 | 269.1 | 261.9 | 278.4 | 268.9 | 268.5 |
| Time on organics, hrs. | 6.5 | 25.5 | 30.5 | 49.5 | 54.5 | 73.5 | 78.5 | 97.0 | 99.2 |
| Duration of run, hrs. | 2 | 2 | 2 | 2 | 2 | 2 | 2 | 2 | 2 |
| MEA SV, gmol/hr/kgcat | 4.48 | 4.16 | 4.21 | 3.93 | 3.96 | 3.98 | 4.08 | 3.40 | 3.96 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.181 | 1.202 | 2.220 | 0.541 | 0.922 | 0.455 | 1.851 | 1.236 | 0.863 |
| MEA | 24.149 | 27.125 | 24.297 | 32.485 | 29.621 | 31.003 | 24.872 | 30.577 | 28.781 |
| PIP | 0.405 | 0.291 | 0.859 | 0.101 | 0.203 | 0.079 | 0.464 | 0.261 | 0.228 |
| DETA | 57.182 | 59.913 | 55.802 | 60.897 | 60.714 | 62.348 | 54.893 | 58.708 | 61.316 |
| AEEA | 0.929 | 1.479 | 1.151 | 1.074 | 1.180 | 0.920 | 1.384 | 1.342 | 1.371 |
| AEP | 0.649 | 0.503 | 0.740 | 0.341 | 0.427 | 0.349 | 0.703 | 0.474 | 0.446 |
| HEP | 0.000 | 0.000 | 0.000 | 0.000 | 0.000 | 0.000 | 0.000 | 0.000 | 0.000 |
| TAEA | 0.720 | 0.473 | 0.644 | 0.321 | 0.303 | 0.320 | 0.553 | 0.276 | 0.291 |
| 1-TETA | 7.014 | 4.341 | 6.500 | 1.844 | 3.136 | 1.875 | 6.108 | 2.942 | 3.059 |
| DAEP | 0.113 | 0.000 | 0.109 | 0.000 | 0.098 | 0.000 | 0.348 | 0.090 | 0.090 |
| PEEDA | 0.098 | 0.000 | 0.111 | 0.000 | 0.000 | 0.000 | 0.583 | 0.000 | 0.000 |
| DPE | 0.000 | 0.000 | 0.083 | 0.000 | 0.000 | 0.000 | 0.182 | 0.000 | 0.000 |
| AE-TAEA | 0.438 | 0.224 | 0.288 | 0.000 | 0.000 | 0.000 | 0.826 | 0.000 | 0.000 |
| 1-TEPA | 1.158 | 0.139 | 0.695 | 0.000 | 0.000 | 0.000 | 1.081 | 0.000 | 0.000 |
| AE-DAEP | 0.000 | 0.000 | 0.000 | 0.000 | 0.000 | 0.000 | 0.000 | 0.000 | 0.000 |
| AE-PEEDA | 0.105 | 0.000 | 0.000 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 1.839 | 1.060 | 2.010 | 0.836 | 1.046 | 0.930 | 2.604 | 0.915 | 0.887 |
| MEA Conversion, % | 34.39 | 26.20 | 33.56 | 12.26 | 19.77 | 16.34 | 32.77 | 16.26 | 21.89 |
| DETA Conversion, % | 7.68 | 3.12 | 9.31 | 2.25 | 2.27 | 0.01 | 11.81 | 4.45 | 1.10 |
| Acyclic(N4), % | 97.35 | 100.00 | 95.92 | 100.00 | 97.24 | 100.00 | 85.69 | 97.27 | 97.40 |
| Acyclic(N5), % | 93.82 | 100.00 | 100.00 | 0.00 | 0.00 | 0.00 | 100.00 | 0.00 | 0.00 |
| Σ(N5)/Σ(N4), weight ratio | 0.21 | 0.08 | 0.13 | 0.00 | 0.00 | 0.00 | 0.25 | 0.00 | 0.00 |
| Acyclic(N4)/cyclic (< × N4), weight ratio | 6.12 | 6.06 | 3.75 | 4.89 | 4.73 | 5.13 | 2.92 | 3.90 | 4.39 |

TABLE XXXVII

| Example No. | 340 | 341 | 342 | 343 | 344 | 345 | 346 | 347 | 348 |
|---|---|---|---|---|---|---|---|---|---|
| Catalyst Type | SS | SS | SS | SS | SS | SS | SS | SS | SS |
| Catalyst weight, gm | 84 | 84 | 84 | 84 | 84 | 84 | 84 | 84 | 84 |
| Pressure, psig | 600 | 600 | 600 | 600 | 600 | 600 | 600 | 600 | 600 |
| Temperature, °C. | 270 | 270 | 280 | 260 | 270 | 260 | 280 | 270 | 270 |
| Time on organics, hrs. | 6.5 | 24.0 | 29.5 | 48.0 | 53.7 | 71.0 | 74.0 | 98.0 | 99.0 |
| Duration of run, hrs. | 2 | 2 | 2 | 2 | 2 | 2 | 1 | 2 | 1 |

TABLE XXXVII-continued

| Example No. | 340 | 341 | 342 | 343 | 344 | 345 | 346 | 347 | 348 |
|---|---|---|---|---|---|---|---|---|---|
| MEA SV, gmol/hr/kgcat | 2.92 | 2.94 | 2.91 | 3.00 | 3.21 | 2.85 | 3.69 | 3.28 | 3.38 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 3.143 | 3.522 | 6.151 | 1.751 | 3.148 | 1.874 | 5.153 | 2.734 | 2.608 |
| MEA | 30.100 | 29.982 | 26.771 | 32.968 | 30.586 | 32.904 | 26.314 | 31.293 | 31.488 |
| PIP | 0.084 | 0.091 | 0.154 | 0.000 | 0.064 | 0.042 | 0.115 | 0.055 | 0.064 |
| DETA | 55.305 | 54.533 | 48.236 | 58.522 | 54.943 | 55.103 | 47.403 | 53.775 | 53.754 |
| AEEA | 0.153 | 0.233 | 0.160 | 0.091 | 0.000 | 0.090 | 0.176 | 0.171 | 0.152 |
| AEP | 0.295 | 0.276 | 0.352 | 0.223 | 0.245 | 0.200 | 0.308 | 0.227 | 0.225 |
| HEP | 0.000 | 0.000 | 0.000 | 0.000 | 0.000 | 0.000 | 0.000 | 0.000 | 0.000 |
| TAEA | 0.380 | 0.387 | 0.555 | 0.226 | 1.227 | 0.630 | 0.434 | 0.277 | 0.290 |
| l-TETA | 1.422 | 1.462 | 1.967 | 0.594 | 0.634 | 0.365 | 1.619 | 0.287 | 0.240 |
| DAEP | 0.097 | 0.089 | 0.101 | 0.117 | 0.081 | 0.068 | 0.090 | 0.088 | 0.095 |
| PEEDA | 0.084 | 0.081 | 0.215 | 0.150 | 0.109 | 0.121 | 0.166 | 0.158 | 0.167 |
| DPE | 0.181 | 0.185 | 0.356 | 0.110 | 0.150 | 0.062 | 0.241 | 0.134 | 0.129 |
| AE-TAEA | 0.000 | 0.000 | 0.184 | 0.000 | 0.000 | 0.000 | 0.122 | 0.000 | 0.000 |
| l-TEPA | 0.133 | 0.000 | 0.123 | 0.000 | 0.148 | 0.103 | 0.000 | 0.000 | 0.000 |
| AE-DAEP | 0.000 | 0.000 | 0.000 | 0.000 | 0.312 | 0.000 | 0.000 | 0.000 | 0.000 |
| AE-PEEDA | 0.000 | 0.000 | 0.104 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 4.933 | 5.408 | 9.890 | 3.207 | 4.813 | 2.118 | 8.097 | 5.003 | 4.889 |
| MEA Conversion, % | 17.10 | 17.35 | 25.92 | 10.37 | 15.66 | 6.14 | 22.88 | 11.56 | 10.89 |
| DETA Conversion, % | 9.47 | 10.66 | 20.67 | 5.44 | 9.96 | 6.58 | 17.43 | 9.67 | 9.59 |
| Acyclic(N4), % | 83.24 | 83.89 | 78.95 | 68.51 | 84.54 | 79.89 | 80.51 | 59.78 | 57.54 |
| Acyclic(N5), % | 100.00 | 0.00 | 74.66 | 0.00 | 52.87 | 100.00 | 100.00 | 0.00 | 0.00 |
| $\Sigma(N5)/\Sigma(N4)$, weight ratio | 0.06 | 0.00 | 0.13 | 0.00 | 0.13 | 0.08 | 0.05 | 0.00 | 0.00 |
| Acyclic(N4)/cyclic ($< \times$ N4), weight ratio | 2.43 | 2.56 | 2.14 | 1.37 | 2.87 | 2.02 | 2.23 | 0.85 | 0.78 |

TABLE XXXVIII

| Example No. | 349 | 350 | 351 | 352 | 353 | 354 | 355 | 356 | 357 |
|---|---|---|---|---|---|---|---|---|---|
| Catalyst Type | TT | TT | TT | TT | TT | TT | TT | TT | TT |
| Catalyst weight, gm | 80.7 | 80.7 | 80.7 | 80.7 | 80.7 | 80.7 | 80.7 | 80.7 | 80.7 |
| Pressure, psig | 600 | 600 | 600 | 600 | 600 | 600 | 600 | 600 | 600 |
| Temperature, °C. | 269.6 | 269.6 | 279.5 | 260.0 | 269.8 | 259.2 | 280.0 | 271.4 | 269.4 |
| Time on organics, hrs. | 20.5 | 24.5 | 44.0 | 49.0 | 68.0 | 73.0 | 92.0 | 97.0 | 116.5 |
| Duration of run, hrs. | 2 | 2 | 2 | 2 | 2 | 2 | 2 | 2 | 2 |
| MEA SV, gmol/hr/kgcat | 3.55 | 3.63 | 3.60 | 3.78 | 3.52 | 3.53 | 3.01 | 3.34 | 3.20 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.354 | 1.094 | 2.246 | 0.684 | 1.032 | 0.457 | 2.918 | 1.351 | 1.546 |
| MEA | 18.152 | 18.204 | 13.314 | 28.101 | 23.557 | 28.629 | 14.287 | 21.618 | 21.329 |
| PIP | 0.850 | 0.723 | 1.703 | 0.353 | 0.902 | 0.303 | 2.036 | 0.844 | 1.106 |
| DETA | 49.396 | 53.187 | 48.982 | 57.642 | 58.104 | 58.959 | 49.804 | 54.426 | 52.827 |
| AEEA | 1.115 | 1.255 | 0.534 | 1.459 | 0.788 | 1.073 | 0.483 | 0.249 | 0.256 |
| AEP | 1.250 | 0.946 | 2.103 | 0.528 | 0.967 | 0.526 | 2.138 | 1.089 | 1.122 |
| HEP | 0.000 | 0.000 | 0.000 | 0.000 | 0.000 | 0.000 | 0.000 | 0.000 | 0.000 |
| TAEA | 0.869 | 1.413 | 1.083 | 0.729 | 0.404 | 0.462 | 0.770 | 1.319 | 1.258 |
| l-TETA | 12.723 | 11.602 | 11.826 | 6.274 | 7.800 | 5.369 | 10.228 | 9.582 | 9.770 |
| DAEP | 0.209 | 0.196 | 0.731 | 0.061 | 0.485 | 0.286 | 0.654 | 0.151 | 0.165 |
| PEEDA | 0.152 | 0.141 | 0.630 | 0.000 | 0.281 | 0.137 | 0.454 | 0.114 | 0.115 |
| DPE | 0.000 | 0.000 | 0.064 | 0.000 | 0.000 | 0.000 | 0.062 | 0.000 | 0.000 |
| AE-TAEA | 0.956 | 1.039 | 2.383 | 0.000 | 0.000 | 0.000 | 1.590 | 0.000 | 0.000 |
| l-TEPA | 3.937 | 3.244 | 5.190 | 0.326 | 0.168 | 0.000 | 3.399 | 0.708 | 0.786 |
| AE-DAEP | 0.509 | 0.284 | 0.454 | 0.000 | 0.000 | 0.000 | 0.085 | 0.000 | 0.000 |
| AE-PEEDA | 0.534 | 0.100 | 0.131 | 0.000 | 0.000 | 0.000 | 0.201 | 0.087 | 0.108 |
| iAE-PEEDA | 0.000 | 0.000 | 0.000 | 0.000 | 0.000 | 0.000 | 0.000 | 0.000 | 0.000 |
| AE-DPE | 1.412 | 0.293 | 0.271 | 0.000 | 0.000 | 0.000 | 0.168 | 0.099 | 0.371 |
| BPEA | 0.000 | 0.000 | 0.000 | 0.000 | 0.000 | 0.000 | 0.000 | 0.000 | 0.000 |
| Others | 1.363 | 1.228 | 2.694 | 1.129 | 0.741 | 0.607 | 2.400 | 3.254 | 3.290 |
| MEA Conversion, % | 51.28 | 50.92 | 64.50 | 24.02 | 35.62 | 22.13 | 60.51 | 41.07 | 41.44 |
| DETA Conversion, % | 21.21 | 14.77 | 22.37 | 7.37 | 5.63 | 4.69 | 18.19 | 11.82 | 13.80 |
| Acyclic(N4), % | 97.41 | 97.47 | 90.05 | 99.13 | 91.45 | 93.23 | 90.38 | 97.63 | 97.53 |
| Acyclic(N5), % | 66.59 | 86.35 | 89.84 | 100.00 | 100.00 | 0.00 | 91.65 | 79.22 | 62.13 |
| $\Sigma(N5)/\Sigma(N4)$, weight ratio | 0.53 | 0.37 | 0.59 | 0.05 | 0.02 | 0.00 | 0.45 | 0.08 | 0.11 |
| Acyclic(N4)/cyclic weight ratio | 5.52 | 6.49 | 2.47 | 7.44 | 3.11 | 4.66 | 2.06 | 4.96 | 4.40 |

TABLE XXXIX

| Example No. | 358 | 359 | 360 | 361 | 362 | 363 | 364 | 365 | 366 |
|---|---|---|---|---|---|---|---|---|---|
| Catalyst Type | UU | UU | UU | UU | UU | UU | UU | UU | UU |
| Catalyst weight, gm | 89 | 89 | 89 | 89 | 89 | 89 | 89 | 89 | 89 |
| Pressure, psig | 600 | 600 | 600 | 600 | 600 | 600 | 600 | 600 | 600 |
| Temperature, °C. | 270 | 270 | 280 | 260 | 270 | 260 | 270 | 270 | 270 |
| Time on organics, hrs. | 6.5 | 24.0 | 29.5 | 48.0 | 53.7 | 71.0 | 24.0 | 98.0 | 99.0 |
| Duration of run, hrs. | 2 | 2 | 2 | 2 | 2 | 2 | 2 | 2 | 2 |
| MEA SV, gmol/hr/kgcat | 2.91 | 2.74 | 2.97 | 2.84 | 3.12 | 2.66 | 2.76 | 2.88 | 3.02 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.718 | 0.645 | 1.457 | 0.333 | 0.542 | 0.310 | 1.234 | 0.585 | 0.539 |
| MEA | 27.595 | 26.525 | 25.356 | 30.520 | 27.336 | 29.634 | 25.529 | 26.745 | 28.074 |
| PIP | 1.107 | 1.105 | 2.119 | 0.588 | 1.024 | 0.549 | 1.947 | 0.000 | 0.917 |
| DETA | 57.184 | 57.402 | 53.992 | 60.160 | 55.509 | 55.391 | 54.113 | 54.836 | 55.562 |
| AEEA | 1.254 | 1.122 | 0.744 | 1.059 | 0.901 | 0.959 | 0.906 | 1.108 | 1.108 |
| AEP | 0.828 | 0.865 | 1.760 | 0.408 | 0.730 | 0.375 | 1.646 | 0.736 | 0.672 |
| HEP | 0.000 | 0.000 | 0.000 | 0.000 | 0.000 | 0.000 | 0.000 | 0.000 | 0.000 |
| TAEA | 0.643 | 0.674 | 0.525 | 0.429 | 0.414 | 0.344 | 0.605 | 0.489 | 0.512 |
| 1-TETA | 5.227 | 5.572 | 5.376 | 3.427 | 4.632 | 2.912 | 6.015 | 5.284 | 4.209 |
| DAEP | 0.127 | 0.144 | 0.312 | 0.000 | 0.117 | 0.000 | 0.350 | 0.115 | 0.094 |
| PEEDA | 0.140 | 0.173 | 0.363 | 0.000 | 0.128 | 0.000 | 0.428 | 0.126 | 0.099 |
| DPE | 0.000 | 0.000 | 0.000 | 0.000 | 0.000 | 0.000 | 0.000 | 0.000 | 0.000 |
| AE-TAEA | 0.366 | 0.492 | 0.490 | 0.169 | 0.040 | 0.124 | 0.669 | 0.166 | 0.274 |
| 1-TEPA | 1.413 | 1.833 | 1.908 | 0.515 | 1.633 | 0.351 | 2.473 | 1.458 | 1.032 |
| AE-DAEP | 0.000 | 0.000 | 0.150 | 0.000 | 0.000 | 0.000 | 0.136 | 0.098 | 0.000 |
| AE-PEEDA | 0.000 | 0.000 | 0.131 | 0.000 | 0.000 | 0.000 | 0.136 | 0.079 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.112 | 0.000 | 0.000 |
| Others | 0.277 | 0.238 | 0.707 | 0.082 | 0.575 | 0.000 | 0.491 | 0.374 | 0.208 |
| MEA Conversion, % | 25.36 | 28.39 | 30.94 | 17.40 | 23.34 | 13.63 | 31.57 | 23.79 | 20.82 |
| DETA Conversion, % | 8.07 | 7.90 | 12.61 | 3.24 | 7.49 | 4.05 | 13.80 | 7.13 | 6.87 |
| Acyclic(N4), % | 95.65 | 95.17 | 89.74 | 100.00 | 95.38 | 100.00 | 89.49 | 95.99 | 96.08 |
| Acyclic(N5), % | 100.00 | 100.00 | 89.50 | 100.00 | 100.00 | 100.00 | 89.11 | 90.17 | 100.00 |
| Σ(N5)/Σ(N4), weight ratio | 0.29 | 0.35 | 0.41 | 0.18 | 0.32 | 0.15 | 0.48 | 0.30 | 0.27 |
| Acyclic(N4)/cyclic (< × N4), weight ratio | 2.67 | 2.73 | 1.30 | 3.87 | 2.52 | 3.52 | 1.51 | 5.90 | 2.65 |

TABLE XL

| Example No. | 367 | 368 | 369 | 370 | 371 | 372 | 373 | 374 |
|---|---|---|---|---|---|---|---|---|
| Catalyst Type | VV | VV | VV | VV | VV | VV | VV | VV |
| Catalyst weight, gm | 89 | 89 | 89 | 89 | 89 | 89 | 89 | 89 |
| Pressure, psig | 600 | 600 | 600 | 600 | 600 | 600 | 600 | 600 |
| Temperature, °C. | 270 | 280 | 260 | 270 | 260 | 260 | 270 | 270 |
| Time on organics, hrs. | 6.5 | 29.5 | 48.0 | 53.7 | 71.0 | 74.0 | 98.0 | 99.0 |
| Duration of run, hrs. | 2 | 2 | 2 | 2 | 2 | 1 | 2 | 1 |
| MEA SV, gmol/hr/kgcat | 3.60 | 4.04 | 3.87 | 3.77 | 3.63 | 3.82 | 3.80 | 4.14 |
| DETA/MEA mole ratio | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 |
| Crude product composition, wt. % | | | | | | | | |
| EDA | 0.213 | 0.589 | 0.063 | 0.237 | 0.132 | 0.597 | 0.268 | 0.221 |
| MEA | 28.924 | 28.276 | 32.679 | 29.051 | 31.767 | 26.401 | 29.867 | 31.406 |
| PIP | 0.577 | 1.302 | 0.331 | 0.637 | 0.305 | 1.250 | 0.636 | 0.606 |
| DETA | 60.693 | 59.604 | 61.967 | 55.284 | 57.693 | 54.502 | 57.225 | 57.491 |
| AEEA | 1.337 | 0.873 | 0.904 | 0.882 | 0.873 | 1.072 | 1.112 | 1.076 |
| AEP | 0.468 | 1.015 | 0.268 | 0.432 | 0.237 | 0.913 | 0.463 | 0.406 |
| HEP | 0.000 | 0.000 | 0.000 | 0.000 | 0.000 | 0.000 | 0.000 | 0.000 |
| TAEA | 0.446 | 0.369 | 0.216 | 0.202 | 0.171 | 0.391 | 0.328 | 0.287 |
| 1-TETA | 3.783 | 3.779 | 1.991 | 2.687 | 1.723 | 4.061 | 2.922 | 2.612 |
| DAEP | 0.000 | 0.182 | 0.000 | 0.064 | 0.000 | 0.133 | 0.000 | 0.000 |
| PEEDA | 0.000 | 0.236 | 0.000 | 0.000 | 0.000 | 0.175 | 0.000 | 0.000 |
| DPE | 0.000 | 0.000 | 0.000 | 0.000 | 0.000 | 0.000 | 0.000 | 0.000 |
| AE-TAEA | 0.194 | 0.224 | 0.000 | 0.000 | 0.000 | 0.289 | 0.138 | 0.000 |
| 1-TEPA | 0.663 | 0.879 | 0.000 | 0.296 | 0.000 | 1.049 | 0.455 | 0.350 |
| AE-DAEP | 0.000 | 0.000 | 0.000 | 0.000 | 0.000 | 0.000 | 0.000 | 0.000 |
| AE-PEEDA | 0.000 | 0.000 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 |
| Others | 0.102 | 0.321 | 0.081 | 0.079 | 0.000 | 0.307 | 0.187 | 0.194 |
| MEA Conversion, % | 21.74 | 24.03 | 11.82 | 14.35 | 8.93 | 24.03 | 15.55 | 11.95 |
| DETA Conversion, % | 2.40 | 4.83 | 0.62 | 3.13 | 1.70 | 6.80 | 3.84 | 4.21 |
| Acyclic(N4), % | 100.00 | 90.85 | 100.00 | 97.82 | 100.00 | 93.54 | 100.00 | 100.00 |
| Acyclic(N5), % | 100.00 | 100.00 | 0.00 | 100.00 | 0.00 | 100.00 | 100.00 | 100.00 |

TABLE XL-continued

| Example No. | 367 | 368 | 369 | 370 | 371 | 372 | 373 | 374 |
|---|---|---|---|---|---|---|---|---|
| Σ(N5)/Σ(N4), weight ratio | 0.20 | 0.24 | 0.00 | 0.10 | 0.00 | 0.28 | 0.18 | 0.12 |
| Acyclic(N4)/cyclic (< × N4), weight ratio | 4.04 | 1.52 | 3.69 | 2.55 | 3.50 | 1.80 | 2.96 | 2.86 |

TABLE XLI

| Example No. | 375 | 376 | 377 | 378 | 379 | 380 | 381 | 382 | 383 |
|---|---|---|---|---|---|---|---|---|---|
| Catalyst Type | WW | WW | WW | WW | WW | WW | WW | WW | WW |
| Catalyst weight, gm | 109.3 | 109.3 | 109.3 | 109.3 | 109.3 | 109.3 | 109.3 | 109.3 | 109.3 |
| Pressure, psig | 600 | 600 | 600 | 600 | 600 | 600 | 600 | 600 | 600 |
| Temperature, °C. | 272.8 | 272.4 | 281.4 | 261.6 | 271.6 | 261.2 | 281.1 | 271.8 | 271.8 |
| Time on organics, hrs. | 4.5 | 25.5 | 30.5 | 49.5 | 54.5 | 73.5 | 78.5 | 96.5 | 98.0 |
| Duration of run, hrs. | 2 | 2 | 2 | 2 | 2 | 2 | 2 | 1 | 1 |
| MEA SV, gmol/hr/kgcat | 2.41 | 2.58 | 2.54 | 2.56 | 2.62 | 2.46 | 2.37 | 2.35 | 2.01 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.497 | 6.772 | 12.561 | 3.271 | 5.650 | 3.027 | 8.398 | 6.989 | 6.342 |
| MEA | 11.926 | 3.136 | 0.306 | 9.052 | 3.533 | 8.556 | 0.344 | 2.253 | 2.052 |
| PIP | 1.508 | 3.617 | 5.688 | 2.203 | 3.219 | 2.114 | 3.924 | 3.679 | 3.432 |
| DETA | 43.663 | 34.939 | 27.007 | 40.944 | 37.212 | 42.204 | 28.868 | 34.736 | 33.388 |
| AEEA | 0.175 | 0.056 | 0.056 | 0.424 | 0.046 | 0.430 | 0.068 | 0.054 | 0.052 |
| AEP | 2.674 | 6.800 | 10.087 | 3.163 | 5.751 | 2.837 | 8.269 | 5.679 | 5.546 |
| HEP | 0.000 | 0.000 | 0.000 | 0.000 | 0.000 | 0.000 | 0.000 | 0.000 | 0.000 |
| TAEA | 5.276 | 2.471 | 0.713 | 3.624 | 2.701 | 3.372 | 1.567 | 2.339 | 2.387 |
| 1-TETA | 13.602 | 13.192 | 7.877 | 15.395 | 13.650 | 14.959 | 10.350 | 13.399 | 13.817 |
| DAEP | 0.031 | 3.410 | 4.966 | 0.050 | 2.804 | 1.167 | 5.005 | 2.753 | 2.852 |
| PEEDA | 0.402 | 1.586 | 3.460 | 0.670 | 1.378 | 0.689 | 3.719 | 1.712 | 1.642 |
| DPE | 0.164 | 0.126 | 0.173 | 0.124 | 0.130 | 0.189 | 0.296 | 0.208 | 0.214 |
| AE-TAEA | 4.114 | 2.399 | 0.888 | 3.396 | 2.480 | 3.259 | 1.667 | 2.421 | 2.684 |
| 1-TEPA | 4.558 | 5.996 | 3.503 | 6.285 | 6.269 | 6.192 | 5.083 | 6.762 | 7.401 |
| AE-DAEP | 0.056 | 1.150 | 2.203 | 0.395 | 0.981 | 0.321 | 2.619 | 1.146 | 1.196 |
| AE-PEEDA | 0.000 | 0.368 | 0.656 | 0.172 | 0.301 | 0.143 | 0.777 | 0.355 | 0.371 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.202 | 0.000 | 0.000 | 0.000 | 0.230 | 0.000 | 0.049 |
| BPEA | 0.019 | 0.170 | 0.043 | 0.198 | 0.142 | 0.105 | 0.056 | 0.133 | 0.249 |
| Others | 2.325 | 4.721 | 8.340 | 3.395 | 3.331 | 1.197 | 7.221 | 4.133 | 4.304 |
| MEA Conversion, % | 67.86 | 91.64 | 99.18 | 75.79 | 90.41 | 76.63 | 99.08 | 93.85 | 94.36 |
| DETA Conversion, % | 30.07 | 44.67 | 56.74 | 34.91 | 39.97 | 31.48 | 53.83 | 43.61 | 45.49 |
| Acyclic(N4), % | 96.93 | 75.36 | 49.97 | 95.75 | 79.13 | 89.96 | 56.92 | 77.11 | 77.49 |
| Acyclic(N5), % | 99.14 | 83.26 | 58.59 | 92.68 | 86.00 | 94.33 | 64.70 | 84.90 | 84.39 |
| Σ(N5)/Σ(N4), weight ratio | 0.45 | 0.49 | 0.44 | 0.53 | 0.49 | 0.49 | 0.50 | 0.53 | 0.57 |
| Acyclic(N4)/cyclic (< × N4), weight ratio | 3.95 | 1.01 | 0.35 | 3.06 | 1.23 | 2.62 | 0.56 | 1.12 | 1.18 |

TABLE XLII

| Example No. | 384 | 385 | 386 | 387 | 388 | 389 | 390 | 391 | 392 |
|---|---|---|---|---|---|---|---|---|---|
| Catalyst Type | XX | XX | XX | XX | XX | XX | XX | XX | XX |
| Catalyst weight, gm | 117 | 117 | 117 | 117 | 117 | 117 | 117 | 117 | 117 |
| Pressure, psig | 600 | 600 | 600 | 600 | 600 | 600 | 600 | 600 | 600 |
| Temperature, °C. | 269.3 | 269.2 | 279.4 | 258.8 | 269.2 | 259.4 | 279.2 | 268.9 | 269.6 |
| Time on organics, hrs. | 23.5 | 27.5 | 47.0 | 52.0 | 71.0 | 76.0 | 95.0 | 100.0 | 120.0 |
| Duration of run, hrs. | 2 | 2 | 2 | 2 | 2 | 2 | 2 | 2 | 2 |
| MEA SV, gmol/hr/kgcat | 2.58 | 2.36 | 2.57 | 2.67 | 2.50 | 2.45 | 1.13 | 0.81 | 1.98 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 3.709 | 3.837 | 8.600 | 2.804 | 3.721 | 0.488 | 9.601 | 7.741 | 3.411 |
| MEA | 9.936 | 9.370 | 5.731 | 16.450 | 9.968 | 25.695 | 3.708 | 7.550 | 16.344 |
| PIP | 2.708 | 2.524 | 4.204 | 1.433 | 2.717 | 0.842 | 4.962 | 3.887 | 2.182 |
| DETA | 38.446 | 38.390 | 33.775 | 45.291 | 38.571 | 55.220 | 34.097 | 37.900 | 43.567 |
| AEEA | 0.291 | 0.324 | 0.317 | 0.339 | 0.292 | 0.367 | 0.388 | 0.526 | 0.391 |
| AEP | 4.686 | 4.502 | 7.284 | 1.974 | 4.702 | 0.717 | 8.582 | 5.708 | 2.836 |
| HEP | 0.000 | 0.000 | 0.000 | 0.000 | 0.000 | 0.000 | 0.000 | 0.000 | 0.000 |
| TAEA | 3.835 | 4.377 | 2.941 | 4.188 | 3.848 | 1.310 | 2.846 | 3.803 | 3.747 |
| 1-TETA | 8.969 | 9.950 | 7.471 | 9.662 | 8.998 | 6.251 | 8.150 | 9.402 | 9.633 |
| DAEP | 1.874 | 1.752 | 2.889 | 0.521 | 1.880 | 0.065 | 2.947 | 1.720 | 0.876 |
| PEEDA | 0.861 | 0.698 | 1.317 | 0.180 | 0.864 | 0.000 | 1.373 | 0.837 | 0.409 |
| DPE | 0.078 | 0.000 | 0.059 | 0.000 | 0.078 | 0.000 | 0.000 | 0.000 | 0.000 |
| AE-TAEA | 0.228 | 0.307 | 0.306 | 0.270 | 0.229 | 0.199 | 0.000 | 0.000 | 0.000 |

TABLE XLII-continued

| Example No. | 384 | 385 | 386 | 387 | 388 | 389 | 390 | 391 | 392 |
|---|---|---|---|---|---|---|---|---|---|
| 1-TEPA | 4.090 | 4.452 | 0.103 | 3.018 | 4.103 | 0.000 | 2.329 | 3.192 | 2.764 |
| AE-DAEP | 0.690 | 0.464 | 0.318 | 0.583 | 0.692 | 0.000 | 0.787 | 0.451 | 0.000 |
| AE-PEEDA | 0.231 | 0.161 | 0.259 | 0.301 | 0.232 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.068 | 0.115 | 0.462 | 1.425 | 0.068 | 0.000 | 0.359 | 0.000 | 0.257 |
| BPEA | 0.160 | 0.349 | 0.515 | 0.765 | 0.161 | 0.000 | 0.358 | 0.278 | 0.000 |
| Others | 8.818 | 8.017 | 13.158 | 2.876 | 8.846 | 1.176 | 7.923 | 4.755 | 2.383 |
| MEA Conversion, % | 72.57 | 74.10 | 84.35 | 54.81 | 72.57 | 27.13 | 89.78 | 78.65 | 53.20 |
| DETA Conversion, % | 36.91 | 36.95 | 45.17 | 26.06 | 36.91 | 6.93 | 44.14 | 36.31 | 25.86 |
| Acyclic(N4), % | 81.99 | 85.39 | 70.94 | 95.19 | 81.99 | 99.14 | 71.79 | 83.78 | 91.24 |
| Acyclic(N5), % | 78.98 | 81.38 | 20.83 | 51.69 | 78.98 | 100.00 | 60.77 | 81.41 | 91.50 |
| Σ(N5)/Σ(N4), weight ratio | 0.35 | 0.35 | 0.13 | 0.44 | 0.35 | 0.03 | 0.25 | 0.25 | 0.21 |
| Acyclic(N4)/cyclic (< × N4), weight ratio | 1.25 | 1.51 | 0.66 | 3.37 | 1.25 | 4.66 | 0.62 | 1.09 | 2.12 |

TABLE XLIII

| Example No. | 393 | 394 | 395 | 396 | 397 | 398 | 399 | 400 | 401 |
|---|---|---|---|---|---|---|---|---|---|
| Catalyst Type | YY | YY | YY | YY | YY | YY | YY | YY | YY |
| Catalyst weight, gm | 109.7 | 109.7 | 109.7 | 109.7 | 109.7 | 109.7 | 109.7 | 109.7 | 109.7 |
| Pressure, psig | 599 | 600 | 600 | 600 | 600 | 600 | 600 | 600 | 600 |
| Temperature, °C. | 272.8 | 272.4 | 281.4 | 261.6 | 271.6 | 261.2 | 281.1 | 271.8 | 271.8 |
| Time on organics, hrs. | 4.5 | 25.5 | 30.5 | 49.5 | 54.5 | 73.5 | 78.5 | 96.5 | 98.0 |
| Duration of run, hrs. | 2 | 2 | 2 | 2 | 2 | 2 | 2 | 1 | 1 |
| MEA SV, gmol/hr/kgcat | 2.30 | 2.46 | 2.44 | 2.27 | 2.30 | 2.79 | 2.53 | 3.81 | 2.50 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.261 | 1.959 | 2.786 | 1.241 | 1.755 | 1.003 | 1.824 | 1.913 | 1.114 |
| MEA | 11.820 | 15.791 | 11.138 | 22.601 | 18.976 | 22.986 | 18.586 | 22.750 | 22.718 |
| PIP | 1.520 | 1.200 | 1.593 | 0.719 | 1.121 | 0.694 | 1.109 | 1.280 | 0.748 |
| DETA | 45.153 | 45.959 | 41.322 | 50.852 | 47.133 | 52.385 | 47.720 | 47.166 | 49.655 |
| AEEA | 0.011 | 0.410 | 0.153 | 0.999 | 0.569 | 0.740 | 0.269 | 0.266 | 0.465 |
| AEP | 2.740 | 1.799 | 2.738 | 1.065 | 1.366 | 0.830 | 1.702 | 2.957 | 1.051 |
| HEP | 0.000 | 0.000 | 0.000 | 0.000 | 0.000 | 0.000 | 0.000 | 0.000 | 0.000 |
| TAEA | 4.881 | 4.991 | 5.095 | 4.056 | 4.454 | 3.564 | 3.729 | 2.475 | 3.404 |
| 1-TETA | 14.240 | 13.568 | 13.497 | 10.800 | 11.889 | 10.434 | 10.309 | 7.038 | 9.572 |
| DAEP | 0.016 | 0.382 | 1.089 | 0.163 | 0.254 | 0.130 | 0.690 | 1.198 | 0.295 |
| PEEDA | 0.211 | 0.138 | 0.463 | 0.071 | 0.110 | 0.061 | 0.347 | 0.648 | 0.149 |
| DPE | 0.149 | 0.000 | 0.194 | 0.034 | 0.000 | 0.066 | 0.208 | 0.175 | 0.058 |
| AE-TAEA | 3.624 | 3.300 | 4.229 | 1.833 | 2.595 | 1.438 | 2.605 | 1.218 | 2.163 |
| 1-TEPA | 4.655 | 3.616 | 5.175 | 2.182 | 2.918 | 1.629 | 3.169 | 1.628 | 2.578 |
| AE-DAEP | 0.025 | 0.000 | 0.194 | 0.047 | 0.000 | 0.000 | 0.138 | 0.331 | 0.250 |
| AE-PEEDA | 0.000 | 0.000 | 0.091 | 0.000 | 0.000 | 0.000 | 0.071 | 0.087 | 0.071 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.044 | 0.000 | 0.126 | 0.000 | 0.000 | 0.000 | 0.000 | 0.000 | 0.000 |
| Others | 1.451 | 0.368 | 1.796 | 0.219 | 0.402 | 0.081 | 0.814 | 2.102 | 0.506 |
| MEA Conversion, % | 68.07 | 57.17 | 69.70 | 39.78 | 48.09 | 38.05 | 49.16 | 37.30 | 38.16 |
| DETA Conversion, % | 27.50 | 25.91 | 33.19 | 19.47 | 23.36 | 16.10 | 22.42 | 22.74 | 19.67 |
| Acyclic(N4), % | 98.07 | 97.27 | 91.41 | 98.23 | 97.82 | 98.20 | 91.85 | 82.48 | 96.27 |
| Acyclic(N5), % | 99.18 | 100.00 | 95.81 | 98.83 | 100.00 | 100.00 | 96.51 | 87.21 | 93.66 |
| Σ(N5)/Σ(N4), weight ratio | 0.43 | 0.36 | 0.48 | 0.27 | 0.33 | 0.22 | 0.39 | 0.28 | 0.38 |
| Acyclic(N4)/cyclic (< = N4), weight ratio | 4.12 | 5.27 | 3.06 | 7.24 | 5.73 | 7.86 | 3.46 | 1.52 | 5.64 |

TABLE XLIV

| Example No. | 402 | 403 | 404 | 405 |
|---|---|---|---|---|
| Catalyst Type | ZZ | ZZ | ZZ | ZZ |
| Catalyst weight, gm | 91.33 | 91.33 | 91.33 | 91.33 |
| Pressure, psig | 597 | 597 | 596 | 596 |
| Temperature, °C. | 270 | 284 | 258 | 272 |
| Time on organics, hrs. | 20.5 | 25.5 | 44.5 | 49.5 |
| Duration of run, hrs. | 2 | 2 | 2 | 2 |
| MEA SV, gmol/hr/kgcat | 2.39 | 2.58 | 2.52 | 2.54 |
| DETA/MEA mole ratio | 1.00 | 1.00 | 1.00 | 1.00 |
| NH$_3$/MEA mole ratio | 5.97 | 5.97 | 5.97 | 5.97 |
| Crude product composition, wt. % | | | | |
| EDA | 4.834 | 8.303 | 4.455 | 3.149 |
| MEA | 5.992 | 2.084 | 9.647 | 10.990 |
| PIP | 2.283 | 3.699 | 1.702 | 1.505 |
| DETA | 24.621 | 19.876 | 30.406 | 33.928 |
| AEEA | 1.216 | 0.261 | 1.338 | 2.268 |
| AEP | 3.659 | 6.379 | 2.728 | 2.013 |
| HEP | 0.000 | 0.000 | 0.000 | 0.000 |
| TAEA | 1.286 | 0.698 | 1.273 | 1.595 |
| 1-TETA | 12.156 | 7.714 | 10.112 | 12.504 |
| DAEP | 2.494 | 4.084 | 1.904 | 1.055 |
| PEEDA | 1.717 | 3.007 | 0.160 | 0.699 |
| DPE | 0.254 | 0.161 | 0.302 | 0.234 |
| AE-TAEA | 2.896 | 1.747 | 2.455 | 2.914 |
| 1-TEPA | 10.186 | 6.866 | 8.071 | 8.571 |
| AE-DAEP | 1.858 | 3.439 | 1.934 | 0.777 |

TABLE XLIV-continued

| Example No. | 402 | 403 | 404 | 405 |
|---|---|---|---|---|
| AE-PEEDA | 0.718 | 0.938 | 0.748 | 0.439 |
| iAE-PEEDA | 0.000 | 0.000 | 0.000 | 0.000 |
| AE-DPE | 0.091 | 0.255 | 0.169 | 0.039 |
| BPEA | 0.403 | 0.377 | 0.505 | 0.558 |
| Others | 14.617 | 19.011 | 15.441 | 9.062 |
| MEA Conversion, % | 84.09 | 94.41 | 74.56 | 70.46 |
| DETA Conversion, % | 61.16 | 68.33 | 52.34 | 45.81 |
| Acyclic(N4), % | 75.07 | 53.70 | 82.79 | 87.64 |
| Acyclic(N5), % | 80.99 | 63.23 | 75.82 | 86.37 |
| Σ(N5)/Σ(N4), weight ratio | 0.90 | 0.87 | 1.01 | 0.83 |
| Acyclic(N4)/cyclic (< = N4), weight ratio | 1.29 | 0.49 | 1.68 | 2.56 |

TABLE XLV

| Example No. | 406 | 407 | 408 | 409 | 410 | 411 |
|---|---|---|---|---|---|---|
| Catalyst Type | AAA | AAA | AAA | AAA | AAA | AAA |
| Catalyst weight, gm | 107 | 107 | 107 | 107 | 107 | 107 |
| Pressure, psig | 600 | 600 | 600 | 600 | 600 | 600 |
| Temperature, °C. | 277 | 277 | 277 | 313 | 314 | 314 |
| Time on organics, hrs. | 3.0 | 18.7 | 20.7 | 26.0 | 42.7 | 44.7 |
| Duration of run, hrs. | 1 | 16 | 2 | 2 | 16 | 2 |
| MEA SV, gmol/hr/kgcat | 2.26 | 2.24 | 2.27 | 2.10 | 2.08 | 2.11 |
| NH3 feedrate, gm/hr | 59 | 59 | 56 | 59 | 59 | 59 |
| Liquid feed composition, wt. % | | | | | | |
| DETA | 77.16 | 77.16 | 77.16 | 77.16 | 77.16 | 77.16 |
| MEA | 22.84 | 22.84 | 22.84 | 22.84 | 22.84 | 22.84 |
| EDA | — | — | — | — | — | — |
| Liquid product composition, wt. % | | | | | | |
| EDA | 1.69 | 1.53 | 1.11 | 5.98 | 5.97 | 6.14 |
| MeEDA | 0.00 | 0.00 | 0.00 | 0.00 | 0.00 | 0.00 |
| MEA | 10.19 | 7.13 | 8.50 | 1.44 | 1.75 | 1.70 |
| EtEDA | 0.00 | 0.00 | 0.00 | 0.00 | 0.00 | 0.00 |
| PIP | 1.17 | 1.29 | 1.08 | 4.26 | 4.38 | 4.67 |
| DETA | 63.75 | 67.41 | 69.62 | 56.36 | 56.78 | 56.34 |
| AEEA | 1.16 | 0.51 | 0.78 | 0.78 | 0.78 | 0.78 |
| AEP | 1.48 | 1.64 | 1.20 | 5.91 | 5.77 | 5.86 |
| HEP | 0.00 | 0.00 | 0.00 | 0.07 | 0.09 | 0.07 |
| TETA's | 13.90 | 13.58 | 11.94 | 14.21 | 13.22 | 13.20 |
| TEPA's | 4.76 | 4.63 | 3.90 | 5.29 | 3.76 | 3.77 |
| ROH Conversion % | 56.11 | 69.33 | 63.43 | 93.70 | 92.18 | 92.41 |
| Acyclic (N4)/cyclic (< = N4), weight ratio | 16.2 | 13.3 | 20.9 | 2.2 | 2.0 | 2.0 |
| Acyclic (N5)/cyclic (< = N5), weight ratio | 11.6 | 10.9 | 16.1 | 1.2 | 2.2 | 2.4 |
| Σ(N5)/Σ(N4), weight ratio | — | — | — | — | — | — |

TABLE XLVI

| Example No. | 412 | 413 | 414 | 415 | 416 | 417 | 418 | 419 | 420 | 421 |
|---|---|---|---|---|---|---|---|---|---|---|
| Catalyst Type | BBB | BBB | BBB | BBB | BBB | BBB | BBB | BBB | BBB | BBB |
| Catalyst weight, gm | 123.7 | 123.7 | 123.7 | 123.7 | 123.7 | 123.7 | 123.7 | 123.7 | 123.7 | 123.7 |
| Pressure, psig | 600 | 600 | 600 | 600 | 600 | 600 | 600 | 600 | 600 | 600 |
| Temperature, °C. | 266 | 272 | 271 | 270 | 298 | 300 | 300 | 299 | 303 | 302 |
| Time on organics, hrs. | 10.5 | 15.5 | 32.5 | 34.5 | 40.5 | 55.5 | 57.5 | 63.0 | 81.5 | 129.5 |
| Duration of run, hrs. | 10 | 2 | 16 | 2 | 2 | 15 | 15 | 2 | 2 | 2 |
| MEA SV, gmol/hr/kgcat | 1.94 | 1.72 | 1.97 | 1.97 | 2.02 | 1.94 | 0.26 | 1.88 | 1.97 | 1.89 |
| NH3 feedrate, gm/hr | 38.4 | 56.0 | 57.0 | 63.0 | 59.0 | 60.2 | 57.5 | 57.0 | 58.5 | 46.5 |
| Liquid feed composition, wt. % | | | | | | | | | | |
| DETA | 77.16 | 77.16 | 77.16 | 77.16 | 77.16 | 77.16 | 77.16 | 77.16 | 77.16 | 77.16 |
| MEA | 22.84 | 22.84 | 22.84 | 22.84 | 22.84 | 22.84 | 22.84 | 22.84 | 22.84 | 22.84 |
| Liquid product composition, wt. % | | | | | | | | | | |
| EDA | 0.97 | 1.21 | 1.01 | 0.94 | 3.46 | 2.86 | 2.63 | 2.72 | 2.46 | 2.44 |
| MeEDA | 0.00 | 0.00 | 0.00 | 0.00 | 0.00 | 0.00 | 0.00 | 0.00 | 0.00 | 0.00 |
| MEA | 13.53 | 11.37 | 11.57 | 12.57 | 4.80 | 6.56 | 7.31 | 7.23 | 8.08 | 7.91 |
| EtEDA | 0.00 | 0.00 | 0.00 | 0.00 | 0.00 | 0.00 | 0.00 | 0.00 | 0.00 | 0.00 |
| PIP | 0.63 | 0.72 | 0.58 | 0.58 | 2.14 | 1.81 | 1.37 | 1.78 | 1.56 | 1.61 |
| DETA | 74.34 | 73.54 | 74.39 | 75.32 | 69.81 | 71.72 | 73.83 | 72.52 | 73.94 | 73.16 |
| AEEA | 0.91 | 0.72 | 0.86 | 0.86 | 0.34 | 0.32 | 0.28 | 0.39 | 0.52 | 0.47 |
| AEP | 0.59 | 0.81 | 0.71 | 0.63 | 2.42 | 1.93 | 1.74 | 1.74 | 1.55 | 1.59 |
| HEP | 0.00 | 0.00 | 0.00 | 0.00 | 0.00 | 0.00 | 0.00 | 0.00 | 0.00 | 0.00 |
| TETA's | 7.74 | 9.46 | 8.96 | 7.68 | 12.10 | 10.11 | 8.91 | 9.43 | 8.16 | 7.76 |
| TEPA's | 1.07 | 1.81 | 1.48 | 1.17 | 2.94 | 2.34 | 1.88 | 2.12 | 1.79 | 1.93 |
| ROH Conversion % | 41.89 | 51.36 | 50.41 | 46.08 | 79.45 | 71.67 | 68.42 | 68.80 | 65.08 | 65.40 |
| Acyclic (N4)/cyclic (< = N4), weight ratio | 100.0 | 73.1 | 38.5 | 74.8 | 8.1 | 8.9 | 10.6 | 9.9 | 10.1 | 9.4 |
| Acyclic (N5)/cyclic (< = N5), weight ratio | — | — | — | — | — | 5.1 | 5.5 | 8.0 | 8.2 | 5.2 |
| Σ(N5)/Σ(N4), | — | — | — | — | — | — | — | — | — | — |

TABLE XLVI-continued

| Example No. | 412 | 413 | 414 | 415 | 416 | 417 | 418 | 419 | 420 | 421 |
|---|---|---|---|---|---|---|---|---|---|---|
| weight ratio | | | | | | | | | | |

TABLE XLVII

| Example No. | 422 | 423 | 424 | 425 | 426 | 427 | 428 | 429 | 430 |
|---|---|---|---|---|---|---|---|---|---|
| Catalyst Type | CCC | CCC | CCC | CCC | CCC | CCC | CCC | CCC | CCC |
| Catalyst weight, gm | 105.7 | 105.7 | 105.7 | 105.7 | 105.7 | 105.7 | 105.7 | 105.7 | 105.7 |
| Pressure, psig | 600 | 600 | 600 | 600 | 600 | 600 | 600 | 600 | 600 |
| Temperature, °C. | 268 | 281 | 275 | 302 | 304 | 304 | 303 | 302 | 302 |
| Time on organics, hrs. | 4.7 | 19.7 | 21.7 | 26.7 | 43.7 | 45.7 | 51.2 | 66.7 | 68.7 |
| Duration of run, hrs. | 2 | 15 | 2 | 2 | 17 | 2 | 2 | 14 | 2 |
| MEA SV, gmol/hr/kgcat | 2.09 | 2.13 | 2.20 | 2.06 | 2.14 | 2.09 | 1.90 | 2.02 | 1.91 |
| NH$_3$ feedrate, gm/hr | 49.5 | 42.8 | 54.5 | 47.5 | 51.0 | 41.5 | 54.5 | 58.8 | 53.0 |
| Liquid feed composition, wt. % | | | | | | | | | |
| DETA | 77.16 | 77.16 | 77.16 | 77.16 | 77.16 | 77.16 | 66.46 | 66.46 | 66.46 |
| MEA | 22.84 | 22.84 | 22.84 | 22.84 | 22.84 | 22.84 | — | — | — |
| AEEA | — | — | — | — | — | — | 33.54 | 33.54 | 33.54 |
| Liquid product composition, wt. % | | | | | | | | | |
| EDA | 2.25 | 1.42 | 1.17 | 4.33 | 4.33 | 4.06 | 2.41 | 2.32 | 2.62 |
| MeEDA | 0.00 | 0.00 | 0.00 | 0.00 | 0.00 | 0.00 | 0.00 | 0.00 | 0.00 |
| MEA | 8.59 | 11.37 | 12.86 | 5.60 | 6.05 | 5.73 | 0.00 | 0.00 | 0.00 |
| EtEDA | 0.00 | 0.00 | 0.00 | 0.00 | 0.00 | 0.00 | 0.00 | 0.00 | 0.00 |
| PIP | 1.36 | 0.68 | 0.49 | 1.69 | 1.70 | 1.69 | 9.19 | 9.15 | 9.13 |
| DETA | 70.30 | 74.76 | 76.82 | 71.05 | 71.22 | 71.97 | 68.27 | 68.90 | 70.40 |
| AEEA | 0.80 | 0.97 | 0.85 | 0.31 | 0.40 | 0.00 | 1.15 | 1.10 | 0.53 |
| AEP | 1.27 | 0.69 | 0.53 | 1.68 | 1.67 | 1.61 | 1.32 | 1.33 | 1.51 |
| HEP | 0.00 | 0.00 | 0.00 | 0.00 | 0.00 | 0.00 | 0.00 | 0.00 | 0.00 |
| TETA's | 10.97 | 8.09 | 5.52 | 9.47 | 8.65 | 7.79 | 6.49 | 6.41 | 6.60 |
| TEPA's | 2.93 | 1.60 | 0.93 | 2.07 | 1.87 | 1.65 | 7.25 | 7.27 | 5.87 |
| ROH Conversion % | 63.07 | 51.25 | 44.36 | 75.40 | 73.30 | 74.34 | 96.50 | 96.70 | 98.40 |
| Acyclic (N4)/cyclic (< = N4), weight ratio | 9.09 | 72.20 | 100.00 | 8.90 | 8.70 | 7.90 | 0.30 | 0.30 | 0.30 |
| Acyclic (N5)/cyclic (< = N5), weight ratio | 28.90 | 100.00 | 100.00 | 15.10 | 10.60 | 9.60 | 13.10 | 13.60 | 9.50 |
| Σ(N5)/Σ(N4), weight ratio | — | — | — | — | — | — | 1.10 | 1.10 | 0.90 |

TABLE XLVIII

| Example No. | 431 | 432 | 433 | 434 | 435 | 436 | 437 | 438 | 439 | 440 | 441 |
|---|---|---|---|---|---|---|---|---|---|---|---|
| Catalyst Type | DDD | DDD | DDD | DDD | DDD | DDD | DDD | DDD | DDD | DDD | DDD |
| Catalyst weight, gm | 121 | 121 | 121 | 121 | 121 | 121 | 121 | 121 | 121 | 121 | 121 |
| Pressure, psig | 600 | 600 | 600 | 600 | 600 | 600 | 600 | 600 | 600 | 600 | 600 |
| Temperature, °C. | 279 | 270 | 270 | 269 | 269 | 275 | 270 | 272 | 274 | 272 | 258 |
| Time on organics, hrs. | 4.5 | 18.5 | 35.5 | 37.5 | 43.5 | 54.5 | 62.5 | 66.0 | 82.0 | 84.0 | 90.7 |
| Duration of run, hrs. | 2 | 2 | 16 | 2 | 2 | 2 | 2 | 2 | 15 | 2 | 2 |
| MEA SV, gmol/hr/kgcat | 2.00 | 1.98 | 1.98 | 2.03 | 2.03 | 2.01 | 1.97 | 1.68 | 1.70 | 1.69 | 1.33 |
| NH$_3$ feedrate, gm/hr | 67.2 | 72.0 | 48.1 | 46.0 | 44.5 | 41.1 | 47.5 | 48.0 | 45.1 | 49.0 | 86.5 |
| Liquid feed composition, wt. % | | | | | | | | | | | |
| DETA | 77.16 | 77.16 | 77.16 | 77.16 | 77.16 | 77.16 | 77.16 | 66.46 | 66.46 | 66.46 | 66.46 |
| MEA | 22.84 | 22.84 | 22.84 | 22.84 | 22.84 | 22.84 | 22.84 | — | — | — | — |
| AEEA | — | — | — | — | — | — | — | 33.54 | 33.54 | 33.54 | 33.54 |
| Liquid product composition, wt. % | | | | | | | | | | | |
| EDA | 5.79 | 1.61 | 1.48 | 1.43 | 1.18 | 1.34 | 1.37 | 1.05 | 1.04 | 1.08 | 0.48 |
| MeEDA | 0.00 | 0.00 | 0.00 | 0.00 | 0.00 | 0.00 | 0.00 | 0.00 | 0.00 | 0.00 | 0.00 |
| MEA | 2.74 | 6.67 | 7.72 | 7.67 | 7.39 | 6.27 | 6.43 | 0.31 | 0.11 | 0.12 | 0.15 |
| EtEDA | 0.00 | 0.00 | 0.00 | 0.00 | 0.00 | 0.00 | 0.00 | 0.00 | 0.00 | 0.00 | 0.00 |
| PIP | 4.65 | 1.25 | 1.17 | 1.16 | 0.99 | 1.15 | 1.21 | 10.37 | 10.57 | 10.55 | 7.06 |
| DETA | 61.98 | 71.25 | 73.17 | 73.07 | 69.92 | 68.69 | 68.71 | 58.64 | 58.83 | 59.53 | 67.06 |
| AEEA | 0.00 | 0.16 | 0.22 | 0.24 | 0.45 | 0.42 | 0.37 | 5.96 | 6.64 | 6.72 | 15.36 |
| AEP | 5.74 | 1.29 | 0.94 | 0.93 | 0.97 | 1.13 | 1.18 | 1.35 | 1.26 | 1.20 | 0.59 |
| HEP | 0.00 | 0.00 | 0.00 | 0.00 | 0.00 | 0.00 | 0.00 | 0.00 | 0.00 | 0.00 | 0.00 |
| TETA's | 13.80 | 14.03 | 12.81 | 12.89 | 14.92 | 16.23 | 15.76 | 8.51 | 8.04 | 7.49 | 3.04 |
| TEPA's | 3.53 | 2.45 | 1.96 | 2.10 | 3.18 | 3.62 | 3.71 | 10.70 | 11.09 | 10.99 | 6.08 |
| ROH Conversion % | 88.45 | 71.55 | 67.20 | 67.43 | 68.55 | 73.37 | 72.65 | 82.40 | 80.50 | 80.30 | 55.20 |
| Acyclic (N4)/cyclic (< = N4), weight ratio | 3.69 | 8.70 | 46.60 | 49.50 | 44.30 | 38.60 | 34.50 | 0.25 | 0.17 | 0.18 | 0.12 |
| Acyclic (N5)/cyclic (< = N5), weight ratio | 2.70 | 100.00 | 100.00 | 100.00 | 100.00 | 100.00 | 100.00 | 34.00 | 38.70 | 44.00 | 100.00 |
| Σ(N5)/Σ(N4), weight ratio | — | — | — | — | — | — | — | 1.30 | 1.40 | 1.50 | 2.00 |

TABLE XLIX

| Example No. | 442 | 443 | 444 | 445 | 446 | 447 | 448 | 449 | 450 |
|---|---|---|---|---|---|---|---|---|---|
| Catalyst Type | EEE | EEE | EEE | EEE | EEE | EEE | EEE | EEE | EEE |
| Catalyst weight, gm | 118.7 | 118.7 | 118.7 | 118.7 | 118.7 | 118.7 | 118.7 | 118.7 | 118.7 |
| Pressure, psig | 600 | 600 | 600 | 600 | 600 | 600 | 600 | 600 | 600 |
| Temperature, °C. | 267 | 268 | 267 | 289 | 284 | 301 | 291 | 298 | 260 |
| Time on organics, hrs. | 8.5 | 19.0 | 21.0 | 25.0 | 28.0 | 32.0 | 35.0 | 39.0 | 43.0 |
| Duration of run, hrs. | 2 | 10 | 2 | 2 | 2 | 2 | 2 | 2 | 2 |
| MEA SV, gmol/hr/kgcat | 2.01 | 2.04 | 2.11 | 2.00 | 1.94 | 1.58 | 1.65 | 1.57 | 1.68 |
| $NH_3$ feedrate, gm/hr | 45.2 | 47.4 | 47.5 | 54.0 | 51.0 | 46.0 | 43.0 | 30.0 | 46.0 |
| Liquid feed composition, wt. % | | | | | | | | | |
| DETA | 77.16 | 77.16 | 77.16 | 77.16 | 77.16 | 66.46 | 66.46 | 66.46 | 66.46 |
| MEA | 22.84 | 22.84 | 22.84 | 22.84 | 22.84 | — | — | — | — |
| AEEA | — | — | — | — | — | 33.54 | 33.54 | 33.54 | 33.54 |
| Liquid product composition, wt. % | | | | | | | | | |
| EDA | 1.12 | 0.95 | 0.83 | 2.89 | 2.86 | 2.46 | 1.69 | 2.41 | 0.31 |
| MeEDA | 0.00 | 0.00 | 0.00 | 0.00 | 0.00 | 0.00 | 0.00 | 0.00 | 0.00 |
| MEA | 11.83 | 12.17 | 12.64 | 6.50 | 6.93 | 0.45 | 0.52 | 0.34 | 0.45 |
| EtEDA | 0.00 | 0.00 | 0.00 | 0.00 | 0.00 | 0.00 | 0.00 | 0.00 | 0.00 |
| PIP | 0.94 | 0.63 | 0.49 | 1.87 | 1.84 | 11.04 | 10.33 | 11.22 | 3.39 |
| DETA | 76.42 | 79.20 | 76.28 | 68.84 | 71.08 | 57.52 | 61.86 | 67.91 | 75.51 |
| AEEA | 0.36 | 0.28 | 0.54 | 0.17 | 0.17 | 0.90 | 2.98 | 0.97 | 17.00 |
| AEP | 0.63 | 0.39 | 0.41 | 1.88 | 1.71 | 2.52 | 1.37 | 1.71 | 0.27 |
| HEP | 0.00 | 0.00 | 0.00 | 0.00 | 0.00 | 0.00 | 0.00 | 0.00 | 0.00 |
| TETA's | 7.47 | 5.50 | 7.52 | 11.98 | 10.95 | 11.25 | 8.74 | 6.93 | 1.01 |
| TEPA's | 1.02 | 0.54 | 0.97 | 3.35 | 2.49 | 8.61 | 9.41 | 5.34 | 2.07 |
| ROH Conversion % | 49.35 | 47.67 | 45.70 | 71.94 | 70.17 | 97.30 | 91.10 | 97.10 | 49.80 |
| Acyclic (N4)/cyclic (< = N4), weight ratio | 100.00 | 100.00 | 100.00 | 10.60 | 13.70 | 0.30 | 0.20 | 0.20 | 0.20 |
| Acyclic (N5)/cyclic (< = N5), weight ratio | 100.00 | 100.00 | 100.00 | 5.78 | 8.20 | 4.40 | 22.80 | 100.00 | 100.00 |
| Σ(N5)/Σ(N4), weight ratio | — | — | — | — | — | 0.80 | 1.10 | 0.80 | 2.00 |

TABLE L

| Example No. | 451 | 452 | 453 | 454 | 455 | 456 | 457 | 458 | 459 | 460 | 461 | 462 |
|---|---|---|---|---|---|---|---|---|---|---|---|---|
| Catalyst Type | FFF | FFF | FFF | FFF | FFF | FFF | FFF | FFF | FFF | FFF | FFF | FFF |
| Catalyst weight, gm | 123.6 | 123.6 | 123.6 | 123.6 | 123.6 | 123.6 | 123.6 | 123.6 | 123.6 | 123.6 | 123.6 | 123.6 |
| Pressure, psig | 600 | 600 | 600 | 600 | 600 | 600 | 600 | 600 | 600 | 600 | 600 | 600 |
| Temperature, °C. | 279 | 277 | 276 | 260 | 263 | 264 | 261 | 262 | 263 | 274 | 277 | 276 |
| Time on organics, hrs. | 4.7 | 22.0 | 24.0 | 29.0 | 45.0 | 47.0 | 52.5 | 69.0 | 71.0 | 76.5 | 93.5 | 95.0 |
| Duration of run, hrs. | 2 | 17 | 2 | 2 | 16 | 2 | 2 | 16 | 2 | 2 | 16 | 1 |
| MEA SV, gmol/hr/kgcat | 1.92 | 1.96 | 1.93 | 1.96 | 1.97 | 1.99 | 1.73 | 1.70 | 1.74 | 1.65 | 1.66 | 1.73 |
| $NH_3$ feedrate, gm/hr | 53.0 | 48.4 | 55.0 | 52.0 | 49.3 | 49.5 | 47.0 | 47.3 | 46.5 | 49.0 | 49.9 | 54.6 |
| Liquid feed composition, wt. % | | | | | | | | | | | | |
| PIP | — | — | — | — | — | — | — | — | — | — | — | — |
| DETA | 77.16 | 77.16 | 77.16 | 77.16 | 77.16 | 77.16 | 66.46 | 66.46 | 66.46 | 66.46 | 66.46 | 66.46 |
| MEA | 22.84 | 22.84 | 22.84 | 22.84 | 22.84 | 22.84 | — | — | — | — | — | — |
| AEEA | — | — | — | — | — | — | 33.54 | 33.54 | 33.54 | 33.54 | 33.54 | 33.54 |
| Liquid product composition, wt. % | | | | | | | | | | | | |
| EDA | 3.96 | 3.55 | 3.17 | 1.21 | 1.14 | 1.30 | 0.77 | 0.77 | 0.67 | 1.58 | 1.88 | 1.60 |
| MeEDA | 0.00 | 0.00 | 0.00 | 0.00 | 0.00 | 0.00 | 0.00 | 0.00 | 0.00 | 0.00 | 0.00 | 0.00 |
| MEA | 2.91 | 2.56 | 2.50 | 7.40 | 7.44 | 7.38 | 0.18 | 0.00 | 0.00 | 0.00 | 0.00 | 0.00 |
| EtEDA | 0.00 | 0.00 | 0.00 | 0.00 | 0.00 | 0.00 | 0.00 | 0.00 | 0.00 | 0.00 | 0.00 | 0.00 |
| PIP | 3.12 | 2.46 | 2.21 | 1.06 | 1.05 | 1.15 | 8.23 | 8.70 | 8.57 | 10.86 | 10.76 | 10.60 |
| DETA | 61.14 | 63.82 | 60.32 | 71.24 | 72.08 | 68.84 | 65.43 | 66.94 | 69.33 | 65.27 | 62.85 | 65.63 |
| AEEA | 0.00 | 0.00 | 0.00 | 0.00 | 0.00 | 0.29 | 3.28 | 3.21 | 3.00 | 0.42 | 0.35 | 0.00 |
| AEP | 4.38 | 3.42 | 3.06 | 1.06 | 0.99 | 1.07 | 0.00 | 0.91 | 0.88 | 1.66 | 1.77 | 1.70 |
| HEP | 0.00 | 0.00 | 0.00 | 0.00 | 0.00 | 0.00 | 0.00 | 0.00 | 0.00 | 0.00 | 0.00 | 0.00 |
| TETA's | 17.74 | 18.49 | 18.86 | 15.11 | 14.78 | 15.71 | 6.46 | 5.73 | 5.20 | 7.71 | 8.60 | 7.54 |
| TEPA's | 4.05 | 4.67 | 5.70 | 2.73 | 2.32 | 3.70 | 14.12 | 13.23 | 12.12 | 11.71 | 11.80 | 11.62 |
| ROH Conversion % | 87.61 | 89.27 | 89.19 | 68.76 | 68.57 | 68.77 | 90.40 | 90.70 | 91.30 | 99.80 | 99.00 | 100.00 |
| Acyclic (N4)/cyclic (< = N4), weight ratio | 7.20 | 11.20 | 11.20 | 80.70 | 100.00 | 46.90 | 0.30 | 0.20 | 0.10 | 0.20 | 0.30 | 0.20 |
| Acyclic (N5)/cyclic (< = N5), weight ratio | 100.00 | 18.00 | 17.30 | 100.00 | 100.00 | 100.00 | 85.10 | 94.20 | 100.00 | 35.10 | 26.40 | 30.80 |
| Σ(N5)/Σ(N4), weight ratio | — | — | — | — | — | — | 2.20 | 2.30 | 2.30 | 1.50 | 1.40 | 1.50 |

TABLE LI

| Example No. | 463 | 464 | 465 | 466 | 467 | 468 | 469 | 470 | 471 | 472 | 473 |
|---|---|---|---|---|---|---|---|---|---|---|---|
| Catalyst Type | GGG | GGG | GGG | GGG | GGG | GGG | GGG | GGG | GGG | GGG | GGG |
| Catalyst weight, gm | 116.6 | 116.6 | 116.6 | 116.6 | 116.6 | 116.6 | 116.6 | 116.6 | 116.6 | 116.6 | 116.6 |
| Pressure, psig | 600 | 600 | 600 | 600 | 600 | 600 | 600 | 600 | 600 | 600 | 600 |
| Temperature, °C. | 277 | 284 | 272 | 272 | 277 | 266 | 267 | 266 | 282 | 282 | 281 |

TABLE LI-continued

| Example No. | 463 | 464 | 465 | 466 | 467 | 468 | 469 | 470 | 471 | 472 | 473 |
|---|---|---|---|---|---|---|---|---|---|---|---|
| Time on organics, hrs. | 4.5 | 20.0 | 22.0 | 27.5 | 44.5 | 52.5 | 69.5 | 71.5 | 76.5 | 94.5 | 96.5 |
| Duration of run, hrs. | 2 | 15 | 2 | 2 | 15 | 2 | 2 | 2 | 2 | 16 | 2 |
| MEA SV, gmol/hr/kgcat | 2.02 | 2.05 | 2.13 | 2.03 | 2.02 | 1.76 | 1.80 | 1.79 | 1.72 | 2.04 | 2.06 |
| $NH_3$ feedrate, gm/hr | 60.5 | 54.7 | 57.0 | 54.5 | 43.5 | 68.5 | 53.1 | 45.5 | 66.0 | 60.6 | 56.0 |
| Liquid feed composition, wt. % | | | | | | | | | | | |
| DETA | 77.16 | 77.16 | 77.16 | 77.16 | 77.16 | 66.46 | 66.46 | 66.46 | 66.46 | 77.16 | 77.16 |
| MEA | 22.84 | 22.84 | 22.84 | 22.84 | 22.84 | — | — | — | — | 22.84 | 22.84 |
| AEEA | — | — | — | — | — | 33.54 | 33.54 | 33.54 | 33.54 | — | — |
| Liquid product composition, wt. % | | | | | | | | | | | |
| EDA | 2.05 | 2.24 | 1.23 | 0.78 | 0.73 | 0.38 | 0.32 | 0.39 | 1.58 | 2.16 | 2.07 |
| MeEDA | 0.00 | 0.00 | 0.00 | 0.00 | 0.00 | 0.00 | 0.00 | 0.00 | 0.00 | 0.00 | 0.00 |
| MEA | 5.90 | 3.75 | 6.68 | 8.22 | 8.34 | 0.26 | 0.00 | 0.19 | 0.00 | 4.77 | 4.91 |
| EtEDA | 0.00 | 0.00 | 0.00 | 0.00 | 0.00 | 0.00 | 0.00 | 0.00 | 0.00 | 0.00 | 0.00 |
| PIP | 2.21 | 2.48 | 1.56 | 1.14 | 1.10 | 6.66 | 6.97 | 6.77 | 9.99 | 2.49 | 2.37 |
| DETA | 74.52 | 75.33 | 75.56 | 79.77 | 81.46 | 72.66 | 76.76 | 73.28 | 65.22 | 73.27 | 75.76 |
| AEEA | 0.00 | 0.00 | 0.00 | 0.00 | 0.00 | 6.14 | 5.08 | 6.32 | 0.00 | 0.00 | 0.00 |
| AEP | 2.09 | 2.54 | 1.56 | 1.05 | 1.06 | 0.64 | 0.61 | 0.59 | 1.90 | 2.48 | 2.38 |
| HEP | 0.00 | 0.00 | 0.00 | 0.00 | 0.00 | 0.00 | 0.00 | 0.00 | 0.00 | 0.00 | 0.00 |
| TETA's | 11.24 | 11.94 | 11.23 | 8.09 | 6.69 | 5.09 | 4.22 | 4.81 | 9.47 | 10.79 | 10.14 |
| TEPA's | 1.89 | 1.67 | 2.03 | 0.92 | 0.62 | 7.62 | 5.92 | 7.17 | 9.26 | 3.34 | 2.36 |
| ROH Conversion % | 75.18 | 84.30 | 71.82 | 65.14 | 64.60 | 82.00 | 85.20 | 81.60 | 100.00 | 79.85 | 79.41 |
| Acyclic (N4)/cyclic (< = N4), weight ratio | 15.00 | 12.40 | 17.20 | 100.00 | 100.00 | 0.11 | 0.00 | 0.10 | 0.20 | 7.30 | 8.40 |
| Acyclic (N5)/cyclic (< = N5), weight ratio | 100.00 | 100.00 | 100.00 | 100.00 | 100.00 | 62.00 | 100.00 | 70.20 | 7.21 | 2.50 | 7.40 |
| $\Sigma(N5)/\Sigma(N4)$, weight ratio | — | — | — | — | — | 1.30 | 1.40 | 1.50 | 1.00 | — | — |

TABLE LII

| Example No. | 474 | 475 | 476 | 477 | 478 | 479 | 480 | 481 | 482 | 483 | 484 | 485 |
|---|---|---|---|---|---|---|---|---|---|---|---|---|
| Catalyst Type | HHH | HHH | HHH | HHH | HHH | HHH | HHH | HHH | HHH | HHH | HHH | HHH |
| Catalyst weight, gm | 118.4 | 118.4 | 118.4 | 118.4 | 118.4 | 118.4 | 118.4 | 118.4 | 118.4 | 118.4 | 118.4 | 118.4 |
| Pressure, psig | 600 | 600 | 600 | 600 | 600 | 600 | 600 | 600 | 600 | 600 | 600 | 600 |
| Temperature, °C. | 267 | 276 | 276 | 295 | 296 | 296 | 298 | 270 | 271 | 266 | 267 | 268 |
| Time on organics, hrs. | 8.0 | 21.0 | 23.0 | 29.0 | 45.0 | 47.0 | 53.0 | 69.0 | 71.0 | 77.0 | 93.0 | 95.0 |
| Duration of run, hrs. | 2 | 13 | 2 | 2 | 16 | 2 | 2 | 16 | 2 | 2 | 16 | 2 |
| MEA SV, gmol/hr/kgcat | 1.96 | 2.00 | 2.06 | 2.01 | 1.99 | 2.01 | 1.68 | 1.72 | 1.71 | 1.98 | 2.00 | 2.01 |
| $NH_3$ feedrate, gm/hr | 65.5 | 57.4 | 53.5 | 59.0 | 46.6 | 36.0 | 64.0 | 49.5 | 51.5 | 51.0 | 49.3 | 49.5 |
| Liquid feed composition, wt. % | | | | | | | | | | | | |
| DETA | 77.16 | 77.16 | 77.16 | 77.16 | 77.16 | 77.16 | 66.46 | 66.46 | 66.46 | 77.16 | 77.16 | 77.16 |
| MEA | 22.84 | 22.84 | 22.84 | 22.84 | 22.84 | 22.84 | — | — | — | 22.84 | 22.84 | 22.84 |
| AEEA | — | — | — | — | — | — | 33.54 | 33.54 | 33.54 | — | — | — |
| Liquid product composition, wt. % | | | | | | | | | | | | |
| EDA | 0.81 | 0.99 | 1.00 | 3.45 | 3.60 | 3.29 | 2.33 | 0.00 | 0.37 | 0.27 | 0.48 | 0.51 |
| MeEDA | 0.00 | 0.00 | 0.00 | 0.00 | 0.00 | 0.00 | 0.00 | 0.00 | 0.00 | 0.00 | 0.00 | 0.00 |
| MEA | 8.16 | 6.51 | 7.10 | 1.45 | 2.25 | 2.43 | 0.00 | 0.00 | 0.00 | 10.27 | 10.50 | 10.46 |
| EtEDA | 0.00 | 0.00 | 0.00 | 0.00 | 0.00 | 0.00 | 0.00 | 0.00 | 0.00 | 0.00 | 0.00 | 0.00 |
| PIP | 1.03 | 1.41 | 1.44 | 3.95 | 4.17 | 4.13 | 12.33 | 6.69 | 6.85 | 0.80 | 0.75 | 0.77 |
| DETA | 77.87 | 78.14 | 74.65 | 76.12 | 72.14 | 74.46 | 69.31 | 82.62 | 77.14 | 84.56 | 84.28 | 84.63 |
| AEEA | 0.00 | 0.00 | 0.00 | 0.00 | 0.00 | 0.00 | 0.00 | 4.62 | 6.65 | 0.00 | 0.00 | 0.00 |
| AEP | 1.04 | 1.43 | 1.38 | 4.56 | 4.28 | 4.25 | 3.27 | 0.72 | 0.61 | 0.74 | 0.72 | 0.71 |
| HEP | 0.00 | 0.00 | 0.00 | 0.00 | 0.00 | 0.00 | 0.00 | 0.00 | 0.00 | 0.00 | 0.00 | 0.00 |
| TETA's | 9.61 | 9.93 | 11.80 | 9.39 | 10.88 | 9.44 | 8.73 | 2.75 | 3.71 | 2.87 | 2.89 | 2.61 |
| TEPA's | 1.49 | 1.59 | 2.63 | 1.08 | 2.34 | 1.86 | 3.29 | 2.60 | 4.50 | 0.49 | 0.39 | 0.00 |
| ROH Conversion % | 65.45 | 72.55 | 70.09 | 93.97 | 90.62 | 89.88 | 100.00 | 86.50 | 80.60 | 56.14 | 55.12 | 55.13 |
| Acyclic (N4)/cyclic (< = N4), weight ratio | 53.30 | 37.90 | 23.80 | 4.10 | 4.40 | 4.10 | 0.20 | 0.00 | 0.00 | 100.00 | 100.00 | 100.00 |
| Acyclic (N5)/cyclic (< = N5), weight ratio | 100.00 | 100.00 | 100.00 | 1.90 | 2.10 | 2.00 | 5.40 | 100.00 | 100.00 | 100.00 | 100.00 | 100.00 |
| $\Sigma(N5)/\Sigma(N4)$, weight ratio | — | — | — | — | — | — | 0.40 | 1.00 | 1.20 | — | — | — |

TABLE LIII

| Example No. | 486 | 487 | 488 | 489 | 490 | 491 | 492 | 493 | 494 | 495 | 496 | 497 |
|---|---|---|---|---|---|---|---|---|---|---|---|---|
| Catalyst Type | III | III | III | III | III | III | III | III | III | III | III | III |
| Catalyst weight, gm | 118.2 | 118.2 | 118.2 | 118.2 | 118.2 | 118.2 | 118.2 | 118.2 | 118.2 | 118.2 | 118.2 | 118.2 |
| Pressure, psig | 600 | 600 | 600 | 600 | 600 | 600 | 600 | 600 | 600 | 600 | 600 | 600 |
| Temperature, °C. | 272 | 271 | 273 | 299 | 301 | 300 | 302 | 302 | 273 | 270 | 272 | 272 |
| Time on organics, hrs. | 4.0 | 17.0 | 19.0 | 25.0 | 42.5 | 44.5 | 50.5 | 59.0 | 62.0 | 72.7 | 82.0 | 84.0 |
| Duration of run, hrs. | 2 | 13 | 2 | 2 | 17 | 2 | 2 | 8 | 2 | 2 | 9 | 2 |
| MEA SV, gmol/hr/kgcat | 1.98 | 1.99 | 1.98 | 1.98 | 1.96 | 2.02 | 1.69 | 1.68 | 1.67 | 1.99 | 2.08 | 2.01 |
| $NH_3$ feedrate, gm/hr | 69.0 | 70.7 | 59.0 | 55.5 | 49.9 | 65.5 | 48.0 | 47.8 | 57.5 | 45.0 | 44.0 | 41.0 |

TABLE LIII-continued

| Example No. | 486 | 487 | 488 | 489 | 490 | 491 | 492 | 493 | 494 | 495 | 496 | 497 |
|---|---|---|---|---|---|---|---|---|---|---|---|---|
| Liquid feed composition, wt. % | | | | | | | | | | | | |
| DETA | 77.16 | 77.16 | 77.16 | 77.16 | 77.16 | 77.16 | 66.46 | 66.46 | 66.46 | 77.16 | 77.16 | 77.16 |
| MEA | 22.84 | 22.84 | 22.84 | 22.84 | 22.84 | 22.84 | — | — | — | 22.84 | 22.84 | 22.84 |
| AEEA | — | — | — | — | — | — | 33.54 | 33.54 | 33.54 | — | — | — |
| Liquid product composition, wt. % | | | | | | | | | | | | |
| EDA | 0.74 | 0.72 | 0.58 | 2.88 | 2.15 | 2.01 | 1.65 | 1.44 | 0.00 | 0.21 | 0.22 | 0.00 |
| MeEDA | 0.00 | 0.00 | 0.00 | 0.00 | 0.00 | 0.00 | 0.00 | 0.00 | 0.00 | 0.00 | 0.00 | 0.00 |
| MEA | 7.89 | 7.63 | 8.40 | 1.99 | 3.10 | 3.86 | 0.00 | 0.00 | 0.19 | 11.14 | 11.57 | 11.60 |
| EtEDA | 0.00 | 0.00 | 0.00 | 0.00 | 0.00 | 0.00 | 0.00 | 0.00 | 0.00 | 0.00 | 0.00 | 0.00 |
| PIP | 1.28 | 1.11 | 0.93 | 3.30 | 3.03 | 2.79 | 12.61 | 12.29 | 7.23 | 0.82 | 0.77 | 0.77 |
| DETA | 79.77 | 73.47 | 73.54 | 76.57 | 79.28 | 79.79 | 71.48 | 70.87 | 78.08 | 84.83 | 84.22 | 85.08 |
| AEEA | 0.23 | 0.50 | 0.70 | 0.00 | 0.00 | 0.00 | 0.00 | 0.00 | 7.36 | 0.00 | 0.00 | 0.00 |
| AEP | 0.78 | 1.01 | 0.88 | 2.61 | 2.05 | 1.80 | 1.93 | 1.71 | 0.19 | 0.29 | 0.25 | 0.21 |
| HEP | 0.00 | 0.00 | 0.00 | 0.00 | 0.00 | 0.00 | 0.00 | 0.00 | 0.00 | 0.00 | 0.00 | 0.00 |
| TETA's | 7.63 | 11.54 | 11.52 | 8.85 | 6.88 | 7.59 | 5.61 | 6.10 | 2.44 | 1.85 | 2.29 | 1.69 |
| TEPA's | 1.03 | 2.90 | 2.71 | 1.72 | 1.36 | 1.22 | 3.11 | 4.22 | 3.46 | 0.37 | 0.26 | 0.19 |
| ROH Conversion % | 66.33 | 67.44 | 64.22 | 91.52 | 86.72 | 83.64 | 100.00 | 100.00 | 78.20 | 52.05 | 50.20 | 50.04 |
| Acyclic (N4)/cyclic (< = N4), weight ratio | 22.50 | 26.60 | 14.70 | 14.70 | 5.70 | 2.30 | 0.20 | 0.20 | 0.10 | 100.00 | 100.00 | 100.00 |
| Acyclic (N5)/cyclic (< = N5), weight ratio | 100.00 | 33.50 | 100.00 | 100.00 | 4.50 | 1.90 | 1.90 | 2.90 | 14.00 | 100.00 | 100.00 | 100.00 |
| Σ(N5)/Σ(N4), weight ratio | — | — | — | — | — | — | 0.60 | 0.70 | 1.40 | — | — | — |

TABLE LIV

| Example No. | 498 | 499 | 500 | 501 | 502 | 503 | 504 | 505 | 506 | 507 | 508 | 509 |
|---|---|---|---|---|---|---|---|---|---|---|---|---|
| Catalyst Type | JJJ | JJJ | JJJ | JJJ | JJJ | JJJ | JJJ | JJJ | JJJ | JJJ | JJJ | JJJ |
| Catalyst weight, gm | 118.3 | 118.3 | 118.3 | 118.3 | 118.3 | 118.3 | 118.3 | 118.3 | 118.3 | 118.3 | 118.3 | 118.3 |
| Pressure, psig | 600 | 600 | 600 | 600 | 600 | 600 | 600 | 600 | 600 | 600 | 600 | 600 |
| Temperature, °C. | 272 | 271 | 272 | 300 | 302 | 302 | 301 | 274 | 275 | 275 | 276 | 276 |
| Time on organics, hrs. | 4.0 | 17.5 | 19.5 | 25.0 | 41.0 | 43.0 | 48.0 | 65.0 | 67.0 | 72.0 | 85.0 | 87.0 |
| Duration of run, hrs. | 2 | 13 | 2 | 2 | 16 | 2 | 2 | 16 | 2 | 2 | 15 | 2 |
| MEA SV, gmol/hr/kgcat | 1.94 | 1.98 | 1.91 | 1.92 | 1.90 | 1.89 | 3.34 | 3.38 | 3.37 | 2.03 | 1.96 | 1.97 |
| NH3 feedrate, gm/hr | 45.0 | 45.9 | 48.5 | 46.0 | 58.4 | 55.0 | 55.5 | 53.0 | 50.5 | 52.5 | 51.0 | 49.5 |
| Liquid feed composition, wt. % | | | | | | | | | | | | |
| DETA | 77.16 | 77.16 | 77.16 | 77.16 | 77.16 | 77.16 | 66.46 | 66.46 | 66.46 | 77.16 | 77.16 | 77.16 |
| MEA | 22.84 | 22.84 | 22.84 | 22.84 | 22.84 | 22.84 | — | — | — | 22.84 | 22.84 | 22.84 |
| AEEA | — | — | — | — | — | — | 33.54 | 33.54 | 33.54 | — | — | — |
| Liquid product composition, wt. % | | | | | | | | | | | | |
| EDA | 0.48 | 0.50 | 0.45 | 2.70 | 2.96 | 2.83 | 2.44 | 0.36 | 0.40 | 0.51 | 0.50 | 0.59 |
| MeEDA | 0.00 | 0.00 | 0.00 | 0.00 | 0.00 | 0.00 | 0.00 | 0.00 | 0.00 | 0.00 | 0.00 | 0.00 |
| MEA | 9.18 | 9.77 | 9.84 | 2.44 | 2.92 | 2.93 | 0.00 | 0.30 | 0.29 | 10.04 | 10.18 | 10.47 |
| EtEDA | 0.00 | 0.00 | 0.00 | 0.00 | 0.00 | 0.00 | 0.00 | 0.00 | 0.00 | 0.00 | 0.00 | 0.00 |
| PIP | 1.10 | 1.10 | 1.07 | 3.88 | 3.86 | 3.85 | 11.79 | 7.03 | 7.40 | 1.33 | 1.23 | 1.21 |
| DETA | 77.40 | 77.67 | 78.15 | 68.03 | 67.03 | 66.76 | 61.93 | 69.26 | 69.84 | 76.33 | 78.33 | 77.59 |
| AEEA | 0.64 | 0.63 | 0.64 | 0.00 | 0.07 | 0.08 | 0.00 | 7.10 | 6.01 | 0.69 | 0.48 | 0.51 |
| AEP | 0.85 | 0.84 | 0.82 | 3.78 | 3.70 | 3.69 | 2.60 | 0.76 | 0.77 | 0.99 | 0.91 | 0.90 |
| HEP | 0.00 | 0.00 | 0.00 | 0.00 | 0.00 | 0.00 | 0.00 | 0.00 | 0.10 | 0.00 | 0.00 | 0.00 |
| TETA's | 7.04 | 6.84 | 6.47 | 11.12 | 10.94 | 11.03 | 9.81 | 5.55 | 5.66 | 7.02 | 6.22 | 6.15 |
| TEPA's | 1.55 | 1.50 | 1.37 | 3.72 | 3.61 | 3.73 | 6.68 | 7.38 | 7.33 | 2.09 | 1.31 | 1.37 |
| ROH Conversion % | 60.31 | 57.98 | 57.64 | 89.42 | 87.25 | 87.18 | 100.00 | 78.90 | 82.20 | 56.92 | 56.32 | 54.87 |
| Acyclic (N4)/cyclic (< = N4), weight ratio | 22.40 | 22.90 | 21.20 | 4.00 | 4.10 | 4.00 | 0.30 | 0.10 | 0.10 | 13.50 | 21.40 | 20.40 |
| Acyclic (N5)/cyclic (< = N5), weight ratio | 100.00 | 100.00 | 100.00 | 2.30 | 2.30 | 2.20 | 2.10 | 19.10 | 20.10 | 9.40 | 100.00 | 100.00 |
| Σ(N5)/Σ(N4), weight ratio | — | — | — | — | — | — | 0.70 | 1.30 | 1.30 | — | — | — |

TABLE LV

| Example No. | 510 | 511 | 512 | 513 | 514 | 515 | 516 | 517 | 518 |
|---|---|---|---|---|---|---|---|---|---|
| Catalyst Type | KKK | KKK | KKK | KKK | KKK | KKK | KKK | KKK | KKK |
| Catalyst weight, gm | 116.2 | 116.2 | 116.2 | 116.2 | 116.2 | 116.2 | 116.2 | 116.2 | 116.2 |
| Pressure, psig | 600 | 600 | 600 | 600 | 600 | 600 | 600 | 600 | 600 |
| Temperature, °C. | 281 | 289 | 255 | 253 | 308 | 300 | 297 | 272 | 268 |
| Time on organics, hrs. | 8.5 | 17.5 | 65.0 | 67.0 | 73.0 | 88.5 | 90.5 | 96.7 | 114.5 |
| Duration of run, hrs. | 2 | 9 | 10 | 2 | 2 | 15 | 2 | 2 | 2 |
| MEA SV, gmol/hr/kgcat | 1.95 | 1.92 | 1.68 | 1.73 | 1.62 | 1.74 | 1.71 | 1.68 | 1.72 |
| NH3 feedrate, gm/hr | 47.2 | 45.6 | 46.8 | 45.0 | 44.0 | 43.3 | 47.0 | 43.0 | 46.5 |
| Liquid feed composition, wt. % | | | | | | | | | |
| DETA | 77.16 | 77.16 | 66.46 | 66.46 | 77.16 | 77.16 | 77.16 | 66.46 | 66.46 |
| MEA | 22.84 | 22.84 | — | — | 22.84 | 22.84 | 22.84 | — | — |
| AEEA | — | — | 33.54 | 33.54 | — | — | — | 33.54 | 33.54 |
| Liquid product composition, | | | | | | | | | |

TABLE LV-continued

| Example No. | 510 | 511 | 512 | 513 | 514 | 515 | 516 | 517 | 518 |
|---|---|---|---|---|---|---|---|---|---|
| wt. % | | | | | | | | | |
| EDA | 2.23 | 1.99 | 0.37 | 0.35 | 9.13 | 5.71 | 5.98 | 1.22 | 1.22 |
| MeEDA | 0.00 | 0.00 | 0.00 | 0.00 | 0.00 | 0.00 | 0.00 | 0.00 | 0.00 |
| MEA | 9.36 | 10.47 | 0.39 | 0.36 | 4.75 | 8.86 | 8.41 | 0.45 | 0.45 |
| EtEDA | 0.00 | 0.00 | 0.00 | 0.00 | 0.00 | 0.00 | 0.00 | 0.00 | 0.00 |
| PIP | 0.65 | 0.44 | 1.26 | 1.29 | 1.40 | 0.90 | 0.92 | 3.43 | 3.43 |
| DETA | 75.37 | 77.92 | 74.89 | 76.09 | 63.34 | 69.29 | 67.65 | 74.85 | 74.85 |
| AEEA | 0.45 | 0.44 | 20.42 | 19.29 | 0.21 | 0.22 | 0.32 | 11.31 | 11.31 |
| AEP | 0.71 | 0.52 | 0.00 | 0.00 | 1.52 | 1.00 | 1.05 | 0.45 | 0.45 |
| HEP | 0.00 | 0.00 | 0.00 | 0.00 | 0.00 | 0.00 | 0.00 | 0.00 | 0.00 |
| TETA's | 6.89 | 4.55 | 0.22 | 0.21 | 6.49 | 5.50 | 6.02 | 2.05 | 2.05 |
| TEPA's | 1.28 | 0.49 | 0.96 | 0.89 | 0.99 | 0.57 | 0.79 | 3.05 | 3.05 |
| ROH Conversion % | 58.81 | 53.66 | 38.40 | 41.80 | 76.90 | 58.71 | 60.45 | 65.60 | 65.60 |
| Acyclic (N4)/cyclic ($\leq$ N4), weight ratio | 20.00 | 41.60 | 0.00 | 0.00 | 4.70 | 7.80 | 8.10 | 0.30 | 0.20 |
| Acyclic (N5)/cyclic ($\leq$ N5), weight ratio | 100.00 | 100.00 | 100.00 | 100.00 | 2.50 | 100.00 | 100.00 | 100.00 | 100.00 |
| $\Sigma(N5)/\Sigma(N4)$, weight ratio | — | — | 4.40 | 4.20 | — | — | — | 1.50 | 1.50 |

TABLE LVI

| Example No. | 519 | 520 | 521 | 522 | 523 | 524 | 525 | 526 | 527 | 528 | 529 |
|---|---|---|---|---|---|---|---|---|---|---|---|
| Catalyst Type | LLL | LLL | LLL | LLL | LLL | LLL | LLL | LLL | LLL | LLL | LLL |
| Catalyst weight, gm | 131.5 | 131.5 | 131.5 | 131.5 | 131.5 | 131.5 | 131.5 | 131.5 | 131.5 | 131.5 | 131.5 |
| Pressure, psig | 600 | 600 | 600 | 600 | 600 | 600 | 600 | 600 | 600 | 600 | 600 |
| Temperature, °C. | 273 | 277 | 277 | 305 | 300 | 300 | 300 | 303 | 301 | 278 | 276 |
| Time on organics, hrs. | 5.0 | 21.7 | 23.7 | 29.0 | 45.0 | 47.0 | 53.0 | 70.0 | 72.0 | 76.0 | 80.0 |
| Duration of run, hrs. | 2 | 15 | 2 | 1 | 16 | 2 | 2 | 16 | 2 | 2 | 2 |
| MEA SV, gmol/hr/kgcat | 1.86 | 1.78 | 1.86 | 1.39 | 1.71 | 1.52 | 1.54 | 1.50 | 1.57 | 1.54 | 1.75 |
| NH$_3$ feedrate, gm/hr | 53.0 | 48.6 | 45.0 | 49.0 | 45.0 | 50.5 | 54.5 | 48.0 | 53.0 | 50.0 | 47.0 |
| Liquid feed composition, wt. % | | | | | | | | | | | |
| DETA | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | — | — | — | — | 22.84 |
| AEEA | — | — | — | — | — | — | 33.54 | 33.54 | 33.54 | 33.54 | — |
| Liquid product composition, wt. % | | | | | | | | | | | |
| EDA | 0.39 | 0.41 | 0.44 | 4.14 | 1.93 | 1.70 | 1.17 | 1.32 | 1.32 | 0.35 | 0.48 |
| McEDA | 0.00 | 0.00 | 0.00 | 0.00 | 0.00 | 0.00 | 0.00 | 0.00 | 0.00 | 0.00 | 0.00 |
| MEA | 12.44 | 11.40 | 11.03 | 1.91 | 5.20 | 5.43 | 0.00 | 0.00 | 0.00 | 0.00 | 10.23 |
| EtEDA | 0.00 | 0.00 | 0.00 | 0.00 | 0.00 | 0.00 | 0.00 | 0.00 | 0.00 | 0.00 | 0.00 |
| PIP | 1.04 | 1.00 | 0.97 | 4.80 | 2.81 | 2.65 | 9.73 | 9.94 | 10.69 | 7.37 | 1.48 |
| DETA | 77.93 | 79.28 | 78.81 | 69.34 | 71.17 | 73.05 | 72.15 | 68.24 | 72.00 | 76.09 | 78.06 |
| AEEA | 0.76 | 0.54 | 0.58 | 0.00 | 0.00 | 0.00 | 0.00 | 0.00 | 0.00 | 3.28 | 0.50 |
| AEP | 0.86 | 0.88 | 0.85 | 5.19 | 2.82 | 2.57 | 2.10 | 2.26 | 2.37 | 0.74 | 1.14 |
| HEP | 0.00 | 0.00 | 0.00 | 0.00 | 0.00 | 0.00 | 0.00 | 0.00 | 0.00 | 0.00 | 0.00 |
| TETA's | 5.36 | 5.49 | 5.87 | 10.35 | 10.83 | 10.10 | 7.69 | 8.66 | 7.72 | 5.03 | 5.65 |
| TEPA's | 0.88 | 0.66 | 0.82 | 1.52 | 2.87 | 2.53 | 5.44 | 6.42 | 4.62 | 6.46 | 1.98 |
| ROH Conversion % | 46.63 | 51.16 | 52.65 | 91.86 | 77.72 | 76.79 | 100.00 | 100.00 | 100.00 | 90.40 | 56.31 |
| Acyclic (N4)/cyclic ($\leq$ N4), weight ratio | 20.20 | 25.50 | 22.70 | 3.20 | 6.60 | 7.30 | 0.20 | 0.20 | 0.20 | 0.10 | 5.90 |
| Acyclic (N5)/cyclic ($\leq$ N5), weight ratio | 100.00 | 100.00 | 100.00 | 1.70 | 6.80 | 8.20 | 11.40 | 7.50 | 8.30 | 52.40 | 18.50 |
| $\Sigma(N5)/\Sigma(N4)$, weight ratio | — | — | — | — | — | — | 0.70 | 0.70 | 0.60 | 1.30 | — |

TABLE LVII

| Example No. | 530 | 531 | 532 | 533 | 534 | 535 | 536 | 537 |
|---|---|---|---|---|---|---|---|---|
| Catalyst Type | MMM | MMM | MMM | MMM | MMM | MMM | MMM | MMM |
| Catalyst weight, gm | 120.5 | 120.5 | 120.5 | 120.5 | 120.5 | 120.5 | 120.5 | 120.5 |
| Pressure, psig | 600 | 600 | 600 | 600 | 600 | 600 | 600 | 600 |
| Temperature, °C. | 268 | 273 | 300 | 301 | 302 | 301 | 302 | 301 |
| Time on organics, hrs. | 5.0 | 21.0 | 27.5 | 45.0 | 47.0 | 55.0 | 68.0 | 71.0 |
| Duration of run, hrs. | 2 | 16 | 2 | 15 | 2 | 2 | 13 | 3 |
| MEA SV, gmol/hr/kgcat | 1.93 | 2.17 | 1.86 | 1.93 | 1.92 | 1.65 | 1.68 | 1.72 |
| NH$_3$ feedrate, gm/hr | 77.0 | 57.7 | 51.5 | 53.0 | 51.5 | 51.5 | 46.4 | 48.7 |
| Liquid feed composition, wt. % | | | | | | | | |
| DETA | 77.16 | 77.16 | 77.16 | 77.16 | 77.16 | 66.46 | 66.46 | 66.46 |
| MEA | 22.84 | 22.84 | 22.84 | 22.84 | 22.84 | — | — | — |
| AEEA | — | — | — | — | — | 33.54 | 33.54 | 33.54 |
| Liquid product composition, wt. % | | | | | | | | |
| EDA | 0.46 | 0.36 | 1.97 | 1.71 | 1.80 | 1.01 | 1.10 | 1.04 |
| MeEDA | 0.00 | 0.00 | 0.00 | 0.00 | 0.00 | 0.00 | 0.00 | 0.00 |
| MEA | 8.19 | 8.94 | 3.30 | 4.02 | 4.32 | 0.00 | 0.00 | 0.00 |

TABLE LVII-continued

| Example No. | 530 | 531 | 532 | 533 | 534 | 535 | 536 | 537 |
|---|---|---|---|---|---|---|---|---|
| EtEDA | 0.00 | 0.00 | 0.00 | 0.00 | 0.00 | 0.00 | 0.00 | 0.00 |
| PIP | 0.71 | 0.58 | 1.70 | 1.53 | 1.45 | 8.12 | 8.21 | 8.14 |
| DETA | 81.58 | 82.37 | 80.61 | 82.51 | 85.17 | 78.02 | 81.61 | 78.10 |
| AEEA | 0.00 | 0.00 | 0.00 | 0.00 | 0.00 | 0.00 | 0.00 | 0.00 |
| AEP | 0.77 | 0.66 | 1.96 | 1.66 | 1.50 | 1.16 | 1.11 | 1.10 |
| HEP | 0.00 | 0.00 | 0.00 | 0.00 | 0.00 | 0.00 | 0.00 | 0.00 |
| TETA's | 7.44 | 6.50 | 8.97 | 6.92 | 4.84 | 5.71 | 4.32 | 5.58 |
| TEPA's | 0.73 | 0.49 | 0.59 | 0.26 | 0.00 | 5.01 | 3.31 | 4.78 |
| ROH Conversion % | 65.18 | 61.92 | 86.01 | 82.82 | 81.58 | 100.00 | 100.00 | 100.00 |
| Acyclic (N4)/cyclic (< = N4), weight ratio | 100.00 | 100.00 | 12.60 | 15.50 | 100.00 | 0.10 | 0.00 | 0.10 |
| Acyclic (N5)/cyclic (< = N5), weight ratio | 100.00 | 100.00 | 100.00 | 100.00 | — | 25.20 | 100.00 | 20.90 |
| $\Sigma$(N5)/$\Sigma$(N4), weight ratio | — | — | — | — | — | 0.90 | 0.80 | 0.86 |

TABLE LVIII

| Example No. | 538 | 539 | 540 | 541 | 542 | 543 | 544 | 545 | 546 | 547 | 548 | 549 |
|---|---|---|---|---|---|---|---|---|---|---|---|---|
| Catalyst Type | NNN | NNN | NNN | NNN | NNN | NNN | NNN | NNN | NNN | NNN | NNN | NNN |
| Catalyst weight, gm | 119.6 | 119.6 | 119.6 | 119.6 | 119.6 | 119.6 | 119.6 | 119.6 | 119.6 | 119.6 | 119.6 | 119.6 |
| Pressure, psig | 600 | 600 | 600 | 600 | 600 | 600 | 600 | 600 | 600 | 600 | 600 | 600 |
| Temperature, °C. | 272 | 274 | 273 | 299 | 301 | 300 | 273 | 300 | 298 | 299 | 272 | 275 |
| Time on organics, hrs. | 4.0 | 20.0 | 22.0 | 27.0 | 44.0 | 46.0 | 49.0 | 66.0 | 68.0 | 70.0 | 74.0 | 86.0 |
| Duration of run, hrs. | 2 | 16 | 2 | 2 | 16 | 2 | 2 | 16 | 2 | 2 | 3 | 3 |
| MEA SV, gmol/hr/kgcat | 2.01 | 2.16 | 2.02 | 1.93 | 1.94 | 2.01 | 1.99 | 1.71 | 1.73 | 1.65 | 1.71 | 1.15 |
| NH3 feedrate, gm/hr | 47.0 | 46.5 | 53.5 | 44.0 | 60.8 | 50.5 | 59.0 | 45.2 | 56.5 | 56.5 | 64.0 | 59.4 |
| Liquid feed composition, wt. % | | | | | | | | | | | | |
| DETA | 77.16 | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | 22.84 | — | — | — | — | 22.84 |
| AEEA | — | — | — | — | — | — | — | 33.54 | 33.54 | 33.54 | 33.54 | — |
| Liquid product composition, wt. % | | | | | | | | | | | | |
| EDA | 0.00 | 0.00 | 0.00 | 2.00 | 1.82 | 1.80 | 0.00 | 1.63 | 1.66 | 1.44 | 0.00 | 0.00 |
| MeEDA | 0.00 | 0.00 | 0.00 | 0.00 | 0.00 | 0.00 | 0.00 | 0.00 | 0.00 | 0.00 | 0.00 | 0.00 |
| MEA | 6.84 | 7.07 | 7.00 | 2.75 | 2.63 | 2.57 | 8.52 | 0.00 | 0.00 | 0.00 | 0.00 | 9.35 |
| EtEDA | 0.00 | 0.00 | 0.00 | 0.00 | 0.00 | 0.00 | 0.00 | 0.00 | 0.00 | 0.00 | 0.00 | 0.00 |
| PIP | 1.21 | 0.85 | 0.69 | 1.96 | 2.02 | 2.11 | 0.58 | 9.79 | 10.05 | 10.16 | 6.52 | 0.72 |
| DETA | 83.64 | 87.98 | 88.48 | 83.40 | 82.22 | 81.77 | 87.13 | 75.36 | 72.92 | 72.45 | 80.94 | 83.87 |
| AEEA | 0.00 | 0.00 | 0.00 | 0.00 | 0.00 | 0.00 | 0.00 | 0.00 | 0.00 | 0.00 | 3.47 | 0.00 |
| AEP | 1.32 | 0.82 | 0.72 | 2.56 | 2.51 | 2.55 | 0.69 | 1.93 | 1.98 | 1.88 | 0.57 | 0.69 |
| HEP | 0.00 | 0.00 | 0.00 | 0.00 | 0.00 | 0.00 | 0.00 | 0.00 | 0.00 | 0.00 | 0.00 | 0.00 |
| TETA's | 6.59 | 3.27 | 3.11 | 6.33 | 7.56 | 7.85 | 3.08 | 7.07 | 7.66 | 7.60 | 3.57 | 4.14 |
| TEPA's | 0.41 | 0.00 | 0.00 | 0.00 | 0.56 | 0.71 | 0.00 | 3.95 | 4.60 | 5.08 | 4.74 | 0.51 |
| ROH Conversion % | 71.08 | 69.97 | 70.25 | 88.33 | 88.90 | 89.16 | 63.70 | 100.00 | 100.00 | 100.00 | 89.80 | 59.87 |
| Acyclic (N4)/cyclic (< = N4), weight ratio | 100.00 | 100.00 | 100.00 | 14.10 | 7.74 | 7.62 | 100.00 | 0.00 | 0.18 | 0.17 | 0.00 | 0.00 |
| Acyclic (N5)/cyclic (< = N5), weight ratio | 100.00 | 0.00 | 00.00 | 0.00 | 0.00 | 0.00 | 0.00 | 11.00 | 9.80 | 11.09 | 100.00 | 100.00 |
| $\Sigma$(N5)/$\Sigma$(N4), weight ratio | — | — | — | — | — | — | — | 0.60 | 0.60 | 0.70 | 1.30 | — |

TABLE LIX

| Example No. | 550 | 551 | 552 | 553 | 554 | 555 | 556 | 557 | 558 | 559 | 560 |
|---|---|---|---|---|---|---|---|---|---|---|---|
| Catalyst Type | OOO | OOO | OOO | OOO | OOO | OOO | OOO | OOO | OOO | OOO | OOO |
| Catalyst weight, gm | 119.0 | 119.0 | 119.0 | 119.0 | 119.0 | 119.0 | 119.0 | 119.0 | 119.0 | 119.0 | 119.0 |
| Pressure, psig | 600 | 600 | 600 | 600 | 600 | 600 | 600 | 600 | 600 | 600 | 600 |
| Temperature, °C. | 272 | 271 | 272 | 293 | 293 | 293 | 293 | 290 | 292 | 270 | 270 |
| Time on organics, hrs. | 6.0 | 22.0 | 24.0 | 29.0 | 46.0 | 48.0 | 53.0 | 69.5 | 71.5 | 76.5 | 93.0 |
| Duration of run, hrs. | 2 | 16 | 2 | 2 | 16 | 2 | 2 | 15 | 2 | 2 | 16 |
| MEA SV, gmol/hr/kgcat | 1.91 | 1.91 | 1.92 | 1.87 | 1.87 | 1.92 | 1.56 | 1.58 | 1.50 | 1.66 | 1.69 |
| NH3 feedrate, gm/hr | 50.0 | 45.0 | 51.0 | 61.0 | 52.0 | 63.5 | 65.0 | 47.8 | 50.5 | 45.0 | 68.6 |
| Liquid feed composition, wt. % | | | | | | | | | | | |
| DETA | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | — | — | — | — | 22.84 |
| AEEA | — | — | — | — | — | — | 33.54 | 33.54 | 33.54 | 33.54 | — |
| Liquid product composition, wt. % | | | | | | | | | | | |
| EDA | 0.63 | 0.69 | 0.72 | 2.72 | 3.02 | 2.99 | 2.68 | 3.21 | 3.67 | 0.60 | 0.78 |
| MeEDA | 0.00 | 0.00 | 0.00 | 0.00 | 0.00 | 0.00 | 0.00 | 0.00 | 0.00 | 0.00 | 0.00 |
| MEA | 15.06 | 14.67 | 14.70 | 7.20 | 6.66 | 6.83 | 0.37 | 0.24 | 0.24 | 0.45 | 14.81 |
| EtEDA | 0.00 | 0.00 | 0.00 | 0.00 | 0.00 | 0.00 | 0.00 | 0.00 | 0.00 | 0.00 | 0.00 |
| PIP | 0.51 | 0.58 | 0.59 | 1.88 | 2.08 | 2.11 | 6.78 | 7.42 | 7.73 | 4.42 | 1.25 |
| DETA | 76.49 | 75.73 | 75.87 | 69.26 | 69.03 | 67.89 | 61.99 | 60.81 | 59.19 | 65.18 | 71.26 |
| AEEA | 0.75 | 0.79 | 0.78 | 0.17 | 0.00 | 0.21 | 0.24 | 0.16 | 0.00 | 10.62 | 1.89 |

TABLE LIX-continued

| Example No. | 550 | 551 | 552 | 553 | 554 | 555 | 556 | 557 | 558 | 559 | 560 |
|---|---|---|---|---|---|---|---|---|---|---|---|
| AEP | 0.53 | 0.59 | 0.60 | 2.19 | 2.37 | 2.41 | 2.12 | 2.49 | 2.81 | 0.51 | 0.71 |
| HEP | 0.00 | 0.00 | 0.00 | 0.00 | 0.00 | 0.00 | 0.00 | 0.00 | 0.00 | 0.00 | 0.00 |
| TETA's | 4.07 | 4.50 | 4.48 | 9.01 | 9.15 | 8.99 | 8.99 | 9.15 | 9.40 | 4.16 | 5.02 |
| TEPA's | 1.66 | 1.99 | 1.94 | 5.81 | 5.97 | 6.10 | 12.71 | 11.71 | 12.96 | 12.13 | 3.62 |
| ROH Conversion % | 35.01 | 36.68 | 36.63 | 69.16 | 71.53 | 70.57 | 99.30 | 99.50 | 100.00 | 68.50 | 36.13 |
| Acyclic (N4)/cyclic (< = N4), weight ratio | 100.00 | 40.70 | 32.30 | 4.40 | 4.00 | 4.20 | 0.67 | 0.30 | 0.30 | 0.10 | 5.00 |
| Acyclic (N5)/cyclic (< = N5), weight ratio | 100.00 | 100.00 | 100.00 | 2.90 | 2.40 | 2.50 | 2.50 | 1.90 | 1.10 | 21.70 | 100.00 |
| Σ(N5)/Σ(N4), weight ratio | — | — | — | — | — | — | 1.40 | 1.30 | 1.40 | 2.90 | — |

TABLE LX

| Example No. | 561 | 562 | 563 | 564 | 565 | 566 | 567 |
|---|---|---|---|---|---|---|---|
| Catalyst Type | PPP | PPP | PPP | PPP | PPP | PPP | PPP |
| Catalyst weight, gm | 113.7 | 113.7 | 113.7 | 113.7 | 113.7 | 113.7 | 113.7 |
| Pressure, psig | 600 | 600 | 600 | 600 | 600 | 600 | 600 |
| Temperature, °C. | 274 | 274 | 299 | 299 | 303 | 294 | 297 |
| Time on organics, hrs. | 18.0 | 20.0 | 25.0 | 41.7 | 43.4 | 49.0 | 65.5 |
| Duration of run, hrs. | 16 | 2 | 2 | 16 | 2 | 2 | 16 |
| MEA SV, gmol/hr/kgcat | 2.15 | 2.19 | 2.20 | 2.10 | 2.19 | 2.11 | 2.14 |
| NH3 feedrate, gm/hr | 55.6 | 43.0 | 52.0 | 55.0 | 38.0 | 84.0 | 52.0 |
| Liquid feed composition, wt. % | | | | | | | |
| DETA | 77.16 | 77.16 | 77.16 | 77.16 | 77.16 | 73.30 | 73.30 |
| MEA | 22.84 | 22.84 | 22.84 | 22.84 | 22.84 | 21.70 | 21.70 |
| EDA | — | — | — | — | — | — | — |
| H2O | — | — | — | — | — | 5.00 | 5.00 |
| Liquid product composition, wt. % | | | | | | | |
| EDA | 0.85 | 0.69 | 2.50 | 1.60 | 1.42 | 1.28 | 1.24 |
| MeEDA | 0.00 | 0.00 | 0.00 | 0.00 | 0.00 | 0.00 | 0.00 |
| MEA | 11.05 | 11.08 | 3.45 | 6.52 | 7.59 | 10.77 | 11.01 |
| EtEDA | 0.00 | 0.00 | 0.00 | 0.00 | 0.00 | 0.00 | 0.00 |
| PIP | 0.46 | 0.37 | 1.22 | 0.77 | 0.70 | 0.53 | 0.50 |
| DETA | 71.01 | 72.32 | 65.63 | 70.92 | 72.86 | 73.67 | 73.65 |
| AEEA | 1.08 | 1.21 | 0.25 | 0.59 | 0.78 | 0.94 | 1.06 |
| AEP | 0.69 | 0.56 | 2.04 | 1.27 | 1.14 | 0.99 | 0.93 |
| HEP | 0.00 | 0.00 | 0.00 | 0.00 | 0.00 | 0.00 | 0.00 |
| TETA's | 11.09 | 10.78 | 15.98 | 11.82 | 10.35 | 8.14 | 8.13 |
| TEPA's | 2.74 | 2.32 | 5.41 | 3.35 | 2.60 | 1.92 | 1.81 |
| ROH Conversion % | 52.50 | 52.51 | 85.08 | 71.61 | 67.04 | 53.28 | 52.25 |
| Acyclic (N4)/cyclic (< = N4), weight ratio | 30.30 | 100.00 | 9.50 | 13.90 | 13.00 | 17.80 | 19.80 |
| Acyclic (N5)/cyclic (< = N5), weight ratio | 31.60 | 100.00 | 6.70 | 10.00 | 13.40 | 12.90 | 31.20 |
| Σ(N5)/Σ(N4), weight ratio | 14.70 | 10.50 | 5.30 | 7.10 | 7.60 | 8.00 | 8.70 |

| Example No. | 568 | 569 | 570 | 571 | 572 | 573 | 574 |
|---|---|---|---|---|---|---|---|
| Catalyst Type | PPP | PPP | PPP | PPP | PPP | PPP | PPP |
| Catalyst weight, gm | 113.7 | 113.7 | 113.7 | 113.7 | 113.7 | 113.7 | 113.7 |
| Pressure, psig | 600 | 600 | 600 | 600 | 600 | 600 | 600 |
| Temperature, °C. | 293 | 299 | 298 | 297 | 300 | 298 | 298 |
| Time on organics, hrs. | 67.4 | 72.4 | 89.5 | 91.5 | 112.2 | 114.2 | 149.2 |
| Duration of run, hrs. | 2 | 2 | 16 | 2 | 15 | 2 | 2 |
| MEA SV, gmol/hr/kgcat | 2.06 | 2.09 | 2.07 | 2.08 | 3.06 | 3.17 | 11.03 |
| NH3 feedrate, gm/hr | 54.0 | 47.0 | 67.0 | 49.5 | 57.0 | 54.0 | 47.0 |
| Liquid feed composition, wt. % | | | | | | | |
| DETA | 73.30 | 77.16 | 77.16 | 77.16 | — | — | — |
| MEA | 21.70 | 22.84 | 22.84 | 22.84 | 33.70 | 33.70 | 100.00 |
| EDA | — | — | — | — | 66.30 | 66.30 | — |
| H2O | 5.00 | — | — | — | — | — | — |
| Liquid product composition, wt. % | | | | | | | |
| EDA | 1.16 | 1.17 | 1.09 | 1.06 | 69.42 | 67.49 | 1.37 |
| MeEDA | 0.00 | 0.00 | 0.00 | 0.00 | 0.00 | 0.00 | 0.00 |
| MEA | 11.46 | 9.15 | 10.15 | 10.62 | 20.41 | 20.60 | 85.05 |
| EtEDA | 0.00 | 0.00 | 0.00 | 0.00 | 0.00 | 0.00 | 0.00 |
| PIP | 0.46 | 0.52 | 0.44 | 0.40 | 0.54 | 0.53 | 0.51 |
| DETA | 74.18 | 72.91 | 74.49 | 75.62 | 4.65 | 6.35 | 1.42 |
| AEEA | 1.07 | 1.21 | 1.18 | 1.20 | 2.23 | 2.29 | 8.02 |
| AEP | 0.88 | 0.90 | 0.83 | 0.80 | 0.62 | 0.62 | 0.58 |
| HEP | 0.00 | 0.06 | 0.00 | 0.00 | 0.00 | 0.00 | 0.39 |
| TETA's | 7.51 | 8.79 | 7.76 | 6.81 | 1.00 | 1.04 | 0.51 |
| TEPA's | 1.57 | 2.10 | 1.50 | 1.19 | 0.11 | 0.82 | 0.00 |
| ROH Conversion % | 50.21 | 59.84 | 55.60 | 53.59 | 40.05 | 35.71 | 15.17 |
| Acyclic (N4)/cyclic (< = N4), | 21.10 | 14.70 | 15.60 | 18.70 | — | — | — |

TABLE LX-continued

| | | | | | | | |
|---|---|---|---|---|---|---|---|
| weight ratio | | | | | | | |
| Acyclic (N5)/cyclic (< = N5), weight ratio | 14.90 | 21.40 | 100.00 | 100.00 | — | — | — |
| Σ(N5)/Σ(N4), weight ratio | 9.00 | 7.60 | 8.10 | 8.70 | — | — | — |

TABLE LXI

| Example No. | 575 | 576 | 577 | 578 | 579 | 580 | 581 |
|---|---|---|---|---|---|---|---|
| Catalyst Type | QQQ | QQQ | QQQ | QQQ | QQQ | QQQ | QQQ |
| Catalyst weight, gm | 123.1 | 123.1 | 123.1 | 123.1 | 123.1 | 123.1 | 123.1 |
| Pressure, psig | 600 | 600 | 600 | 600 | 600 | 600 | 600 |
| Temperature, °C. | 278 | 280 | 279 | 308 | 306 | 305 | 305 |
| Time on organics, hrs. | 31.2 | 19.5 | 21.5 | 26.2 | 32.2 | 49.2 | 51.2 |
| Duration of run, hrs. | 1 | 16 | 2 | 2 | 2 | 16 | 2 |
| MEA SV, gmol/hr/kgcat | 2.14 | 1.96 | 1.95 | 1.93 | 1.91 | 1.64 | 1.65 |
| NH₃ feedrate, gm/hr | 80.0 | 53.0 | 53.5 | 58.5 | 59.5 | 56.0 | 47.0 |
| Liquid feed composition, wt. % | | | | | | | |
| DETA | 77.16 | 77.16 | 77.16 | 77.16 | 77.16 | 66.46 | 66.46 |
| MEA | 22.84 | 22.84 | 22.84 | 22.84 | 22.84 | — | — |
| AEEA | — | — | — | — | — | 33.54 | 33.54 |
| Liquid product composition, wt. % | | | | | | | |
| EDA | 0.93 | 0.49 | 0.46 | 1.74 | 1.34 | 1.17 | 1.12 |
| MeEDA | 0.00 | 0.00 | 0.00 | 0.00 | 0.00 | 0.00 | 0.00 |
| MEA | 15.52 | 14.20 | 14.55 | 7.82 | 10.95 | 0.58 | 0.25 |
| EtEDA | 0.00 | 0.00 | 0.00 | 0.00 | 0.00 | 0.00 | 0.00 |
| PIP | 0.08 | 0.13 | 0.11 | 0.66 | 0.36 | 4.33 | 4.26 |
| DETA | 79.78 | 80.09 | 80.45 | 79.71 | 78.22 | 72.69 | 71.85 |
| AEEA | 0.63 | 0.82 | 0.84 | 0.58 | 0.97 | 4.41 | 5.88 |
| AEP | 0.38 | 0.42 | 0.39 | 1.19 | 0.85 | 0.97 | 0.80 |
| HEP | 0.00 | 0.00 | 0.00 | 0.00 | 0.12 | 0.15 | 0.08 |
| TETA's | 2.32 | 3.12 | 2.68 | 6.54 | 3.78 | 8.89 | 8.53 |
| TEPA's | 0.00 | 0.22 | 0.16 | 1.09 | 0.55 | 4.30 | 4.08 |
| ROH Conversion % | 32.65 | 38.51 | 37.03 | 65.50 | 51.72 | 86.80 | 82.30 |
| Acyclic (N4)/cyclic (< = N4), weight ratio | — | — | 100.00 | 11.57 | 12.90 | 7.79 | 10.00 |
| Acyclic (N5)/cyclic (< = N5), weight ratio | — | — | — | — | — | 0.10 | 0.10 |
| Σ(N5)/Σ(N4), weight ratio | — | — | — | — | — | 0.50 | 0.50 |

TABLE LXII

| Example No. | 582 | 583 | 584 | 585 | 586 | 587 | 588 | 589 |
|---|---|---|---|---|---|---|---|---|
| Catalyst Type | RRR | RRR | RRR | RRR | RRR | RRR | RRR | RRR |
| Catalyst weight, gm | 116.4 | 116.4 | 116.4 | 116.4 | 116.4 | 116.4 | 116.4 | 116.4 |
| Pressure, psig | 600 | 600 | 600 | 600 | 600 | 600 | 600 | 600 |
| Temperature, °C. | 274 | 274 | 274 | 303 | 301 | 303 | 301 | 301 |
| Time on organics, hrs. | 3.0 | 18.8 | 20.8 | 26.5 | 43.0 | 45.0 | 50.4 | 55.1 |
| Duration of run, hrs. | 1 | 16 | 2 | 2 | 16 | 2 | 2 | 2 |
| MEA SV, gmol/hr/kgcat | 2.05 | 2.07 | 2.11 | 2.03 | 2.02 | 1.97 | 3.24 | 3.26 |
| NH₃ feedrate, gm/hr | 70.0 | 60.3 | 53.5 | 93.0 | 60.8 | 61.0 | 53.0 | 78.5 |
| Liquid feed composition, wt. % | | | | | | | | |
| DETA | 77.16 | 77.16 | 77.16 | 77.16 | 77.16 | 77.16 | 62.81 | 62.81 |
| MEA | 22.84 | 22.84 | 22.84 | 22.84 | 22.84 | 22.84 | 37.19 | 37.19 |
| Liquid product composition, wt % | | | | | | | | |
| EDA | 1.07 | 1.05 | 0.86 | 3.00 | 2.27 | 1.97 | 2.25 | 1.86 |
| MeEDA | 0.00 | 0.00 | 0.00 | 0.00 | 0.00 | 0.00 | 0.00 | 0.00 |
| MEA | 10.34 | 10.06 | 11.47 | 3.86 | 6.06 | 7.28 | 15.71 | 21.10 |
| EtEDA | 0.00 | 0.00 | 0.00 | 0.00 | 0.00 | 0.00 | 0.00 | 0.00 |
| PIP | 1.07 | 0.69 | 0.44 | 1.44 | 1.06 | 0.87 | 1.14 | 0.71 |
| DETA | 71.40 | 71.74 | 74.72 | 68.70 | 70.45 | 72.29 | 62.19 | 63.50 |
| AEEA | 2.14 | 1.02 | 1.02 | 0.29 | 0.47 | 0.62 | 1.27 | 1.68 |
| AEP | 1.05 | 0.89 | 0.63 | 2.17 | 1.54 | 1.30 | 1.61 | 1.01 |
| HEP | 0.00 | 0.00 | 0.00 | 0.00 | 0.00 | 0.00 | 0.00 | 0.00 |
| TETA's | 8.90 | 10.65 | 8.62 | 13.51 | 11.60 | 10.01 | 9.86 | 5.67 |
| TEPA's | 3.00 | 2.71 | 1.52 | 3.58 | 2.99 | 2.10 | 2.09 | 1.32 |
| ROH Conversion % | 55.63 | 56.77 | 50.69 | 83.26 | 73.52 | 68.05 | 57.95 | 43.18 |
| Acyclic (N4)/cyclic (< = N4), weight ratio | 14.20 | 26.00 | 40.00 | 7.30 | 9.40 | 11.10 | 8.40 | 13.00 |
| Acyclic (N5)/cyclic (< = N5), weight ratio | 21.70 | 25.90 | 100.00 | 3.90 | 5.60 | 26.00 | 13.70 | 2.97 |
| Σ(N5)/Σ(N4), | 5.00 | 9.50 | 13.00 | 3.90 | — | — | 4.00 | 4.70 |

TABLE LXII-continued

| Example No. | 582 | 583 | 584 | 585 | 586 | 587 | 588 | 589 |
|---|---|---|---|---|---|---|---|---|
| weight ratio | | | | | | | | |

TABLE LXIII

| Example No. | 590 | 591 | 592 | 593 | 594 | 595 | 596 | 597 | 598 | 599 | 600 | 601 |
|---|---|---|---|---|---|---|---|---|---|---|---|---|
| Catalyst Type | SSS | SSS | SSS | SSS | SSS | SSS | SSS | SSS | SSS | SSS | SSS | SSS |
| Catalyst weight, gm | 105.1 | 105.1 | 105.1 | 105.1 | 105.1 | 105.1 | 105.1 | 105.1 | 105.1 | 105.1 | 105.1 | 105.1 |
| Pressure, psig | 600 | 600 | 600 | 600 | 600 | 600 | 600 | 600 | 600 | 600 | 600 | 600 |
| Temperature, °C. | 284 | 286 | 284 | 304 | 303 | 276 | 276 | 280 | 306 | 311 | 311 | 311 |
| Time on organics, hrs. | 3.0 | 19.0 | 20.0 | 41.6 | 43.6 | 49.0 | 65.0 | 67.0 | 71.0 | 78.0 | 92.0 | 94.0 |
| Duration of run, hrs. | 1 | 16 | 2 | 16 | 2 | 2 | 15 | 2 | 2 | 2 | 2 | 2 |
| MEA SV, gmol/hr/kgcat | 2.30 | 2.34 | 2.35 | 2.26 | 2.29 | 2.00 | 1.97 | 1.94 | 1.96 | 1.84 | 1.90 | 1.98 |
| NH$_3$ feedrate, gm/hr | 60.5 | 59.0 | 52.5 | 53.4 | 56.5 | 54.5 | 61.5 | 54.0 | 48.0 | 63.0 | 45.0 | 53.0 |
| Liquid feed composition, wt. % | | | | | | | | | | | | |
| EDA | — | — | — | — | — | — | — | — | — | 18.29 | 18.29 | 18.29 |
| DETA | 77.16 | 77.16 | 77.16 | 77.16 | 77.16 | 66.46 | 66.46 | 66.46 | 66.46 | 31.41 | 31.41 | 31.41 |
| MEA | 22.84 | 22.84 | 22.84 | 22.84 | 22.84 | — | — | — | — | 18.59 | 18.59 | 18.59 |
| AEEA | — | — | — | — | — | 33.54 | 33.54 | 33.54 | 33.54 | 31.71 | 31.71 | 31.71 |
| Liquid product composition, wt. % | | | | | | | | | | | | |
| EDA | 1.42 | 1.51 | 1.58 | 4.01 | 4.05 | 0.68 | 0.62 | 0.57 | 3.04 | 27.12 | 23.79 | 25.27 |
| MeEDA | 0.00 | 0.00 | 0.00 | 0.00 | 0.00 | 0.00 | 0.00 | 0.00 | 0.00 | 0.00 | 0.00 | 0.00 |
| MEA | 9.68 | 8.49 | 9.09 | 3.41 | 3.82 | 0.36 | 0.19 | 0.16 | 0.00 | 3.52 | 3.25 | 3.40 |
| EtEDA | 0.00 | 0.00 | 0.00 | 0.00 | 0.00 | 0.00 | 0.00 | 0.00 | 0.00 | 0.00 | 0.00 | 0.00 |
| PIP | 1.16 | 1.29 | 1.28 | 2.99 | 2.95 | 6.65 | 6.30 | 5.94 | 9.68 | 10.98 | 9.83 | 10.11 |
| DETA | 71.42 | 70.10 | 71.52 | 65.54 | 64.54 | 71.47 | 69.54 | 69.17 | 57.76 | 28.16 | 27.11 | 27.67 |
| AEEA | 0.59 | 0.59 | 0.55 | 0.23 | 0.18 | 8.21 | 9.71 | 10.06 | 0.27 | 0.42 | 0.37 | 0.33 |
| AEP | 1.08 | 1.25 | 1.22 | 3.33 | 3.12 | 0.89 | 0.75 | 0.73 | 3.14 | 6.78 | 7.24 | 6.99 |
| HEP | 0.00 | 0.00 | 0.00 | 0.00 | 0.00 | 0.00 | 0.00 | 0.00 | 0.00 | 0.00 | 0.00 | 0.00 |
| TETA's | 11.29 | 12.78 | 11.42 | 13.94 | 14.12 | 4.16 | 3.83 | 3.84 | 11.05 | 12.22 | 14.47 | 13.61 |
| TEPA's | 2.65 | 3.21 | 2.53 | 3.96 | 4.53 | 6.84 | 8.00 | 8.60 | 10.52 | 6.38 | 7.75 | 7.53 |
| ROH Conversion % | 58.68 | 63.87 | 61.20 | 85.42 | 83.62 | 75.90 | 71.50 | 70.50 | 99.20 | 81.42 | 82.82 | 81.99 |
| Acyclic (N4)/cyclic (< = N4), weight ratio | 28.50 | 26.30 | 26.00 | 6.70 | 6.80 | 0.40 | 0.30 | 0.30 | 0.50 | 0.90 | 0.90 | 0.90 |
| Acyclic (N5)/cyclic (< = N5), weight ratio | — | — | 100.00 | 4.10 | 4.00 | 61.00 | 79.00 | 28.20 | 4.10 | 0.70 | 0.80 | 0.80 |
| Σ(N5)/Σ(N4), weight ratio | — | — | — | — | — | 1.64 | 2.10 | 2.20 | 1.00 | — | — | — |

TABLE LXIV

| Example No. | 602 | 603 | 604 | 605 | 606 | 607 | 608 | 609 | 610 | 611 | 612 |
|---|---|---|---|---|---|---|---|---|---|---|---|
| Catalyst Type | TTT | TTT | TTT | TTT | TTT | TTT | TTT | TTT | TTT | TTT | TTT |
| Catalyst weight, gm | 117.9 | 117.9 | 117.9 | 117.9 | 117.9 | 117.9 | 117.9 | 117.9 | 117.9 | 117.9 | 117.9 |
| Pressure, psig | 600 | 600 | 600 | 600 | 600 | 600 | 600 | 600 | 600 | 600 | 600 |
| Temperature, °C. | 278 | 277 | 301 | 302 | 301 | 300 | 300 | 303 | 301 | 302 | 302 |
| Time on organics, hrs. | 18.0 | 20.0 | 25.0 | 40.0 | 42.0 | 47.5 | 65.5 | 87.0 | 88.5 | 109.0 | 111.0 |
| Duration of run, hrs. | 16 | 2 | 2 | 14 | 2 | 2 | 2 | 19 | 2 | 20 | 2 |
| MEA SV, gmol/hr/kgcat | 2.03 | 2.06 | 1.98 | 2.00 | 2.11 | 1.74 | 1.32 | 3.51 | 3.79 | 3.30 | 3.45 |
| NH$_3$ feedrate, gm/hr | 56.0 | 54.0 | 54.0 | 63.0 | 61.0 | 60.0 | 10.0 | 67.8 | 54.0 | 67.9 | 48.5 |
| Liquid feed composition, wt. % | | | | | | | | | | | |
| DETA | 77.16 | 77.16 | 77.16 | 77.16 | 77.16 | 66.46 | 66.46 | 62.81 | 62.81 | 62.81 | 62.81 |
| MEA | 22.84 | 22.84 | 22.84 | 22.84 | 22.84 | — | — | 37.19 | 37.19 | 37.19 | 37.19 |
| AEEA | — | — | — | — | — | 33.54 | 33.54 | — | — | — | — |
| Liquid product composition, wt. % | | | | | | | | | | | |
| EDA | 1.02 | 0.88 | 3.46 | 2.84 | 2.51 | 1.46 | 2.23 | 2.44 | 2.31 | 2.15 | 2.01 |
| MeEDA | 0.00 | 0.00 | 0.00 | 0.00 | 0.00 | 0.00 | 0.00 | 0.00 | 0.00 | 0.00 | 0.00 |
| MEA | 12.18 | 11.85 | 5.47 | 5.76 | 6.66 | 0.35 | 0.15 | 15.93 | 16.51 | 17.85 | 18.61 |
| EtEDA | 0.00 | 0.00 | 0.00 | 0.00 | 0.00 | 0.00 | 0.00 | 0.00 | 0.00 | 0.00 | 0.00 |
| PIP | 0.50 | 0.49 | 1.74 | 1.49 | 1.27 | 5.41 | 5.82 | 1.39 | 1.23 | 1.13 | 1.02 |
| DETA | 74.13 | 74.56 | 70.50 | 71.81 | 70.37 | 70.92 | 61.30 | 60.00 | 61.02 | 61.91 | 62.27 |
| AEEA | 1.14 | 1.11 | 0.39 | 0.48 | 0.56 | 3.78 | 4.31 | 1.92 | 1.89 | 2.00 | 2.10 |
| AEP | 0.64 | 0.64 | 2.16 | 1.91 | 1.65 | 1.24 | 2.04 | 1.64 | 1.58 | 1.42 | 1.26 |
| HEP | 0.00 | 0.00 | 0.00 | 0.00 | 0.00 | 0.00 | 0.00 | 0.00 | 0.00 | 0.00 | 0.00 |
| TETA's | 7.19 | 7.69 | 10.84 | 10.30 | 10.16 | 6.34 | 7.31 | 9.54 | 9.36 | 8.29 | 8.01 |
| TEPA's | 2.28 | 1.79 | 2.96 | 2.74 | 3.47 | 8.47 | 12.87 | 3.31 | 2.80 | 2.39 | 2.35 |
| ROH Conversion % | 47.45 | 48.87 | 76.39 | 75.07 | 70.93 | 88.80 | 87.00 | 57.42 | 56.04 | 52.52 | 50.66 |
| Acyclic (N4)/cyclic (< = N4), weight ratio | 30.70 | 29.40 | 6.40 | 7.90 | 8.10 | 0.30 | 0.50 | 6.70 | 6.40 | 8.40 | 9.20 |
| Acyclic (N5)/cyclic (< = N5), weight ratio | 2.70 | 100.00 | 3.50 | 4.40 | 5.20 | 11.70 | 12.20 | 4.70 | 3.90 | 4.80 | 5.10 |
| Σ(N5)/Σ(N4), | — | — | — | — | — | 1.30 | 1.80 | — | — | — | — |

TABLE LXIV-continued

| Example No. | 602 | 603 | 604 | 605 | 606 | 607 | 608 | 609 | 610 | 611 | 612 |
|---|---|---|---|---|---|---|---|---|---|---|---|
| weight ratio | | | | | | | | | | | |

TABLE LXV

| Example No. | 613 | 614 | 615 | 616 | 617 | 618 | 619 | 620 | 621 |
|---|---|---|---|---|---|---|---|---|---|
| Catalyst Type | UUU | UUU | UUU | UUU | UUU | UUU | UUU | UUU | UUU |
| Catalyst weight, gm | 116.4 | 116.4 | 116.4 | 116.4 | 116.4 | 116.4 | 116.4 | 116.4 | 116.4 |
| Pressure, psig | 600 | 600 | 600 | 600 | 600 | 600 | 600 | 600 | 600 |
| Temperature, °C. | 278 | 291 | 278 | 304 | 307 | 306 | 301 | 302 | 302 |
| Time on organics, hrs. | 18.0 | 20.2 | 22.2 | 28.0 | 44.5 | 46.5 | 55.5 | 68.5 | 70.5 |
| Duration of run, hrs. | 16 | 16 | 2 | 2 | 16 | 2 | 2 | 13 | 2 |
| MEA SV, gmol/hr/kgcat | 2.03 | 2.05 | 2.06 | 2.07 | 2.00 | 2.02 | 1.73 | 1.72 | 1.78 |
| $NH_3$ feedrate, gm/hr | 56.0 | 51.2 | 51.5 | 56.0 | 56.0 | 53.5 | 64.0 | 59.7 | 59.7 |
| Liquid feed composition, wt. % | | | | | | | | | |
| DETA | 77.16 | 77.16 | 77.16 | 77.16 | 77.16 | 77.16 | 66.46 | 66.46 | 66.46 |
| MEA | 22.84 | 22.84 | 22.84 | 22.84 | 22.84 | 22.84 | — | — | — |
| AEEA | — | — | — | — | — | — | 33.54 | 33.54 | 33.54 |
| Liquid product composition, wt. % | | | | | | | | | |
| EDA | 1.02 | 1.12 | 0.70 | 2.22 | 2.31 | 2.54 | 1.67 | 1.70 | 1.86 |
| MeEDA | 0.00 | 0.00 | 0.00 | 0.00 | 0.00 | 0.00 | 0.00 | 0.00 | 0.00 |
| MEA | 12.18 | 10.60 | 11.71 | 6.34 | 6.10 | 6.24 | 0.21 | 0.00 | 0.20 |
| EtEDA | 0.00 | 0.00 | 0.00 | 0.00 | 0.00 | 0.00 | 0.00 | 0.00 | 0.00 |
| PIP | 0.50 | 0.56 | 0.35 | 1.18 | 1.19 | 1.22 | 7.01 | 6.71 | 7.26 |
| DETA | 74.13 | 76.35 | 76.18 | 74.45 | 74.51 | 74.81 | 73.57 | 73.53 | 73.22 |
| AEEA | 1.14 | 0.90 | 1.00 | 0.49 | 0.42 | 0.43 | 1.39 | 1.52 | 1.41 |
| AEP | 0.64 | 0.79 | 0.61 | 1.53 | 1.60 | 1.58 | 1.22 | 1.17 | 1.15 |
| HEP | 0.00 | 0.00 | 0.00 | 0.00 | 0.00 | 0.00 | 0.00 | 0.00 | 0.00 |
| TETA's | 7.19 | 7.58 | 7.18 | 9.57 | 8.76 | 8.18 | 7.33 | 7.38 | 7.12 |
| TEPA's | 2.28 | 1.36 | 1.47 | 1.86 | 3.57 | 1.80 | 4.61 | 5.25 | 4.68 |
| ROH Conversion % | 47.45 | 54.45 | 49.55 | 72.57 | 73.87 | 72.74 | 95.90 | 95.50 | 95.80 |
| Acyclic (N4)/cyclic (< = N4), weight ratio | 30.70 | 24.30 | 30.50 | 11.20 | 10.20 | 8.90 | 0.20 | 0.10 | 0.10 |
| Acyclic (N5)/cyclic (< = N5), weight ratio | 2.70 | 100.00 | 100.00 | 10.00 | 5.80 | 7.40 | 11.80 | 9.80 | 11.00 |
| $\Sigma(N5)/\Sigma(N4)$, weight ratio | — | — | — | — | — | — | 0.60 | 0.70 | 0.70 |

TABLE LXVI

| Example No. | 622 | 623 | 624 | 625 | 626 | 627 | 628 | 629 |
|---|---|---|---|---|---|---|---|---|
| Catalyst Type | VVV | VVV | VVV | VVV | VVV | VVV | VVV | VVV |
| Catalyst weight, gm | 117.2 | 117.2 | 117.2 | 117.2 | 117.2 | 117.2 | 117.2 | 117.2 |
| Pressure, psig | 600 | 600 | 600 | 600 | 600 | 600 | 600 | 600 |
| Temperature, °C. | 276 | 277 | 275 | 299 | 290 | 302 | 300 | 308 |
| Timer on organics, hrs. | 4.0 | 11.0 | 20.0 | 26.0 | 36.0 | 40.0 | 45.0 | 57.0 |
| Duration of run, hrs. | 2 | 2 | 2 | 2 | 10 | 2 | 2 | 2 |
| MEA SV, gmol/hr/kgcat | 1.76 | 2.31 | 2.08 | 2.00 | 2.03 | 1.95 | 1.81 | 1.69 |
| $NH_3$ feedrate, gm/hr | 29.0 | 37.5 | 58.0 | 55.0 | 55.0 | 52.0 | 59.0 | 49.5 |
| Liquid feed composition, wt. % | | | | | | | | |
| DETA | 77.16 | 77.16 | 77.16 | 77.16 | 77.16 | 77.16 | 66.46 | 66.46 |
| MEA | 22.84 | 22.84 | 22.84 | 22.84 | 22.84 | 22.84 | — | — |
| AEEA | — | — | — | — | — | — | 33.54 | 33.54 |
| Liquid product composition, wt. % | | | | | | | | |
| EDA | 1.54 | 1.38 | 1.38 | 2.84 | 2.73 | 3.56 | 1.85 | 2.20 |
| MeEDA | 0.00 | 0.00 | 0.00 | 0.00 | 0.00 | 0.00 | 0.00 | 0.00 |
| MEA | 8.33 | 7.66 | 13.37 | 5.58 | 5.61 | 6.07 | 0.33 | 0.00 |
| EtEDA | 0.00 | 0.00 | 0.00 | 0.00 | 0.00 | 0.00 | 0.00 | 0.00 |
| PIP | 1.26 | 1.16 | 0.29 | 1.49 | 1.48 | 1.46 | 7.47 | 6.84 |
| DETA | 74.34 | 74.58 | 80.12 | 74.81 | 70.27 | 70.19 | 71.84 | 71.91 |
| AEEA | 1.27 | 0.89 | 0.00 | 0.00 | 0.00 | 0.13 | 1.65 | 1.10 |
| AEP | 0.64 | 1.29 | 0.54 | 1.97 | 1.90 | 1.84 | 1.31 | 1.68 |
| HEP | 0.00 | 0.00 | 0.00 | 0.00 | 0.00 | 0.00 | 0.00 | 0.00 |
| TETA's | 10.00 | 10.98 | 4.25 | 10.18 | 11.99 | 10.45 | 5.91 | 6.40 |
| TEPA's | 2.07 | 1.86 | 0.00 | 1.74 | 3.50 | 2.98 | 7.79 | 6.50 |
| ROH Conversion % | 64.49 | 67.56 | 42.44 | 76.15 | 75.80 | 73.51 | 95.10 | 96.70 |
| Acyclic (N4)/cyclic (< = N4), weight ratio | 17.80 | 20.40 | 20.40 | 9.50 | 11.40 | 9.80 | 0.20 | 0.30 |
| Acyclic (N5)/cyclic (< = N5), weight ratio | — | — | — | 5.30 | 7.30 | — | 22.60 | 11.20 |
| $\Sigma(N5)/\Sigma(N4)$, weight ratio | — | — | — | — | — | — | 1.30 | 1.00 |

TABLE LXVII

| Example No. | 630 | 631 | 632 | 633 | 634 | 635 | 636 | 637 |
|---|---|---|---|---|---|---|---|---|
| Catalyst Type | WWW | WWW | WWW | WWW | WWW | WWW | WWW | WWW |
| Catalyst weight, gm | 107.3 | 107.3 | 107.3 | 107.3 | 107.3 | 107.3 | 107.3 | 107.3 |
| Pressure, psig | 600 | 600 | 600 | 600 | 600 | 600 | 600 | 600 |
| Temperature, °C. | 276 | 275 | 276 | 300 | 301 | 300 | 301 | 301 |
| Time on organics, hrs. | 4.0 | 14.0 | 16.0 | 21.0 | 37.5 | 39.5 | 47.5 | 44.0 |
| Duration of run, hrs. | 2 | 10 | 2 | 2 | 16 | 2 | 2 | 2 |
| MEA SV, gmol/hr/kgcat | 2.22 | 2.22 | 2.28 | 2.18 | 2.06 | 1.92 | 1.90 | 1.82 |
| $NH_3$ feedrate, gm/hr | 49.0 | 53.7 | 51.0 | 49.0 | 52.3 | 60.0 | 61.0 | 49.5 |
| Liquid feed composition, wt. % | | | | | | | | |
| DETA | 77.16 | 77.16 | 77.16 | 77.16 | 77.16 | 66.46 | 66.46 | 66.46 |
| MEA | 22.84 | 22.84 | 22.84 | 22.84 | 22.84 | — | — | — |
| AEEA | — | — | — | — | — | 33.54 | 33.54 | 33.54 |
| Liquid product composition, wt. % | | | | | | | | |
| EDA | 0.59 | 0.48 | 0.42 | 1.39 | 1.39 | 1.17 | 1.18 | 1.35 |
| MeEDA | 0.00 | 0.00 | 0.00 | 0.00 | 0.00 | 0.00 | 0.00 | 0.00 |
| MEA | 11.78 | 12.64 | 12.69 | 7.30 | 8.85 | 0.48 | 0.00 | 8.79 |
| EtEDA | 0.00 | 0.00 | 0.00 | 0.00 | 0.00 | 0.00 | 0.00 | 0.00 |
| PIP | 0.32 | 0.18 | 0.14 | 0.65 | 0.57 | 5.50 | 5.68 | 0.57 |
| DETA | 81.41 | 81.70 | 81.91 | 81.16 | 82.83 | 79.81 | 81.98 | 84.88 |
| AEEA | 1.12 | 0.89 | 0.89 | 0.00 | 0.00 | 2.01 | 1.94 | 1.08 |
| AEP | 0.57 | 0.50 | 0.48 | 1.17 | 1.08 | 1.14 | 1.08 | 0.00 |
| HEP | 0.00 | 0.00 | 0.00 | 0.00 | 0.00 | 0.00 | 0.00 | 0.00 |
| TETA's | 3.71 | 3.08 | 2.89 | 5.97 | 3.52 | 6.18 | 5.18 | 1.83 |
| TEPA's | 0.00 | 0.00 | 0.00 | 0.65 | 0.00 | 1.97 | 1.34 | 0.00 |
| ROH Conversion % | 49.22 | 45.39 | 45.13 | 68.46 | 61.55 | 94.00 | 94.20 | 96.70 |
| Acyclic (N4)/cyclic (< = N4), weight ratio | 100.00 | 100.00 | 100.00 | 25.40 | 18.40 | 100.00 | 100.00 | 100.00 |
| Acyclic (N5)/cyclic (< = N5), weight ratio | — | — | — | 100.00 | — | 0.00 | 0.00 | — |
| $\Sigma(N5)/\Sigma(N4)$, weight ratio | — | — | — | — | — | 0.30 | 0.30 | — |

TABLE LXVIII

| Example No. | 638 | 639 | 640 | 641 | 642 | 643 | 644 | 645 |
|---|---|---|---|---|---|---|---|---|
| Catalyst Type | XXX | XXX | XXX | XXX | XXX | XXX | XXX | XXX |
| Catalyst weight, gm | 126.9 | 126.9 | 126.9 | 126.9 | 126.9 | 126.9 | 126.9 | 126.9 |
| Pressure, psig | 600 | 600 | 600 | 600 | 600 | 600 | 600 | 600 |
| Temperature, °C. | 282 | 264 | 269 | 296 | 283 | 290 | 299 | 272 |
| Time on organics, hrs. | 4.0 | 24.0 | 27.0 | 48.0 | 50.0 | 67.5 | 69.5 | 75.0 |
| Duration of run, hrs. | 2 | 2 | 2 | 2 | 2 | 2 | 2 | 2 |
| MEA SV, gmol/hr/kgcat | 1.87 | 1.84 | 1.86 | 1.71 | 1.87 | 1.63 | 1.67 | 1.64 |
| $NH_3$ feedrate, gm/hr | 53.5 | 54.0 | 51.0 | 55.0 | 50.0 | 45.0 | 41.0 | 51.0 |
| Liquid feed composition, wt. % | | | | | | | | |
| DETA | 77.16 | 77.16 | 77.16 | 77.16 | 77.16 | 66.46 | 66.46 | 66.46 |
| MEA | 22.84 | 22.84 | 22.84 | 22.84 | 22.84 | — | — | — |
| AEEA | — | — | — | — | — | 33.54 | 33.54 | 33.54 |
| Liquid product composition, wt. % | | | | | | | | |
| EDA | 2.60 | 1.08 | 0.73 | 2.34 | 1.57 | 1.64 | 1.62 | 0.00 |
| MeEDA | 0.00 | 0.00 | 0.00 | 0.00 | 0.00 | 0.00 | 0.00 | 0.00 |
| MEA | 2.38 | 8.61 | 10.46 | 5.48 | 7.30 | 0.00 | 0.00 | 0.00 |
| EtEDA | 0.00 | 0.00 | 0.00 | 0.00 | 0.00 | 0.00 | 0.00 | 0.00 |
| PIP | 2.30 | 0.91 | 0.71 | 2.12 | 1.59 | 11.97 | 12.36 | 6.27 |
| DETA | 72.97 | 78.50 | 79.50 | 76.30 | 78.68 | 68.16 | 71.00 | 77.31 |
| AEEA | 0.00 | 0.00 | 0.00 | 0.00 | 0.00 | 1.42 | 1.38 | 14.18 |
| AEP | 3.04 | 1.12 | 0.68 | 2.28 | 1.55 | 1.79 | 1.72 | 0.47 |
| HEP | 0.00 | 0.00 | 0.00 | 0.00 | 0.00 | 0.00 | 0.00 | 0.00 |
| TETA's | 13.55 | 7.63 | 6.79 | 7.81 | 7.22 | 8.73 | 7.12 | 1.57 |
| TEPA's | 3.04 | 1.60 | 0.92 | 1.88 | 1.11 | 4.32 | 3.21 | 0.00 |
| ROH Conversion % | 90.08 | 63.26 | 55.30 | 76.51 | 68.80 | 95.90 | 96.00 | 58.30 |
| Acyclic (N4)/cyclic (< = N4), weight ratio | 7.10 | 10.50 | 100.00 | 5.40 | 9.90 | 0.10 | 0.00 | 0.00 |
| Acyclic (N5)/cyclic (< = N5), weight ratio | 7.80 | 100.00 | 100.00 | 2.90 | 100.00 | 10.50 | 100.00 | 100.00 |
| $\Sigma(N5)/\Sigma(N4)$, weight ratio | — | — | — | — | — | 0.50 | 0.50 | — |

TABLE LXIX

| Example No. | 646 | 647 | 648 | 649 | 650 | 651 | 652 | 653 | 654 | 655 | 656 |
|---|---|---|---|---|---|---|---|---|---|---|---|
| Catalyst Type | YYY | YYY | YYY | YYY | YYY | YYY | YYY | YYY | YYY | YYY | YYY |
| Catalyst weight, gm | 120.2 | 120.2 | 120.2 | 120.2 | 120.2 | 120.2 | 120.2 | 120.2 | 120.2 | 120.2 | 120.2 |
| Pressure, psig | 600 | 600 | 600 | 600 | 600 | 600 | 600 | 600 | 600 | 600 | 600 |
| Temperature, °C. | 272 | 273 | 273 | 289 | 300 | 299 | 297 | 300 | 299 | 272 | 272 |
| Time on organics, hrs. | 3.5 | 19.5 | 21.5 | 27.5 | 43.5 | 45.5 | 50.5 | 66.5 | 68.5 | 70.5 | 73.5 |

TABLE LXIX-continued

| Example No. | 646 | 647 | 648 | 649 | 650 | 651 | 652 | 653 | 654 | 655 | 656 |
|---|---|---|---|---|---|---|---|---|---|---|---|
| Duration of run, hrs. | 2 | 16 | 2 | 2 | 16 | 2 | 2 | 16 | 2 | 2 | 1 |
| MEA SV, gmol/hr/kgcat | 1.92 | 1.95 | 2.06 | 2.09 | 1.94 | 1.99 | 1.56 | 1.58 | 1.55 | 1.66 | 2.03 |
| $NH_3$ feedrate, gm/hr | 111.0 | 50.9 | 66.0 | 80.0 | 58.0 | 55.0 | 68.0 | 64.5 | 84.8 | 67.0 | 49.0 |
| Liquid feed composition, wt. % | | | | | | | | | | | |
| DETA | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | — | — | — | — | 22.84 |
| AEEA | — | — | — | — | — | — | 33.54 | 33.54 | 33.54 | 33.54 | — |
| Liquid product composition, wt. % | | | | | | | | | | | |
| EDA | 0.00 | 0.00 | 0.00 | 0.00 | 1.08 | 0.00 | 0.00 | 0.00 | 0.00 | 0.00 | 0.00 |
| MeEDA | 0.00 | 0.00 | 0.00 | 0.00 | 0.00 | 0.00 | 0.00 | 0.00 | 0.00 | 0.00 | 0.00 |
| MEA | 8.22 | 8.33 | 7.82 | 2.98 | 3.36 | 3.69 | 1.08 | 1.14 | 0.00 | 0.00 | 9.79 |
| EtEDA | 0.00 | 0.00 | 0.00 | 0.00 | 0.00 | 0.00 | 0.00 | 0.00 | 0.00 | 0.00 | 0.00 |
| PIP | 0.00 | 0.00 | 0.00 | 0.91 | 0.73 | 0.71 | 5.15 | 4.86 | 4.64 | 3.87 | 0.43 |
| DETA | 88.30 | 87.01 | 88.01 | 84.49 | 81.52 | 83.00 | 83.96 | 79.07 | 83.12 | 84.96 | 87.16 |
| AEEA | 0.00 | 0.00 | 0.00 | 0.00 | 0.00 | 0.00 | 0.00 | 0.65 | 0.73 | 5.72 | 0.00 |
| AEP | 0.37 | 0.38 | 0.38 | 1.42 | 1.30 | 1.22 | 1.35 | 1.06 | 1.01 | 0.43 | 0.49 |
| HEP | 0.00 | 0.00 | 0.00 | 0.00 | 0.00 | 0.00 | 0.00 | 0.00 | 0.00 | 0.00 | 0.00 |
| TETA's | 3.10 | 4.29 | 3.79 | 8.95 | 10.19 | 8.57 | 4.93 | 6.53 | 5.81 | 2.15 | 2.13 |
| TEPA's | 0.00 | 0.00 | 0.00 | 0.75 | 1.14 | 0.79 | 2.69 | 5.45 | 4.13 | 2.87 | 0.00 |
| ROH Conversion % | 64.92 | 64.48 | 66.67 | 87.43 | 85.77 | 84.16 | 99.30 | 99.50 | 100.00 | 68.50 | 58.15 |
| Acyclic (N4)/cyclic (< = N4), weight ratio | 100.00 | 100.00 | 100.00 | 26.20 | 17.50 | 17.80 | 0.31 | 0.10 | 0.06 | 0.00 | 100.00 |
| Acyclic (N5)/cyclic (< = N5), weight ratio | — | — | — | 100.00 | 100.00 | 100.00 | 100.00 | 22.20 | 100.00 | 100.00 | — |
| $\Sigma(N5)/\Sigma(N4)$, weight ratio | — | — | — | — | — | — | — | — | — | — | — |

TABLE LXX

| Example No. | 657 | 658 | 659 | 660 | 661 | 662 | 663 | 664 | 665 | 666 | 667 |
|---|---|---|---|---|---|---|---|---|---|---|---|
| Catalyst Type | ZZZ | ZZZ | ZZZ | ZZZ | ZZZ | ZZZ | ZZZ | ZZZ | ZZZ | ZZZ | ZZZ |
| Catalyst weight, gm | 116.3 | 116.3 | 116.3 | 116.3 | 116.3 | 116.3 | 116.3 | 116.3 | 116.3 | 116.3 | 116.3 |
| Pressure, psig | 600 | 600 | 600 | 600 | 600 | 600 | 600 | 600 | 600 | 600 | 600 |
| Temperature, °C. | 275 | 275 | 275 | 300 | 303 | 300 | 299 | 299 | 300 | 274 | 275 |
| Time on organics, hrs. | 6.0 | 23.0 | 25.0 | 29.0 | 47.0 | 49.0 | 54.0 | 71.0 | 73.0 | 78.0 | 95.0 |
| Duration of run, hrs. | 2 | 16 | 2 | 2 | 16 | 2 | 2 | 17 | 2 | 2 | 16 |
| MEA SV, gmol/hr/kgcat | 1.92 | 2.00 | 2.03 | 1.96 | 1.96 | 1.95 | 1.74 | 1.51 | 1.60 | 1.78 | 1.99 |
| $NH_3$ feedrate, gm/hr | 70.0 | 61.1 | 57.5 | 49.5 | 51.3 | 52.0 | 55.5 | 48.8 | 50.5 | 55.0 | 48.3 |
| Liquid feed composition, wt. % | | | | | | | | | | | |
| DETA | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | — | — | — | — | 22.84 |
| AEEA | — | — | — | — | — | — | 33.54 | 33.54 | 33.54 | 33.54 | — |
| Liquid product composition, wt. % | | | | | | | | | | | |
| EDA | 1.09 | 0.80 | 0.74 | 1.86 | 1.69 | 1.60 | 1.45 | 1.55 | 1.62 | 0.58 | 0.58 |
| MeEDA | 0.00 | 0.00 | 0.00 | 0.00 | 0.00 | 0.00 | 0.00 | 0.00 | 0.00 | 0.00 | 0.00 |
| MEA | 13.57 | 15.03 | 15.47 | 8.52 | 10.49 | 11.24 | 0.62 | 0.38 | 0.38 | 0.46 | 16.94 |
| EtEDA | 0.00 | 0.00 | 0.00 | 0.00 | 0.00 | 0.00 | 0.00 | 0.00 | 0.00 | 0.00 | 0.00 |
| PIP | 0.34 | 0.20 | 0.18 | 0.56 | 0.47 | 0.42 | 3.49 | 3.53 | 3.46 | 1.39 | 0.14 |
| DETA | 71.01 | 74.43 | 74.82 | 71.47 | 73.78 | 74.30 | 72.62 | 70.62 | 71.21 | 69.66 | 76.98 |
| AEEA | 1.11 | 1.21 | 1.24 | 0.65 | 0.87 | 0.99 | 4.28 | 4.09 | 4.36 | 20.93 | 2.65 |
| AEP | 0.51 | 0.33 | 0.31 | 0.91 | 0.77 | 0.73 | 0.76 | 0.68 | 0.67 | 0.22 | 0.25 |
| HEP | 0.00 | 0.00 | 0.00 | 0.00 | 0.00 | 0.00 | 0.00 | 0.00 | 0.00 | 0.00 | 0.00 |
| TETA's | 7.40 | 5.81 | 5.25 | 8.79 | 6.82 | 5.83 | 6.63 | 6.99 | 6.60 | 1.40 | 1.67 |
| TEPA's | 3.76 | 1.88 | 1.60 | 4.50 | 2.87 | 2.23 | 8.06 | 8.11 | 7.70 | 4.25 | 0.37 |
| ROH Conversion % | 41.20 | 35.13 | 33.09 | 62.86 | 54.23 | 50.62 | 87.20 | 87.50 | 86.70 | 37.40 | 26.29 |
| Acyclic (N4)/cyclic (< = N4), weight ratio | 24.50 | 100.00 | 100.00 | 12.00 | 12.80 | 11.60 | 0.12 | 0.10 | 0.10 | 0.10 | 100.00 |
| Acyclic (N5)/cyclic (< =N5), weight ratio | 9.60 | 100.00 | 100.00 | 5.90 | 8.70 | 17.10 | 10.20 | 11.50 | 12.70 | 100.00 | 100.00 |
| $\Sigma(N5)/\Sigma(N4)$, weight ratio | — | — | — | — | — | — | 1.20 | 1.20 | 1.20 | 3.00 | — |

TABLE LXXI

| Example No. | 668 | 669 | 670 | 671 | 672 | 673 | 674 | 675 | 676 | 677 | 678 |
|---|---|---|---|---|---|---|---|---|---|---|---|
| Catalyst Type | AAAA | AAAA | AAAA | AAAA | AAAA | AAAA | AAAA | AAAA | AAAA | AAAA | AAAA |
| Catalyst weight, gm | 117.7 | 117.7 | 117.7 | 117.7 | 117.7 | 117.7 | 117.7 | 117.7 | 117.7 | 117.7 | 117.7 |
| Pressure, psig | 600 | 600 | 600 | 600 | 600 | 600 | 600 | 600 | 600 | 600 | 600 |
| Temperature, °C. | 275 | 275 | 277 | 303 | 302 | 302 | 273 | 301 | 301 | 274 | 274 |
| Time on organics, hrs. | 6.0 | 22.0 | 24.0 | 29.0 | 45.6 | 47.6 | 52.6 | 69.7 | 71.7 | 76.7 | 93.7 |
| Duration of run, hrs. | 2 | 16 | 2 | 2 | 16 | 2 | 2 | 16 | 2 | 2 | 16 |
| MEA SV, gmol/hr/kgcat | 1.98 | 1.99 | 2.03 | 1.99 | 1.99 | 2.03 | 2.00 | 1.58 | 1.70 | 1.75 | 1.98 |
| $NH_3$ feedrate, gm/hr | 68.0 | 54.3 | 50.5 | 55.5 | 47.8 | 48.5 | 79.0 | 68.3 | 72.5 | 79.5 | 68.1 |
| Liquid feed composition, wt. % | | | | | | | | | | | |
| DETA | 77.16 | 77.16 | 77.16 | 77.16 | 77.16 | 77.16 | 77.16 | 66.46 | 66.46 | 66.46 | 77.16 |

TABLE LXXI-continued

| Example No. | 668 | 669 | 670 | 671 | 672 | 673 | 674 | 675 | 676 | 677 | 678 |
|---|---|---|---|---|---|---|---|---|---|---|---|
| MEA | 22.84 | 22.84 | 22.84 | 22.84 | 22.84 | 22.84 | 22.84 | — | — | — | 22.84 |
| AEEA | — | — | — | — | — | — | — | 33.54 | 33.54 | 33.54 | — |
| Liquid product composition, wt. % | | | | | | | | | | | |
| EDA | 0.97 | 0.91 | 0.90 | 2.63 | 2.07 | 1.73 | 0.53 | 1.35 | 1.32 | 0.42 | 0.48 |
| MeEDA 0.00 | 0.00 | 0.00 | 0.00 | 0.00 | 0.00 | 0.00 | 0.00 | 0.00 | 0.00 | 0.00 | 0.00 |
| MEA | 11.59 | 11.42 | 11.61 | 3.72 | 5.41 | 7.22 | 15.50 | 0.39 | 0.26 | 0.39 | 15.13 |
| EtEDA | 0.00 | 0.00 | 0.00 | 0.00 | 0.00 | 0.00 | 0.00 | 0.00 | 0.00 | 0.00 | 0.00 |
| PIP | 0.35 | 0.33 | 0.33 | 0.84 | 0.64 | 0.53 | 0.12 | 3.59 | 3.54 | 1.45 | 0.22 |
| DETA | 71.40 | 70.89 | 71.27 | 67.56 | 69.33 | 71.24 | 76.04 | 68.79 | 68.37 | 66.67 | 74.89 |
| AEEA | 1.15 | 1.26 | 1.28 | 0.23 | 0.44 | 0.85 | 1.39 | 2.48 | 3.15 | 20.08 | 3.01 |
| AEP | 0.52 | 0.49 | 0.47 | 1.53 | 1.12 | 0.91 | 0.30 | 0.81 | 0.69 | 0.23 | 0.29 |
| HEP | 0.00 | 0.00 | 0.00 | 0.00 | 0.00 | 0.00 | 0.00 | 0.00 | 0.00 | 0.00 | 0.00 |
| TETA's | 9.08 | 9.52 | 9.30 | 12.67 | 11.55 | 9.77 | 4.68 | 6.58 | 6.06 | 1.62 | 3.65 |
| TEPA's | 4.20 | 4.41 | 4.17 | 7.89 | 6.69 | 5.30 | 1.17 | 13.35 | 12.33 | 7.56 | 1.63 |
| ROH Conversion % | 50.26 | 51.01 | 50.20 | 83.98 | 76.63 | 68.73 | 33.00 | 92.60 | 90.40 | 39.90 | 34.34 |
| Acrylic (N4)/cyclic (< = N4), weight ratio | 38.80 | 46.80 | 50.10 | 9.60 | 13.90 | 17.20 | 100.00 | 0.30 | 0.20 | 0.20 | 15.70 |
| Acrylic (N5)/cyclic (< = N5), weight ratio | 21.00 | 24.40 | 22.90 | 4.10 | 6.10 | 8.90 | 100.00 | 13.50 | 16.00 | 100.00 | 8.20 |
| Σ(N5)/Σ(N4)), weight ratio | — | — | — | — | — | — | — | 2.00 | 12.00 | 4.70 | — |

TABLE LXXII

| Example No. | 679 | 680 | 681 | 682 | 683 | 684 | 685 | 686 | 687 | 688 | 689 | 690 |
|---|---|---|---|---|---|---|---|---|---|---|---|---|
| Catalyst Type | BBBB | BBBB | BBBB | BBBB | BBBB | BBBB | BBBB | BBBB | BBBB | BBBB | BBBB | BBBB |
| Catalyst weight, gm | 78.74 | 78.74 | 78.74 | 78.74 | 78.74 | 78.74 | 78.74 | 78.74 | 78.74 | 78.74 | 78.74 | 78.74 |
| Pressure, psig | 606 | 603 | 603 | 602 | 603 | 603 | 603 | 598 | 603 | 603 | 604 | 603 |
| Temperature, °C. | 270 | 270 | 280 | 269 | 259 | 280 | 280 | 270.1 | 270 | 280 | 259 | 269 |
| Time on organics, hrs. | 4.5 | 4.5 | 28.5 | 51.5 | 71.5 | 76.5 | 100.5 | 120 | 167.5 | 172.5 | 191.5 | 196.5 |
| Duration of run, hrs. | 2 | 2 | 2 | 2 | 2 | 2 | 2 | 2 | 2 | 2 | 2 | 2 |
| MEA SV, gmol/hr/kgcat | 3.46 | 3.84 | 3.94 | 3.87 | 3.77 | 3.63 | 3.78 | 3.83 | 3.81 | 3.71 | 3.89 | 3.89 |
| DETA/MEA mole ratio | 1.00 | 1.00 | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 | 5.97 | 5.97 |
| Crude product composition, wt. % | | | | | | | | | | | | |
| EDA | 0.874 | 1.232 | 1.585 | 0.847 | 0.433 | 1.400 | 1.565 | 0.773 | 0.551 | 1.445 | 0.461 | 0.791 |
| MEA | 12.473 | 11.945 | 7.517 | 13.370 | 17.877 | 6.436 | 7.199 | 12.823 | 16.111 | 5.976 | 18.787 | 12.858 |
| PIP | 0.965 | 1.116 | 1.414 | 1.070 | 0.651 | 1.400 | 1.451 | 1.028 | 0.807 | 1.387 | 0.691 | 1.023 |
| DETA | 39.228 | 39.867 | 35.453 | 41.854 | 47.014 | 35.668 | 35.534 | 41.213 | 44.005 | 33.430 | 47.586 | 40.957 |
| AEEA | 1.227 | 1.108 | 0.479 | 1.371 | 2.399 | 0.486 | 0.502 | 1.388 | 1.922 | 0.443 | 2.282 | 1.404 |
| AEP | 1.183 | 1.533 | 1.814 | 1.158 | 0.708 | 1.977 | 1.886 | 1.126 | 0.824 | 1.827 | 0.682 | 1.103 |
| HEP | 0.000 | 0.000 | 0.000 | 0.000 | 0.000 | 0.000 | 0.000 | 0.000 | 0.000 | 0.000 | 0.000 | 0.000 |
| TAEA | 2.760 | 2.694 | 2.611 | 2.646 | 2.564 | 2.683 | 2.567 | 2.662 | 2.560 | 2.553 | 2.310 | 2.681 |
| l-TETA | 12.867 | 13.297 | 13.364 | 12.613 | 12.062 | 14.170 | 13.658 | 12.943 | 12.257 | 13.506 | 10.647 | 12.732 |
| DAEP | 0.519 | 0.744 | 0.968 | 0.425 | 0.180 | 0.018 | 0.985 | 0.432 | 0.232 | 1.004 | 0.173 | 0.386 |
| PEEDA | 0.110 | 0.111 | 0.154 | 0.082 | 0.152 | 0.059 | 0.710 | 0.336 | 0.206 | 0.710 | 0.146 | 0.310 |
| DPE | 0.118 | 0.120 | 0.127 | 0.085 | 0.097 | 0.087 | 0.322 | 0.227 | 0.120 | 0.335 | 0.085 | 0.184 |
| AE-TAEA | 4.110 | 3.926 | 4.516 | 3.704 | 2.640 | 4.497 | 4.572 | 3.788 | 3.014 | 4.645 | 2.372 | 3.629 |
| l-TEPA | 7.436 | 7.679 | 8.979 | 7.093 | 5.411 | 8.403 | 9.298 | 7.467 | 6.239 | 9.538 | 4.500 | 6.990 |
| AE-DAEP | 0.140 | 0.117 | 0.182 | 0.100 | 0.097 | 0.000 | 0.808 | 0.390 | 0.275 | 0.848 | 0.213 | 0.276 |
| AE-PEEDA | 0.099 | 0.100 | 0.129 | 0.096 | 0.000 | 0.720 | 0.173 | 0.127 | 0.099 | 0.185 | 0.000 | 0.057 |
| iAE-PEEDA | 0.000 | 0.000 | 0.000 | 0.000 | 0.000 | 0.000 | 0.000 | 0.000 | 0.000 | 0.000 | 0.000 | 0.000 |
| AE-DPE | 0.304 | 0.169 | 0.301 | 0.160 | 0.065 | 0.160 | 1.020 | 0.739 | 0.467 | 1.089 | 0.315 | 0.667 |
| BPEA | 0.639 | 0.578 | 0.844 | 0.573 | 0.045 | 0.211 | 1.060 | 0.835 | 0.435 | 1.026 | 0.247 | 0.634 |
| Others | 8.068 | 6.841 | 11.264 | 5.414 | 2.775 | 11.735 | 8.190 | 6.222 | 3.695 | 9.232 | 1.904 | 3.598 |
| MEA conversion, % | 66.60 | 68.06 | 79.87 | 63.84 | 52.17 | 82.68 | 80.79 | 66.20 | 56.64 | 83.70 | 48.64 | 64.40 |
| DETA conversion, % | 37.56 | 36.64 | 43.59 | 32.72 | 25.25 | 42.94 | 43.64 | 35.44 | 29.62 | 45.82 | 22.68 | 32.60 |
| Acyclic(N4), wt. % | 95.43 | 94.25 | 92.75 | 96.27 | 97.15 | 93.54 | 88.94 | 94.00 | 96.37 | 88.68 | 96.98 | 94.60 |
| Acyclic(N5), wt. % | 90.71 | 92.25 | 90.26 | 92.08 | 97.50 | 92.20 | 81.92 | 84.33 | 87.88 | 81.83 | 89.87 | 86.66 |
| Σ(N5)/Σ(N4), weight ratio | 0.78 | 0.74 | 0.87 | 0.74 | 0.55 | 0.78 | 0.93 | 0.80 | 0.68 | 0.96 | 0.57 | 0.75 |
| Acyclic(Nr)/cyclic(< = N4), weight ratio | 5.40 | 4.41 | 3.57 | 5.41 | 8.18 | 3.71 | 3.03 | 4.96 | 6.77 | 3.05 | 7.29 | 5.13 |

| Example No. | 691 | 692 | 693 | 694 | 695 | 696 |
|---|---|---|---|---|---|---|
| Catalyst Type | BBBB | BBBB | BBBB | BBBB | BBBB | BBBB |
| Catalyst weight, gm | 78.74 | 78.74 | 78.74 | 78.74 | 78.74 | 78.74 |
| Pressure, psig | 604 | 603 | 603 | 603 | 604 | 604 |
| Temperature, °C. | 260 | 280 | 270 | 280 | 270 | 270 |
| Time on organics, hrs. | 214.5 | 219.5 | 238.5 | 243.5 | 262.5 | 266 |
| Duration of run, hrs. | 2 | 2 | 2 | 2 | 2 | 2 |
| MEA SV, gmol/hr/kgcat | 3.81 | 3.78 | 3.79 | 3.51 | 3.51 | 3.71 |
| DETA/MEA mole ratio | 1.00 | 1.00 | 1.00 | 1.00 | 1.00 | 1.00 |
| NH3/MEA mole ratio | 5.97 | 5.97 | 5.97 | 5.97 | 5.97 | 5.97 |
| Crude product composition, wt. % | | | | | | |
| EDA | 0.658 | 1.456 | 0.910 | 1.122 | 1.072 | 1.017 |
| MEA | 18.141 | 6.956 | 13.064 | 13.239 | 11.990 | 12.608 |

TABLE LXXII-continued

| | | | | | | |
|---|---|---|---|---|---|---|
| PIP | 0.811 | 1.416 | 1.148 | 1.024 | 1.234 | 1.186 |
| DETA | 45.580 | 35.955 | 41.603 | 42.624 | 40.482 | 40.928 |
| AEEA | 1.879 | 0.493 | 1.322 | 1.350 | 1.216 | 1.269 |
| AEP | 0.881 | 1.832 | 1.184 | 1.192 | 1.267 | 1.191 |
| HEP | 0.000 | 0.000 | 0.000 | 0.000 | 0.000 | 0.000 |
| TAEA | 2.359 | 2.571 | 2.654 | 2.361 | 2.647 | 2.627 |
| 1-TETA | 10.997 | 13.341 | 12.720 | 11.438 | 12.833 | 12.755 |
| DAEP | 0.275 | 0.888 | 0.410 | 0.490 | 0.472 | 0.422 |
| EEDA | 0.222 | 0.654 | 0.336 | 0.382 | 0.369 | 0.339 |
| DPE | 0.086 | 0.309 | 0.196 | 0.271 | 0.070 | 0.135 |
| AE-TAEA | 2.706 | 4.368 | 3.735 | 3.951 | 3.951 | 3.751 |
| 1-TEPA | 5.378 | 8.945 | 7.412 | 6.576 | 7.610 | 7.246 |
| AE-DAEP | 0.183 | 0.700 | 0.300 | 0.385 | 0.331 | 0.291 |
| AE-PEEDA | 0.056 | 0.084 | 0.065 | 0.085 | 0.035 | 0.028 |
| iAE-PEEDA | 0.000 | 0.000 | 0.000 | 0.000 | 0.000 | 0.000 |
| AE-DPE | 4.434 | 1.016 | 0.698 | 0.091 | 0.064 | 0.062 |
| BPEA | 0.403 | 0.932 | 0.638 | 0.093 | 0.594 | 0.053 |
| Others | 2.311 | 6.162 | 3.686 | 6.348 | 5.045 | 5.231 |
| MEA conversion, % | 50.59 | 80.69 | 64.55 | 64.31 | 67.22 | 65.36 |
| DETA conversion, % | 26.22 | 40.67 | 32.91 | 31.71 | 34.22 | 33.16 |
| Acyclic(N4), wt. % | 95.81 | 89.58 | 94.23 | 92.35 | 94.45 | 94.49 |
| Acyclic(N5), wt. % | 88.25 | 82.97 | 86.76 | 94.15 | 91.86 | 96.21 |
| Σ(N5)/Σ(N4), weight ratio | 0.66 | 0.90 | 0.79 | 0.75 | 0.77 | 0.70 |
| Acyclic(N4)/cyclic(< = N4), weight ratio | 5.86 | 3.12 | 4.70 | 4.11 | 4.54 | 4.70 |

TABLE LXXIII

| | Example No. | | | | | | | | | | |
|---|---|---|---|---|---|---|---|---|---|---|---|
| Catalyst Type | 697 CCCC | 698 CCCC | 699 CCCC | 700 CCCC | 701 CCCC | 702 CCCC | 703 CCCC | 704 CCCC | 705 CCCC | 706 CCCC | 707 CCCC |
| Catalyst weight, gm | 84.66 | 84.66 | 84.66 | 84.66 | 84.66 | 84.66 | 84.66 | 84.66 | 84.66 | 84.66 | 84.66 |
| Pressure, psig | 598 | 598 | 598 | 598 | 598 | 599 | 599 | 598 | 603 | 598 | 598 |
| Temperature, °C. | 270 | 270 | 280 | 259 | 269 | 259 | 280 | 280 | 270.1 | 270 | 280 |
| Time on organics, hrs. | 4.5 | 23.5 | 28.5 | 47.5 | 51.5 | 71.5 | 76.5 | 100.5 | 120 | 167.5 | 172.5 |
| Duration of run, hrs. | 2 | 2 | 2 | 2 | 2 | 2 | 2 | 2 | 2 | 2 | 2 |
| MEA SV, g mol/hr/kg cat | 2.95 | 2.82 | 2.91 | 2.90 | 2.89 | 2.81 | 2.72 | 2.85 | 2.92 | 2.92 | 2.51 |
| DETA/MEA mole ratio | 1.00 | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 | 5.97 |
| Crude product composition, wt. % | | | | | | | | | | | |
| EDA | 0.387 | 0.451 | 0.942 | 0.263 | 0.472 | 0.251 | 0.768 | 0.805 | 0.481 | 0.768 | 0.935 |
| MEA | 18.211 | 18.550 | 12.561 | 24.117 | 18.908 | 22.270 | 11.181 | 11.851 | 17.815 | 11.617 | 9.895 |
| PIP | 0.711 | 0.768 | 1.105 | 0.411 | 0.731 | 0.450 | 1.013 | 1.082 | 0.763 | 1.012 | 1.112 |
| DETA | 45.762 | 47.529 | 39.025 | 52.023 | 46.902 | 51.519 | 38.122 | 38.925 | 46.516 | 38.660 | 37.291 |
| AEEA | 1.902 | 2.077 | 1.192 | 2.582 | 2.111 | 2.804 | 1.247 | 1.088 | 2.005 | 1.321 | 0.909 |
| AEP | 0.846 | 0.787 | 1.214 | 0.446 | 0.718 | 0.519 | 1.229 | 1.254 | 0.767 | 1.097 | 1.308 |
| HEP | 0.000 | 0.000 | 0.000 | 0.000 | 0.000 | 0.000 | 0.000 | 0.000 | 0.000 | 0.000 | 0.000 |
| TAEA | 2.031 | 2.252 | 2.423 | 1.674 | 2.273 | 2.036 | 2.764 | 2.429 | 2.345 | 2.638 | 2.623 |
| 1-TETA | 10.921 | 11.106 | 12.012 | 8.125 | 11.140 | 9.812 | 13.613 | 12.691 | 11.657 | 12.643 | 12.534 |
| DAEP | 0.186 | 0.202 | 0.477 | 0.080 | 0.175 | 0.097 | 0.523 | 0.523 | 0.191 | 0.461 | 0.560 |
| PEEDA | 0.159 | 0.178 | 0.147 | 0.057 | 0.157 | 0.084 | 0.424 | 0.443 | 0.174 | 0.353 | 0.455 |
| DPE | 0.084 | 0.096 | 0.095 | 0.052 | 0.114 | 0.086 | 0.094 | 0.303 | 0.105 | 0.353 | 0.332 |
| AE-TAEA | 2.341 | 2.390 | 3.575 | 1.205 | 2.444 | 1.558 | 4.042 | 3.853 | 2.650 | 3.971 | 4.248 |
| 1-TEPA | 3.918 | 5.171 | 7.286 | 2.186 | 6.082 | 3.822 | 8.123 | 8.109 | 6.868 | 8.051 | 8.471 |
| AE-DAEP | 0.366 | 0.189 | 0.131 | 0.129 | 0.081 | 0.000 | 0.417 | 0.508 | 0.093 | 0.479 | 0.536 |
| AE-PEEDA | 0.080 | 0.079 | 0.101 | 0.068 | 0.000 | 0.000 | 0.113 | 0.139 | 0.000 | 0.163 | 0.150 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.403 | 0.061 | 0.264 | 0.051 | 0.078 | 0.066 | 0.220 | 0.797 | 0.055 | 0.793 | 0.918 |
| BPEA | 0.328 | 0.276 | 0.649 | 0.076 | 0.291 | 0.128 | 0.215 | 0.930 | 0.371 | 0.949 | 1.033 |
| Others | 6.126 | 2.669 | 9.532 | 1.845 | 2.513 | 1.388 | 8.524 | 7.390 | 2.594 | 7.450 | 7.630 |
| MEA conversion, % | 51.16 | 50.15 | 66.20 | 34.36 | 49.36 | 40.71 | 70.01 | 68.44 | 52.59 | 68.95 | 73.17 |
| DETA conversion, % | 27.06 | 24.09 | 37.59 | 15.85 | 25.35 | 18.49 | 39.22 | 38.40 | 26.43 | 38.60 | 39.91 |
| Acyclic(N4), wt. % | 96.80 | 96.56 | 95.26 | 98.11 | 96.78 | 97.79 | 94.03 | 92.26 | 96.75 | 92.90 | 91.84 |
| Acyclic(N5), wt. % | 84.17 | 92.59 | 90.47 | 91.27 | 94.99 | 96.53 | 92.65 | 83.44 | 94.83 | 83.45 | 82.83 |
| Σ(N5)/Σ(N4), weight ratio | 0.56 | 0.59 | 0.79 | 0.37 | 0.65 | 0.46 | 0.75 | 0.87 | 0.69 | 0.88 | 0.93 |
| Acyclic(N4)/cyclic (< = N4), weight ratio | 6.52 | 6.58 | 4.75 | 9.37 | 7.08 | 9.58 | 4.99 | 4.20 | 7.00 | 4.66 | 4.02 |

| | Example No. | | | | | | | |
|---|---|---|---|---|---|---|---|---|
| Catalyst Type | 708 CCCC | 709 CCCC | 710 CCCC | 711 CCCC | 712 CCCC | 713 CCCC | 714 CCCC | 715 CCCC |
| Catalyst weight, gm | 84.66 | 84.66 | 84.66 | 84.66 | 84.66 | 84.66 | 84.66 | 84.66 |
| Pressure, psig | 598 | 598 | 598 | 599 | 599 | 604 | 604 | 604 |
| Temperature, °C. | 259 | 269 | 260 | 280 | 270 | 280 | 270 | 270 |
| Time on organics, hrs. | 191.5 | 196.5 | 214.5 | 219.5 | 238.5 | 243.5 | 262.5 | 266 |
| Duration of run, hrs. | 2 | 2 | 2 | 2 | 2 | 2 | 2 | 2 |
| MEA SV, g mol/hr/kg cat | 2.94 | 2.91 | 3.37 | 2.82 | 2.90 | 2.83 | 2.69 | 2.83 |
| DETA/MEA mole ratio | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 |
| Crude product composition, wt. % | | | | | | | | |

TABLE LXXIII-continued

| | | | | | | | | |
|---|---|---|---|---|---|---|---|---|
| EDA | 0.259 | 0.554 | 0.303 | 0.984 | 0.731 | 1.166 | 0.772 | 0.727 |
| MEA | 22.504 | 16.654 | 25.518 | 10.278 | 15.594 | 9.688 | 14.486 | 15.223 |
| PIP | 0.501 | 0.801 | 0.351 | 1.163 | 0.969 | 1.258 | 0.984 | 0.967 |
| DETA | 50.906 | 44.882 | 53.431 | 38.532 | 43.211 | 37.652 | 42.240 | 43.621 |
| AEEA | 2.608 | 1.955 | 2.502 | 0.852 | 1.707 | 0.755 | 1.601 | 1.652 |
| AEP | 0.480 | 0.827 | 0.406 | 1.361 | 1.004 | 1.440 | 1.010 | 0.980 |
| HEP | 0.000 | 0.000 | 0.000 | 0.000 | 0.000 | 0.000 | 0.000 | 0.000 |
| TAEA | 2.028 | 2.607 | 1.424 | 2.641 | 2.659 | 2.671 | 2.744 | 2.666 |
| l-TETA | 9.067 | 11.734 | 6.423 | 12.393 | 11.936 | 12.701 | 12.439 | 12.081 |
| DAEP | 0.119 | 0.241 | 0.079 | 0.538 | 0.298 | 0.622 | 0.320 | 0.282 |
| PEEDA | 0.081 | 0.211 | 0.068 | 0.431 | 0.263 | 0.498 | 0.276 | 0.248 |
| DPE | 0.103 | 0.133 | 0.127 | 0.308 | 0.161 | 0.109 | 0.118 | 0.100 |
| AE-TAEA | 1.719 | 2.992 | 1.105 | 4.215 | 3.423 | 4.647 | 3.605 | 3.411 |
| l-TEPA | 3.147 | 5.870 | 1.995 | 8.144 | 6.762 | 8.696 | 6.609 | 6.249 |
| AE-DAEP | 0.073 | 0.161 | 0.074 | 0.499 | 0.236 | 0.581 | 0.204 | 0.181 |
| AE-PEEDA | 0.064 | 0.000 | 0.053 | 0.132 | 0.054 | 0.123 | 0.034 | 0.030 |
| iAE-PEEDA | 0.000 | 0.000 | 0.000 | 0.000 | 0.000 | 0.000 | 0.000 | 0.000 |
| AE-DPE | 0.151 | 0.456 | 0.092 | 0.892 | 0.536 | 0.306 | 0.061 | 0.063 |
| BPEA | 0.115 | 0.459 | 0.108 | 0.885 | 0.576 | 0.724 | 0.059 | 0.402 |
| Others | 1.713 | 2.553 | 2.042 | 6.020 | 3.491 | 7.953 | 4.671 | 3.839 |
| MEA conversion, % | 39.26 | 54.71 | 30.82 | 71.85 | 58.06 | 73.87 | 60.45 | 58.58 |
| DETA conversion, % | 18.34 | 27.46 | 13.91 | 37.28 | 30.93 | 39.64 | 31.46 | 29.46 |
| Acyclic(N4), wt. % | 97.34 | 96.08 | 96.64 | 92.17 | 95.29 | 92.60 | 95.51 | 95.90 |
| Acyclic(N5), wt. % | 92.34 | 89.17 | 90.46 | 83.69 | 87.90 | 88.50 | 96.63 | 93.47 |
| Σ(N5)/Σ(N4), weight ratio | 0.46 | 0.67 | 0.42 | 0.91 | 0.76 | 0.91 | 0.67 | 0.67 |
| Acyclic(N4)/cyclic (< = N4), weight ratio | 8.64 | 6.48 | 7.62 | 3.95 | 5.42 | 3.91 | 5.61 | 5.72 |

TABLE LXXIV

| | Example No. | | | | | | | | |
|---|---|---|---|---|---|---|---|---|---|
| Catalyst Type | 716 DDDD | 717 DDDD | 718 DDDD | 719 DDDD | 720 DDDD | 721 DDDD | 722 DDDD | 723 DDDD | 724 DDDD |
| Catalyst weight, gm | 75 | 75 | 75 | 75 | 75 | 75 | 75 | 75 | 75 |
| Pressure, psig | 607.5 | 600 | 600 | 600 | 600 | 600 | 600 | 600 | 600 |
| Temperature, °C. | 267.9 | 267.8 | 277.8 | 259.9 | 270.1 | 259.9 | 280.1 | 269.6 | 269 |
| Time on organics, hrs. | 5 | 7.5 | 26 | 31.5 | 50 | 55.5 | 74 | 78 | 80 |
| Duration of run, hrs. | 1 | 1 | 2 | 2 | 2 | 2 | 2 | 2 | 1.5 |
| MEA SV, g mol/hr/kg cat | 8.48 | 8.57 | 4.17 | 3.96 | 3.90 | 4.22 | 4.15 | 4.01 | 3.97 |
| DETA/MEA mole ratio | 1.00 | 1.00 | 1.00 | 1.00 | 1.00 | 1.00 | 1.00 | 1.00 | 1.00 |
| NH₃/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.673 | 0.822 | 1.742 | 0.612 | 1.367 | 0.688 | 2.430 | 1.370 | 1.341 |
| MEA | 33.641 | 24.246 | 13.234 | 26.804 | 16.396 | 24.443 | 8.046 | 15.672 | 15.462 |
| PIP | 0.585 | 1.113 | 0.000 | 0.823 | 1.584 | 0.886 | 1.994 | 1.506 | 1.484 |
| DETA | 51.838 | 49.325 | 40.936 | 52.117 | 49.168 | 51.904 | 40.046 | 47.408 | 47.941 |
| AEEA | 2.205 | 0.926 | 0.312 | 1.512 | 0.754 | 1.506 | 0.202 | 0.925 | 0.850 |
| AEP | 0.502 | 0.953 | 1.969 | 0.613 | 1.431 | 0.666 | 2.287 | 1.330 | 1.326 |
| HEP | 0.000 | 0.000 | 0.000 | 0.000 | 0.000 | 0.000 | 0.000 | 0.000 | 0.000 |
| TAEA | 0.488 | 2.104 | 2.220 | 1.660 | 2.270 | 1.751 | 2.342 | 2.219 | 2.195 |
| l-TETA | 4.586 | 9.252 | 11.293 | 7.569 | 10.817 | 7.792 | 12.031 | 10.555 | 10.356 |
| DAEP | 0.000 | 0.167 | 0.922 | 0.114 | 0.307 | 0.112 | 1.101 | 0.290 | 0.271 |
| PEEDA | 0.000 | 0.113 | 0.678 | 0.000 | 0.217 | 0.075 | 0.791 | 0.209 | 0.196 |
| DPE | 0.000 | 0.000 | 0.205 | 0.000 | 0.000 | 0.000 | 0.096 | 0.000 | 0.000 |
| AE-TAEA | 0.234 | 1.259 | 3.575 | 0.885 | 2.431 | 1.011 | 3.561 | 2.057 | 2.019 |
| l-TEPA | 0.541 | 2.471 | 6.977 | 1.667 | 5.274 | 1.895 | 7.683 | 4.176 | 3.991 |
| AE-DAEP | 0.000 | 0.000 | 0.676 | 0.000 | 0.134 | 0.000 | 0.783 | 0.149 | 0.124 |
| AE-PEEDA | 0.000 | 0.000 | 0.710 | 0.000 | 0.089 | 0.000 | 0.718 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.882 | 0.000 | 0.270 | 0.091 | 1.072 | 0.423 | 0.395 |
| BPEA | 0.000 | 0.000 | 0.729 | 0.000 | 0.340 | 0.077 | 0.874 | 0.385 | 0.362 |
| Others | 0.455 | 0.399 | 3.890 | 0.125 | 1.112 | 0.488 | 5.301 | 1.685 | 1.506 |
| MEA conversion, % | 6.59 | 32.47 | 63.69 | 25.82 | 54.29 | 31.29 | 78.37 | 56.01 | 56.32 |
| DETA conversion, % | 14.45 | 18.36 | 33.25 | 14.28 | 23.51 | 14.64 | 36.03 | 20.92 | 19.52 |
| Acyclic(N4), wt. % | 100.00 | 97.59 | 88.22 | 98.78 | 96.15 | 98.08 | 87.85 | 96.23 | 96.41 |
| Acyclic(N5), wt. % | 100.00 | 100.00 | 77.88 | 100.00 | 90.24 | 94.53 | 76.53 | 86.69 | 87.22 |
| Σ(N5)/Σ(N4), weight ratio | 0.15 | 0.32 | 0.88 | 0.27 | 0.63 | 0.32 | 0.90 | 0.54 | 0.53 |
| Acyclic(N4)/cyclic (< = N4), weight ratio | 4.67 | 4.84 | 3.58 | 5.96 | 3.70 | 5.49 | 2.29 | 3.83 | 3.83 |

TABLE LXXV

| | Example No. | | | | | | | | | | |
|---|---|---|---|---|---|---|---|---|---|---|---|
| Catalyst Type | 725 EEEE | 726 EEEE | 727 EEEE | 728 EEEE | 729 EEEE | 730 EEEE | 731 EEEE | 732 EEEE | 733 EEEE | 734 EEEE | 735 EEEE |
| Catalyst weight, gm | 68.38 | 68.38 | 68.38 | 68.38 | 68.38 | 68.38 | 68.38 | 68.38 | 68.38 | 68.38 | 68.38 |
| Pressure, psig | 602 | 602 | 602 | 602 | 602 | 603 | 603 | 602 | 602 | 602 | 602 |
| Temperature, °C. | 270 | 270 | 280 | 259 | 269 | 259 | 280 | 280 | 270.1 | 270 | 280 |
| Time on organics, hrs. | 4.5 | 23.5 | 28.5 | 47.5 | 51.5 | 71.5 | 76.5 | 100.5 | 120 | 167.5 | 172.5 |

TABLE LXXV-continued

| | | | | | | | | | | | |
|---|---|---|---|---|---|---|---|---|---|---|---|
| Duration of run, hrs. | 2 | 2 | 2 | 2 | 2 | 2 | 2 | 2 | 2 | 2 | 2 |
| MEA SV, g mol/hr/kg cat | 3.96 | 3.87 | 4.09 | 3.96 | 3.90 | 3.87 | 3.92 | 3.90 | 4.03 | 3.92 | 3.98 |
| DETA/MEA mole ratio | 1.00 | 1.00 | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 | 5.97 | 5.97 |
| Crude product composition, wt. % | | | | | | | | | | | |
| EDA | 0.223 | 0.361 | 0.675 | 0.212 | 0.396 | 0.180 | 0.730 | 0.795 | 0.461 | 0.516 | 0.878 |
| MEA | 24.445 | 22.069 | 16.449 | 26.779 | 21.362 | 24.727 | 13.740 | 14.037 | 20.260 | 18.745 | 12.739 |
| PIP | 0.470 | 0.526 | 0.892 | 0.297 | 0.553 | 0.298 | 0.888 | 0.897 | 0.585 | 0.611 | 0.931 |
| DETA | 53.878 | 51.806 | 46.950 | 56.278 | 50.889 | 55.710 | 44.046 | 42.839 | 49.907 | 47.493 | 41.921 |
| AEEA | 2.281 | 2.479 | 1.818 | 2.578 | 2.565 | 2.914 | 1.871 | 1.449 | 2.318 | 2.331 | 1.424 |
| AEP | 0.515 | 0.624 | 1.064 | 0.387 | 0.663 | 0.447 | 1.193 | 1.137 | 0.672 | 0.691 | 1.141 |
| HEP | 0.000 | 0.000 | 0.000 | 0.000 | 0.000 | 0.000 | 0.000 | 0.000 | 0.000 | 0.000 | 0.000 |
| TAEA | 1.420 | 1.640 | 2.118 | 1.210 | 1.747 | 1.411 | 2.465 | 2.237 | 1.931 | 2.040 | 2.361 |
| l-TETA | 7.238 | 7.768 | 10.879 | 5.638 | 8.217 | 6.704 | 12.235 | 11.091 | 9.032 | 9.416 | 11.410 |
| DAEP | 0.092 | 0.160 | 0.324 | 0.058 | 0.188 | 0.079 | 0.480 | 0.476 | 0.204 | 0.223 | 0.454 |
| PEEDA | 0.097 | 0.137 | 0.289 | 0.053 | 0.154 | 0.073 | 0.398 | 0.393 | 0.166 | 0.181 | 0.371 |
| DPE | 0.075 | 0.095 | 0.046 | 0.052 | 0.063 | 0.100 | 0.355 | 0.333 | 0.191 | 0.211 | 0.323 |
| AE-TAEA | 1.219 | 1.522 | 2.583 | 0.752 | 1.679 | 0.945 | 3.598 | 3.115 | 2.003 | 2.229 | 3.445 |
| l-TEPA | 2.039 | 2.628 | 5.427 | 1.366 | 3.512 | 1.934 | 6.530 | 6.472 | 4.096 | 4.517 | 6.679 |
| AE-DAEP | 0.173 | 0.187 | 0.318 | 0.000 | 0.179 | 0.087 | 0.390 | 0.491 | 0.208 | 0.250 | 0.419 |
| AE-PEEDA | 0.066 | 0.063 | 0.068 | 0.000 | 0.071 | 0.080 | 0.096 | 0.129 | 0.079 | 0.091 | 0.113 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.141 | 0.121 | 0.160 | 0.073 | 0.175 | 0.115 | 0.175 | 0.301 | 0.139 | 0.100 | 0.642 |
| BPEA | 0.101 | 0.141 | 0.381 | 0.047 | 0.197 | 0.060 | 0.186 | 0.732 | 0.292 | 0.316 | 0.649 |
| Others | 2.821 | 3.594 | 4.790 | 1.260 | 3.582 | 1.974 | 6.576 | 7.895 | 3.856 | 4.550 | 5.879 |
| MEA conversion, % | 34.76 | 40.66 | 56.27 | 27.73 | 42.89 | 34.28 | 64.11 | 62.93 | 46.18 | 49.40 | 65.33 |
| DETA conversion, % | 14.55 | 17.21 | 25.83 | 9.80 | 19.14 | 12.00 | 31.61 | 32.77 | 21.21 | 23.81 | 32.19 |
| Acyclic(N4), wt. % | 97.05 | 96.00 | 95.18 | 97.67 | 96.10 | 96.98 | 92.27 | 91.72 | 95.13 | 94.90 | 92.30 |
| Acyclic(N5), wt. % | 87.14 | 89.01 | 89.63 | 94.66 | 89.31 | 89.37 | 92.28 | 85.30 | 89.48 | 89.91 | 84.74 |
| Σ(N5)/Σ(N4), weight ratio | 0.42 | 0.48 | 0.65 | 0.32 | 0.56 | 0.38 | 0.69 | 0.77 | 0.59 | 0.62 | 0.80 |
| Acyclic(N4)/cyclic (<= N4), weight ratio | 7.31 | 6.11 | 4.97 | 8.08 | 6.15 | 8.14 | 4.44 | 4.12 | 6.03 | 5.98 | 4.28 |

| | Example No. | | | | | | | |
|---|---|---|---|---|---|---|---|---|
| Catalyst Type | 736 EEEE | 737 EEEE | 738 EEEE | 739 EEEE | 740 EEEE | 741 EEEE | 742 EEEE | 743 EEEE |
| Catalyst weight, gm | 68.38 | 68.38 | 68.38 | 68.38 | 68.38 | 68.38 | 68.38 | 68.38 |
| Pressure, psig | 603 | 602 | 603 | 603 | 602 | 603 | 603 | 603 |
| Temperature, °C. | 259 | 269 | 260 | 280 | 270 | 280 | 270 | 270 |
| Time on organics, hrs. | 191.5 | 196.5 | 214.5 | 219.5 | 238.5 | 243.5 | 262.5 | 266 |
| Duration of run, hrs. | 2 | 2 | 2 | 2 | 2 | 2 | 2 | 2 |
| MEA SV, g mol/hr/kg cat | 4.05 | 4.06 | 3.59 | 4.00 | 3.95 | 4.40 | 3.76 | 3.89 |
| DETA/MEA mole ratio | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 |
| Crude product composition, wt. % | | | | | | | | |
| EDA | 0.251 | 0.489 | 0.337 | 0.945 | 0.600 | 1.593 | 0.706 | 0.676 |
| MEA | 24.769 | 19.980 | 21.647 | 14.371 | 19.473 | 6.716 | 18.311 | 19.235 |
| PIP | 0.340 | 0.589 | 0.483 | 0.985 | 0.679 | 1.480 | 0.743 | 0.731 |
| DETA | 53.539 | 49.348 | 49.438 | 44.879 | 48.790 | 36.170 | 47.421 | 48.217 |
| AEEA | 2.555 | 2.352 | 2.505 | 1.539 | 2.260 | 0.475 | 2.170 | 2.155 |
| AEP | 0.402 | 0.686 | 0.479 | 1.175 | 0.770 | 1.905 | 0.803 | 0.752 |
| HEP | 0.000 | 0.000 | 0.000 | 0.000 | 0.000 | 0.000 | 0.000 | 0.000 |
| TAEA | 1.480 | 1.962 | 2.037 | 2.311 | 2.070 | 2.556 | 2.174 | 1.990 |
| l-TETA | 6.735 | 8.956 | 8.928 | 10.980 | 9.466 | 13.448 | 10.036 | 9.225 |
| DAEP | 0.082 | 0.179 | 0.113 | 0.411 | 0.216 | 0.992 | 0.260 | 0.214 |
| PEEDA | 0.072 | 0.153 | 0.087 | 0.337 | 0.181 | 0.685 | 0.205 | 0.176 |
| DPE | 0.103 | 0.188 | 0.090 | 0.336 | 0.229 | 0.084 | 0.151 | 0.130 |
| AE-TAEA | 1.148 | 1.988 | 1.704 | 3.208 | 2.190 | 4.698 | 2.609 | 2.255 |
| l-TEPA | 2.110 | 3.632 | 3.226 | 6.048 | 4.274 | 8.949 | 4.512 | 4.130 |
| AE-DAEP | 0.072 | 0.068 | 0.065 | 0.302 | 0.149 | 0.729 | 0.156 | 0.129 |
| AE-PEEDA | 0.055 | 0.000 | 0.051 | 0.055 | 0.000 | 0.083 | 0.027 | 0.026 |
| iAE-PEEDA | 0.000 | 0.000 | 0.000 | 0.000 | 0.000 | 0.000 | 0.000 | 0.000 |
| AE-DPE | 0.059 | 0.074 | 0.169 | 0.596 | 0.296 | 0.104 | 0.073 | 0.070 |
| BPEA | 0.081 | 0.221 | 0.152 | 0.558 | 0.257 | 0.781 | 0.053 | 0.056 |
| Others | 1.898 | 3.066 | 1.779 | 4.582 | 3.140 | 7.552 | 4.192 | 3.803 |
| MEA conversion, % | 32.69 | 45.43 | 40.15 | 61.44 | 47.63 | 81.50 | 50.64 | 47.61 |
| DETA conversion, % | 13.53 | 19.90 | 18.77 | 28.43 | 22.01 | 40.80 | 24.03 | 21.95 |
| Acyclic(N4), wt. % | 96.97 | 95.46 | 97.43 | 92.46 | 94.85 | 90.08 | 95.20 | 95.57 |
| Acyclic(N5), wt. % | 92.45 | 93.93 | 91.87 | 85.96 | 90.20 | 88.94 | 95.85 | 95.78 |
| Σ(N5)/Σ(N4), weight ratio | 0.42 | 0.52 | 0.48 | 0.75 | 0.59 | 0.86 | 0.58 | 0.57 |
| Acyclic(N4)/cyclic (<= N4), weight ratio | 8.23 | 6.09 | 8.76 | 4.10 | 5.56 | 3.11 | 5.65 | 5.60 |

TABLE LXXVI

| | Example No. | | | | | | | | | | |
|---|---|---|---|---|---|---|---|---|---|---|---|
| Catalyst Type | 744 FFFF | 745 FFFF | 746 FFFF | 747 FFFF | 748 FFFF | 749 FFFF | 750 FFFF | 751 FFFF | 752 FFFF | 753 FFFF | 754 FFFF |
| Catalyst weight, gm | 68 | 68 | 68 | 68 | 68 | 68 | 68 | 68 | 68 | 68 | 68 |
| Pressure, psig | 606 | 599 | 602 | 606 | 593 | 593 | 601 | 600 | 600 | 596 | 598 |

TABLE LXXVI-continued

| | | | | | | | | | | | |
|---|---|---|---|---|---|---|---|---|---|---|---|
| Temperature, °C. | 270 | 270 | 280 | 260 | 270 | 260 | 280 | 280 | 270 | 271 | 282 |
| Time on organics, hrs. | 7 | 26 | 30.5 | 50 | 55 | 74 | 79 | 98.8 | 123 | 158 | 163 |
| Duration of run, hrs. | 2 | 2 | 1 | 2 | 2 | 2 | 2 | 2 | 2 | 2 | 2 |
| MEA SV, g mol/hr/kg cat | 3.97 | 3.90 | 3.93 | 3.98 | 3.96 | 3.94 | 3.97 | 3.93 | 3.85 | 3.92 | 3.89 |
| DETA/MEA mole ratio | 1.00 | 1.00 | 1.00 | 1.00 | 1.00 | 1.00 | 1.00 | 1.00 | 1.00 | 1.00 | 1.00 |
| NH₃/MEA mole ratio | 5.97 | 5.97 | 5.97 | 5.97 | 5.97 | 5.97 | 5.97 | 5.97 | 5.97 | 5.97 | 5.97 |
| Crude product composition, wt. % | | | | | | | | | | | |
| EDA | 0.750 | 0.869 | 1.269 | 0.502 | 0.696 | 1.589 | 1.188 | 1.273 | 0.810 | 1.086 | 1.518 |
| MEA | 14.139 | 13.058 | 7.841 | 19.884 | 13.962 | 19.078 | 8.661 | 6.995 | 13.582 | 13.203 | 6.960 |
| PIP | 0.946 | 1.041 | 1.264 | 0.614 | 0.883 | 0.667 | 1.206 | 1.218 | 0.953 | 1.186 | 1.446 |
| DETA | 42.338 | 40.333 | 34.679 | 47.727 | 41.491 | 46.874 | 37.218 | 33.635 | 40.430 | 40.181 | 35.494 |
| AEEA | 1.641 | 1.480 | 0.679 | 2.213 | 1.609 | 2.241 | 0.609 | 0.617 | 1.541 | 1.261 | 0.505 |
| AEP | 0.987 | 1.041 | 1.527 | 0.599 | 0.913 | 0.603 | 1.467 | 1.500 | 0.961 | 1.136 | 1.798 |
| HEP | 0.000 | 0.000 | 0.000 | 0.000 | 0.000 | 0.000 | 0.000 | 0.000 | 0.000 | 0.000 | 0.000 |
| TAEA | 2.657 | 2.786 | 2.699 | 2.233 | 2.513 | 2.246 | 2.703 | 2.625 | 2.555 | 2.661 | 2.671 |
| l-TETA | 12.825 | 13.469 | 13.932 | 10.488 | 12.891 | 10.468 | 13.856 | 13.911 | 12.446 | 13.232 | 14.206 |
| DAEP | 0.340 | 0.387 | 0.763 | 0.170 | 0.305 | 0.165 | 0.693 | 0.770 | 0.335 | 0.452 | 0.939 |
| PEEDA | 0.302 | 0.336 | 0.601 | 0.150 | 0.277 | 0.146 | 0.549 | 0.605 | 0.284 | 0.372 | 0.692 |
| DPE | 0.132 | 0.150 | 0.301 | 0.094 | 0.099 | 0.099 | 0.088 | 0.118 | 0.077 | 0.076 | 0.107 |
| AE-TAEA | 3.574 | 3.998 | 4.830 | 2.253 | 3.538 | 2.309 | 4.432 | 4.606 | 3.500 | 4.013 | 4.667 |
| l-TEPA | 7.216 | 7.943 | 9.991 | 4.612 | 7.184 | 4.724 | 9.147 | 9.831 | 7.304 | 8.152 | 9.680 |
| AE-DAEP | 0.088 | 0.082 | 0.204 | 0.154 | 0.134 | 0.064 | 0.601 | 0.879 | 0.328 | 0.401 | 0.783 |
| AE-PEEDA | 0.155 | 0.158 | 0.380 | 0.028 | 0.223 | 0.074 | 0.067 | 0.125 | 0.039 | 0.047 | 0.080 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.038 | 0.067 | 0.403 | 0.056 | 0.248 | 0.075 | 0.078 | 0.313 | 0.048 | 0.057 | 0.105 |
| BPEA | 0.508 | 0.179 | 1.040 | 0.229 | 0.611 | 0.231 | 0.804 | 0.839 | 0.472 | 0.607 | 0.902 |
| Others | 5.025 | 5.875 | 9.178 | 2.946 | 5.812 | 3.348 | 7.734 | 8.939 | 4.826 | 5.537 | 8.116 |
| MEA conversion, % | 62.09 | 64.96 | 79.02 | 46.40 | 62.51 | 48.13 | 76.57 | 80.72 | 62.33 | 64.77 | 81.20 |
| DETA conversion, % | 32.54 | 35.67 | 44.85 | 23.54 | 33.79 | 24.26 | 40.15 | 44.90 | 33.36 | 36.28 | 43.03 |
| Acyclic(N4), wt. % | 95.24 | 94.91 | 90.90 | 96.85 | 95.77 | 96.87 | 92.56 | 91.71 | 95.57 | 94.64 | 90.67 |
| Acyclic(N5), wt. % | 93.19 | 96.09 | 87.98 | 93.64 | 89.81 | 94.07 | 89.76 | 87.00 | 92.42 | 91.63 | 88.47 |
| Σ(N5)/Σ(N4), weight ratio | 0.71 | 0.73 | 0.92 | 0.56 | 0.74 | 0.57 | 0.85 | 0.92 | 0.74 | 0.79 | 0.87 |
| Acyclic(N4)/cyclic (< = N4), weight ratio | 5.72 | 5.50 | 3.73 | 7.82 | 6.22 | 7.57 | 4.14 | 3.93 | 5.75 | 4.93 | 3.39 |

| | Example No. | | | | | | | | | | |
|---|---|---|---|---|---|---|---|---|---|---|---|
| | 755 | 756 | 757 | 758 | 759 | 760 | 761 | 762 | 763 | 764 | 765 |
| Catalyst Type | FFFF | FFFF | FFFF | FFFF | FFFF | FFFF | FFFF | FFFF | FFFF | FFFF | FFFF |
| Catalyst weight, gm | 68 | 68 | 68 | 68 | 68 | 68 | 68 | 68 | 67.2 | 67.2 | 67.2 |
| Pressure, psig | 602 | 603 | 602 | 602 | 603 | 603 | 603 | 603 | 600 | 600 | 600 |
| Temperature, °C. | 260 | 270 | 260 | 281 | 272 | 280 | 272 | 271 | 267.7 | 267.9 | 278 |
| Time on organics, hrs. | 182 | 187 | 206 | 211 | 272 | 235 | 254 | 257.5 | 4 | 6.5 | 28.5 |
| Duration of run, hrs. | 2 | 2 | 83.7 | 2 | 2 | 2 | 2 | 2 | 2 | 2 | 2 |
| MEA SV, g mol/hr/kg cat | 3.99 | 3.83 | 0.09 | 3.85 | 3.80 | 3.88 | 3.86 | 4.03 | 4.59 | 4.81 | 4.66 |
| DETA/MEA mole ratio | 1.00 | 1.00 | 1.00 | 1.00 | 1.00 | 1.00 | 1.00 | 1.00 | 1.00 | 1.00 | 1.00 |
| NH₃/MEA mole ratio | 5.97 | 5.97 | 5.97 | 5.97 | 5.97 | 5.97 | 5.97 | 5.97 | 5.97 | 5.97 | 5.97 |
| Crude product composition, wt. % | | | | | | | | | | | |
| EDA | 0.564 | 0.960 | 0.630 | 1.769 | 1.921 | 2.220 | 1.641 | 1.650 | 0.515 | 0.541 | 1.593 |
| MEA | 18.056 | 12.558 | 17.829 | 6.838 | 12.002 | 5.827 | 11.663 | 13.072 | 23.588 | 25.727 | 18.012 |
| PIP | 0.765 | 1.101 | 0.770 | 1.362 | 1.263 | 1.380 | 1.178 | 1.205 | 0.888 | 1.118 | 1.953 |
| DETA | 45.781 | 40.874 | 44.267 | 34.368 | 39.115 | 30.652 | 38.907 | 40.441 | 54.811 | 54.100 | 50.845 |
| AEEA | 2.117 | 1.385 | 2.108 | 0.517 | 1.158 | 0.441 | 1.197 | 1.308 | 0.344 | 0.802 | 0.233 |
| AEP | 0.738 | 1.161 | 0.699 | 1.725 | 1.205 | 1.595 | 1.179 | 1.119 | 0.883 | 0.858 | 1.884 |
| HEP | 0.000 | 0.000 | 0.000 | 0.000 | 0.000 | 0.000 | 0.000 | 0.000 | 0.000 | 0.000 | 0.000 |
| TAEA | 2.384 | 2.732 | 2.320 | 2.531 | 2.548 | 2.402 | 2.575 | 2.513 | 1.618 | 1.490 | 1.878 |
| l-TETA | 11.386 | 13.549 | 11.117 | 13.437 | 12.752 | 13.162 | 12.893 | 12.524 | 7.964 | 7.269 | 9.198 |
| DAEP | 0.225 | 0.438 | 0.196 | 0.889 | 0.485 | 0.981 | 0.469 | 0.410 | 0.114 | 0.093 | 0.645 |
| PEEDA | 0.187 | 0.630 | 0.175 | 0.670 | 0.383 | 0.728 | 0.375 | 0.335 | 0.081 | 0.064 | 0.387 |
| DPE | 0.056 | 0.091 | 0.033 | 0.111 | 0.077 | 0.133 | 0.082 | 0.076 | 0.000 | 0.000 | 0.000 |
| AE-TAEA | 2.669 | 3.990 | 2.705 | 4.603 | 4.023 | 4.890 | 3.878 | 3.770 | 0.000 | 0.088 | 0.246 |
| l-TEPA | 5.588 | 8.225 | 5.696 | 9.840 | 8.145 | 10.433 | 8.054 | 7.706 | 0.664 | 0.704 | 1.555 |
| AE-DAEP | 0.156 | 0.382 | 0.201 | 0.171 | 0.377 | 0.235 | 0.379 | 0.324 | 0.000 | 0.223 | 0.372 |
| AE-PEEDA | 0.028 | 0.051 | 0.028 | 0.114 | 0.042 | 0.161 | 0.048 | 0.037 | 0.000 | 0.000 | 0.099 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.046 | 0.043 | 0.036 | 0.053 | 0.049 | 0.706 | 0.047 | 0.046 | 0.168 | 0.000 | 0.059 |
| BPEA | 0.324 | 0.630 | 0.311 | 0.897 | 0.644 | 1.020 | 0.619 | 0.582 | 0.000 | 0.000 | 0.000 |
| Others | 3.310 | 5.711 | 3.339 | 10.005 | 5.502 | 13.484 | 5.564 | 5.184 | 1.532 | 0.963 | 2.990 |
| MEA conversion, % | 51.33 | 66.74 | 50.94 | 81.35 | 67.32 | 84.30 | 67.93 | 64.52 | 34.18 | 28.60 | 49.97 |
| DETA conversion, % | 26.65 | 35.67 | 27.60 | 44.30 | 36.70 | 50.93 | 36.43 | 34.77 | 9.11 | 10.77 | 16.06 |
| Acyclic(N4), wt. % | 96.72 | 94.81 | 97.08 | 90.53 | 94.19 | 89.41 | 94.35 | 94.83 | 98.01 | 98.23 | 91.48 |
| Acyclic(N5), wt. % | 93.71 | 91.70 | 93.58 | 92.12 | 91.63 | 87.84 | 91.61 | 92.07 | 79.79 | 78.07 | 77.26 |
| Σ(N5)/Σ(N4), weight ratio | 0.62 | 0.78 | 0.65 | 0.89 | 0.82 | 1.00 | 0.79 | 0.79 | 0.09 | 0.11 | 0.19 |
| Acyclic(N4)/cyclic (< = N4), weight ratio | 6.99 | 5.16 | 7.17 | 3.36 | 4.48 | 3.23 | 4.71 | 4.78 | 4.87 | 4.11 | 2.27 |

| | Example No. | | | | | |
|---|---|---|---|---|---|---|
| | 766 | 767 | 768 | 769 | 770 | 771 |
| Catalyst Type | FFFF | FFFF | FFFF | FFFF | FFFF | FFFF |
| Catalyst weight, gm | 67.2 | 67.2 | 67.2 | 67.2 | 67.2 | 67.2 |
| Pressure, psig | 600 | 600 | 600 | 600 | 600 | 600 |
| Temperature, °C. | 257.8 | 269.6 | 259.3 | 279.3 | 269.8 | 270.1 |

TABLE LXXVI-continued

| | | | | | | |
|---|---|---|---|---|---|---|
| Time on organics, hrs. | 47.5 | 52.5 | 71 | 76.5 | 96.5 | 99 |
| Duration of run, hrs. | 2 | 2 | 2 | 2 | 2 | 2 |
| MEA SV, g mol/hr/kg cat | 4.74 | 4.80 | 4.79 | 4.46 | 4.63 | 4.60 |
| DETA/MEA mole ratio | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 |
| Crude product composition, wt. % | | | | | | |
| EDA | 0.567 | 0.832 | 0.445 | 1.675 | 0.932 | 0.995 |
| MEA | 26.580 | 21.992 | 27.189 | 13.854 | 20.859 | 20.291 |
| PIP | 1.009 | 1.390 | 0.957 | 1.810 | 1.493 | 1.486 |
| DETA | 55.433 | 53.042 | 56.685 | 51.796 | 53.039 | 51.623 |
| AEEA | 0.360 | 0.208 | 0.377 | 0.150 | 0.478 | 0.210 |
| AEP | 0.856 | 1.352 | 0.775 | 2.177 | 1.423 | 1.423 |
| HEP | 0.000 | 0.000 | 0.000 | 0.000 | 0.000 | 0.000 |
| TAEA | 1.474 | 1.695 | 1.397 | 1.977 | 1.858 | 1.955 |
| l-TETA | 6.586 | 8.327 | 6.490 | 9.962 | 8.880 | 10.270 |
| DAEP | 0.301 | 0.154 | 0.207 | 0.692 | 0.412 | 0.178 |
| PEEDA | 0.144 | 0.104 | 0.117 | 0.359 | 0.162 | 0.125 |
| DPE | 0.000 | 0.000 | 0.000 | 0.000 | 0.000 | 0.000 |
| AE-TAEA | 0.000 | 0.102 | 0.000 | 1.894 | 0.109 | 0.000 |
| l-TEPA | 0.500 | 0.975 | 0.246 | 3.556 | 1.157 | 1.321 |
| AE-DAEP | 0.000 | 0.000 | 0.000 | 0.114 | 0.133 | 0.326 |
| AE-PEEDA | 0.000 | 0.175 | 0.000 | 0.075 | 0.000 | 0.069 |
| iAE-PEEDA | 0.000 | 0.000 | 0.000 | 0.000 | 0.000 | 0.000 |
| AE-DPE | 0.000 | 0.423 | 0.000 | 0.000 | 0.083 | 0.512 |
| BPEA | 0.000 | 0.000 | 0.000 | 0.000 | 0.000 | 0.000 |
| Others | 1.492 | 2.047 | 0.994 | 0.880 | 1.861 | 2.579 |
| MEA conversion, % | 27.10 | 38.81 | 25.75 | 61.46 | 42.13 | 44.20 |
| DETA conversion, % | 9.64 | 12.29 | 7.99 | 14.37 | 12.55 | 15.64 |
| Acyclic(N4), wt. % | 94.77 | 97.49 | 96.05 | 91.91 | 94.93 | 97.59 |
| Acyclic(N5), wt. % | 100.00 | 64.30 | 100.00 | 96.64 | 85.40 | 59.30 |
| $\Sigma(N5)/\Sigma(N4)$, weight ratio | 0.06 | 0.16 | 0.03 | 0.43 | 0.13 | 0.18 |
| Acyclic(N4)/cyclic ($\leq$ N4), weight ratio | 3.49 | 3.34 | 3.83 | 2.37 | 3.08 | 3.81 |

TABLE LXXVII

| | Example No. | | | | | | |
|---|---|---|---|---|---|---|---|
| Catalyst Type | 772 GGGG | 773 GGGG | 774 GGGG | 775 GGGG | 776 GGGG | 777 GGGG | 778 GGGG |
| Catalyst weight, gm | 69.34 | 69.34 | 69.34 | 69.34 | 69.34 | 69.34 | 69.34 |
| Pressure, psig | 604 | 603 | 603 | 604 | 604 | 603 | 603 |
| Temperature, °C. | 270 | 270 | 280 | 260 | 270 | 260 | 280 |
| Time on organics, hrs. | 7 | 26 | 30.5 | 50 | 55 | 74 | 79 |
| Duration of run, hrs. | 2 | 2 | 1 | 2 | 2 | 2 | 2 |
| MEA SV, g mol/hr/kg cat | 4.33 | 4.26 | 4.21 | 4.20 | 4.33 | 4.20 | 4.17 |
| DETA/MEA mole ratio | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 |
| Crude product composition, wt. % | | | | | | | |
| EDA | 0.805 | 1.034 | 1.662 | 0.510 | 0.908 | 0.544 | 1.363 |
| MEA | 14.316 | 13.747 | 10.093 | 20.646 | 15.418 | 19.410 | 8.991 |
| PIP | 0.832 | 0.927 | 1.260 | 0.542 | 0.841 | 0.555 | 1.085 |
| DETA | 41.647 | 40.641 | 36.709 | 48.819 | 43.537 | 47.902 | 35.150 |
| AEEA | 1.392 | 1.332 | 0.661 | 2.056 | 1.526 | 2.142 | 0.718 |
| AEP | 0.990 | 1.057 | 1.455 | 0.554 | 0.915 | 0.588 | 1.336 |
| HEP | 0.000 | 0.000 | 0.000 | 0.000 | 0.000 | 0.000 | 0.000 |
| TAEA | 2.980 | 2.906 | 2.683 | 2.272 | 2.709 | 2.329 | 2.593 |
| l-TETA | 13.276 | 13.074 | 12.859 | 9.750 | 12.028 | 10.013 | 12.850 |
| DAEP | 0.416 | 0.470 | 0.726 | 0.152 | 0.358 | 0.171 | 0.754 |
| PEEDA | 0.321 | 0.347 | 0.527 | 0.130 | 0.270 | 0.147 | 0.531 |
| DPE | 0.151 | 0.167 | 0.208 | 0.055 | 0.159 | 0.073 | 0.126 |
| AE-TAEA | 4.148 | 4.074 | 4.997 | 2.219 | 3.441 | 2.254 | 4.357 |
| l-TEPA | 7.057 | 7.074 | 8.378 | 3.718 | 6.209 | 3.871 | 8.283 |
| AE-DAEP | 0.081 | 0.074 | 0.124 | 0.145 | 0.075 | 0.247 | 1.053 |
| AE-PEEDA | 0.148 | 0.141 | 0.238 | 0.027 | 0.117 | 0.067 | 0.154 |
| iAE-PEEDA | 0.000 | 0.000 | 0.000 | 0.000 | 0.000 | 0.000 | 0.000 |
| AE-DPE | 0.051 | 0.069 | 0.286 | 0.266 | 0.175 | 0.261 | 0.309 |
| BPEA | 0.582 | 0.570 | 0.800 | 0.207 | 0.479 | 0.205 | 0.737 |
| Others | 5.099 | 5.415 | 7.215 | 2.423 | 4.615 | 2.781 | 8.931 |
| MEA conversion, % | 61.90 | 63.00 | 72.52 | 43.91 | 58.54 | 46.90 | 75.19 |
| DETA conversion, % | 34.13 | 35.00 | 40.60 | 21.18 | 30.42 | 22.12 | 42.36 |
| Acyclic(N4), wt. % | 94.82 | 94.20 | 91.41 | 97.28 | 94.93 | 96.93 | 91.63 |
| Acyclic(N5), wt. % | 92.86 | 92.88 | 90.23 | 90.21 | 91.94 | 88.71 | 84.88 |
| $\Sigma(N5)/\Sigma(N4)$, weight ratio | 0.70 | 0.71 | 0.87 | 0.53 | 0.68 | 0.54 | 0.88 |
| Acyclic(N4)/cyclic ($\leq$ N4), weight ratio | 6.00 | 5.38 | 3.72 | 8.39 | 5.80 | 8.05 | 4.03 |

| | Example No. | | | | | | |
|---|---|---|---|---|---|---|---|
| Catalyst Type | 779 GGGG | 780 GGGG | 781 GGGG | 782 GGGG | 783 GGGG | 784 GGGG | 785 GGGG |
| Catalyst weight, gm | 69.34 | 69.34 | 69.34 | 69.34 | 69.34 | 69.34 | 69.34 |

TABLE LXXVII-continued

| | | | | | | | |
|---|---|---|---|---|---|---|---|
| Pressure, psig | 600 | 600 | 603 | 604 | 603 | 604 | 603 |
| Temperature, °C. | 280 | 270 | 271 | 282 | 260 | 270 | 260 |
| Time on organics, hrs. | 98.8 | 123 | 158 | 163 | 182 | 187 | 206 |
| Duration of run, hrs. | 2 | 2 | 2 | 2 | 2 | 2 | 2 |
| MEA SV, g mol/hr/kg cat | 4.26 | 4.16 | 4.01 | 4.31 | 4.28 | 4.05 | 4.11 |
| DETA/MEA mole ratio | 1.00 | 1.00 | 1.00 | 1.00 | 1.00 | 1.00 | 1.00 |
| NH₃/MEA mole ratio | 5.97 | 5.97 | 5.97 | 5.97 | 5.97 | 5.97 | 5.97 |
| Crude product composition, wt. % | | | | | | | |
| EDA | 2.077 | 0.963 | 1.212 | 1.778 | 0.757 | 0.980 | 0.861 |
| MEA | 9.550 | 15.047 | 12.554 | 9.298 | 20.034 | 13.105 | 18.882 |
| PIP | 1.325 | 0.906 | 1.009 | 1.387 | 0.734 | 0.962 | 0.794 |
| DETA | 32.997 | 41.105 | 37.117 | 36.552 | 46.016 | 38.892 | 44.565 |
| AEEA | 0.580 | 1.445 | 1.046 | 0.554 | 1.888 | 1.280 | 1.745 |
| AEP | 1.810 | 0.927 | 1.212 | 1.598 | 0.679 | 0.976 | 0.784 |
| HEP | 0.000 | 0.000 | 0.000 | 0.000 | 0.000 | 0.000 | 0.000 |
| TAEA | 1.994 | 2.443 | 2.311 | 2.549 | 2.223 | 2.513 | 2.187 |
| l-TETA | 10.946 | 11.547 | 11.703 | 13.076 | 10.211 | 11.973 | 10.178 |
| DAEP | 1.270 | 0.373 | 0.669 | 0.839 | 0.209 | 0.394 | 0.335 |
| PEEDA | 0.858 | 0.292 | 0.476 | 0.594 | 0.174 | 0.318 | 0.240 |
| DPE | 0.164 | 0.196 | 0.112 | 0.468 | 0.072 | 0.186 | 0.150 |
| AE-TAEA | 3.447 | 3.193 | 3.397 | 4.484 | 2.580 | 3.922 | 2.727 |
| l-TEPA | 7.231 | 6.092 | 7.003 | 8.450 | 5.015 | 7.390 | 5.407 |
| AE-DAEP | 1.912 | 0.489 | 0.928 | 0.694 | 0.198 | 0.427 | 0.351 |
| AE-PEEDA | 0.294 | 0.065 | 0.153 | 0.085 | 0.045 | 0.079 | 0.059 |
| iAE-PEEDA | 0.000 | 0.000 | 0.000 | 0.000 | 0.000 | 0.000 | 0.000 |
| AE-DPE | 0.130 | 0.070 | 0.287 | 0.093 | 0.051 | 0.166 | 0.042 |
| BPEA | 0.613 | 0.415 | 0.510 | 0.761 | 0.054 | 0.563 | 0.330 |
| Others | 12.620 | 4.609 | 7.302 | 7.358 | 3.390 | 6.493 | 3.912 |
| MEA conversion, % | 73.83 | 57.94 | 64.82 | 74.69 | 45.65 | 63.83 | 48.59 |
| DETA conversion, % | 46.26 | 31.71 | 38.19 | 40.86 | 25.81 | 36.20 | 27.88 |
| Acyclic(N4), wt. % | 84.95 | 94.20 | 91.77 | 89.15 | 96.47 | 94.16 | 94.46 |
| Acyclic(N5), wt. % | 78.36 | 89.93 | 84.70 | 88.79 | 95.62 | 90.16 | 91.23 |
| Σ(N5)/Σ(N4), weight ratio | 0.89 | 0.70 | 0.80 | 0.83 | 0.62 | 0.82 | 0.68 |
| Acyclic(N4)/cyclic (< = N4), weight ratio | 2.38 | 5.19 | 4.03 | 3.20 | 6.65 | 5.11 | 5.37 |

| | Example No. | | | | |
|---|---|---|---|---|---|
| Catalyst Type | 786 GGGG | 787 GGGG | 788 GGGG | 789 GGGG | 790 GGGG |
| Catalyst weight, gm | 69.34 | 69.34 | 69.34 | 69.34 | 69.34 |
| Pressure, psig | 604 | 604 | 604 | 603 | 604 |
| Temperature, °C. | 281 | 272 | 280 | 272 | 271 |
| Time on organics, hrs. | 211 | 272 | 235 | 254 | 257.5 |
| Duration of run, hrs. | 2 | 2 | 2 | 2 | 2 |
| MEA SV, g mol/hr/kg cat | 4.41 | 4.13 | 4.11 | 4.22 | 4.43 |
| DETA/MEA mole ratio | 1.00 | 1.00 | 1.00 | 1.00 | 1.00 |
| NH₃/MEA mole ratio | 5.97 | 5.97 | 5.97 | 5.97 | 5.97 |
| Crude product composition, wt. % | | | | | |
| EDA | 2.156 | 1.946 | 2.350 | 1.794 | 1.594 |
| MEA | 8.720 | 12.941 | 7.170 | 13.118 | 13.362 |
| PIP | 1.385 | 1.150 | 1.343 | 1.147 | 1.045 |
| DETA | 34.824 | 39.610 | 33.663 | 39.912 | 39.851 |
| AEEA | 0.521 | 1.185 | 0.478 | 1.195 | 1.279 |
| AEP | 1.518 | 1.109 | 1.669 | 1.094 | 1.015 |
| HEP | 0.000 | 0.000 | 0.000 | 0.000 | 0.000 |
| TAEA | 2.296 | 2.546 | 2.452 | 2.458 | 2.496 |
| l-TETA | 12.160 | 12.466 | 13.106 | 12.081 | 12.149 |
| DAEP | 0.916 | 0.518 | 1.012 | 0.454 | 0.423 |
| PEEDA | 0.634 | 0.377 | 0.766 | 0.348 | 0.321 |
| DPE | 0.127 | 0.092 | 0.123 | 0.079 | 0.072 |
| AE-TAEA | 4.290 | 3.863 | 4.417 | 3.624 | 3.540 |
| l-TEPA | 8.840 | 7.583 | 9.218 | 7.097 | 6.990 |
| AE-DAEP | 0.189 | 0.411 | 0.892 | 0.342 | 0.038 |
| AE-PEEDA | 0.132 | 0.052 | 0.135 | 0.036 | 0.038 |
| iAE-PEEDA | 0.000 | 0.000 | 0.000 | 0.000 | 0.000 |
| AE-DPE | 0.411 | 0.073 | 0.390 | 0.091 | 0.061 |
| BPEA | 0.822 | 0.597 | 0.843 | 0.577 | 0.535 |
| Others | 10.339 | 5.881 | 9.704 | 5.473 | 5.321 |
| MEA conversion, % | 76.20 | 64.94 | 80.41 | 63.82 | 62.91 |
| DETA conversion, % | 43.50 | 36.22 | 45.35 | 34.58 | 34.25 |
| Acyclic(N4), wt. % | 89.61 | 93.83 | 89.12 | 94.28 | 94.72 |
| Acyclic(N5), wt. % | 89.42 | 91.00 | 85.78 | 91.11 | 91.63 |
| Σ(N5)/Σ(N4), weight ratio | 0.91 | 0.79 | 0.91 | 0.76 | 0.74 |
| Acyclic(N4)/cyclic (< = N4), weight ratio | 3.16 | 4.63 | 3.17 | 4.66 | 5.09 |

TABLE LXXVIII

| | Example No. | | | | | | | | |
|---|---|---|---|---|---|---|---|---|---|
| Catalyst Type | 791 HHHH | 792 HHHH | 793 HHHH | 794 HHHH | 795 HHHH | 796 HHHH | 797 HHHH | 798 HHHH | 799 HHHH |
| Catalyst weight, gm | 70.6 | 70.6 | 70.6 | 70.6 | 70.6 | 70.6 | 70.6 | 70.6 | 70.6 |
| Pressure, psig | 600 | 600 | 600 | 600 | 600 | 600 | 600 | 600 | 600 |
| Temperature, °C | 267.7 | 267.9 | 278 | 257.8 | 269.6 | 259.3 | 279.3 | 269.8 | 270.1 |
| Time on organics, hrs. | 4 | 6.5 | 30.5 | 49.5 | 54.5 | 73 | 78.5 | 98 | 101 |
| Duration of run, hrs. | 2 | 2 | 2 | 2 | 2 | 2 | 2 | 2 | 2 |
| MEA SV, g mol/hr/kg cat | 4.23 | 4.29 | 4.10 | 4.04 | 4.14 | 4.15 | 3.89 | 3.94 | 3.95 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.162 | 0.169 | 0.783 | 0.192 | 0.397 | 0.176 | 1.073 | 0.529 | 0.553 |
| MEA | 29.144 | 31.908 | 24.483 | 32.053 | 27.952 | 31.487 | 22.456 | 25.861 | 26.009 |
| PIP | 0.349 | 0.340 | 1.209 | 0.251 | 0.651 | 0.248 | 1.406 | 0.768 | 0.760 |
| DETA | 59.742 | 58.534 | 56.565 | 58.955 | 59.279 | 59.506 | 54.811 | 57.648 | 57.364 |
| AEEA | 0.310 | 0.929 | 0.200 | 0.321 | 0.342 | 0.351 | 0.776 | 0.366 | 0.370 |
| AEP | 0.544 | 0.498 | 1.287 | 0.436 | 0.711 | 0.471 | 1.454 | 0.793 | 0.801 |
| HEP | 0.000 | 0.000 | 0.000 | 0.000 | 0.000 | 0.000 | 0.000 | 0.000 | 0.000 |
| TAEA | 0.578 | 0.706 | 0.873 | 0.618 | 0.733 | 0.669 | 1.573 | 0.874 | 1.310 |
| l-TETA | 4.153 | 2.968 | 6.200 | 2.623 | 4.926 | 2.835 | 6.907 | 5.628 | 5.841 |
| DAEP | 0.177 | 0.175 | 0.342 | 0.144 | 0.238 | 0.180 | 0.520 | 0.239 | 0.184 |
| PEEDA | 0.076 | 0.000 | 0.220 | 0.000 | 0.135 | 0.000 | 0.347 | 0.085 | 0.125 |
| DPE | 0.000 | 0.000 | 0.000 | 0.000 | 0.000 | 0.000 | 0.060 | 0.000 | 0.000 |
| AE-TAEA | 0.000 | 0.000 | 0.000 | 0.000 | 0.000 | 0.000 | 0.236 | 0.000 | 0.000 |
| l-TEPA | 0.000 | 0.000 | 0.463 | 0.000 | 0.000 | 0.000 | 0.848 | 0.318 | 0.401 |
| AE-DAEP | 0.000 | 0.000 | 0.000 | 0.000 | 0.000 | 0.000 | 0.181 | 0.000 | 0.000 |
| AE-PEEDA | 0.000 | 0.000 | 0.000 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.279 | 0.000 | 0.000 |
| BPEA | 0.000 | 0.000 | 0.000 | 0.000 | 0.000 | 0.000 | 0.000 | 0.000 | 0.000 |
| Others | 0.976 | 0.215 | 1.483 | 1.078 | 1.416 | 1.247 | 1.734 | 1.491 | 2.212 |
| MEA conversion, % | 20.13 | 12.23 | 32.26 | 12.02 | 24.15 | 14.16 | 38.70 | 28.47 | 29.14 |
| DETA conversion, % | 2.69 | 4.31 | 6.99 | 3.83 | 4.40 | 3.59 | 11.07 | 5.24 | 7.12 |
| Acyclic(N4), wt. % | 94.94 | 95.46 | 92.64 | 95.76 | 93.82 | 95.11 | 90.14 | 95.25 | 95.85 |
| Acyclic(N5), wt. % | — | — | 100.00 | — | — | — | 70.20 | 100.00 | 100.00 |
| Σ(N5)/Σ(N4), weight ratio | 0.00 | 0.00 | 0.00 | 0.00 | 0.00 | 0.00 | 0.16 | 0.05 | 0.05 |
| Acyclic(N4)/cyclic (< = N4), weight ratio | 4.13 | 3.63 | 2.31 | 3.90 | 3.26 | 3.90 | 2.24 | 3.45 | 3.82 |

TABLE LXXIX

| | Example No. | | | | | | | | | | |
|---|---|---|---|---|---|---|---|---|---|---|---|
| Catalyst Type | 800 IIII | 801 IIII | 802 IIII | 803 IIII | 804 IIII | 805 IIII | 806 IIII | 807 IIII | 808 IIII | 809 IIII | 810 IIII |
| Catalyst weight, gm | 67.5 | 67.5 | 67.5 | 67.5 | 67.5 | 67.5 | 67.5 | 67.5 | 67.5 | 67.5 | 67.5 |
| Pressure, psig | 598 | 597 | 597 | 598 | 598 | 598 | 598 | 600 | 600 | 585 | 598 |
| Temperature, °C | 270 | 270 | 280 | 260 | 270 | 260 | 280 | 280 | 270 | 271 | 282 |
| Time on organics, hrs. | 7 | 26 | 30.5 | 50 | 55 | 74 | 79 | 98.8 | 123 | 158 | 163 |
| Duration of run, hrs. | 2 | 2 | 1 | 2 | 2 | 2 | 2 | 2 | 2 | 2 | 2 |
| MEA SV, g mol/hr/kg cat | 3.62 | 3.73 | 3.53 | 3.46 | 3.70 | 3.56 | 3.47 | 3.46 | 3.40 | 2.97 | 3.69 |
| DETA/MEA mole ratio | 1.00 | 1.00 | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 | 5.97 | 5.97 |
| Crude product composition, wt. % | | | | | | | | | | | |
| EDA | 0.294 | 0.424 | 0.706 | 0.273 | 0.506 | 0.342 | 0.979 | 1.001 | 0.624 | 0.764 | 1.129 |
| MEA | 25.314 | 22.475 | 18.589 | 26.092 | 22.747 | 25.743 | 18.317 | 16.142 | 21.635 | 20.571 | 16.885 |
| PIP | 0.421 | 0.496 | 0.707 | 0.266 | 0.485 | 0.297 | 0.712 | 0.692 | 0.469 | 0.531 | 0.826 |
| DETA | 54.036 | 51.203 | 48.723 | 54.115 | 53.329 | 54.167 | 48.580 | 42.653 | 47.745 | 47.941 | 46.768 |
| AEEA | 1.899 | 2.033 | 1.670 | 2.115 | 2.193 | 2.258 | 1.799 | 1.403 | 1.963 | 1.707 | 1.530 |
| AEP | 0.488 | 0.616 | 0.869 | 0.374 | 0.614 | 0.438 | 0.855 | 0.848 | 0.588 | 0.697 | 1.034 |
| HEP | 0.000 | 0.000 | 0.000 | 0.000 | 0.000 | 0.000 | 0.000 | 0.000 | 0.000 | 0.000 | 0.000 |
| TAEA | 1.340 | 1.728 | 1.888 | 1.215 | 1.590 | 1.290 | 1.768 | 1.764 | 1.551 | 1.641 | 1.964 |
| l-TETA | 6.203 | 8.239 | 9.101 | 5.680 | 7.515 | 6.023 | 8.740 | 9.202 | 7.737 | 8.006 | 9.717 |
| DAEP | 0.091 | 0.205 | 0.282 | 0.096 | 0.157 | 0.110 | 0.267 | 0.415 | 0.216 | 0.239 | 0.408 |
| PEEDA | 0.093 | 0.162 | 0.229 | 0.076 | 0.133 | 0.090 | 0.209 | 0.313 | 0.172 | 0.186 | 0.297 |
| DPE | 0.048 | 0.111 | 0.178 | 0.076 | 0.126 | 0.084 | 0.220 | 0.387 | 0.232 | 0.211 | 0.069 |
| AE-TAEA | 1.230 | 1.884 | 2.347 | 1.338 | 1.704 | 1.006 | 1.902 | 2.806 | 1.832 | 1.858 | 2.661 |
| l-TEPA | 2.363 | 3.385 | 4.197 | 1.841 | 2.798 | 1.882 | 3.504 | 5.099 | 3.159 | 3.247 | 5.154 |
| AE-DAEP | 0.139 | 0.145 | 0.257 | 0.143 | 0.273 | 0.114 | 0.392 | 0.812 | 0.539 | 0.401 | 0.342 |
| AE-PEEDA | 0.066 | 0.034 | 0.101 | 0.042 | 0.061 | 0.024 | 0.100 | 0.168 | 0.078 | 0.057 | 0.062 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.000 | 0.043 | 0.117 | 0.077 | 0.157 | 0.090 | 0.062 | 0.343 | 0.035 | 0.053 | 0.067 |
| BPEA | 0.110 | 0.211 | 0.290 | 0.056 | 0.110 | 0.069 | 0.063 | 0.209 | 0.048 | 0.051 | 0.390 |
| Others | 2.415 | 3.286 | 4.610 | 2.509 | 3.660 | 2.432 | 4.633 | 8.202 | 4.835 | 4.459 | 5.997 |
| MEA conversion, % | 31.77 | 40.08 | 50.03 | 29.37 | 39.57 | 30.42 | 49.72 | 55.92 | 40.42 | 42.93 | 55.07 |
| DETA conversion, % | 13.44 | 18.87 | 22.15 | 12.94 | 17.39 | 12.99 | 20.75 | 30.77 | 21.85 | 20.95 | 26.04 |
| Acyclic(N4), wt. % | 97.01 | 95.43 | 94.10 | 96.54 | 95.63 | 96.27 | 93.80 | 90.77 | 93.73 | 93.81 | 93.79 |
| Acyclic(N5), wt. % | 91.93 | 92.41 | 89.53 | 90.91 | 88.22 | 90.67 | 89.75 | 83.77 | 87.68 | 90.08 | 90.08 |
| Σ(N5)/Σ(N4), weight ratio | 0.50 | 0.55 | 0.63 | 0.49 | 0.54 | 0.42 | 0.54 | 0.78 | 0.57 | 0.55 | 0.70 |

TABLE LXXIX-continued

| | | | | | | | | | | |
|---|---|---|---|---|---|---|---|---|---|---|
| Acyclic(N4)/cyclic (< = N4), weight ratio | 6.61 | 6.27 | 4.85 | 7.78 | 6.01 | 7.18 | 4.65 | 4.13 | 5.53 | 5.17 | 4.43 |

| | Example No. | | | | | | | |
|---|---|---|---|---|---|---|---|---|
| Catalyst Type | 811 IIII | 812 IIII | 813 IIII | 814 IIII | 815 IIII | 816 IIII | 817 IIII | 818 IIII |
| Catalyst weight, gm | 67.5 | 67.5 | 67.5 | 67.5 | 67.5 | 67.5 | 67.5 | 67.5 |
| Pressure, psig | 598 | 598 | 598 | 598 | 598 | 598 | 598 | 598 |
| Temperature, °C. | 260 | 270 | 260 | 281 | 272 | 280 | 272 | 271 |
| Time on organics, hrs. | 182 | 187 | 206 | 211 | 272 | 235 | 254 | 257.5 |
| Duration of run, hrs. | 2 | 2 | 2 | 2 | 2 | 2 | 2 | 2 |
| MEA SV, g mol/hr/kg cat | 3.58 | 3.41 | 3.41 | 3.54 | 3.99 | 3.53 | 3.50 | 3.70 |
| DETA/MEA mole ratio | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 |
| Crude product composition, wt. % | | | | | | | | |
| EDA | 0.479 | 0.786 | 0.509 | 1.756 | 1.803 | 1.993 | 1.749 | 1.597 |
| MEA | 25.262 | 21.504 | 25.342 | 18.397 | 20.631 | 15.100 | 20.996 | 22.350 |
| PIP | 0.351 | 0.538 | 0.352 | 0.865 | 0.634 | 0.781 | 0.638 | 0.567 |
| DETA | 52.656 | 48.687 | 51.138 | 47.357 | 46.647 | 42.162 | 46.440 | 48.370 |
| AEEA | 2.132 | 1.979 | 2.129 | 1.620 | 1.738 | 1.446 | 1.730 | 1.824 |
| AEP | 0.470 | 0.636 | 0.432 | 0.927 | 0.707 | 0.935 | 0.676 | 0.626 |
| HEP | 0.000 | 0.000 | 0.000 | 0.000 | 0.000 | 0.000 | 0.000 | 0.000 |
| TAEA | 1.408 | 1.541 | 1.337 | 1.743 | 1.648 | 1.942 | 1.596 | 1.530 |
| l-TETA | 6.641 | 7.305 | 6.278 | 8.432 | 8.037 | 9.595 | 7.922 | 7.422 |
| DAEP | 0.135 | 0.174 | 0.125 | 0.291 | 0.359 | 0.442 | 0.295 | 0.232 |
| PEEDA | 0.101 | 0.138 | 0.094 | 0.224 | 0.234 | 0.314 | 0.215 | 0.169 |
| DPE | 0.110 | 0.183 | 0.114 | 0.089 | 0.099 | 0.103 | 0.182 | 0.107 |
| AE-TAEA | 1.266 | 1.659 | 1.462 | 2.013 | 2.165 | 2.975 | 2.063 | 1.905 |
| l-TEPA | 2.314 | 2.935 | 2.396 | 3.688 | 3.984 | 5.395 | 3.860 | 3.394 |
| AE-DAEP | 0.130 | 0.223 | 0.173 | 0.261 | 0.335 | 0.507 | 0.256 | 0.234 |
| AE-PEEDA | 0.025 | 0.068 | 0.063 | 0.045 | 0.076 | 0.117 | 0.056 | 0.042 |
| iAE-PEEDA | 0.000 | 0.000 | 0.000 | 0.000 | 0.000 | 0.000 | 0.000 | 0.000 |
| AE-DPE | 0.086 | 0.211 | 0.083 | 0.034 | 0.229 | 0.080 | 0.055 | 0.040 |
| BPEA | 0.040 | 0.087 | 0.037 | 0.225 | 0.294 | 0.465 | 0.272 | 0.231 |
| Others | 2.874 | 5.176 | 3.565 | 5.035 | 6.180 | 8.307 | 5.107 | 4.381 |
| MEA conversion, % | 31.89 | 40.98 | 31.07 | 49.41 | 44.79 | 58.84 | 42.66 | 32.29 |
| DETA conversion, % | 15.63 | 20.58 | 17.33 | 22.60 | 25.81 | 31.71 | 24.63 | 31.91 |
| Acyclic(N4), wt. % | 95.88 | 94.70 | 95.80 | 94.40 | 93.33 | 93.06 | 93.21 | 94.64 |
| Acyclic(N5), wt. % | 92.72 | 88.64 | 91.56 | 90.98 | 86.82 | 87.74 | 90.25 | 90.67 |
| Σ(N5)/Σ(N4), weight ratio | 0.46 | 0.55 | 0.53 | 0.58 | 0.68 | 0.77 | 0.64 | 0.62 |
| Acyclic(N4)/cyclic (< = N4), weight ratio | 6.90 | 5.30 | 6.82 | 4.25 | 4.76 | 4.48 | 4.47 | 5.26 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process of making polyalkylene polyamines which comprises condensing an amino compound comprising at least one of ammonia and one or more organic compounds containing nitrogen to which is bonded an active hydrogen, with a high surface area Group IVB metal oxide condensation catalyst selected from the group consisting of hafnium oxide having a surface area greater than about 70 m$^2$/gm, zirconium oxide having a surface area greater than about 70 m$^2$/gm, titanium oxide having a surface area greater than about 140 m$^2$/gm and mixtures thereof.

2. The process of claim 1 wherein the titanium oxide condensation catalyst comprises titanium dioxide.

3. The process of claim 1 wherein the zirconium oxide condensation catalyst comprises zirconium dioxide.

4. The process of claim 1 wherein the condensation catalyst comprises a mixture of titanium dioxide and zirconium dioxide.

5. The process of claim 1 wherein the catalyst is associated with a support material.

6. The process of claim 5 wherein the support comprises an alumina material or an alumina-silica material.

7. The process of claim 5 wherein the support comprises a silica material or a silica-alumina material.

8. The process of claim 5 wherein the support comprises from about 5 to about 50 percent by weight of the catalyst.

9. The process of claim 1 wherein the catalyst contains a performance moderator that enhances product selectivity of the process.

10. The process of claim 9 wherein the performance moderator comprises one or more metal oxides.

11. The process of claim 11 wherein the performance moderator comprises one or more Group IA metal oxides, Group IIA metal oxides, Group IIIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, other Group IVB metal oxides or mixtures thereof.

12. The process of claim 11 wherein the performance moderator comprises one or more oxides of scandium, yttrium, lanthanum, cerium, gadolinium, lutetium, ytterbium, niobium, tantalum, chromium, molybdenum, tungsten, titanium, zirconium, iron, cobalt, nickel, zinc, cadmium, boron, aluminum, gallium, indium, silicon, germanium, tin, lead, arsenic, antimony and bismuth.

13. The process of claim 9 wherein the performance moderator comprises one or more metallic phosphates having a cyclic structure or an acylic structure, metallic polyphosphates having a condensed structure, metallic metaphosphimates, metallic phosphoramidates, metallic amidophosphates, metallic imidophosphates or mixtures thereof.

14. The process of claim 13 wherein the performance moderator comprises sodium dihydrogen phosphate, sodium trimetaphosphate, disodium dihydrogen pyrophosphate, sodium tripolyphosphate or mixtures thereof.

15. The process of claim 1 wherein the Group IVB metal oxide condensation catalyst comprises a mixed oxide of a Group IVB metal oxide and one or more other metal oxides.

16. The process of claim 15 wherein the metal oxide comprises one or more Group IA metal oxides, Group IIA metal oxides, Group IIIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, other Group IVB metal oxides or mixtures thereof.

17. The process of claim 15 wherein the metal oxide comprises one or more oxides of scandium, yttrium, lanthanum, cerium, gadolinium, lutetium, ytterbium, niobium, tantalum, chromium, molybdenum, tungsten, titanium, zirconium, iron, cobalt, nickel, zinc, cadmium, boron, aluminum, gallium, indium, silicon, germanium, tin, lead, arsenic, antimony and bismuth.

18. The process of claim 1 wherein the Group IVB metal oxide condensation catalyst comprises a Group IVB metal oxide in an amount of from about 50 weight percent to about 100 weight percent of the weight of the catalyst.

19. The process of claim 1 wherein the Group IVB metal oxide condensation catalyst comprises a Group IVB metal oxide in an amount of from about 75 weight percent to about 100 weight percent of the weight of the catalyst.

20. The process of claim 1 wherein the Group IVB metal oxide condensation catalyst comprises a Group IVB metal oxide in an amount of from about 90 weight percent to about 100 weight percent of the weight of the catalyst.

21. The process of claim 1 wherein the amino compound comprises an alkyleneamine.

22. The process of claim 1 wherein the condensation further comprises condensing the amino compound with a compound containing an alcoholic hydroxy group.

23. The process of claim 22 wherein the amino compound is ammonia.

24. The process of claim 133 wherein the compound containing an alcoholic hydroxy group is an alkanolamine or an alkylene glycol.

25. The process of claim 24 wherein the alkanolamine is aminoethylethanolamine.

26. The process of claim 22 wherein the amino compound comprises ethylenediamine or diethylenetriamine and the compound containing the alcoholic hydroxy group is ethylene glycol.

27. The process of claim 1 wherein the amino compound comprises a mixture of monoethanolamine and ethylenediamine.

28. The process of claim 1 wherein the amino compound comprises a mixture of monoethanolamine and diethylenetriamine.

29. The process of claim 1 wherein the amino compound comprises a mixture of monoethanolamine, ethylenediamine and ammonia.

30. The process of claim 1 wherein the amino compound comprises a mixture of monoethanolamine, diethylenetriamine and ammonia.

31. The process of claim 1 wherein the amino compound comprises a mixture of aminoethylethanolamine and ethylenediamine.

32. The process of claim 1 wherein the amino compound comprises a mixture of aminoethylethanolamine and diethylenetriamine.

33. The process of claim 1 wherein the amino compound comprises a mixture of aminoethylethanolamine, ethylenediamine and ammonia.

34. The process of claim 1 wherein the amino compound comprises a mixture of aminoethylethanolamine, diethylenetriamine and ammonia.

35. The process of claim 1 wherein the amino compound comprises a mixture of diethanolamine and ethylenediamine or a mixture of diethanolamine and diethylenetriamine.

36. The process of claim 1 wherein the amino compound comprises a mixture of dihydroxyethylethylenediamine and ethylenediamine or a mixture of dihydroxyethylethylenediamine and diethylenetriamine.

37. The process of claim 1 wherein the amino compound comprises a mixture of hydroxyethyldiethylenetriamine and ethylenediamine or a mixture of hydroxyethyldiethylenetriamine and diethylenetriamine.

38. The process of claim 1 wherein the amino compound comprises a mixture of hydroxyethyltriethylenetetramine and ethylenediamine or a mixture of hydroxyethyltriethylenetetramine and diethylenetriamine.

39. The process of claim 1 which is effected in the liquid phase, vapor phase, supercritical liquid phase or mixtures thereof.

40. A process of making alkylamines which comprises condensing an alcohol and at least one of a primary amine, a secondary amine or a tertiary amine with a high surface area Group IVB metal oxide condensation catalyst.

* * * * *